US007115795B1

(12) United States Patent
Forsberg et al.

(10) Patent No.: US 7,115,795 B1
(45) Date of Patent: Oct. 3, 2006

(54) TRANSGENIC ANIMALS EXPRESSING SALIVARY PROTEINS

(75) Inventors: Cecil W. Forsberg, Guelph (CA); Serguei Golovan, Guelph (CA); John P. Phillips, Arkell (CA)

(73) Assignee: University of Guelph, Guelph (CA)

( * ) Notice: Subject to any disclaimer, the term of this patent is extended or adjusted under 35 U.S.C. 154(b) by 0 days.

(21) Appl. No.: 09/926,375

(22) PCT Filed: Apr. 20, 2000

(86) PCT No.: PCT/CA00/00430

§ 371 (c)(1),
(2), (4) Date: Feb. 28, 2002

(87) PCT Pub. No.: WO00/64247

PCT Pub. Date: Nov. 2, 2000

Related U.S. Application Data

(60) Provisional application No. 60/130,508, filed on Apr. 23, 1999.

(51) Int. Cl.
*A01K 67/027* (2006.01)
*A01K 67/00* (2006.01)
*C12P 21/00* (2006.01)
*C12N 15/00* (2006.01)

(52) U.S. Cl. .................. 800/14; 800/4; 800/8; 800/17; 800/24

(58) Field of Classification Search .................... 800/4, 800/14, 17, 18–20
See application file for complete search history.

(56) References Cited

U.S. PATENT DOCUMENTS 5,837,693 A * 11/1998 German et al. ............... 514/44
5,939,303 A 8/1999 Cheng
5,985,605 A 11/1999 Cheng

FOREIGN PATENT DOCUMENTS

WO WO 97/48812 12/1997
WO WO 99/08539 2/1999
WO WO 99/17610 4/1999

OTHER PUBLICATIONS

Hammer, 1990, Spontaneous inflammatory disease in transgenic rats expressing HLA-B27 and human beta-2m : An animal model of HLA-B27-associated human disorders, Cell, vol. 63, pp. 1099-1112.*
Mullins, 1990, Nature, Fulminant hypertension in transgenic rats harbouring the mose Ren-2 gene, vol. 344, pp. 541-544.*
Sang, 2004, Mech. Dev., vol. 121, pp. 1179-1186.*
Mozdziak, 2994, Dev. Dynam., vol. 229, pp. 414-421.*
Higashijima, 1997, Dev. Biol., vol. 192, pp. 289-299.*
Samuelson, 1996, Mol. Biol. Evol., vol. 13, pp. 767-779.*
Saito, 1999, Jour. Immunol., vol. 162, pp. 2488-2494.*
Velander (1992, PNAS, vol. 89, pp. 12003-12007.*
Li, J et al., 1997, Plant Physiol., 114;1103-1111.*
Hong, C-Y et al., 2004, Transgenic Research, 13:29-39.*
Abelson, P.H. 1999. A potential phosphate crisis. Science 283: 2015.
Altschul,S.F., Gish, W., Miller, W., Myers, E.W. and Lipman, D.J. 1990. Basic local alignment search tool. J. Mol. Biol. 215: 403-410.
Ann, D.K. and Carlson, D.M. 1985. The structure and organization of a proline-rich protein gene of a mouse multigene family. J. Biol. Chem. 260: 15863-15872.
AOAC 1984. Official Methods of analysis (14th Ed.).
Ausbel, F.M., Brent, R., Kingston, R.E., Moore, D.D., Seidman, J.G., Smith, J.A. and Struhl, K. 1992. Short protocols in molecular biology. John Wiley & Sons.
Barsh, G.S. and Epstein, C.J. 1989. Physical and genetic characterization of a 75-kilobase deletion associated with al, a recessive lethal allele at the mouse agouti locus. Genetics 121: 811-818.
Bennick, A. 1982. Salivary proline-rich proteins. Mol.Cell Biochem. 45: 83-99.
Bitar, K. and Reinhold, J.G. 1972. Phytase and alkaline phosphatase activities in intestinal mucosae of rat, chicken, calf, and man. Biochim. Biophys. Acta 268: 442-452.
Burge, C. and Karlin S. 1997. Prediction of complete gene structures in human genomic DNA. J. Mol. Biol. 288: 78-94.
Burge, C.B. and Karlin, S. 1998. Finding the genes in genomic DNA. Curr. Opin. Struct. Biol. 8: 346-354.
Carlson, D.M. 1993. Salivary proline-rich proteins: Biochemistry, molecular biology, and regulation of expression. Crit. Rev.Oral Biol.Med. 4: 495-502.
Carswell, S. and Alwine, J.C. 1989. Efficiency of utilization of the simian virus 40 late polyadenylation site: effects of upstream sequences. Mol. Cell. Biol. 9: 4248-4258.
Chi, T.H. and Crabtree, G.R. 2000. Inositol phosphates in the nucleus. Science 287: 1937-1939.
Clark, A.J., Archibald, A.L., McClenaghan, M., Simons, J.P., Wallace, R. and Whitelaw, C.B.A. 1993. Enhancing the efficiency of transgene expression. Phil.Trans.R.Soc.Lond. B 330: 225-232.
Clements, S., Mehansho, H. and Carlson, D.M. 1985. Novel multigene families encoding highly repetitive peptide sequences. J.Biol.Chem. 260: 13471-13477.
Corring,T. 1980. Endogenous secretions in the pig. In Current concepts of digestion and absorption in pigs. Edited by A.G.Low and I.G.Partridge. National Institute for Research in Dairying. Reading. pp.136-150.Ed.Technical Bulletin 3.

(Continued)

*Primary Examiner*—Scott D. Priebe
*Assistant Examiner*—Valarie Bertoglio
(74) *Attorney, Agent, or Firm*—Micheline Gravelle; Bereskin & Parr

(57) ABSTRACT

The invention provides a transgenic animal having within its genome a transgene construct for gastrointestinal tract specific expression of a protein. In a preferred embodiment, the protein is a phytase or a homologue thereof. Such proteins may be heterologous and may be specifically expressed in the salivary gland of the animal by operably linking the nucleic acid sequence encoding the protein with regulatory sequence including a salivary gland protein promoter/enhancer. Also provided are methods of expressing and producing proteins using such nucleic acid constructs. Further, antibodies specific to such proteins and immunological diagnostic kits are also provided.

23 Claims, 58 Drawing Sheets

OTHER PUBLICATIONS

Cosgrove, D.J. 1980. Inositol phosphates. Their chemistry, biochemistry and physiology. Elsevier, Amsterdam.
Crameri, A., Dawes, G., Rodriguez, E.Jr., Silver, S. and Stemmer, W.P.C. 1997. Molecular evolution of an arsenate detoxification pathway by DNA shuffling. Nature Biotechnol. 15: 436-438.
Dassa, J., Marck, C. and Boquet, P.L. 1990. The complete nucleotide sequence of the *Escheriichia coli* gene *appA* reveals significant homology between pH 2.5 acid phosphatase and glucose-1-phosphatase. J. Bacteriol. 172: 5497-5500.
Denny, H.R. and Messervy, A. 1972. Surgical techniques for the extirpation of the submandibular salivary glands and the collection of salivary secretions in the pig. Vet.Rec. 90: 650-654.
Dobrinsky, J.R., Johnson, L.A. and Rath, D. 1996. Developmental of a culture medium (BECM-3) for porcine embryos: Effect of bovine serum albumin and fetal bovine serum on embryo development. Biol.Reprod. 55: 1069-1074.
Dvorakova, J. 1998. Phytase: Sources, preparation and exploitation. Folia Microbiol Prague. 43: 323-338.
Engelen, A.J., Vanderheeft, F.C., Randsdorp, P.H.G. and Smit, E.L.C. 1994. Simple and rapid determination of phytase activity, J.Aoac. Int. 77: 760-764.
Frandson, R.D. and Spurgeon, T.L. 1992. Anatomy and physiology of farm animals. Lea & Febiger, Philadelphia.
Galfre, G. and Milstein, C. 1981. Preparation of monoclonal antibodies: strategies and procedures. Methods Enzymol. 73: 3-46.
Geyer, P.K. 1997. The role of insulator elements in defining domains of gene expression. Curr.Opin.Genet.Dev. 7: 242-248.
Gish, W. and States, D.J. 1993. Identification of protein coding regions by database similarity search. Nature Genetics. 3: 266-272.
Golovan, S., Wang, G., Zhang, J. and Forsberg, C.W. 2000. Characterization and overproduction of the *Escherichia coli* appA encoded bifunctional enzyme which exhibits both phytase and acid phosphatase activities. Can.J. Microbiol. 46: 59-71.
Gordon, J.W., Scangos, G.A., Plotkin, D.J., Barbosa, J.A. and Ruddle, F.H. 1980. Genetic transformation of mouse embryos by microinjection of purified DNA. Proc. Natl. Acad. Sci. USA 77: 7380-7384.
Gorman, C., Padmanabhan, R. and Howard, B.H. 1983. High efficiency DNA-mediated transformation of primate cells. Science 221: 551-553.
Greiner, R. and Jany, K.-D. 1991. Characterization of a phytase from *Escherichia coli* . Herbsttagung der Gesellschaft fur Biologische Chemie 372 (Abstract).
Greiner, R., Konietzny, U. and Jany, K. 1993. Purification and characterization of two phytases from *Escherichia coli* . Arch. Biochem.Biophys. 303: 107-113.
Hall, J., Hazelwood, G.P., Surani, M.A., Hirst, B.H. and Gilbert, H.J. 1990. Eukaryotic and prokaryotic signal peptides direct secretion of a bacterial endoglucanase by mammalian cells. J. Biol. Chem. 275: 19996-19999.
Harayama, S. 1998. Artificial evolution by DNA shuffling. Trends Biotechnol. 16: 76-81.
Harland, B.F. and Morris, E.R. 1995. Phytate: A good or a bad food component? Nutr.Res. 15: 733-754.
Harlow, E. and Lane, D. 1988. Antibodies: a laboratory manual. Cold Spring Harbor Laboratory, New York.
Heinoen, J.K. and Lahti, R.J. 1981. A new and convenient colorimetric determination of inorganic orthophosphate and its application to the assay of inorganic pyrophosphate. Anal. Biochem. 133: 313-317.
Heneine, W. and Switzer, W.M. 1996. Highly sensitive and specific polymerase chain reaction assays for detection of baboon and pig cells following xenotransplantation in humans. Transplantation 62: 1360-1362.
Higuchi, R. 1989. Simple and rapid preparation of samples for PCR. In PCR technology: principles and applications for DNA amplification. Edited by H.A. Erlich. MacMillan Publishers; Stockton Press. New York. pp. 31-38.
Hu, Y., Nakagwa, Y., Purushotham, K.R. and Humphreys-Beher, G. 1992. Functional changes in salivary glands of autoimmune disease-prone NOD mice. Am. J. Physiol. 263: E607-E614.
Huang, X. 1996. An improved sequence assembly program. Genomics 33: 21-31.
Huang, X. 1999. A contig assembly program based on sensitive detection of fragment overlaps. Genomics 14: 18-25.
Huff, W.E., Moore, P.A.J. Waldroup, P.W., Waldroup, J.M., Balog, J.M., Huff, G.R., Rath, N.C., Daniel, T.C. and Raboy, V. 1998. Effect of dietary phytase and high available phosphorus corn on broiler chicken performance. J Anim. Sci. 77: 1899-1904.
Iqbal, T.H., Lewis, K.O. and Cooper, B.T. 1994. Phytase activity in the human and rat small intestine. Gut 35: 1233-1236.
Jia, Z., Golovan, S., Ye, Q. and Forsberg, C.W. 1998. Purification, crystallization and preliminary X-ray analysis of the *Escherichia coli* phytase. Acta Crystallographica D54: 647-649.
Kazazian, H.H. Jr. 1999. Mobile elements and disease. Curr.Opin. Genet.Dev. 8: 350.
Kim, H.S. and Maeda, N. 1986. Structures of two HaeIII-type genes in the human salivary proline-rich protein multigene family. J.Biol. Chem. 261: 6712-6718.
Kohler, G. and Milstein, C. 1976. Derivation of specific antibody-producing tissue culture and tumor lines by cell fusion. Eur.J. Immunol. 7: 511-519.
Kozak, M. 1987. At least six nucleotides preceding the AUG initiator codon enhance translation in mammalian cells. J.Mol.Biol. 196: 947-950.
Kuchner, O. and Arnold, F.H. 1997. Directed evolution of enzyme catalysts. Trends Biotechnol. 15: 523-530.
Laemmli, U.K. 1970. Cleavage of structural proteins during the assembly of the head of bacteriophage T4. Nature 227: 680-685.
Lam, J.S., MacDonald, L.A., Lam, M.Y.C., Duchesne, L.G.M. and Southam, G.G. 1987. Production and characterization of monoclonal antibodies against serotype strains of *Pseudomonas aeruginosa*. Infect.Immun. 55: 1051-1057.
Larsen, H.J., Brodersen, C.H. and Hjorth, J.P. 1994. High-level salivary gland expression in transgenic mice. Transgenic Res. 3: 311-316.
Laursen, J. and Hjorth, J.P. 1997. A cassette for high-level expression in the mouse salivary glands. Gene 198: 367-372.
Levitt, N., Briggs, D., Gil, A. and Proudfoot, N.J. 1989. Definition of an efficient synthetic poly(A) site. Genes Dev. 3: 1019-1025.
Lim, D., Golovan, S., Forsberg, C.W. and Jia, Z. 2000. Crystal structures of *Escherichia coli* phytase and its complex with phytate. Nature Struct.Biol. 7: 108-113.
Low, A.G. 1989. Research into the digestive physiology of pigs. In Nutrition and digestive physiology in monogastric farm animals. Edited by E.J. van Weerden and J. Huisman. Pudoc. Wageningen. pp. 1-15.
Madsen, H.O. and Hjorth, J.P. 1985. Molecular cloning of mouse PSP mRNA. Nucleic Acids Res. 13: 1-13.
Mallin, M.A. 2000. Impacts of industrial animal production on rivers and estuaries. American Scientist Jan.-Feb. 26-37.
Mehansho, H., Ann, D.K., Butler, L.G., Rogler, J. and Carlson, D.M. 1987. Induction of proline-rich proteins in hamster salivary glands by isoproterenol treatment and an unusual growth inhibition by tannins. J.Biol.Chem. 262: 12344-12350.
Menniti, F.S., Oliver, K.G., Putney, J.J.W. and Shears, S.B. 1993. Inositol phosphates and cell signaling: new views of InsP5 and InsP6. Trends Biochem.Sci. 18: 53-56.
Mikkelsen, T.R., Brandt, J., Larsen, H.J., Larsen, B.B., Poulsen, K., Ingerslev, J., Din, N. and Hjorth, J.P. 1992. Tissue-specific expression in the salivary glands of transgenic mice. Nucl.Acid Res. 20:2249-2255.
Miner, J.R. 1999. Alternatives to minimize the environmental impact of large swine production units. J.Anim.Sci. 77: 440-444.
Nakai, K. and Kanehisa, M. 1992. A knowledge base for predicting protein localization sites in eukaryotic cells. Genomics 14: 897-911.
Nesterenko, M.V., Tilley, M. and Upton, S.J. 1994. A simple modification of Blum's silver stain method allows for 30 minute detection of proteins in polyacrylamide gels. J. Biochem.Biophys. Methods 28: 239-242.
O'Shannessy, D.J., Voorstad, P.J. and Quarles, R.H. 1987. Quantitation of glycoproteins on electroblots using the biotin-streptavidin complex. Anal.Biochem. 163: 204-209.

Owerbach, D. and Hjorth, J.P. 1980. Inheritance of a parotid secretory protein in mice and its use In determining salivary amylase quantative variants. Genetics 95: 129-141.
Pen, J., Verwoerd, T.C., Vanparidon, P.A., Beudeker, R.F., Vandenelzen, P.J.M. Geerse, K., Vanderklis, J.D., Versteegh, H.A.J., Vanooyen, A.J.J. and Hoekema, A. 1993. Phytase-containing transgenic seeds as a novel feed additive for improved phosphorus utilization. Biotechnology 11: 811-814.
Petitclerc, D., Attal, J., Theron, M.C., Bearzotti, M., Bolifraud, P., Kann, G., Stinnakre, M.G., Pointu, H., Puissant, C. and Houdebine, L.M. 1995. The effect of various introns and transcription terminators on the efficiency of expression vectors in various cultured cell lines and in the mammary gland of transgenic mice. J.Biotechnol. 40: 169-178.
Pinkert, C.A., Dyer, T.J., Kooyman, D.L. and Kiehm, D.J. 1990. Characterization of transgenic livestock production. Domest.Anim. Endocrinol 7: 1-18.
Quissell. D.O., Barzen, K.A., Redman, R.S., Camden, J.M. and Turner, J.T. 1998. Development and characterization of SV40 immortalized rat parotid acinar cell lines. In Vitro Cell Dev.Biol.-Animal. 34: 58-67.
Reddy, N.R., Sathe, S.K. and Salunkhe, D.K. 1982. Phytates in legumes and cereals. In Advances in food chemistry. Edited by C.O. Chichester, E.M. Mrak and G.F. Stewart. Academic Press. New York. pp. 1-92.
Rozhkov, Y.I. and Galimov, I.R. 1990. Salivary gland polymorphism in pigs and cattle detected by affinity electrophoresis. Anim. Genet. 21: 277-283.
Samuelson, L.C. 1996. Transgenic approaches to salivary gland research, Annu.Rev.Physiol.58: 209-229.
Shaw, P. and Schibler, U. 1986. Structure and expression of the parotid secretory protein gene of mouse. J.Mol.Biol.192: 567-576.
Simons, P.C.M., Versteegh, H.A.J., Jongbloed, A.W., Kemme, P.A., Slump, P., Bos, K.D., Wolters, M.G.E., Beudeker, R.F. and Verschoor, G.J. 1990. Improvement of phosphorus availability by microbial phytase in broilers and pigs. Brit.J.Nutr. 64: 525-540.
Smit, A.F.A. 1996. The origin of interspersed repeats in the human genome. Curr.Opin.Genet.Dev.8: 343-350.
Stahl, C.H., Han, Y.M., Roneker, K.R., House, W.A. and Lei, X.G. 1999. Phytase improves iron bioavailability for hemoglobin synthesis in young pigs. J.Anim.Sci. 77: 2135-2142.
Svendsen, P., Laursen, J., Krogh-Pedersen, H. and Hjorth, J.P. 1998. Novel salivary gland specific binding elements located in the PSP proximal enhancer core. Nuc.Acid Res. 26: 2761-2770.
Taboit-Dameron, F., Malassagne, B., Viglietta,C., Puissant, C., Leroux-Coyau, M., Chereau, C., Attal, J., Weill, B. and Houdebine, L.M. 1999. Association of the 5'HS4 sequence of the chicken beta-globin locus control region with human EF1 alpha gene promoter induces ubiquitous and high expression of human CD55 and CD59 cDNAs in transgenic rabbits. Transgenic Res. 8: 223-235.
Terada, T. and Nakanuma, Y. 1993. An immunohistochemical survey of amylase isoenzymes in cholangiocarcinoma and hepatocelluar carcinoma. Arch.Pathol.Lab.Med. 117: 160-162.
Towbin, H. and Staehelin, T.G.J. 1979. Electrophoretic transfer of proteins from polyacrylamide gets to nitrocellulose sheets: Procedure and some applications. Proc.Natl.Acad.Sci.USA 76: 4350-4354.
Tryon, A.F. and Bibby, B.G. 1966. Preliminary studies on pig saliva. Arch.Oral Biol. 11: 527-531.
Tu, Z.J., Lazowski, K.W., Ehlenfeldt, R.G., Wu, G., Lin, H.H., Kousvelari, E. and Ann, D.K. 1993. Isoproterenol/tannin-dependent R15 expression in transgenic mice is mediated by an upstream parotid control region. Gene Expr. 3: 289-305.
Verwoerd, T.C., van Paridon, P.A., van Ooyen, A.J.J., van Lent, J.W.M., Hoekema, A. and Pen, J. 1995. Stable accumulation of *Asperigillus niger* phytase in transgenic tobacco leaves. Plant Physiol. 109: 1199-1205.
Wall, R.J., Hyman, P., Kerr, D., Pintado, B. and Wells, K. 1997. Transgenic animal technology. J.Androl. 18: 236-239.
Wall, R.J., Pursel, V.G., Hammer, R.E. and Brinster, R.L. 1985. Development of porcine ova that were centrifuged to permit visualization of pronuclei and nuclei. Biol.Reprod. 32: 645-651.
Wessel, D. and Flugge, U.I. 1984. A method for the quantitative recovery of protein in dilute solution in the presence of detergents and lipids. Anal.Biochem. 138: p141-143.
Whitelaw, C.B., Archibald, A.L., Harris, S., McClenaghan, M., Simons, J.P. and Clark, A.J. 1991. Targeting expression to the mammary gland: intronic sequences can enhance the efficiency of gene expression in transgenic mice. Transgenic Res. 1: 3-13.
Williamson, C.M., Bramley, A.J. and Lax, A.J. 1994. Expression of the lysostaphin gene of *Staphylococcus simulans* in a eukaryotic system. Appl.Environ.Microbiol. 60: 771-776.
Wodzinski, R.J. and Ullah, A.H.J. 1996. Phytase. Adv.Appl. Microbiol. 42: 263-302.
Xiong, Y. and Eickbush, T.H. 1990. Origin and evolution of retroelements based upon their reverse transcriptase sequences. EMBO J. 9: 3353-3362.
Selinger, L.B., Forsberg, C.W. and Cheng, K.J. 1996. The Rumen: A Unique Source of Enzymes for Enhancing Livestock Production. Anaerobe. 2: 263-284.
Zhang, J.X., Krell, P.J., Philips, J.P. and Forsberg, C.W. 1997. Expression of a bacterial endo (1-4)-β-glucanase gene in mammalian cells and post translational modification of the gene product. Biochimica et Biophysica Acta. 1357: 215-224.
Database EMBL 'Online! ID: AF062078, May 18, 1998. Dennis et al.: "Cloning vector p34s-Cm".
Database EMBL 'Online! ID: MMPSPG, Nov. 3, 1992. Mikkelsen: "M. musculus Psp gene for parotid secretory protein".
Database EMBL 'Online! ID: BLCAT3DNA, Feb. 26, 1992. Luckow: "Plasmid pBLCAT3 gene for beta-lactamase and CAT gene for chloramphenicol acetyltransferase".
Database EMBL 'Online! ID: MMU73190, Nov. 4, 1996. Laursen et al.: "Mus musculus positive acting regulatory region of the parotid secretory protein (PSP) gene".
Database EMBL 'Online! ID: CVCATBLA, Jan. 24, 1992. Boshart et al.: "Cloning vector pBLCAT6 encoding chloramphenicol acetyltransferase (CAT) and beta-lactamase (bla) genes".
Database EMBL 'Online! ID: RNRP15, May 12, 1991. Lin et al.: "Rat salivary protein-rich protein (RP15) gene".
Database EMBL 'Online! ID: ECAPPAA, Feb. 5, 1991. Dassa et al., "*E. Coli* periplasmic phosphoanhydride phosphohydrolase (appA) gene".

* cited by examiner

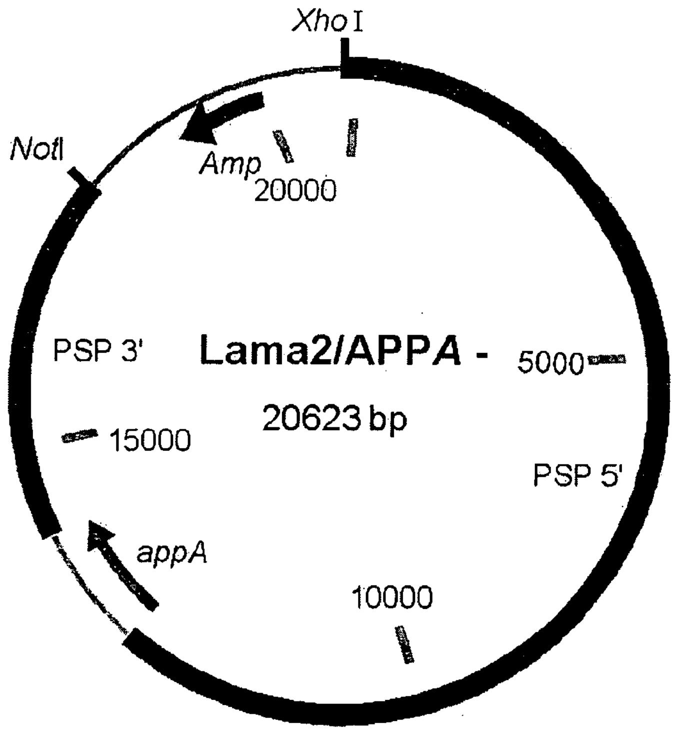
Figure 4. Schematic diagram of the Lama2/APPA construct.

Figure 5. The nucleic acid sequence of the Lama2/APPA plasmid (SEQ ID NO: 1)

```
LOCUS         Lama-appA  20623 bp    DNA   CIRCULAR SYN       17-JAN-2000
DEFINITION    Lama 2/APPA transgenic construct
ACCESSION     Lama 2-appA,
KEYWORDS      parotid secretory protein; acid glucose-1-phosphatase; appA
              gene;
              periplasmic phosphoanhydride phosphohydrolase; artificial
              sequence;
              cloning vector
REFERENCE     1  (bases 1 to 20623)
AUTHORS       Golovan, S., Forsberg, C.W., Phillips, J.
JOURNAL       Unpublished.
FEATURES
DEFINITION  M. musculus Psp gene for parotid secretory protein.
   ACCESSION   X68699
   VERSION     X68699.1  GI:53809
   SOURCE      house mouse.
   ORGANISM  Mus musculus
      Eukaryota; Metazoa; Chordata; Craniata; Vertebrata; Mammalia;
      Eutheria; Rodentia; Sciurognathi; Muridae; Murinae; Mus.
      REFERENCE   1  (bases 3777 to 5332;)
      AUTHORS   Svendsen,P., Laursen,J., Krogh-Pedersen,H. and Hjorth,J.P.
      TITLE     Novel salivary gland specific binding elements located in the PSP
             proximal enhancer core
      JOURNAL   Nucleic Acids Res. 26 (11), 2761-2770 (1998)
      MEDLINE   98256451
      REFERENCE   2  (bases 7147 to 12653; 13952 to 17731)
      AUTHORS   Mikkelsen,T.R.
      TITLE     Direct Submission
      JOURNAL   Submitted (07-OCT-1992) T.R. Mikkelsen, Department of Molecular
                   Biology, University of Aarhus, CF Mollers Alle 130, 8000
                   Aarhus, DENMARK
      REFERENCE  3  (bases 7147 to 12653; 13952 to 17731)
      AUTHORS   Laursen J, Hjorth JP
      TITLE A cassette for high-level expression in the mouse salivary glands.
      JOURNAL   Gene 1997 Oct 1;198(1-2):367-72
      MEDLINE   9370303

FEATURES                 Location/Qualifiers
                    source         1.to 12653; 13952 to 17731
                   /organism="Mus musculus"
                   /strain="C3H/As"
                   /db_xref="taxon:10090"
                   /chromosome="2"
                   /map="Estimate: 69 cM from centromere"
                   /clone="Lambda YP1, Lambda YP3, Lambda YP7"
                   /clone_lib="Lambda-PHAGE (Lambda L47.1)"
                   /germline
                   /note="Allele: b"
      misc_feature   3777-5332
                   /gene="PSP"
                   /function="salivary gland specific positive acting
                   regulatory region"
      enhancer     7147..8724
                   /evidence=experimental
      exon         11778..11824
                   /gene="Psp"
                   /note="exon a"
                   /number=1
                   /evidence=experimental
      exon         12626.. 14190
                   /gene="Psp"
                   /note="exon b fused with exons h and i"
      misc_feature 12644-12652
```

Figure 5A:

```
                /function=" consensus sequence for initiation in higher
                eukaryotes "
     misc_feature 13952-13965
                /function=" M13mp18 polylinker"

DEFINITION  E. coli periplasmic phosphoanhydride phosphohydrolase (appA) gene,

     ACCESSION    M58708 L03370 L03371 L03372 L03373 L03374 L03375
     VERSION      M58708.1  GI:145283
     SOURCE       Escherichia coli DNA.
     ORGANISM     Escherichia coli
           Bacteria; Proteobacteria; gamma subdivision; Enterobacteriaceae;
           Escherichia.

REFERENCE   1  (bases 12653..13951)
     AUTHORS    Dassa,J., Marck,C. and Boquet,P.L.
     TITLE      The complete nucleotide sequence of the Escherichia coli gene appA
                  reveals significant homology between pH 2.5 acid phosphatase
                  and glucose-1-phosphatase
     JOURNAL    J. Bacteriol. 172 (9), 5497-5500 (1990)
     MEDLINE    90368616

FEATURES                 Location/Qualifiers
     Source                    12653..13951
                         /organism="Escherichia coli"
                         /db_xref="taxon:562"
     sig_peptide         12653..12718
     /gene="appA"
     CDS12653            13951
                         /gene="appA"
                         /standard_name="acid phosphatase/phytase"
                         /transl_table=11
                         /product="periplasmic phosphoanhydride phosphohydrolase"
                         /protein_id="AAA72086.1"
                         /db_xref="GI:145285"

     mat_peptide         12719  13948
                         /gene="appA"
                         /product="periplasmic phosphoanhydride phosphohydrolase"

     mutation       replace(12659.. 12661,"gcg changed to gcc")
                    /gene="appA"
                    /standard_name="A3 mutant"
                    /note="created by site directed mutagenesis"
                    /citation=[3]
                    /phenotype="silent mutation"
     mutation       replace(13934..13936," ccg changed to ccc")
                    /gene="appA"
                    /standard_name=" P428 mutant"
                    /note="created by site directed mutagenesis"
                    /citation=[3]
                    /phenotype=" silent mutation "
     mutation       replace(13937..13939," gcg changed to gct")
                    /gene="appA"
                    /standard_name=" A429 mutant"
                    /note="created by site directed mutagenesis"
```

Figure 5B:

```
                 /citation=[3]
                 /phenotype=" silent mutation "

DEFINITION       pBluescript II KS(+) vector DNA,
ACCESSION        X52327
VERSION          X52327.1  GI:58061
KEYWORDS         artificial sequence; cloning vector; expression vector; vector.
SOURCE           synthetic construct.
ORGANISM         synthetic construct
                 artificial sequence.
REFERENCE        1      (bases 17732 to 20623)
AUTHORS          Thomas,E.A.
TITLE            Direct Submission
JOURNAL          Submitted (20-FEB-1990) Thomas E.A., Stratagene Cloning
                 Systems, 11099 North Torney Pines Rd., La Jolla, CA 92037, USA
REFERENCE        2      (bases 17732 to 20623)
AUTHORS          Short,J.M., Fernandez,J.M., Sorge,J.A. and Huse,W.D.
TITLE            Lambda ZAP: a bacteriophage lambda expression vector with in
                 vivo excision properties
JOURNAL          Nucleic Acids Res. 16 (15), 7583-7600 (1988)
MEDLINE          88319944
REFERENCE        3      (bases 17732 to 20623)
AUTHORS          Alting-Mees,M.A. and Short,J.M.
TITLE            pBluescript II: gene mapping vectors
JOURNAL          Nucleic Acids Res. 17 (22), 9494 (1989)
MEDLINE          90067967
FEATURES                Location/Qualifiers
Source                  17732 to 20623
                        /organism="synthetic construct"
                        /db_xref="taxon:32630"
CDS                     complement (18967..19827)
                 /gene="Amp"
                 /product="b-lactamase"

BASE COUNT     5449 a   4847 c   4902 g   5424 t
ORIGIN
      1 TCGAGAGTAT CTTTGTCAGC TGTGCCTCCA ACAAAGGGGT ACTGTTGCCC ACATAGAAAG
     61 ATCTAAACTA ATTAATTAAT CCCTCACCCG CAAATCTTTC AGTCACTAAG TTAGCACGAT
    121 TGTTGAACAA GTTCTCCAAA GGAGAGATAC AGATGAGTGC GTATAGGGTG GACCTGGCTG
    181 CTGAGGAGAC ACCTGCATCT GACTAAGAAG AGCCACGGTG TTAGTTGAAT GGTGTGGAGT
    241 AGGGTGGTTC TGTGGGACAG TAGAAAATCG AGAGGCATGT GCCGTTTAGT GAACTGATGG
    301 AAGCTACCCC AAACGACAGA GATTGTCAGT CAGGCCAATC CGTTTCGAGT TTGATGGGCA
    361 GCCGGACAGT GAGACAGACA CACCTACTCA GTTGGAGGAA GGATGAGAAC AATGGCCAGC
    421 AGGGATTGAG AGACCCTGAC AGGCGCAAGG CCCTAACACA CACACCTACC ACCTCACTTG
    481 ACAAAGCTGC CAAAGACCAA AGACTTGTTC TCCATTAGAA ATGACAGCTG GCTTGACCCG
    541 ACAGCATAAT AAGCAGAGTG TACTCTGATT GGAGAACTTT AATGTGTTTC ATTCAGTATT
    601 ATAAAAGGAC AGTATTACAG ATTTTGTTGT ACACTGCTGT TACATGTGGG GCAGTGTGTC
    661 TTTAAGTAGG GTAAAGTACT CTTTAAAAAT GGGTCCTAGA TATTTTTTCC TTTAACTCAA
    721 GTCTCTTACT GTTTAAATGA TTTTTATTTT GTTTAATATG GAGGAAAAAG AAGCGTAAAT
    781 GGACAATATA TATTTAGAGA AAGATGGTTA GCTGTCAGAA AAATATGCAA ATCAAAATCA
    841 CACCAAGACT GCAGCACACC CCTGTCAGAT GGCTGTGATC AAGAAAATAA ATGACAATGA
    901 GTGGTGGTGA AGATGTACTA AAGGGAAACA CACACACACA CACACACACA CACACACACA
    961 CACACTGGAG CAACCACTGT GGAAATCAGT ATGAATGGTC CTCAAAAACC TGAAGATAGA
   1021 GCGGGGCGTG GTGGCATACA CTTTTATTCC CAGCACTGGG GAGGCAGAGG CAGGTGGATC
   1081 TCTGAGTTCC AGGCCAGCCT GGTCTATAGC ACAGGTTCTA GGACAGCCAG GGCTACACAG
   1141 AAAAACCCTG CCTTGATTAA ACCAAACCAA ACCAAACCAA ACCAAACCAA ACCAAACCAA
   1201 ACCAAACCAA ACCAAACCAG ACCAAACCAA AACACTGAAG ATAGAACTTC AGTATTCCAT
   1261 TCCTAGATAT ATACCCAATG GAGACTAAGT CAGCAAGACA CCTGCACAGC CATGTTCACT
   1321 ACTACACTGT TCACCACAGC CAGGCTGTGG AACCAGCCTG AGTGTCCATG ATAAATGAAT
   1381 GGATAGGTAA CTTTCAAGGT AAATGGACTC TGCTGTGTAC ATGCCTCACA TTCTGTTTAT
   1441 TCATTTTTCT TTATGAGGTG TCCATTCAGG AGTCACATGG TAGTTCTATT TTCAGTCTTC
   1501 TGAAGATACT ACACTGGTCC CCACAGTTTA CACTTTTATC AGCAGTGAAT AAGGGTTCCT
   1561 CTATCCTTAC CATCATTTGT TGTAATTTTT CTTGATGACC CTCTTTCTGA CAGGGATAGG
   1621 ATGTAATATC AGTGTGAGGA AGTACAACTT GTTTTCTAAG TATTTATTGG CCCCTTGCAT
   1681 TTCTTCTTTT GAAAACTGTC GGTTCCTGAC ATCTGCTCAG GTATTCATTG GATGTTGTTT
```

Figure 5C:

```
1741 CTTTGGTGTT TGAGTTCTTA TGAATTCTAG ATGTTAAATC CCTGCCTGTG GTTCTCTCCC
1801 ATTCTGTAGG CTGCCTCCTC ACCCTGGCAA TTGTTGTCCT TGTTTTGCAG AAACTTTTGA
1861 CTTCATGGAA TCTCATTTGT CAGTTTTCCC TCCTCTGCTA TAGCCTGAGC TAATGCACTG
1921 GTTTTTACAG AGCCCTGGTC TATGCCTTTA TCCTCCTCTG GCAGCTTCGG AGTTTCATTT
1981 CTTACATTTA GATCTTTGAT CCACTTTGAA CAAGTTTTGG AGCAGGGTGA GAGATACGAA
2041 TCTAGTTCCA TTCTTCCATA TGTGATCCTA GTTTACATAG CATCGTTGGT TGAAGAGGTT
2101 TTATTTTATT TTTAAATAAT GTGTCATAAA AAACGAGGTG GTTGTAGCAG TGTGGATTTG
2161 TTTCTTTGTC CTTTGATCTA CAGGTCTTGT TTTGTGTCAG TCTCATGATG TTTTATTGCT
2221 ATGGCTCTGT CATACAGTCT GAGGTCAGGT ATTGTGATAT ACCTTCAGTA TTGCTCCCTC
2281 AGACTCAGGT TTGCTTTGGC CAGGAGTCAT CTTACTCAGT GCTCTTAGAG CTCCCCCAGC
2341 ATGTAGCTGC TACTATTCTT AGTTGATAAA TCAGGAAACT GGGGCTCAGA GAGATTAACT
2401 GTCTTGAACT ACTTCTGGGG AGGTGAAACG TGGAGACACT AAACTGTGTT TACCCTGTAC
2461 TGCTCCAGTA GCTGTCGGGT GCTGGGCTAC AGCAAAGCAC CTATACTATA TATTACTCAG
2521 GAGGTGGAAA AACTCAGCCT CCCTTGGGGT TCCCAAGCTC CCAGGTGTCC AGTCACTGCT
2581 GGAAACCTCA TGGAGTCTGA AAGGAAGGGT TGAGGGTACA TGGGGCAGCG ATGAGGAGCC
2641 TGGGGCTGGG ATCTCCCAAA CACCTGGATA TCCAGATGCC ACTGGGTCAG GGGGAGTTGG
2701 GAACAGAGTT GGGATGTCCA TGGACCTGTG ACAAGGCCAG GGCCAGGGGG AGGATAACTC
2761 TGGCTTTACT AATTTGCGAA AGTCCTTAGC TTAGCAGCAG TTGTCTGGGA GCACAGAGGG
2821 GCCTTCTGTA AGAGGCTCAG GCAGTGCCGC TCTGTAGGCG AAGGTCTTCT CCATGTTCCC
2881 CATGGTGGTT CTTGATGAAA GAGACAGTCC TTGGCTCCAA ACTGGTTTAT TGATTGTTCA
2941 TTGTGGAAAA TGGGTGCACA CCACCTTCTC AGGGTGGACC AGAGATCAAA TACCTTTTGC
3001 AGGGAGGAAT ATCTGGGAAG GGACGCTTAC TGGCTAAACC CTCAGGGCCT CTAGATACAT
3061 CATTAGCATG GAGAACTCTG TTCTGGGCTA CATGACCACA GGCCACATTT CCACAAGCCA
3121 CATGTGGGAA GTGTGGCACA TGTTCTAGGC CAGGAATCTG GTAGGGAGCG TGGAGCCACC
3181 TACCATCCCA GGTGGGTGCC TGGGTGCCAG GGACCCTGAA CCCGCTCAAC CTTACCAAGT
3241 TTCCTGGCAG GGTCCACTGT CCTACACAGA AGCTGGAGGA GGTGTGAGGG TTGTGTCTTT
3301 GTGGAATGTC CCATGCTGCT TGGGGCTCAG TTTCTCCACC TGTACCTCAT TGGTTTGGGT
3361 ATAAAAAGTG GGGATACTTT ATTATTCTCT GACTCGGTCC TGAGGAAAAA GCATCGTGGC
3421 AGTCCAGGAA CCACACCCTG AGGTTCCTGC ACTGAAGGGA CTCCCTAAGT CTCTGGAGTC
3481 TCTCCCCTTC ACAGAGCTGC CAAAGTCTAG GTTCTTTTGA GGATAACAGA GCCATGCTTG
3541 GTAAGCAGAC AACAGCATTT GTTTACTCAA CCTTCTTTTG TCAGCTCCCT CTTCATAAAC
3601 AAGTTGAGAC ACCATGCTGG CTTGAGGAAG ACTTCTAAAG CCAGACAACT GTGCAAGGAA
3661 GAAGAAGAAG GGGCAAGTGG AGTTAGCCTG GATGTAGCCC TCAAAGTCTC CAGAGACCAG
3721 CCATGAAGGC TCAAGTGGAG GGCAAGACCT GCAGCAGCCA AGCATCTGGC AGGAGAGGAT
3781 CCTGGGAACC CCTCTACCAT GACACACATT CTTCCTGCAG GTCACACTTA ATAGGCCATT
3841 TCTTATTTGG ATCTATCATG GTGTTCTGTG CGAGATTAAT GAGGTGTTAT GCTGCGAACA
3901 GAAAGTTATA TAAAAACAAG TCCCCCCCCC TTGTCACTGC TGCTAAGAAT GTAGCAGAAA
3961 TTGTCTCAAG TGTCTCTCTA ATCAGAAACA ATAAAGGTCT CCTTGGATTC AAGCCCTCCA
4021 GTTTCCTCCT TCCTTGCTGA GCCTTGGACA CCCATACAAA CCTCCTGGAT GCTACAGCTC
4081 TGGGCAGAGA CTCCAAGGTG GGGAGAGACT GATGGTACAA AAGCAAAATA CTTGTTTGGG
4141 GGTACACCCA CTCCTCTGCC TGTGTGGTTC CTGCAGTCAG TCCTGCAGAC AGGCCCTCAG
4201 TGGGTCTTCC ATGGGCAACA CGCAGAGGGA GGCAATGGAT GGGAATACCC ACACCCTGGT
4261 TAGTTTACCC CGGCCATGCT CTCTGCTCTT CATCCCTCCT CTGCCCTCTG CCACGGCTTT
4321 CTCTGCAGGA ATCATATCTT CATATTGGCC CACAGGTGTT CTCCTCACCC TAGCTATGAT
4381 GTTTACTTTA GAGTGACCTT AGCAGGGCTG GTGGGAATGA GTTCTAGAAG GCTCACGGAG
4441 ATGCTAGGGA AGAAACGTCT TCTAACTACT GAGGTTACTA AGTTCCTGGT GGTTGTCTCT
4501 GCCTTTCCCT TGTTAAAGTC ACCTTGAAGT TAGTGCAGAA GAAATCAGAG CCCAGTCACA
4561 GAGTAAATAT GGTCCTGAAG ATTTCCTTTG AGTGCCCAGA ATCCATGACA TTTCAAGAGC
4621 CCTCTTTGTA CCTTAAGTCA TTTGGGGTTG TATCTTCTGC TTGATGTATG TGTGTGTGTT
4681 TATCAAAGAG TGAGATGGTT ACATAAGAGG TGCTCTAAAG GACAGAGAGG ATTTGCAATT
4741 GTGGCATGTG ACATCCTCAG GCCTTGCTCT GGTGCCAGGA GGAACTGATG CAGAAAAGAG
4801 TAAGAGGTCA TTTCCTGGAG GCTGTCACTA TAGAGGAGAT CTTACAGTGC ATTCCCTCCT
4861 CCAGGCCCTG CCTGAGGATA GACATGTGCT GACTGCAACT GAAACAGAGG CTTGGGATGG
4921 AGAGTTAGGT TCACAGAAGG GAGGGTGGGA GATGGATGCT TGCTGGGTTC TGGGTCTCAT
4981 CACCAGCTCC TGACCACCCG GTCAGCCCAT GTGCTTATTC CATAGCTTTC TTTTGCTATG
5041 TTTACTCAGT GTGGTGTTTG TTGGGACCCA GCAGAAGCCA GTCCCAGGCT GACAGCTGTG
5101 GATACACAGG GCAGCATGAG GGTCCTCAGC CTGAAGCAGT CAGGCTGGCA GAAGAGAAAG
5161 ACCAGCACAC ATTCCTTCAA CCAACTATGT CTTGAAAAAC AAACATATTA TATCACATAT
5221 ATTGCATTTA TGAGACAGCT AAAATGTACT CGGGTAGCAT GACTCCAGGT GGGGATATCT
5281 GCAAGTGCCA TGAGTGGCAG AGGGACAGCC AATGTGAGGC AAGAAGGAAT TCTGGCTCAA
5341 CACAGCTTAG CTCCCTGGTG TTGGTTCAAA CTTTGAGAGT TTGACCACAA GCACTTTATT
5401 TTTGACATAT TTAAACAGAG CACAACTTTG GGAAAAAGTT TTCTTATGAA AATTATCACA
5461 ATAAAGCTTA AGGCATGACT ACATTAAAAT GCCTTTGCAA AGTATATGTG CCCTCTTCCA
5521 CAAGAATGGT TCTATTGACT GAGAAATAAT GTTCAGGATA AAGATCCAGG AAGAAAAGAT
5581 CAGGGATAAG TAAAATACTA AACTCTTTTG CAAAGTACAT AGACCCTCTT TCATAACAAT
```

Figure 5D:

```
5641 GGGTTCTATT GACTGACAAG CACTGCTCAG GAGTTGGGAA AGAGTCTAGC ATAAGCACGA
5701 TAGCCTGGAG ACTCTAGTGA GGTCTAGTCT TACAGACAGC AAAAATCACC AGGTTACAAA
5761 CTACATTCAT TTCCAGTTTT CTGATCAGGC ACAGGTATGA ATCCCTTCTG TTGAAGAGAA
5821 AAGTCCATGT GTTTAAAATA TCTGGTTTCT CCAGTGCTAT TAGCGAGAAG ACTTGAGCCC
5881 TATACAACTC CCACCTGGAG TGACATCCTG TCTTCATGGT ATATTACATA CCTAGACACG
5941 CTCATCTCAC AGACTTAGGA CTTTGTCTTC TGATCTCCAT TTCTGATCCC ACTTCCACCT
6001 TTGCCTTGAT AGTGTCATTT TCTTCACTGC CTTGGTGACA ACCATGTTAT CCTCTGTGTA
6061 TTTGAGTGTT ACCATTTTCA GATTTTACCT GTATGCAAGA TCACACAGTC TTTGTCTTTC
6121 TGTCTGGATG CATGCTAATC TCTACACAAC AACCCTTCCC CGTCACTCAG ATCTTCCTCC
6181 ATTAACACAT ACATGGTGCT GAAGAGGCTA GGGAGCTTCC CTTCAGTGGG GAGCTAGCTG
6241 GCTATTGGGC CTTTTTGACT GTCCAGGAAG GCCCCCAATT GCTGAGACAA GAACTTAGAT
6301 TCTTCATTAT TGACTCTAAC TCATGTATCA AGCAGAAGCT AATGAATAGT TATCAACAGG
6361 ATCAGAGGTT CCAGTGTAAG ACACTTTGAC ATGAAAGAAC GGAGGAAGGA CAGATGGATG
6421 CATAAAAGCA GGACCACTGC CCCAGGAAGG TCCTGGAAAC TGATGCAGGG CAAAGGACAG
6481 GTTATAAACC AAATCTTAGG GAGTCAGGAA GAGCACAGAG GAGCTCAACC AACTGACCAC
6541 TGCTTAGGGG CTACCAACCC AATCCTCCCT GTGGGAACAG CTAAGCTATC AGCCAAGGGT
6601 AATAAACAGG CAGGACCTGT GGATGACATG GAGAGCATAG GGACCCTGGG TCCAGCCTTT
6661 AGCACCTGCA CTCTCAGGAT ACTCCACCAT TGTGTCTTAG AGAGCCTAGG GATACTGGGT
6721 CCAGCCTTTG GTACCTTCAC TCTCAGGGTA CCCCATCACT GTGTCTTGGA GAGCCTAGGC
6781 ACCCTGGGTC CAGCCTTCAG TACCTGCGCT CTCAGGACAC CCCACCATTG TCTCTTGCCC
6841 CGTCTCTTCT TCCTCTTCCT CCCTTTCATT GTCTCTTCTC TGTTTCTTTC TTGACTCTCC
6901 TTTCCCCTCA CACCCTCACT CTAGTTCTCC CCTTCCCTCT CTGCATCACC CTATTCTCTC
6961 TGTGGTCCCT CCACTTTCCT TTATCTCTCA TGCTTCTCTC CTCCCTCAAA TACTTGTCAC
7021 CCACTATACT TCAGGGGCCA GCTCTAGTGA CAAAGCTGTT AATAGCAAGA CTCTCAGATC
7081 TCCAACGGCT CAGAGGAGCC AGACCCACCA AGAACTCTCT CCAGGTCCAA TTTCAGGTTC
7141 CTTCGAAAGC TTTCAGCAAA TGCTCAGGGA ACATGCCACT AACAAGAAGA TGCAAATTCC
7201 AGTTGAGAGT GGGAAAGGCC CTTGCGTAGG TCCCATCTTC CAGGCCAAGG TCAGAGGGGC
7261 TCTGTGTAAT CCGGATTGAC AGGGCTCAGA ACAATGTTTT GTTTTTAAGG TTTATTTATT
7321 TTAGGTGTTA GTGTCTTTGC TTGCATGACC TTATGTGCAT CATGTGTGTG CAGGTTCCTG
7381 ATGACAGTAG AGGAGGGCTT TGAATCCCTG GGGATAGGAA GTTACAGGAA ATTATAAGCT
7441 GCTTTGTGGG TCTTCTAGCT TTCCCAACAG AAGTGAATGC TCTTCACCAC TGAGCCATCT
7501 CTCTAGGCCC AAGAGACATT GCTTTATGGA TATAATTGTG TGTGTGTGTC AACATTGAGG
7561 AAAGGGAAAT AAAAAAAAAA CTTCAGCCGC TAAGGTTGTA CAGTTTCACT AATTGCTACT
7621 TTTAGTTGTG ATAAAATGGC AGGTGCTTCA ACATTTATAT ATACAAAAAC TTCCCTGCTG
7681 GTGGTTCAAC TGTGAGAACT GGGGTAAGTG GGTGAGTTCT CTTTTTCTGT CTCTGTCTCT
7741 GTCTCTCTCC TTCCATTCTT TCTTAAAGGA AATAAACATT GCAGCTGGGT TATAGCTCAT
7801 CAATATGGAA GTTACAGAAG TGAAAAAAGG CATTGCCTTG GTGGGTGGTG TTACCAGCTG
7861 ATTTTTGGTT GTCCTGCAAG GAGGTCTGGG GACTGGCTGC TCTGTCTCTG TCTGTATGAG
7921 TGAGGGAAGT CTGGGGAGCA GATTCCCTAA CCTTCAGCCT GGCCTGGTTC CTGAGTGAAC
7981 CCAGCCTCTC TGGTCCTAGT AGCTTTTTCC AAACAGGAAT CTGAGTGGTG ACAGGGAACA
8041 AGTACCAGCC CATTGCTTAA GTGCCAGGGT TAGTGAGGGC AGGAAGCTGC CATAGCTGGG
8101 ATTAGTAGTT GTATTGGATG TAGGAAGTCC TATCCTGGGA CAGCTAATCC TTAATGCTTC
8161 ACTGGAGATT TTCAATGAGA AATTTATCCC ACGGCCCATA TGGCCCCATC CTTTTGTCTC
8221 CAACAGCCAA GTATTTTCCA TTAGAGGAGA CTTCCTGTAC ACTTGATGGA TGCTCATTCC
8281 AAGGTGACTT GGGGCAGTCA GTACAGACTT GGGATGACCT CTGACAGCCT AACCTCTCCC
8341 CAACAAGGGC CCTCTATGTT TGCTATGTAA TGTAATGTCA GACATTGTCA GGAGTGTCCG
8401 CAGCACAGCC TGCCCAGTGT GAGGGCTCTC ATAGGTTTCC CACTGTCTTA TCTACACAGG
8461 GATAACGAGG AGGTAAGCTG CAGTTCCCAG TCTCACTTCA CAGAGGAAGA GATAACCCCA
8521 TCCCAGGTCA TGTAGCCAGC AGTGGAAAGA ATGAGGATTT GAACTCAGGT CTTCCAAGTC
8581 CCATTGATAG CATCTCCTCA CAAGTCCCTT GCCACCCTCA CGATGCCTTA GACACTTGCC
8641 TGCCCTTTAT ACTAAGGAGA TGCAGGTACA AGGGGGTTTAC CCATGTAGCA GCTGAGGCAG
8701 CTGGGGATAG ATACCAGCAG CAGGCCTGAT GTCACCACTC TAACTCCAGC ATCCCCAGTC
8761 TGTGTTCCTG GAGTGTGAAA ATCCCTACTT AACAAGATTG TGCAACAGTC CTTGGCTCTG
8821 TGACCCATAG CTGGAAACAG GATTCTCATT GATTTGTGGA ACATGGTGGC AGCCAGCCAA
8881 AAAGAGGGTC TGCATACAGA AGACACGTGT GGCAAGGCCA CAGCAGACTC TGACTACCTT
8941 AGCTTACAGA ATTACAAGGT CATAATGTCC TCTGCTTTGG TCACCTCATG TTAAGGACAG
9001 GCCCTAATGA AGATGGGGCA GAAGACTGAA GGAATGGCCA ACCAATAACT GGCCCAACTT
9061 GAGACCCATC CTACAGGCAA GCATCAATTC CTGACACTAC TAATGATACT CTGTTATGCT
9121 TGCAGACAGA AGCCTAGCAT AACTATCCTC CGAGAGGTCC ACCCAGCAAC TGACTGAAAC
9181 AGAAAAAGAT ATCCACAGGC AAACAGTGGA TGGAGGTCAG GGACTATTAT GGGAGAGCTG
9241 TGGGAAGGAT TAAAAACCCT GAAGGGGATA GGAACCCCAC AGGAAGACCA ACAGAGTCAA
9301 CTAAGAGACC TGTGGGAGCT CTCAGAGACT GAGCCACCAA CCAAAGAGCA TACACAGGCC
9361 GGTCCGAGGC ACCTGGCACG TGTGAAGCAG ACATGCAGCT CAGTCTCCAT GTAGGTCCTC
9421 CAATAAGCGG TAGCCTGACT GCAGTATCCA ATCCCCAACA GGGCTGCATA GTCTGGCCTC
9481 AGTGGGGGAG GATGCCCCTA ATCCTGCAGA GACTTGATGA GTGGAGAGCT ATCCAGGGGG
```

Figure 5E:

```
 9541 AACCCACCCT CTCTGAGAAG GGAATGGGGA TGGGGGAGGG ACTCTGTGAA GAGGGGACAA
 9601 GGACAAACAA GAACCTCAAA TAGGTCAGGC CCTAAAGGCT TGCTAAGTAG CAGTGGCCCA
 9661 GCTCTGTCCT GTTCCTCAGC CCAAGGCTCA GCTCCCACCT GTTTCTGTGT TTTTCTGGCT
 9721 TTTCATGGGC CTAGGACTTG GTGACCAGTT CAAACAATGG GGCCTGTGGA AGACACAATA
 9781 TACAAGACTA GGGACATTCC TGTTCTGCTG ACTATCCATA GCCTGATGTA GGTGGAAGGA
 9841 CCCAATCACT GGATTTCTAC CCTTGCACAA CCTTGACAGC TGAGGGCCTC TCAGAAACCT
 9901 ATTTCTTCCA CTGAAAAATG AGACTCTCAA ATGAACGTCG TGACAATCAT CAGGCTTATT
 9961 AAAGAGGTGT ATCTAACCTG AATGGCAAGC AGACAGCAGG CAAATGTCTG TATCAACCTC
10021 TAGGAAGGAC AAGAACTGCT CACTGCTGCC CCCCAGGAGG CCATTTGCTG AAACAGCTGC
10081 TCTCCTGCTG GTGCACAGGC CCTGCCTTCT CATTGCAGCC ACAGCCCCTT CCTGTCTGAA
10141 CCTCCTGTCA GGTCACTGGG AAACAGATCA AGATGGAACA GGACAGCTCC TGATGGTAAA
10201 TAAAAAACAG TGGTCATGGC TATTCATAGG GGTTTATGCT TCTTCAGTCC ACACTGTGAA
10261 GAGCTGTGGG CATGAACCAC AGTGTTCGAG GTAGAGTTGG GGTTCTGAAA TTCACAGTGG
10321 GGTGAGCTCA GTAAATGTGA GCTGGAGGTC ACTCGTGAGA CACACAGTCC TGCTGCTTCT
10381 GTTCCCAATA TCCTGAGGAG ACGACACATC TACTTTGTTC AGAGGCCACA GTCTAGTTGA
10441 CCTGAGAGTT ACCAGTTTCT TATTTGTGTG TGTGTGTGTG TGTGTGTGTG TGTGTGTGTG
10501 TGTTGTTCGT GTGTGAGTGC AGGTGCACAT ATGATAGCGT ACACGTTGAG GTCAGAGGAT
10561 AACTATCAGG CGTTGTCCCC TCCTACTTTT CCTCGGACTC TGGAGAACAA ACATGGGTCC
10621 TTATTCCAGG GGAGCAAGTC GCTGTTGGCT GACACATCTT GCTCACATAC ATTTTACCTA
10681 GACAATGGAG CCTCCATCAG AGTATTACTT TAGCTCCTCA CCGATGGCAA TGCACCACCT
10741 CTCTACCCAC ATAGGAGTTG GGTCTCCACA CACCCCCACA CCCCCTTCAC CAAAACGTTT
10801 TCAGTTACTT TATCTGGTAA AGTTCATCAG AGAATGAAGC CAGTATTAAG AACATGGAAT
10861 CATTTGGGAA CCTGGATCTA GCAATACCCC ACCCTAGATG GAGTTGCTGA GTTTTCACCT
10921 CAGATTATAA TTCCCCCCTA GCTTCTATGG TTTATTCTGA AACCAGGGGA ACTCGATTCC
10981 TCCCTTTGGA CCACAGACAT CCTGGCTTGT GAATTCACAT GTCATCTACT GCTAATCCAT
11041 TGGTAGTATG TGGCTCACAG AGACACACTA CAGTCATGGC CAATGTCAAG GTAGGACAGA
11101 TGTGAATCAT TCCCCCAGTC CTGCTGTTTT CATGACTAAC CCTCCTCAGC ACAGTGACCA
11161 TGAACCTACT TTTCCCCTCC TTTTATTTTT AGAATTGCTG GAATTTTCTA TTTTGAGAAA
11221 TAATAGCCTT GGGCAGCATT AAACAAAATC ATCTAGAAAG CTGGTTTAAA ATACAGATGG
11281 TTGAGTCAGT GAAAGAGTGA GGAATGTCAT TATTGGCCCC TCACAGAGGC TGGCTCACTC
11341 CAGCAGAGGT GGTTGAAGCT CTTGGACACG GGTCAGGTGC ATAGGAAAGG TNGTCTGGGA
11401 CACTGAGAAC CACAATTGAA CAAACAGAAC TGTTGGCTTT TTTTTTTTTA AATGAGTTCT
11461 CAAAAAATGA CTGGCTAGCT TAGGCAAATA CTTCGAGCCA ACCCAACAGA ACATTCTTCC
11521 ATTGATTCAT TCTGGATCTT CTTTCTAGAC AATACTGAAC TGACCCCTTG TTGGCAGTCT
11581 CAAGTTTGAC AACATAGGGC TTTGAACTTG GCACAAGGTC CATCACTGTC ACCCAAGCAT
11641 CCTGGGTGAC CTTTGGGTTG GAATATCTTG GCTAACCTTA GATATTTTCT TTGGAGTATC
11701 TTTAGAACAT CCAGGAAATA GGGCTTGATT CTCATCCTGG GACCACAATA TAAGTCACCC
11761 TAGAATCCCA GGAGATCGTG CAGAGAAACA AGGATCTCTC TCGTGTGCAT CCTTCTTCAA
11821 AGCAGTGAGT AGTGACTCCA CTAAACTGAG TTCCCATCTG AGAGTCCACA GGAGGCTTTG
11881 GGGCAAGAAG CAGAGGGAAG GCACTGTTTG TGTTGGTAAA GTTTTGACTC TAACAAATTT
11941 GAAGACATAG ATGACATTGT GTCAGACTAA CAACAACCTA GACTCATGTG GGTTCTGTTT
12001 AGGGATCAGA TTTTATTCAT CAATGACTTG TCTTAGTGTA TAGAGAAAGG CTTCCTACTG
12061 GAGTGTAGGC TCAATAATGA CAGAAGAGAT AGCTATTTCC CCTAGGGACT GTGCTGCTCC
12121 AAGTTTGGTG GAGAAAGGCA GTGGGGAACC TAGATGTGCT CTCTGGGGAG GGGGTCTGAA
12181 GCTGGCTTCA TAGAAGGTGT GAAGTTTTGC TGAAACATCT AAACAGAATT ATAGCTTAGG
12241 AAAGTGAGCA GGCAAGGCAG GGAATGTGTT GCATATGTAT ATGTACATGA ATATATTATG
12301 TTATAGATAC ACACACATTT GAACCTCATT TGCAGATGAC AGAAAATAGG TTATTTTGCC
12361 TCTCTTAACT GCTAAGCACA ATGACTTCCA GTTCCATCCA TTTCCTGAAA TGCCACAATT
12421 TCATTTTTCA TTGTGGCTGA ATAAAATTCC ATTGCAGACT GGGCCCTACT TCATCCACTC
12481 CTGAGGGCAG GCATATCCCC TGGCTCCATT TCTTACCTAT TGTGAAGAGA AGTGCAACTG
12541 TCTTGTTGAA AGGCAAGCGT GAGAGAGGCA GGCACTAATT GTGGGTTTTT GTTTCTTCTT
12601 CCTGCTATGA CTCTCCATTT GTCAGAACCA AAGATCGATA AAAGCCGCCA CCATGAAAGC
12661 CATCTTAATC CCATTTTTAT CTCTTCTGAT TCCGTTAACC CCGCAATCTG CATTCGCTCA
12721 GAGTGAGCCG GAGCTGAAGC TGGAAAGTGT GGTGATTGTC AGTCGTCATG GTGTGCGTGC
12781 TCCAACCAAG GCCACGCAAC TGATGCAGGA TGTCACCCCA GACGCATGGC CAACCTGGCC
12841 GGTAAAACTG GGTTGGCTGA CACCGCGCGG TGGTGAGCTA ATCGCCTATC TCGGACATTA
12901 CCAACGCCAG CGTCTGGTAG CCGACGGATT GCTGGCGAAA AAGGGCTGCC CGCAGTCTGG
12961 TCAGGTCGCG ATTATTGCTG ATGTCGACGA GCGTACCCGT AAAACAGGCG AAGCCTTCGC
13021 CGCCGGGCTG GCACCTGACT GTGCAATAAC CGTACATACC CAGGCAGATA CGTCCAGTCC
13081 CGATCCGTTA TTTAATCCTC TAAAAACTGG CGTTTGCCAA CTGGATAACG CGAACGTGAC
13141 TGACGCGATC CTCAGCAGGG CAGGAGGGTC AATTGCTGAC TTTACCGGGC ATCGGCAAAC
13201 GGCGTTTCGC GAACTGGAAC GGGTGCTTAA TTTTCCGCAA TCAAACTTGT GCCTTAAACG
13261 TGAGAAACAG GACGAAAGCT GTTCATTAAC GCAGGCATTA CCATCGGAAC TCAAGGTGAG
13321 CGCCGACAAT GTCTCATTAA CCGGTGCGGT AAGCCTCGCA TCAATGCTGA CGGAGATATT
13381 TCTCCTGCAA CAAGCACAGG GAATGCCGGA GCCGGGGTGG GGAAGGATCA CCGATTCACA
```

Figure 5F:

```
13441 CCAGTGGAAC ACCTTGCTAA GTTTGCATAA CGCGCAATTT TATTTGCTAC AACGCACGCC
13501 AGAGGTTGCC CGCAGCCGCG CCACCCCGTT ATTAGATTTG ATCAAGACAG CGTTGACGCC
13561 CCATCCACCG CAAAAACAGG CGTATGGTGT GACATTACCC ACTTCAGTGC TGTTTATCGC
13621 CGGACACGAT ACTAATCTGG CAAATCTCGG CGGCGCACTG GAGCTCAACT GGACGCTTCC
13681 CGGTCAGCCC CATAACACGC CGCCAGGTGG TGAACTGGTG TTTGAACGCT GGCGTCGGCT
13741 AAGCGATAAC AGCCAGTGGA TTCAGGTTTC GCTGGTCTTC CAGACTTTAC AGCAGATGCG
13801 TGATAAAACG CCGCTGTCAT TAAATACGCC GCCCGGAGAG GTGAAACTGA CCCTGGCAGG
13861 ATGTGAAGAG CGAAATGCGC AGGGCATGTG TTCGTTGGCA GGTTTTACGC AAATCGTGAA
13921 TGAAGCACGC ATACCCGCTT GCAGTTTGTA AGGTACCCGG GGATCACAAC TTGCCCTCTG
13981 AAGAGGAAGA ACAGAAGGAT GCCACAACTC TCCTGCTGGC TACTCTCCAG TGGTTTCATC
14041 TTACTTCTGA TGGCATTTCC CTCTAGAAAG TGCTACTATC ATCCACACAT TTCTACCTGA
14101 GACCACCCAA AGGACCCTCC CAAATTCTCT TCCTCTCTGA GTAGTCTCCA CACCTGTTAC
14161 CACCATCCCA GAATTAAAAT CCTAACTGCA CTCTGGCGTG TGACTTGCCT CAGTCCTTGC
14221 AATAAGAGTT GTTGGCAGTG CCAGGCGTGG TGGCGCACGC CTTTAATTCC AGCACTTGGG
14281 AGGCAGAGGC AGGCGGATTT CTGAGTTCGA GGCCAGCCTG GTCTACAGAG TGAGTTCCAG
14341 GACAGCCAGG GCTATACAGA GAAACCCTGT GTCGAAAAAC CAAAAAAAAA AAAAAAAGTT
14401 GTTGGCAGAG TGTGGGTTAT ATACCAGGTG GAGATTTCAA ATGAGTGGCT GAAGCTGTAG
14461 CCAGAAGGAA CTTAGAGGAT AGCTCATAAC TTAAAAAGAA ATGTAGAGAG TAGCAGAAAC
14521 ATTGAGAGAG TGGGCACACA GCCACTGTGT GAATGTGGCA GAACACAATC CAGCCAGCTA
14581 TACATGCATA AGTGTATATT GGCGCCATCC TGACTGATGA GACACAGGAA AACAGATAGA
14641 CGGGGTTAGG TGGCCATGGC CTTTCCTGCC TGCCTCTTCC TAAGGGTCAT CTCAAGACCT
14701 TATGCTCTCT TAACTCTTCC ATTGCTACTT AGCTTCTAGA TATCACCTCC AGATTAGTCT
14761 CCTTGGGTAC ATCAGTGATC CTGGTGATAT CCAGGGCTTC CTGATTCCAT CTTTGTCATA
14821 GAGGCTGCAA CTAAAGAGGT CTTCTTAATA CTTCACACCC TGATGCCAAA AGGAAGACAC
14881 AGAAGTTCAC AGAGGTGAAG TGATTCATGT AGGACATACA GTGAGCAAGC ATCAGGGTCC
14941 GGATTATCTG ACTCTACTCT AACTTTTATG TAAATGTGCT TTATGCCATT AACACTGTCA
15001 TTCCTGTGCT TCAGCTCTGG GAGACTCCCA AGCACTCTTA GGCACAAGCC ACAATTAAGG
15061 GACTCTGACA CTCTGCATTG ATTAATTAGC ATGGTGGTCT CTATGTTTCC AGATTCATGA
15121 TTGTTTCACT TTCCATATAG GCTATGAAGG GTGTGAGGAA ATTTTTTGGG GACAGAATTG
15181 GAGGCAATCC ACCTCTCTCA GGAAGCCTCT ATCTGGAAAA GCTTACAACT CAGGGACAGT
15241 AACTGTAGGC CCAGTCCTTG GTGTCCAAAA TGGGTTTTAT GGTTTGAATC TGCAAAGCCT
15301 TCCATGTGCT CAAAGGTTTG AACATGGAGC CTCCTCCTGG TAACACTGTA TTGGAGGCTT
15361 TTGAGACTGG ATGCTCTTTG GTCCCATGTT TTGCTACATC ATCTGTCAAG ATATGACCCA
15421 GGCATGCTAC CAGCTACCAC AGACTATGCC TCTCCAGCTT TCATGTTCTC CCCACCATGA
15481 TAGACTTGTA TCTCCTAAAA ATGGAATCAA AGCAAACTTT TCCTGCATTA AGTTTTTTTT
15541 TTTCTGTTAA GTGTTTGGTC ACAGGGACAA GAAAACACTC AATACAGATA ATTAGTACCA
15601 GAGTTGAGGT TCATTGCTCT AGCAAGTTGG ATCAAATTTT TAGGGCTTTG GAACTGATTT
15661 ATAAGAGACA TGTAGAAGAG TCTGAAGCTG TGGGCTACAG AAGTGTCACC AGTTTTTAAG
15721 AATAGTTTAA TACACCATGG GAATTGTGAA AATCAGAATG CTCACACAAA GGCAGACAGG
15781 AAAACGTGAG CATGTGGCGT GTGAGAGGGC ATAAGAAGGA ACCTAGGGGG AAATGAGCTA
15841 GAAGCCATTC GGCTACGTTA GGGAACGTGT GTGGCTGTGC TTGGCCCATG CCCTGGCAAT
15901 CTGAATGAGG CCAAATTTTA AAGGAGTGGA CTAACTCGAT TGTCAGAGAA AATATCAAGA
15961 CAGACCACCA CTCAGGCTAT GCCGTGTTTG TGACCGACCA GCTACTCTTA GCCAGCTCTA
16021 TTGTGAAATT CCAGAGCAAT TATCAGAGCA TGAAGATACA TACAGTTTAG TGAAGTAAGG
16081 GGTGTGGGTC CCTAAGTGGA TGGTGCATAA ATCTATGTAG GTGATGCCTA AGTGACACTT
16141 GATAATCCAA AATATCAGCA ATGTGGAATG TCTTCCAAGG AGACCTGTAG ACACACATTT
16201 TAGAACTTTG CTCATGGCTG TAATAAATAG CTAGCTAGAA ATCATTTCCT GAAGAGGTTA
16261 GTCTGAGTTA CGGTTCCAGG GCAAACATTC AGTGATGGCA AGGAAGGCAT TGCAGTCAGG
16321 AGCCAAAGGT CAGCTGGTCA CATTGCATCA AGAGTAGAGA GTCAGAGTGT GAGTAGAAAG
16381 AGGATACAGG TTATAAAACC TCACTGTCCA CTCTCAGCAA TCCATTTTCT CCTAAAAGGC
16441 TTTACCTTCT AAAGATTTTA GTCTTCAAAA CCAGTACCAG TAGCCTGGGA ACAAAAGTTG
16501 AAACAAATGA GCCTTTGTGG GGCATTTCAC ACTTAAAACA GGGCATCACC TAGGAGGAGC
16561 CCTGTGTGCA GTAGGAAGTG TGGCCTCTGT GTCAGGAATG CTCAGGCTAA TAAGGGGTCC
16621 TCTATCTGAG GGACCCTATG AAGATTCAAC AAGTAGTTGT GAGAATTCCC TGTAAATGGA
16681 TGCTACCAAT TTGACATTTG TAGACCTGCT ATTGTGTGCT TCTTTATTGG GCTCTCCCAT
16741 CTCCCAACTT TCCAACCCAT ATTCCACATT AATCCCTTCC ACCACCATGC AACACTAGGT
16801 AGGAGAGAAG GAAGGTTAGA AGAGAAAGTG GGTATAGATC TATTTAGACT ACTTCCTGCT
16861 GATTAGGGGC AAGTCCAATC GTCATTGTCA GGATACCTCC AACCAGCAAC CAGCAAACCA
16921 GCAAATCAGA AACAGCAAAA GCAGCCAACA AGGCAGCACT AACCAGCAGG ATTGGGGTCG
16981 GTAGCGTGGG AGCAGTCACT ACTGGTCTTC TCATGGCTTT GGCATTAATA CTCTCTCAAG
17041 AAATTCCGTA ATTTTTTCCC CACCACCTGA AATTCCGTAA TTTTAAATGC AAACTATCTA
17101 CAGCTGGCAA AAATCACATC TCTCCTAGAG CACAAGACAA ATCATAGTTA CTGGCTATTT
17161 GCAATCTGAA GCATCTCAAT ATCCCACACC TGGGATTAAA ACAAAAACAT ATTCACATCA
17221 CATAACTGTT TTTTTTTTCC AATTTTTTAT TAGGTATTTT CTTTATTTAC ATTTCAAATG
17281 CTATCCCGAA AGTCCCCTAT ACCCTCCCAC CTCCCTGCTC CCCTACACAC CCACTCCCAC
```

Figure 5G:

```
17341 TTTTTGACCC TGGAGTTCCC CGGTACTGGG GCATATAAAG TTTGCAAGAC CAAGGGGCCT
17401 CTCTTCCCAG TGATGGCCGA CTAAGCCATC TTCTGCTACA TATGCAGATA GAGACACGAG
17461 CTCTGGGGGT ACTAGTTAGT TCATATTGTT GTTCCACCTA TAGGGTCGCA GACCCCTTCA
17521 GCTCCTTGGG TACTTTGTCT AGCTCCTCCA CTGGGGGCTC TGTGTTTTAT CTAATAGATG
17581 ACTGTGAGCA TCCACTTCTG TATTTGACAG GCACTGGCCT AGCGTCACAT GAGCCAGCTA
17641 TATCAGGGTC CTTTCAGCAA AACCTTGCTG GCATGTGCAA TAGTGTCTGC GTTTGGTGGT
17701 TGATTATGGG ATGGATCCAC TAGTTCTAGA GCGGCCGCCA CCGCGGTGGA GCTCCAGCTT
17761 TTGTTCCCTT TAGTGAGGGT TAATTGCGCG CTTGGCGTAA TCATGGTCAT AGCTGTTTCC
17821 TGTGTGAAAT TGTTATCCGC TCACAATTCC ACACAACATA CGAGCCGGAA GCATAAAGTG
17881 TAAAGCCTGG GGTGCCTAAT GAGTGAGCTA ACTCACATTA ATTGCGTTGC GCTCACTGCC
17941 CGCTTTCCAG TCGGGAAACC TGTCGTGCCA GCTGCATTAA TGAATCGGCC AACGCGCGGG
18001 GAGAGGCGGT TTGCGTATTG GGCGCTCTTC CGCTTCCTCG CTCACTGACT CGCTGCGCTC
18061 GGTCGTTCGG CTGCGGCGAG CGGTATCAGC TCACTCAAAG GCGGTAATAC GGTTATCCAC
18121 AGAATCAGGG GATAACGCAG GAAAGAACAT GTGAGCAAAA GGCCAGCAAA AGGCCAGGAA
18181 CCGTAAAAAG GCCGCGTTGC TGGCGTTTTT CCATAGGCTC CGCCCCCCTG ACGAGCATCA
18241 CAAAAATCGA CGCTCAAGTC AGAGGTGGCG AAACCCGACA GGACTATAAA GATACCAGGC
18301 GTTTCCCCCT GGAAGCTCCC TCGTGCGCTC TCCTGTTCCG ACCCTGCCGC TTACCGGATA
18361 CCTGTCCGCC TTTCTCCCTT CGGGAAGCGT GGCGCTTTCT CATAGCTCAC GCTGTAGGTA
18421 TCTCAGTTCG GTGTAGGTCG TTCGCTCCAA GCTGGGCTGT GTGCACGAAC CCCCCGTTCA
18481 GCCCGACCGC TGCGCCTTAT CCGGTAACTA TCGTCTTGAG TCCAACCCGG TAAGACACGA
18541 CTTATCGCCA CTGGCAGCAG CCACTGGTAA CAGGATTAGC AGAGCGAGGT ATGTAGGCGG
18601 TGCTACAGAG TTCTTGAAGT GGTGGCCTAA CTACGGCTAC ACTAGAAGGA CAGTATTTGG
18661 TATCTGCGCT CTGCTGAAGC CAGTTACCTT CGGAAAAAGA GTTGGTAGCT CTTGATCCGG
18721 CAAACAAACC ACCGCTGGTA GCGGTGGTTT TTTTGTTTGC AAGCAGCAGA TTACGCGCAG
18781 AAAAAAAGGA TCTCAAGAAG ATCCTTTGAT CTTTTCTACG GGGTCTGACG CTCAGTGGAA
18841 CGAAAACTCA CGTTAAGGGA TTTTGGTCAT GAGATTATCA AAAAGGATCT TCACCTAGAT
18901 CCTTTTAAAT TAAAAATGAA GTTTTAAATC AATCTAAAGT ATATATGAGT AAACTTGGTC
18961 TGACAGTTAC CAATGCTTAA TCAGTGAGGC ACCTATCTCA GCGATCTGTC TATTTCGTTC
19021 ATCCATAGTT GCCTGACTCC CCGTCGTGTA GATAACTACG ATACGGGAGG GCTTACCATC
19081 TGGCCCCAGT GCTGCAATGA TACCGCGAGA CCCACGCTCA CCGGCTCCAG ATTTATCAGC
19141 AATAAACCAG CCAGCCGGAA GGGCCGAGCG CAGAAGTGGT CCTGCAACTT TATCCGCCTC
19201 CATCCAGTCT ATTAATTGTT GCCGGGAAGC TAGAGTAAGT AGTTCGCCAG TTAATAGTTT
19261 GCGCAACGTT GTTGCCATTG CTACAGGCAT CGTGGTGTCA CGCTCGTCGT TTGGTATGGC
19321 TTCATTCAGC TCCGGTTCCC AACGATCAAG GCGAGTTACA TGATCCCCCA TGTTGTGCAA
19381 AAAAGCGGTT AGCTCCTTCG GTCCTCCGAT CGTTGTCAGA AGTAAGTTGG CCGCAGTGTT
19441 ATCACTCATG GTTATGGCAG CACTGCATAA TTCTCTTACT GTCATGCCAT CCGTAAGATG
19501 CTTTTCTGTG ACTGGTGAGT ACTCAACCAA GTCATTCTGA GAATAGTGTA TGCGGCGACC
19561 GAGTTGCTCT TGCCCGGCGT CAATACGGGA TAATACCGCG CCACATAGCA GAACTTTAAA
19621 AGTGCTCATC ATTGGAAAAC GTTCTTCGGG GCGAAAACTC TCAAGGATCT TACCGCTGTT
19681 GAGATCCAGT TCGATGTAAC CCACTCGTGC ACCCAACTGA TCTTCAGCAT CTTTTACTTT
19741 CACCAGCGTT TCTGGGTGAG CAAAAACAGG AAGGCAAAAT GCCGCAAAAA AGGGAATAAG
19801 GGCGACACGG AAATGTTGAA TACTCATACT CTTCCTTTTT CAATATTATT GAAGCATTTA
19861 TCAGGGTTAT TGTCTCATGA GCGGATACAT ATTTGAATGT ATTTAGAAAA ATAAACAAAT
19921 AGGGGTTCCG CGCACATTTC CCCGAAAAGT GCCACCTAAA TTGTAAGCGT TAATATTTTG
19981 TTAAAATTCG CGTTAAATTT TTGTTAAATC AGCTCATTTT TTAACCAATA GGCCGAAATC
20041 GGCAAAATCC CTTATAAATC AAAAGAATAG ACCGAGATAG GGTTGAGTGT TGTTCCAGTT
20101 TGGAACAAGA GTCCACTATT AAAGAACGTG GACTCCAACG TCAAAGGGCG AAAAACCGTC
20161 TATCAGGGCG ATGGCCCACT ACGTGAACCA TCACCCTAAT CAAGTTTTTT GGGGTCGAGG
20221 TGCCGTAAAG CACTAAATCG GAACCCTAAA GGGAGCCCCC GATTTAGAGC TTGACGGGGA
20281 AAGCCGGCGA ACGTGGCGAG AAAGGAAGGG AAGAAAGCGA AAGGAGCGGG CGCTAGGGCG
20341 CTGGCAAGTG TAGCGGTCAC GCTGCGCGTA ACCACCACAC CCGCCGCGCT TAATGCGCCG
20401 CTACAGGGCG CGTCCCATTC GCCATTCAGG CTGCGCAACT GTTGGGAAGG GCGATCGGTG
20461 CGGGCCTCTT CGCTATTACG CCAGCTGGCG AAAGGGGGAT GTGCTGCAAG GCGATTAAGT
20521 TGGGTAACGC CAGGGTTTTC CCAGTCACGA CGTTGTAAAA CGACGGCCAG TGAGCGCGCG
20581 TAATACGACT CACTATAGGG CGAATTGGGT ACCGGGCCCC CCC
```

//

Figure 18: Nucleic acid sequence of the known segment of the R15/appa+intron plasmid, including the vector sequences of pBLCAT3 (SEQ ID NO:2).

```
LOCUS       R15/appa+intron    6708 bp   DNA     SYN        15-APR-2000
DEFINITION  R15/appa+intron transgene  with vector cut 13543 to 4954
ACCESSION R15/appa+intron
REFERENCE   1  (bases 1 to 6708))
SOURCE      synthetic construct.
       ORGANISM  synthetic construct
                 artificial sequence.
KEYWORDS    salivary proline-rich protein, acid glucose-1-phosphatase; appA
            gene; periplasmic phosphoanhydride phosphohydrolase; artificial
            sequence;
AUTHORS     Golovan, S., Forsberg, C.W., Phillips, J.
  JOURNAL   Unpublished.

     DEFINITION  Rat salivary proline-rich protein (RP15) gene.
     ACCESSION   M64793 M36414
     VERSION     M64793.1  GI:206711
     SOURCE      Rat (Sprague-Dawley) liver DNA.
       ORGANISM  Rattus norvegicus
                 Eukaryota; Metazoa; Chordata; Craniata; Vertebrata;
Mammalia;
                 Eutheria; Rodentia; Sciurognathi; Muridae; Murinae;
Rattus.
     REFERENCE   1  (bases 1 to 1748)
       AUTHORS   Lin,H.H. and Ann,D.K.
       TITLE     Molecular characterization of rat multigene family
encoding
                 proline-rich proteins
       JOURNAL   Genomics 10, 102-113 (1991)
       MEDLINE   91257817
     FEATURES             Location/Qualifiers
          source          1..1748
                          /organism="Rattus norvegicus"
                          /strain="Sprague-Dawley"
                          /db_xref="taxon:10116"
                          /tissue_type="liver"
                          /tissue_lib="cosmid genomic library"
           misc_feature         1802-1810
                          /function=" consensus sequence for initiation in
                                higher eukaryotes "


FEATURES             Location/Qualifiers
DEFINITION  E. coli periplasmic phosphoanhydride phosphohydrolase (appA)
gene,

      ACCESSION   M58708 L03370 L03371 L03372 L03373 L03374 L03375
      VERSION     M58708.1  GI:145283
      SOURCE            Escherichia coli DNA.
      ORGANISM    Escherichia coli
            Bacteria; Proteobacteria; gamma subdivision;
      Enterobacteriaceae;
            Escherichia.

REFERENCE   1   (bases 1811..3109)
      AUTHORS   Dassa,J., Marck,C. and Boquet,P.L.
```

Figure 18A:

```
        TITLE      The complete nucleotide sequence of the Escherichia coli
                     gene appA reveals significant homology between pH 2.5
                     acid phosphatase and glucose-1-phosphatase
        JOURNAL    J. Bacteriol. 172 (9), 5497-5500 (1990)
        MEDLINE    90368616

FEATURES                    Location/Qualifiers
        Source                    1811..3109
                            /organism="Escherichia coli"
                            /db_xref="taxon:562"
        sig_peptide         1811.. 1876
        /gene="appA"
        CDS                  1811..3109
                            /gene="appA"
                            /standard_name="acid phosphatase/phytase"
                            /transl_table=11
                            /product="periplasmic phosphoanhydride
                            phosphohydrolase"
                            /protein_id="AAA72086.1"
                            /db_xref="GI:145285"

        mat_peptide         1877  3106
                            /gene="appA"
                            /product="periplasmic phosphoanhydride
                                  phosphohydrolase"

        mutation       replace(1817.. 1819,"gcg changed to gcc")
                       /gene="appA"
                       /standard_name="A3 mutant"
                       /note="created by site directed mutagenesis"
                       /phenotype="silent mutation"
        mutation       replace(3092..3094," ccg changed to ccc")
                       /gene="appA"
                       /standard_name=" P428 mutant"
                       /note="created by site directed mutagenesis"
                       /phenotype=" silent mutation "
        mutation       replace(3095..3097," gcg changed to gct")
                       /gene="appA"
                       /standard_name=" A429 mutant"
                       /note="created by site directed mutagenesis"
                       /phenotype=" silent mutation "
```

Figure 18B:

```
DEFINITION  Plasmid pBLCAT3  (bases 3109 to 6708)
     ACCESSION   X64409
     VERSION     X64409.1  GI:58163
     SOURCE      synthetic construct.
       ORGANISM  synthetic construct
                 artificial sequence.
     REFERENCE   1  (bases 3109 to 6708)
       AUTHORS   Luckow,B.H.R.
       TITLE     Direct Submission
       JOURNAL   Submitted (06-FEB-1992) B.H.R. Luckow, German Cancer Res
                 Center, Im Neuenheimer Feld 280, W-6900 Heidelberg, FRG
     REFERENCE   2  (bases 3109 to 6708)
       AUTHORS   Luckow,B. and Schutz,G.
       TITLE     CAT constructions with multiple unique restriction sites
for
                 the functional analysis of eukaryotic promoters and
regulatory
                 elements
       JOURNAL   Nucleic Acids Res. 15 (13), 5490 (1987)
       MEDLINE   87260024
     COMMENT     Promoterless CAT vector for transient transfection
experiments
                  with eukaryotic cells. Allows the analysis of foreign
                  promoters and  enhancers.
     FEATURES             Location/Qualifiers
          source          3109 to 6116
                          /organism="synthetic construct"
                          /db_xref="taxon:32630"

          SV40 t intron   3197..3810
                          /note="SV40 signals"
          polyA_signal    3807..4047
                          /note="SV40 signals"
          CDS             complement(5244..6104)
                          /codon_start=1
                          /transl_table=11
                          /gene="Amp"
                          /product="beta-lactamase"
                          /protein_id="CAA45753.1"
                          /db_xref="GI:58165"

BASE COUNT     1916 a   1479 c   1515 g   1798 t
ORIGIN
        1 GGATCCCCTT TGCTATGTAG TTTTTAATGG AAATTACAAC CCATAGTGTG TTGATAAATA
       61 GAGAGTCCTG TTTGGTTTAA GCAACCTCTG TTTCTCATAA ACTCCATAAA AACAGGAATA
      121 CTCTTTGTTT CTAGCATAAC CAAAAGATTT AGTGAATTGA AAACAATGTT CCCTTAGAGT
      181 ATAGGTCTAA TAACCCCGAA AATATTACCA TGATACTGAG CATTTGTAAG TATCTCATAG
      241 CATGTAGTAT CCATAGTCCA TCAATGAGAG AGACATTTAA CATGATTTTC ATTAATCAGG
      301 TGGAAAAGAC ATGACAACAT TCACAGGCAC TGCACAGAAC ATAGTGGTCC ACCTTGCACA
      361 TATTTCACTA AACTAGGTTT ATCTATTTTG TTGCTTTCTC TAACATCTCT GCAATGAAGC
      421 AGGTCAACAG TGCCACATAT CCTTTACTTA ACCTAAGGAA CACAAAAAAT TTTCTACATA
      481 TATCCTGGTT AGAGAGTGCT TAAAATAAGT TTTCCAAGAA TGGAAAAGAA ATGTTCTGAC
      541 TTAACAATTA AGACAGTATT TATTTAAAGC AAGAAATATG AGGCACACAA GAAAATATTT
      601 TGGGAAGAAA CCATTTGGTG AACAATATTT CAAATAAAAA TAGACAAACA TAGTTAATTG
      661 TAAAACATAT GTTTGACCAG CCCTTCTTTT CAATAGGCTT AATGTGAATA AAATGTTAAA
      721 GATTCTCTTT GGGTGGCTGC AAATTGTCCA CGAATAAGAC AAAATATAAA AATAAGGACT
      781 GAGTCTCACA AAATGAAAAG GAAATATATT CAGAAAGAGA ATCTTGAGAG AATGTGTTGT
      841 CACAAATTAA AGAAAACCTG TGGTGAATGA CATCCTGAGG CCTGAGCTAT TACTGACATT
```

Figure 18C:

```
 901 TAAGATAAAG GTAACTGTAT ACATTTGTCC CATTGAGGGG ACAAGAAAGC TGCTCTCATG
 961 TTCAGCTCTA TAATTCTTGC CTTAAACAAC TTAAATAGAA TGATTTAAAA TATGGAGCTG
1021 TCCATGGACC TTTGAAATAT AAAATAGTCA AGCAACTTAT CAAGGAATTA CAGATTCCTT
1081 GATACTAACA CAGGTAAATC CCACACGTGT TTTCACACTA CATTTGCTGG GATTTTATTG
1141 ATGTAATAGG TCACATGTTT TTCGGGCCAA TGTTGCTGTT ATTCGGTTAC TTCAAGAGAA
1201 TAGTGGCAAC TGATGCTATG TATTCTAGGG GTTTGAAGTG ATGTTTCATG ATTGAAATTT
1261 GTAAAAGAAT AACATCATCA TTCTTAACAA TAGAACATAT AAAGTCACAC AGAAGTGACA
1321 GTGTTTAAGC TGTACTATTG ATCAAAGAAA TTTATTACCT TCAGTTTCAA TGGAAATAAT
1381 TACTGATAAT ACAAACATGT GTGAACACAC ACTAATCCTA TCCAAATGCA CAGTGATACA
1441 CAGAAAATAT TAGCAAGTAG AATGCAATAT TTATATAACG ATTGTATTTA TCAATCAATT
1501 GTATGTATCA ATATATGGGC TATTTTCTTA CACATGATTT TATTCAAATT TACTCTAATC
1561 ATTGTTGAAC CATTTAGAAA AGGCATACTG GCAACTTTTC CTTACCTCAT CCAGCTGGGC
1621 AAAAGTCCCA GTGTGGAGTA AAGGATGCAA GATTTCCTGC TCTGTTAAGT ATAAAATAAT
1681 AGTATGAATT CAAAGGTGCC ATTCTTCTGC TTCTAGTTAT AAAGGCAGTG CTTGCTTCTT
1741 CCAGCACAGA TCTGGATCTC GAGGAGCTTG GCGAGATTTT CAGGAGCTAA GGAAGCTAAA
1801 AGCCGCCACC ATGAAAGCCA TCTTAATCCC ATTTTTATCT CTTCTGATTC CGTTAACCCC
1861 GCAATCTGCA TTCGCTCAGA GTGAGCCGGA GCTGAAGCTG GAAAGTGTGG TGATTGTCAG
1921 TCGTCATGGT GTGCGTGCTC CAACCAAGGC CACGCAACTG ATGCAGGATG TCACCCCAGA
1981 CGCATGGCCA ACCTGGCCGG TAAAACTGGG TTGGCTGACA CCGCGCGGTG GTGAGCTAAT
2041 CGCCTATCTC GGACATTACC AACGCCAGCG TCTGGTAGCC GACGGATTGC TGGCGAAAAA
2101 GGGCTGCCCG CAGTCTGGTC AGGTCGCGAT TATTGCTGAT GTCGACGAGC GTACCCGTAA
2161 AACAGGCGAA GCCTTCGCCG CCGGGCTGGC ACCTGACTGT GCAATAACCG TACATACCCA
2221 GGCAGATACG TCCAGTCCCG ATCCGTTATT TAATCCTCTA AAAACTGGCG TTTGCCAACT
2281 GGATAACGCG AACGTGACTG ACGCGATCCT CAGCAGGGCA GGAGGGTCAA TTGCTGACTT
2341 TACCGGGCAT CGGCAAACGG CGTTTCGCGA ACTGGAACGG GTGCTTAATT TTCCGCAATC
2401 AAACTTGTGC CTTAAACGTG AGAAACAGGA CGAAAGCTGT TCATTAACGC AGGCATTACC
2461 ATCGGAACTC AAGGTGAGCG CCGACAATGT CTCATTAACC GGTGCGGTAA GCCTCGCATC
2521 AATGCTGACG GAGATATTTC TCCTGCAACA AGCACAGGGA ATGCCGGAGC CGGGGTGGGG
2581 AAGGATCACC GATTCACACC AGTGGAACAC CTTGCTAAGT TTGCATAACG CGCAATTTTA
2641 TTTGCTACAA CGCACGCCAG AGGTTGCCCG CAGCCGCGCC ACCCCGTTAT TAGATTTGAT
2701 CAAGACAGCG TTGACGCCCC ATCCACCGCA AAAACAGGCG TATGGTGTGA CATTACCCAC
2761 TTCAGTGCTG TTTATCGCCG GACACGATAC TAATCTGGCA AATCTCGGCG GCGCACTGGA
2821 GCTCAACTGG ACGCTTCCCG GTCAGCCGGA TAACACGCCG CCAGGTGGTG AACTGGTGTT
2881 TGAACGCTGG CGTCGGCTAA GCGATAACAG CCAGTGGATT CAGGTTTCGC TGGTCTTCCA
2941 GACTTTACAG CAGATGCGTG ATAAAACGCC GCTGTCATTA AATACGCCGC CCGGAGAGGT
3001 GAAACTGACC CTGGCAGGAT GTGAAGAGCG AAATGCGCAG GGCATGTGTT CGTTGGCAGG
3061 TTTTACGCAA ATCGTGAATG AAGCACGCAT ACCCGCTTGC AGTTTGTAAG GTATAAGGCA
3121 GTTATTGGTG CCCTTAAACG CCTGGTGCTA CGCCTGAATA AGTGATAATA AGCGGATGAA
3181 TGGCAGAAAT TCGCCGGATC TTTGTGAAGG AACCTTACTT CTGTGGTGTG ACATAATTGG
3241 ACAAACTACC TACAGAGATT TAAAGCTCTA AGGTAAATAT AAAATTTTTA AGTGTATAAT
3301 GTGTTAAACT ACTGATTCTA ATTGTTTGTG TATTTTAGAT TCCAACCTAT GGAACTGATG
3361 AATGGGAGCA GTGGTGGAAT GCCTTTAATG AGGAAAACCT GTTTTGCTCA GAAGAAATGC
3421 CATCTAGTGA TGATGAGGCT ACTGCTGACT CTCAACATTC TACTCCTCCA AAAAAGAAGA
3481 GAAAGGTAGA AGACCCCAAG GACTTTCCTT CAGAATTGCT AAGTTTTTTG AGTCATGCTG
3541 TGTTTAGTAA TAGAACTCTT GCTTGCTTTG CTATTTACAC CACAAAGGAA AAAGCTGCAC
3601 TGCTATACAA GAAAATTATG GAAAAATATT CTGTAACCTT TATAAGTAGG CATAACAGTT
3661 ATAATCATAA CATACTGTTT TTTCTTACTC CACACAGGCA TAGAGTGTCT GCTATTAATA
3721 ACTATGCTCA AAAATTGTGT ACCTTTAGCT TTTTAATTTG TAAAGGGGTT AATAAGGAAT
3781 ATTTGATGTA TAGTGCCTTG ACTAGAGATC ATAATCAGCC ATACCACATT TGTAGAGGTT
3841 TTACTTGCTT TAAAAAACCT CCCACACCTC CCCCTGAACC TGAAACATAA AATGAATGCA
3901 ATTGTTGTTG TTAACTTGTT TATTGCAGCT TATAATGGTT ACAAATAAAG CAATAGCATC
3961 ACAAATTTCA CAAATAAAGC ATTTTTTTCA CTGCATTCTA GTTGTGGTTT GTCCAAACTC
4021 ATCAATGTAT CTTATCATGT CTGGATCGAT CCCCGGGTAC CGAGCTCGAA TTCGTAATCA
4081 TGGTCATAGC TGTTTCCTGT GTGAAATTGT TATCCGCTCA CAATTCCACA CAACATACGA
4141 GCCGGAAGCA TAAAGTGTAA AGCCTGGGGT GCCTAATGAG TGAGCTAACT CACATTAATT
4201 GCGTTGCGCT CACTGCCCGC TTTCCAGTCG GGAAACCTGT CGTGCCAGCT GCATTAATGA
4261 ATCGGCCAAC GCGCGGGGAG AGGCGGTTTG CGTATTGGGC GCTCTTCCGC TTCCTCGCTC
4321 ACTGACTCGC TGCGCTCGGT CGTTCGGCTG CGGCGAGCGG TATCAGCTCA CTCAAAGGCG
```

Figure 18D:

```
4381 GTAATACGGT TATCCACAGA ATCAGGGGAT AACGCAGGAA AGAACATGTG AGCAAAAGGC
4441 CAGCAAAAGG CCAGGAACCG TAAAAAGGCC GCGTTGCTGG CGTTTTTCCA TAGGCTCCGC
4501 CCCCCTGACG AGCATCACAA AAATCGACGC TCAAGTCAGA GGTGGCGAAA CCCGACAGGA
4561 CTATAAAGAT ACCAGGCGTT TCCCCCTGGA AGCTCCCTCG TGCGCTCTCC TGTTCCGACC
4621 CTGCCGCTTA CCGGATACCT GTCCGCCTTT CTCCCTTCGG GAAGCGTGGC GCTTTCTCAA
4681 TGCTCACGCT GTAGGTATCT CAGTTCGGTG TAGGTCGTTC GCTCCAAGCT GGGCTGTGTG
4741 CACGAACCCC CCGTTCAGCC CGACCGCTGC GCCTTATCCG GTAACTATCG TCTTGAGTCC
4801 AACCCGGTAA GACACGACTT ATCGCCACTG GCAGCAGCCA CTGGTAACAG GATTAGCAGA
4861 GCGAGGTATG TAGGCGGTGC TACAGAGTTC TTGAAGTGGT GGCCTAACTA CGGCTACACT
4921 AGAAGGACAG TATTTGGTAT CTGCGCTCTG CTGAAGCCAG TTACCTTCGG AAAAAGAGTT
4981 GGTAGCTCTT GATCCGGCAA ACAAACCACC GCTGGTAGCG GTGGTTTTTT TGTTTGCAAG
5041 CAGCAGATTA CGCGCAGAAA AAAAGGATCT CAAGAAGATC CTTTGATCTT TTCTACGGGG
5101 TCTGACGCTC AGTGGAACGA AAACTCACGT TAAGGGATTT TGGTCATGAG ATTATCAAAA
5161 AGGATCTTCA CCTAGATCCT TTTAAATTAA AAATGAAGTT TTAAATCAAT CTAAAGTATA
5221 TATGAGTAAA CTTGGTCTGA CAGTTACCAA TGCTTAATCA GTGAGGCACC TATCTCAGCG
5281 ATCTGTCTAT TTCGTTCATC CATAGTTGCC TGACTCCCCG TCGTGTAGAT AACTACGATA
5341 CGGGAGGGCT TACCATCTGG CCCCAGTGCT GCAATGATAC CGCGAGACCC ACGCTCACCG
5401 GCTCCAGATT TATCAGCAAT AAACCAGCCA GCCGGAAGGG CCGAGCGCAG AAGTGGTCCT
5461 GCAACTTTAT CCGCCTCCAT CCAGTCTATT AATTGTTGCC GGGAAGCTAG AGTAAGTAGT
5521 TCGCCAGTTA ATAGTTTGCG CAACGTTGTT GCCATTGCTA CAGGCATCGT GGTGTCACGC
5581 TCGTCGTTTG GTATGGCTTC ATTCAGCTCC GGTTCCCAAC GATCAAGGCG AGTTACATGA
5641 TCCCCCATGT TGTGCAAAAA AGCGGTTAGC TCCTTCGGTC CTCCGATCGT TGTCAGAAGT
5701 AAGTTGGCCG CAGTGTTATC ACTCATGGTT ATGGCAGCAC TGCATAATTC TCTTACTGTC
5761 ATGCCATCCG TAAGATGCTT TTCTGTGACT GGTGAGTACT CAACCAAGTC ATTCTGAGAA
5821 TAGTGTATGC GGCGACCGAG TTGCTCTTGC CCGGCGTCAA TACGGGATAA TACCGCGCCA
5881 CATAGCAGAA CTTTAAAAGT GCTCATCATT GGAAAACGTT CTTCGGGGCG AAAACTCTCA
5941 AGGATCTTAC CGCTGTTGAG ATCCAGTTCG ATGTAACCCA CTCGTGCACC CAACTGATCT
6001 TCAGCATCTT TTACTTTCAC CAGCGTTTCT GGGTGAGCAA AAACAGGAAG GCAAAATGCC
6061 GCAAAAAAGG GAATAAGGGC GACACGGAAA TGTTGAATAC TCATACTCTT CCTTTTTCAA
6121 TATTATTGAA GCATTTATCA GGGTTATTGT CTCATGAGCG GATACATATT TGAATGTATT
6181 TAGAAAAATA AACAAATAGG GGTTCCGCGC ACATTTCCCC GAAAAGTGCC ACCTGACGTC
6241 TAAGAAACCA TTATTATCAT GACATTAACC TATAAAAATA GGCGTATCAC GAGGCCCTTT
6301 CGTCTCGCGC GTTTCGGTGA TGACGGTGAA AACCTCTGAC ACATGCAGCT CCCGGAGACG
6361 GTCACAGCTT GTCTGTAAGC GGATGCCGGG AGCAGACAAG CCCGTCAGGG CGCGTCAGCG
6421 GGTGTTGGCG GGTGTCGGGG CTGGCTTAAC TATGCGGCAT CAGAGCAGAT TGTACTGAGA
6481 GTGCACCATA TGCGGTGTGA AATACCGCAC AGATGCGTAA GGAGAAAATA CCGCATCAGG
6541 CGCCATTCGC CATTCAGGCT GCGCAACTGT TGGGAAGGGC GATCGGTGCG GGCCTCTTCG
6601 CTATTACGCC AGCTGGCGAA AGGGGGATGT GCTGCAAGGC GATTAAGTTG GGTAACGCCA
6661 GGGTTTTCCC AGTCACGACG TTGTAAAACG ACGGCCAGTG CCAAGCTT
//
```

Figure 19: Nucleic acid sequence of the known segment of the R15/appa+intron transgene used for the generation of transgenic mice (SEQ ID NO: 3).

```
LOCUS       R15/appa     4060 bp    DNA        SYN      15-APR-2000
DEFINITION  R15/appa transgene  without vector
ACCESSION R15/appa
REFERENCE   1  (bases 1 to 4060)
SOURCE      synthetic construct.
       ORGANISM  synthetic construct
                 artificial sequence.
KEYWORDS    salivary proline-rich protein, acid glucose-1-phosphatase; appA
            gene; periplasmic phosphoanhydride phosphohydrolase; artificial
            sequence;
AUTHORS     Golovan, S., Forsberg, C.W., Phillips, J.
  JOURNAL   Unpublished.

     DEFINITION  Rat salivary proline-rich protein (RP15) gene.
     ACCESSION   M64793 M36414
     VERSION     M64793.1  GI:206711
     SOURCE      Rat (Sprague-Dawley) liver DNA.
       ORGANISM  Rattus norvegicus
                 Eukaryota; Metazoa; Chordata; Craniata; Vertebrata;
Mammalia;
                 Eutheria; Rodentia; Sciurognathi; Muridae; Murinae;
Rattus.
     REFERENCE   1  (bases 1 to 1748)
       AUTHORS   Lin,H.H. and Ann,D.K.
       TITLE     Molecular characterization of rat multigene family
encoding
                 proline-rich proteins
       JOURNAL   Genomics 10, 102-113 (1991)
       MEDLINE   91257817
     FEATURES             Location/Qualifiers
          source          1..1748
                          /organism="Rattus norvegicus"
                          /strain="Sprague-Dawley"
                          /db_xref="taxon:10116"
                          /tissue_type="liver"
                          /tissue_lib="cosmid genomic library"
           misc_feature          1802-1810
                          /function=" consensus sequence for initiation in
                                 higher eukaryotes "


FEATURES             Location/Qualifiers
DEFINITION  E. coli periplasmic phosphoanhydride phosphohydrolase (appA)
gene,

      ACCESSION   M58708 L03370 L03371 L03372 L03373 L03374 L03375
      VERSION     M58708.1  GI:145283
      SOURCE             Escherichia coli DNA.
      ORGANISM    Escherichia coli
            Bacteria; Proteobacteria; gamma subdivision;
      Enterobacteriaceae;
            Escherichia.

REFERENCE   1    (bases 1811..3109)
      AUTHORS   Dassa,J., Marck,C. and Boquet,P.L.
```

Figure 19A:

```
     TITLE      The complete nucleotide sequence of the Escherichia coli
                  gene appA reveals significant homology between pH 2.5
                  acid phosphatase and glucose-1-phosphatase
     JOURNAL    J. Bacteriol. 172 (9), 5497-5500 (1990)
     MEDLINE    90368616

FEATURES                 Location/Qualifiers
     Source                    1811..3109
                         /organism="Escherichia coli"
                         /db_xref="taxon:562"
     sig_peptide         1811.. 1876
     /gene="appA"
CDS                 1811..3109
                         /gene="appA"
                         /standard_name="acid phosphatase/phytase"
                         /transl_table=11
                         /product="periplasmic phosphoanhydride
                         phosphohydrolase"
                         /protein_id="AAA72086.1"
                         /db_xref="GI:145285"

     mat_peptide         1877  3106
                         /gene="appA"
                         /product="periplasmic phosphoanhydride
                               phosphohydrolase"

     mutation      replace(1817.. 1819,"gcg changed to gcc")
                   /gene="appA"
                   /standard_name="A3 mutant"
                   /note="created by site directed mutagenesis"
                   /phenotype="silent mutation"
     mutation      replace(3092..3094," ccg changed to ccc")
                   /gene="appA"
                   /standard_name=" P428 mutant"
                   /note="created by site directed mutagenesis"
                   /phenotype=" silent mutation "
     mutation      replace(3095..3097," gcg changed to gct")
                   /gene="appA"
                   /standard_name=" A429 mutant"
                   /note="created by site directed mutagenesis"
                   /phenotype=" silent mutation "
```

Figure 19B:

```
        SV40 t intron   3197..3810
                        /note="SV40 signals"
        polyA_signal    3807..4047
                        /note="SV40 signals"

BASE COUNT     1257 a    814 c    843 g   1146 t
ORIGIN
        1 GGATCCCCTT TGCTATGTAG TTTTTAATGG AAATTACAAC CCATAGTGTG TTGATAAATA
       61 GAGAGTCCTG TTTGGTTTAA GCAACCTCTG TTTCTCATAA ACTCCATAAA AACAGGAATA
      121 CTCTTTGTTT CTAGCATAAC CAAAAGATTT AGTGAATTGA AAACAATGTT CCCTTAGAGT
      181 ATAGGTCTAA TAACCCCGAA AATATTACCA TGATACTGAG CATTTGTAAG TATCTCATAG
      241 CATGTAGTAT CCATAGTCCA TCAATGAGAG AGACATTTAA CATGATTTTC ATTAATCAGG
      301 TGGAAAAGAC ATGACAACAT TCACAGGCAC TGCACAGAAC ATAGTGGTCC ACCTTGCACA
      361 TATTTCACTA AACTAGGTTT ATCTATTTTG TTGCTTTCTC TAACATCTCT GCAATGAAGC
      421 AGGTCAACAG TGCCACATAT CCTTTACTTA ACCTAAGGAA CACAAAAAAT TTTCTACATA
      481 TATCCTGGTT AGAGAGTGCT TAAAATAAGT TTTCCAAGAA TGGAAAAGAA ATGTTCTGAC
      541 TTAACAATTA AGACAGTATT TATTTAAAGC AAGAAATATG AGGCACACAA GAAAATATTT
      601 TGGGAAGAAA CCATTTGGTG AACAATATTT CAAATAAAAA TAGACAAACA TAGTTAATTG
      661 TAAAACATAT GTTTGACCAG CCCTTCTTTT CAATAGGCTT AATGTGAATA AAATGTTAAA
      721 GATTCTCTTT GGGTGGCTGC AAATTGTCCA CGAATAAGAC AAAATATAAA AATAAGGACT
      781 GAGTCTCACA AAATGAAAAG GAAATATATT CAGAAAGAGA ATCTTGAGAG AATGTGTTGT
      841 CACAAATTAA AGAAAACCTG TGGTGAATGA CATCCTGAGG CCTGAGCTAT TACTGACATT
      901 TAAGATAAAG GTAACTGTAT ACATTTGTCC CATTGAGGGG ACAAGAAAGC TGCTCTCATG
      961 TTCAGCTCTA TAATTCTTGC CTTAAACAAC TTAAATAGAA TGATTTAAAA TATGGAGCTG
     1021 TCCATGGACC TTTGAAATAT AAAATAGTCA AGCAACTTAT CAAGGAATTA CAGATTCCTT
     1081 GATACTAACA CAGGTAAATC CCACACGTGT TTTGAGACTA CATTTGCTGG GATTTTATTG
     1141 ATGTAATAGG TCACATGTTT TTCGGGCCAA TGTTGCTGTT ATTCGGTTAC TTCAAGAGAA
     1201 TAGTGGCAAC TGATGCTATG TATTCTAGGG GTTTGAAGTG ATGTTTCATG ATTGAAATTT
     1261 GTAAAAGAAT AACATCATCA TTCTTAACAA TAGAACATAT AAAGTCACAC AGAAGTGACA
     1321 GTGTTTAAGC TGTACTATTG ATCAAAGAAA TTTATTACCT TCAGTTTCAA TGGAAATAAT
     1381 TACTGATAAT ACAAACATGT GTGAACACAC ACTAATCCTA TCCAAATGCA CAGTGATACA
     1441 CAGAAAATAT TAGCAAGTAG AATGCAATAT TTATATAACG ATTGTATTTA TCAATCAATT
     1501 GTATGTATCA ATATATGGGC TATTTTCTTA CACATGATTT TATTCAAATT TACTCTAATC
     1561 ATTGTTGAAC CATTTAGAAA AGGCATACTG GCAACTTTTC CTTACCTCAT CCAGCTGGGC
     1621 AAAAGTCCCA GTGTGGAGTA AAGGATGCAA GATTTCCTGC TCTGTTAAGT ATAAAATAAT
     1681 AGTATGAATT CAAAGGTGCC ATTCTTCTGC TTCTAGTTAT AAAGGCAGTG CTTGCTTCTT
     1741 CCAGCACAGA TCTGGATCTC GAGGAGCTTG GCGAGATTTT CAGGAGCTAA GGAAGCTAAA
     1801 AGCCGCCACC ATGAAAGCCA TCTTAATCCC ATTTTTATCT CTTCTGATTC CGTTAACCCC
     1861 GCAATCTGCA TTCGCTCAGA GTGAGCCGGA GCTGAAGCTG GAAAGTGTGG TGATTGTCAG
     1921 TCGTCATGGT GTGCGTGCTC CAACCAAGGC CACGCAACTG ATGCAGGATG TCACCCCAGA
     1981 CGCATGGCCA ACCTGGCCGG TAAAACTGGG TTGGCTGACA CCGCGCGGTG GTGAGCTAAT
     2041 CGCCTATCTC GGACATTACC AACGCCAGCG TCTGGTAGCC GACGGATTGC TGGCGAAAAA
     2101 GGGCTGCCCG CAGTCTGGTC AGGTCGCGAT TATTGCTGAT GTCGACGAGC GTACCCGTAA
     2161 AACAGGCGAA GCCTTCGCCG CCGGGCTGGC ACCTGACTGT GCAATAACCG TACATACCCA
     2221 GGCAGATACG TCCAGTCCCG ATCCGTTATT TAATCCTCTA AAAACTGGCG TTTGCCAACT
     2281 GGATAACGCG AACGTGACTG ACGCGATCCT CAGCAGGGCA GGAGGGTCAA TTGCTGACTT
     2341 TACCGGGCAT CGGCAAACGG CGTTTCGCGA ACTGGAACGG GTGCTTAATT TTCCGCAATC
     2401 AAACTTGTGC CTTAAACGTG AGAAACAGGA CGAAAGCTGT TCATTAACGC AGGCATTACC
     2461 ATCGGAACTC AAGGTGAGCG CCGACAATGT CTCATTAACC GGTGCGGTAA GCCTCGCATC
     2521 AATGCTGACG GAGATATTTC TCCTGCAACA AGCACAGGGA ATGCCGGAGC CGGGGTGGGG
     2581 AAGGATCACC GATTCACACC AGTGGAACAC CTTGCTAAGT TTGCATAACG CGCAATTTTA
     2641 TTTGCTACAA CGCACGCCAG AGGTTGCCCG CAGCCGCGCC ACCCCGTTAT TAGATTTGAT
     2701 CAAGACAGCG TTGACGCCCC ATCCACCGCA AAAACAGGCG TATGGTGTGA CATTACCCAC
     2761 TTCAGTGCTG TTTATCGCCG GACACGATAC TAATCTGGCA AATCTCGGCG GCGCACTGGA
     2821 GCTCAACTGG ACGCTTCCCG GTCAGCCGGA TAACACGCCG CCAGGTGGTG AACTGGTGTT
     2881 TGAACGCTGG CGTCGGCTAA GCGATAACAG CCAGTGGATT CAGGTTTCGC TGGTCTTCCA
```

Figure 19C:

```
2941 GACTTTACAG CAGATGCGTG ATAAAACGCC GCTGTCATTA AATACGCCGC CCGGAGAGGT
3001 GAAACTGACC CTGGCAGGAT GTGAAGAGCG AAATGCGCAG GGCATGTGTT CGTTGGCAGG
3061 TTTTACGCAA ATCGTGAATG AAGCACGCAT ACCCGCTTGC AGTTTGTAAG GTATAAGGCA
3121 GTTATTCCTC CCCTTAAACG CCTGGTGCTA CGCCTGAATA AGTGATAATA AGCGGATGAA
3181 TGGCAGAAAT TCGCCGGATC TTTGTGAAGG AACCTTACTT CTGTGGTGTG ACATAATTGG
3241 ACAAACTACC TACAGAGATT TAAAGCTCTA AGGTAAATAT AAAATTTTTA AGTGTATAAT
3301 GTGTTAAACT ACTGATTCTA ATTGTTTGTG TATTTTAGAT TCCAACCTAT GGAACTGATG
3361 AATGGGAGCA GTGGTGGAAT GCCTTTAATG AGGAAAACCT GTTTTGCTCA GAAGAAATGC
3421 CATCTAGTGA TGATGAGGCT ACTGCTGACT CTCAACATTC TACTCCTCCA AAAAAGAAGA
3481 GAAAGGTAGA AGACCCCAAG GACTTTCCTT CAGAATTGCT AAGTTTTTTG AGTCATGCTG
3541 TGTTTAGTAA TAGAACTCTT GCTTGCTTTG CTATTTACAC CACAAAGGAA AAAGCTGCAC
3601 TGCTATACAA GAAAATTATG GAAAAATATT CTGTAACCTT TATAAGTAGG CATAACAGTT
3661 ATAATCATAA CATACTGTTT TTTCTTACTC CACACAGGCA TAGAGTGTCT GCTATTAATA
3721 ACTATGCTCA AAAATTGTGT ACCTTTAGCT TTTTAATTTG TAAAGGGGTT AATAAGGAAT
3781 ATTTGATGTA TAGTGCCTTG ACTAGAGATC ATAATCAGCC ATACCACATT TGTAGAGGTT
3841 TTACTTGCTT TAAAAAACCT CCCACACCTC CCCCTGAACC TGAAACATAA AATGAATGCA
3901 ATTGTTGTTG TTAACTTGTT TATTGCAGCT TATAATGGTT ACAAATAAAG CAATAGCATC
3961 ACAAATTTCA CAAATAAAGC ATTTTTTTCA CTGCATTCTA GTTGTGGTTT GTCCAAACTC
4021 ATCAATGTAT CTTATCATGT CTGGATCGAT CCCCGGGTAC
```
//

Figure 20: Nucleic acid sequence of the known segment of the R15/appa plasmid (including the vector sequences of pBLCAT3 (SEQ ID NO:4).

```
LOCUS       R15/appa        6116 bp    DNA             SYN       15-APR-2000
DEFINITION  R15/appa transgene  with vector
ACCESSION   R15/appa
REFERENCE   1  (bases 1 to 6116)
SOURCE      synthetic construct.
       ORGANISM  synthetic construct
                 artificial sequence.
KEYWORDS    salivary proline-rich protein, acid glucose-1-phosphatase; appA
            gene; periplasmic phosphoanhydride phosphohydrolase; artificial
            sequence;
AUTHORS     Golovan, S., Forsberg, C.W., Phillips, J.
  JOURNAL   Unpublished.

     DEFINITION  Rat salivary proline-rich protein (RP15) gene.
     ACCESSION   M64793 M36414
     VERSION     M64793.1  GI:206711
     SOURCE      Rat (Sprague-Dawley) liver DNA.
       ORGANISM  Rattus norvegicus
                 Eukaryota; Metazoa; Chordata; Craniata; Vertebrata;
Mammalia;
                 Eutheria; Rodentia; Sciurognathi; Muridae; Murinae;
Rattus.
     REFERENCE   1  (bases 1 to 1748)
       AUTHORS   Lin,H.H. and Ann,D.K.
       TITLE     Molecular characterization of rat multigene family
encoding
                 proline-rich proteins
       JOURNAL   Genomics 10, 102-113 (1991)
       MEDLINE   91257817
     FEATURES             Location/Qualifiers
          source          1..1748
                          /organism="Rattus norvegicus"
                          /strain="Sprague-Dawley"
                          /db_xref="taxon:10116"
                          /tissue_type="liver"
                          /tissue_lib="cosmid genomic library"
          misc_feature          1802-1810
                          /function=" consensus sequence for initiation in
                                higher eukaryotes "


FEATURES             Location/Qualifiers
DEFINITION  E. coli periplasmic phosphoanhydride phosphohydrolase (appA)
gene,

      ACCESSION    M58708 L03370 L03371 L03372 L03373 L03374 L03375
      VERSION      M58708.1  GI:145283
      SOURCE       Escherichia coli DNA.
      ORGANISM     Escherichia coli
             Bacteria; Proteobacteria; gamma subdivision; Enterobacteriaceae;
             Escherichia.

REFERENCE   1    (bases 1811..3109)
      AUTHORS    Dassa,J., Marck,C. and Boquet,P.L.
      TITLE      The complete nucleotide sequence of the Escherichia coli gene appA
                     reveals significant homology between pH 2.5 acid phosphatase
                     and glucose-1-phosphatase
      JOURNAL    J. Bacteriol. 172 (9), 5497-5500 (1990)
```

Figure 20A:

```
      MEDLINE   90368616

FEATURES                    Location/Qualifiers
      Source                      1811..3109
                            /organism="Escherichia coli"
                            /db_xref="taxon:562"
      sig_peptide           1811.. 1876
      /gene="appA"
      CDS                    1811..3109
                                  /gene="appA"
                            /standard_name="acid phosphatase/phytase"
                            /transl_table=11
                            /product="periplasmic phosphoanhydride phosphohydrolase"
                            /protein_id="AAA72086.1"
                            /db_xref="GI:145285"

      mat_peptide           1877  3106
                            /gene="appA"
                            /product="periplasmic phosphoanhydride phosphohydrolase"

      mutation        replace(1817.. 1819,"gcg changed to gcc")
                      /gene="appA"
                      /standard_name="A3 mutant"
                      /note="created by site directed mutagenesis"
                      /phenotype="silent mutation"
      mutation        replace(3092..3094," ccg changed to ccc")
                      /gene="appA"
                      /standard_name=" P428 mutant"
                      /note="created by site directed mutagenesis"
                      /phenotype=" silent mutation "
      mutation        replace(3095..3097," gcg changed to gct")
                      /gene="appA"
                      /standard_name=" A429 mutant"
                      /note="created by site directed mutagenesis"
                      /phenotype=" silent mutation "


DEFINITION  Plasmid pBLCAT3  (bases 3109 to 6116)
     ACCESSION   X64409
     VERSION     X64409.1  GI:58163
     SOURCE      synthetic construct.
       ORGANISM  synthetic construct
                 artificial sequence.
     REFERENCE   1  (bases 3109 to 6116)
       AUTHORS   Luckow,B.H.R.
       TITLE     Direct Submission
       JOURNAL   Submitted (06-FEB-1992) B.H.R. Luckow, German Cancer Res
                 Center, Im Neuenheimer Feld 280, W-6900 Heidelberg, FRG
```

Figure 20B:

```
     REFERENCE   2  (bases 3109 to 6116)
       AUTHORS   Luckow,B. and Schutz,G.
       TITLE     CAT constructions with multiple unique restriction sites
for
                 the functional analysis of eukaryotic promoters and
regulatory
                 elements
       JOURNAL   Nucleic Acids Res. 15 (13), 5490 (1987)
       MEDLINE   87260024
     COMMENT     Promoterless CAT vector for transient transfection
experiments
                  with eukaryotic cells. Allows the analysis of foreign
                  promoters and  enhancers.
     FEATURES             Location/Qualifiers
          source          3109 to 6116
                          /organism="synthetic construct"
                          /db_xref="taxon:32630"
          polyA_signal    3262..3457
                          /note="SV40 signals"

          CDS             complement(4654..5514)
                          /codon_start=1
                          /transl_table=11
                          /gene="Amp"
                          /product="beta-lactamase"
                          /protein_id="CAA45753.1"
                          /db_xref="GI:58165"

BASE COUNT     1724 a   1386 c   1407 g   1599 t
ORIGIN
        1 GGATCCCCTT TGCTATGTAG TTTTTAATGG AAATTACAAC CCATAGTGTG TTGATAAATA
       61 GAGAGTCCTG TTTGGTTTAA GCAACCTCTG TTTCTCATAA ACTCCATAAA AACAGGAATA
      121 CTCTTTGTTT CTAGCATAAC CAAAAGATTT AGTGAATTGA AAACAATGTT CCCTTAGAGT
      181 ATAGGTCTAA TAACCCCGAA AATATTACCA TGATACTGAG CATTTGTAAG TATCTCATAG
      241 CATGTAGTAT CCATAGTCCA TCAATGAGAG AGACATTTAA CATGATTTTC ATTAATCAGG
      301 TGGAAAAGAC ATGACAACAT TCACAGGCAC TGCACAGAAC ATAGTGGTCC ACCTTGCACA
      361 TATTTCACTA AACTAGGTTT ATCTATTTTG TTGCTTTCTC TAACATCTCT GCAATGAAGC
      421 AGGTCAACAG TGCCACATAT CCTTTACTTA ACCTAAGGAA CACAAAAAAT TTTCTACATA
      481 TATCCTGGTT AGAGAGTGCT TAAAATAAGT TTTCCAAGAA TGGAAAAGAA ATGTTCTGAC
      541 TTAACAATTA AGACAGTATT TATTTAAAGC AAGAAATATG AGGCACACAA GAAAATATTT
      601 TGGGAAGAAA CCATTTGGTG AACAATATTT CAAATAAAAA TAGACAAACA TAGTTAATTG
      661 TAAAACATAT GTTTGACCAG CCCTTCTTTT CAATAGGCTT AATGTGAATA AAATGTTAAA
      721 GATTCTCTTT GGGTGGCTGC AAATTGTCCA CGAATAAGAC AAAATATAAA AATAAGGACT
      781 GAGTCTCACA AAATGAAAAG GAAATATATT CAGAAAGAGA ATCTTGAGAG AATGTGTTGT
      841 CACAAATTAA AGAAAACCTG TGGTGAATGA CATCCTGAGG CCTGAGCTAT TACTGACATT
      901 TAAGATAAAG GTAACTGTAT ACATTTGTCC CATTGAGGGG ACAAGAAAGC TGCTCTCATG
      961 TTCAGCTCTA TAATTCTTGC CTTAAACAAC TTAAATAGAA TGATTTAAAA TATGGAGCTG
     1021 TCCATGGACC TTTGAAATAT AAAATAGTCA AGCAACTTAT CAAGGAATTA CAGATTCCTT
     1081 GATACTAACA CAGGTAAATC CCACACGTGT TTTGAGACTA CATTTGCTGG GATTTTATTG
     1141 ATGTAATAGG TCACATGTTT TTCGGGCCAA TGTTGCTGTT ATTCGGTTAC TTCAAGAGAA
     1201 TAGTGGCAAC TGATGCTATG TATTCTAGGG GTTTGAAGTG ATGTTTCATG ATTGAAATTT
     1261 GTAAAAGAAT AACATCATCA TTCTTAACAA TAGAACATAT AAAGTCACAC AGAAGTGACA
     1321 GTGTTTAAGC TGTACTATTG ATCAAAGAAA TTTATTACCT TCAGTTTCAA TGGAAATAAT
     1381 TACTGATAAT ACAAACATGT GTGAACACAC ACTAATCCTA TCCAAATGCA CAGTGATACA
     1441 CAGAAAATAT TAGCAAGTAG AATGCAATAT TTATATAACG ATTGTATTTA TCAATCAATT
     1501 GTATGTATCA ATATATGGGC TATTTTCTTA CACATGATTT TATTCAAATT TACTCTAATC
     1561 ATTGTTGAAC CATTTAGAAA AGGCATACTG GCAACTTTTC CTTACCTCAT CCAGCTGGGC
     1621 AAAAGTCCCA GTGTGGAGTA AAGGATGCAA GATTTCCTGC TCTGTTAAGT ATAAAATAAT
```

Figure 20C:

```
1681 AGTATGAATT CAAAGGTGCC ATTCTTCTGC TTCTAGTTAT AAAGGCAGTG CTTGCTTCTT
1741 CCAGCACAGA TCTGGATCTC GAGGAGCTTG GCGAGATTTT CAGGAGCTAA GGAAGCTAAA
1801 AGCCGCCACC ATGAAAGCCA TCTTAATCCC ATTTTTATCT CTTCTGATTC CGTTAACCCC
1861 GCAATCTGCA TTCGCTCAGA GTGAGCCGGA GCTCAAGCTG GAAAGTGTGG TGATTGTCAG
1921 TCGTCATGGT GTGCGTGCTC CAACCAAGGC CACGCAACTG ATGCAGGATG TCACCCCAGA
1981 CGCATGGCCA ACCTGGCCGG TAAAACTGGG TTGGCTGACA CCGCGCGGTG GTGAGCTAAT
2041 CGCCTATCTC GGACATTACC AACGCCAGCG TCTGGTAGCC GACGGATTGC TGGCGAAAAA
2101 GGGCTGCCCG CAGTCTGGTC AGGTCGCGAT TATTGCTGAT GTCGACGAGC GTACCCGTAA
2161 AACAGGCGAA GCCTTCGCCG CCGGGCTGGC ACCTGACTGT GCAATAACCG TACATACCCA
2221 GGCAGATACG TCCAGTCCCG ATCCGTTATT TAATCCTCTA AAAACTGGCG TTTGCCAACT
2281 GGATAACGCG AACGTGACTG ACGCGATCCT CAGCAGGGCA GGAGGGTCAA TTGCTGACTT
2341 TACCGGGCAT CGGCAAACGG CGTTTCGCGA ACTGGAACGG GTGCTTAATT TTCCGCAATC
2401 AAACTTGTGC CTTAAACGTG AGAAACAGGA CGAAAGCTGT TCATTAACGC AGGCATTACC
2461 ATCGGAACTC AAGGTGAGCG CCGACAATGT CTCATTAACC GGTGCGGTAA GCCTCGCATC
2521 AATGCTGACG GAGATATTTC TCCTGCAACA AGCACAGGGA ATGCCGGAGC CGGGGTGGGG
2581 AAGGATCACC GATTCACACC AGTGGAACAC CTTGCTAAGT TTGCATAACG CGCAATTTTA
2641 TTTGCTACAA CGCACGCCAG AGGTTGCCCG CAGCCGCGCC ACCCCGTTAT TAGATTTGAT
2701 CAAGACAGCG TTGACGCCCC ATCCACCGCA AAAACAGGCG TATGGTGTGA CATTACCCAC
2761 TTCAGTGCTG TTTATCGCCG GACACGATAC TAATCTGGCA AATCTCGGCG GCGCACTGGA
2821 GCTCAACTGG ACGCTTCCCG GTCAGCCGGA TAACACGCCG CCAGGTGGTG AACTGGTGTT
2881 TGAACGCTGG CGTCGGCTAA GCGATAACAG CCAGTGGATT CAGGTTTCGC TGGTCTTCCA
2941 GACTTTACAG CAGATGCGTG ATAAAACGCC GCTGTCATTA AATACGCCGC CCGGAGAGGT
3001 GAAACTGACC CTGGCAGGAT GTGAAGAGCG AAATGCGCAG GGCATGTGTT CGTTGGCAGG
3061 TTTTACGCAA ATCGTGAATG AAGCACGCAT ACCCGCTTGC AGTTTGTAAG GTATAAGGCA
3121 GTTATTGGTG CCCTTAAACG CCTGGTGCTA CGCCTGAATA AGTGATAATA AGCGGATGAA
3181 TGGCAGAAAT TCGCCGGATC TTTGTGAAGG AACCTTACTT CTGTGGTGTG ACATAATTGG
3241 ACAAACTACC TACAGAGATT TAAAAAACCT CCCACACCTC CCCCTGAACC TGAAACATAA
3301 AATGAATGCA ATTGTTGTTG TTAACTTGTT TATTGCAGCT TATAATGGTT ACAAATAAAG
3361 CAATAGCATC ACAAATTTCA CAAATAAAGC ATTTTTTTCA CTGCATTCTA GTTGTGGTTT
3421 GTCCAAACTC ATCAATGTAT CTTATCATGT CTGGATCGAT CCCCGGGTAC CGAGCTCGAA
3481 TTCGTAATCA TGGTCATAGC TGTTTCCTGT GTGAAATTGT TATCCGCTCA CAATTCCACA
3541 CAACATACGA GCCGGAAGCA TAAAGTGTAA AGCCTGGGGT GCCTAATGAG TGAGCTAACT
3601 CACATTAATT GCGTTGCGCT CACTGCCCGC TTTCCAGTCG GGAAACCTGT CGTGCCAGCT
3661 GCATTAATGA ATCGGCCAAC GCGCGGGGAG AGGCGGTTTG CGTATTGGGC GCTCTTCCGC
3721 TTCCTCGCTC ACTGACTCGC TGCGCTCGGT CGTTCGGCTG CGGCGAGCGG TATCAGCTCA
3781 CTCAAAGGCG GTAATACGGT TATCCACAGA ATCAGGGGAT AACGCAGGAA AGAACATGTG
3841 AGCAAAAGGC CAGCAAAAGG CCAGGAACCG TAAAAAGGCC GCGTTGCTGG CGTTTTTCCA
3901 TAGGCTCCGC CCCCCTGACG AGCATCACAA AAATCGACGC TCAAGTCAGA GGTGGCGAAA
3961 CCCGACAGGA CTATAAAGAT ACCAGGCGTT TCCCCCTGGA AGCTCCCTCG TGCGCTCTCC
4021 TGTTCCGACC CTGCCGCTTA CCGGATACCT GTCCGCCTTT CTCCCTTCGG GAAGCGTGGC
4081 GCTTTCTCAA TGCTCACGCT GTAGGTATCT CAGTTCGGTG TAGGTCGTTC GCTCCAAGCT
4141 GGGCTGTGTG CACGAACCCC CCGTTCAGCC CGACCGCTGC GCCTTATCCG GTAACTATCG
4201 TCTTGAGTCC AACCCGGTAA GACACGACTT ATCGCCACTG GCAGCAGCCA CTGGTAACAG
4261 GATTAGCAGA GCGAGGTATG TAGGCGGTGC TACAGAGTTC TTGAAGTGGT GGCCTAACTA
4321 CGGCTACACT AGAAGGACAG TATTTGGTAT CTGCGCTCTG CTGAAGCCAG TTACCTTCGG
4381 AAAAAGAGTT GGTAGCTCTT GATCCGGCAA ACAAACCACC GCTGGTAGCG GTGGTTTTTT
4441 TGTTTGCAAG CAGCAGATTA CGCGCAGAAA AAAAGGATCT CAAGAAGATC CTTTGATCTT
4501 TTCTACGGGG TCTGACGCTC AGTGGAACGA AAACTCACGT TAAGGGATTT TGGTCATGAG
4561 ATTATCAAAA AGGATCTTCA CCTAGATCCT TTTAAATTAA AAATGAAGTT TTAAATCAAT
4621 CTAAAGTATA TATGAGTAAA CTTGGTCTGA CAGTTACCAA TGCTTAATCA GTGAGGCACC
4681 TATCTCAGCG ATCTGTCTAT TTCGTTCATC CATAGTTGCC TGACTCCCCG TCGTGTAGAT
4741 AACTACGATA CGGGAGGGCT TACCATCTGG CCCCAGTGCT GCAATGATAC CGCGAGACCC
4801 ACGCTCACCG GCTCCAGATT TATCAGCAAT AAACCAGCCA GCCGGAAGGG CCGAGCGCAG
4861 AAGTGGTCCT GCAACTTTAT CCGCCTCCAT CCAGTCTATT AATTGTTGCC GGGAAGCTAG
4921 AGTAAGTAGT TCGCCAGTTA ATAGTTTGCG CAACGTTGTT GCCATTGCTA CAGGCATCGT
4981 GGTGTCACGC TCGTCGTTTG GTATGGCTTC ATTCAGCTCC GGTTCCCAAC GATCAAGGCG
5041 AGTTACATGA TCCCCCATGT TGTGCAAAAA AGCGGTTAGC TCCTTCGGTC CTCCGATCGT
5101 TGTCAGAAGT AAGTTGGCCG CAGTGTTATC ACTCATGGTT ATGGCAGCAC TGCATAATTC
```

Figure 20D:

```
5161 TCTTACTGTC ATGCCATCCG TAAGATGCTT TTCTGTGACT GGTGAGTACT CAACCAAGTC
5221 ATTCTGAGAA TAGTGTATGC GGCGACCGAG TTGCTCTTGC CCGGCGTCAA TACGGGATAA
5281 TACCGCGCCA CATAGCAGAA CTTTAAAAGT GCTCATCATT GGAAAACGTT CTTCGGGGCG
5341 AAAACTCTCA AGGATCTTAC CGCTGTTGAG ATCCAGTTCG ATGTAACCCA CTCGTGCACC
5401 CAACTGATCT TCAGCATCTT TTACTTTCAC CAGCGTTTCT GGGTGAGCAA AAACAGGAAG
5461 GCAAAATGCC GCAAAAAAGG GAATAAGGGC GACACGGAAA TGTTGAATAC TCATACTCTT
5521 CCTTTTTCAA TATTATTGAA GCATTTATCA GGGTTATTGT CTCATGAGCG GATACATATT
5581 TGAATGTATT TAGAAAAATA AACAAATAGG GGTTCCGCGC ACATTTCCCC GAAAAGTGCC
5641 ACCTGACGTC TAAGAAACCA TTATTATCAT GACATTAACC TATAAAAATA GGCGTATCAC
5701 GAGGCCCTTT CGTCTCGCGC GTTTCGGTGA TGACGGTGAA AACCTCTGAC ACATGCAGCT
5761 CCCGGAGACG GTCACAGCTT GTCTGTAAGC GGATGCCGGG AGCAGACAAG CCCGTCAGGG
5821 CGCGTCAGCG GGTGTTGGCG GGTGTCGGGG CTGGCTTAAC TATGCGGCAT CAGAGCAGAT
5881 TGTACTGAGA GTGCACCATA TGCGGTGTGA AATACCGCAC AGATGCGTAA GGAGAAAATA
5941 CCGCATCAGG CGCCATTCGC CATTCAGGCT GCGCAACTGT TGGGAAGGGC GATCGGTGCG
6001 GGCCTCTTCG CTATTACGCC AGCTGGCGAA AGGGGGATGT GCTGCAAGGC GATTAAGTTG
6061 GGTAACGCCA GGGTTTTCCC AGTCACGACG TTGTAAAACG ACGGCCAGTG CCAAGC
//
```

Figure 21: Nucleic acid sequence of the known segment of the R15/appa transgene used for the generation of transgenic mice (SEQ ID NO:5).

```
LOCUS       R15/appa    3470 bp    DNA             SYN        15-APR-2000
DEFINITION  R15/appa transgene with vector sequences removed.
ACCESSION   R15/appa
REFERENCE   1  (bases 1 to 3470)
SOURCE      synthetic construct.
       ORGANISM  synthetic construct
                 artificial sequence.
KEYWORDS    salivary proline-rich protein, acid glucose-1-phosphatase; appA
            gene; periplasmic phosphoanhydride phosphohydrolase; artificial
            sequence;
AUTHORS     Golovan, S., Forsberg, C.W., Phillips, J.
  JOURNAL   Unpublished.

     DEFINITION  Rat salivary proline-rich protein (RP15) gene.
     ACCESSION   M64793 M36414
     VERSION     M64793.1  GI:206711
     SOURCE      Rat (Sprague-Dawley) liver DNA.
       ORGANISM  Rattus norvegicus
                 Eukaryota; Metazoa; Chordata; Craniata; Vertebrata;
Mammalia;
                 Eutheria; Rodentia; Sciurognathi; Muridae; Murinae;
Rattus.
     REFERENCE   1  (bases 1 to 1748)
       AUTHORS   Lin,H.H. and Ann,D.K.
       TITLE     Molecular characterization of rat multigene family
encoding
                 proline-rich proteins
       JOURNAL   Genomics 10, 102-113 (1991)
       MEDLINE   91257817
     FEATURES             Location/Qualifiers
          source          1..1748
                          /organism="Rattus norvegicus"
                          /strain="Sprague-Dawley"
                          /db_xref="taxon:10116"
                          /tissue_type="liver"
                          /tissue_lib="cosmid genomic library"
          misc_feature          1802-1810
                          /function=" consensus sequence for initiation in
                                higher eukaryotes "


FEATURES             Location/Qualifiers

DEFINITION  E. coli periplasmic phosphoanhydride phosphohydrolase (appA)
gene,

      ACCESSION    M58708 L03370 L03371 L03372 L03373 L03374 L03375
      VERSION      M58708.1  GI:145283
      SOURCE       Escherichia coli DNA.
      ORGANISM     Escherichia coli
            Bacteria; Proteobacteria; gamma subdivision; Enterobacteriaceae;
            Escherichia.

REFERENCE   1     (bases 1811..3109)
      AUTHORS     Dassa,J., Marck,C. and Boquet,P.L.
      TITLE       The complete nucleotide sequence of the Escherichia coli gene appA
                     reveals significant homology between pH 2.5 acid phosphatase
                     and glucose-1-phosphatase
```

Figure 21A:

```
        JOURNAL    J. Bacteriol. 172 (9), 5497-5500 (1990)
        MEDLINE    90368616

FEATURES                      Location/Qualifiers
        Source                      1811..3109
                              /organism="Escherichia coli"
                              /db_xref="taxon:562"
        sig_peptide           1811.. 1876
                              /gene="appA"
        CDS                    1811..3109
                              /gene="appA"
                              /standard_name="acid phosphatase/phytase"
                              /transl_table=11
                              /product="periplasmic phosphoanhydride phosphohydrolase"
                              /protein_id="AAA72086.1"
                              /db_xref="GI:145285"

        mat_peptide           1877   3106
                              /gene="appA"
                              /product="periplasmic phosphoanhydride phosphohydrolase"

        mutation        replace(1817.. 1819,"gcg changed to gcc")
                        /gene="appA"
                        /standard_name="A3 mutant"
                        /note="created by site directed mutagenesis"
                        /phenotype="silent mutation"
        mutation        replace(3092..3094," ccg changed to ccc")
                        /gene="appA"
                        /standard_name=" P428 mutant"
                        /note="created by site directed mutagenesis"
                        /phenotype=" silent mutation "
        mutation        replace(3095..3097," gcg changed to gct")
                        /gene="appA"
                        /standard_name=" A429 mutant"
                        /note="created by site directed mutagenesis"
                        /phenotype=" silent mutation "

            polyA_signal     3262..3457
                             /note="SV40 signals"

BASE COUNT     1065 a     721 c     735 g     949 t
ORIGIN
        1 GGATCCCCTT TGCTATGTAG TTTTTAATGG AAATTACAAC CCATAGTGTG TTGATAAATA
       61 GAGAGTCCTG TTTGGTTTAA GCAACCTCTG TTTCTCATAA ACTCCATAAA AACAGGAATA
      121 CTCTTTGTTT CTAGCATAAC CAAAAGATTT AGTGAATTGA AAACAATGTT CCCTTAGAGT
      181 ATAGGTCTAA TAACCCCGAA AATATTACCA TGATACTGAG CATTTGTAAG TATCTCATAG
      241 CATGTAGTAT CCATAGTCCA TCAATGAGAG AGACATTTAA CATGATTTTC ATTAATCAGG
```

Figure 21B:

```
 301 TGGAAAAGAC ATGACAACAT TCACAGGCAC TGCACAGAAC ATAGTGGTCC ACCTTGCACA
 361 TATTTCACTA AACTAGGTTT ATCTATTTTG TTGCTTTCTC TAACATCTCT GCAATGAAGC
 421 AGGTCAACAG TGCCACATAT CCTTTACTTA ACCTAAGGAA CACAAAAAAT TTTCTACATA
 481 TATCCTGGTT AGAGAGTGCT TAAAATAAGT TTTCCAAGAA TGGAAAAGAA ATGTTCTGAC
 541 TTAACAATTA AGACAGTATT TATTTAAAGC AAGAAATATG AGGCACACAA GAAAATATTT
 601 TGGGAAGAAA CCATTTGGTG AACAATATTT CAAATAAAAA TAGACAAACA TAGTTAATTG
 661 TAAAACATAT GTTTGACCAG CCCTTCTTTT CAATAGGCTT AATGTGAATA AAATGTTAAA
 721 GATTCTCTTT GGGTGGCTGC AAATTGTCCA CGAATAAGAC AAAATATAAA AATAAGGACT
 781 GAGTCTCACA AAATGAAAAG GAAATATATT CAGAAAGAGA ATCTTGAGAG AATGTGTTGT
 841 CACAAATTAA AGAAAACCTG TGGTGAATGA CATCCTGAGG CCTGAGCTAT TACTGACATT
 901 TAAGATAAAG GTAACTGTAT ACATTTGTCC CATTGAGGGG ACAAGAAAGC TGCTCTCATG
 961 TTCAGCTCTA TAATTCTTGC CTTAAACAAC TTAAATAGAA TGATTTAAAA TATGGAGCTG
1021 TCCATGGACC TTTGAAATAT AAAATAGTCA AGCAACTTAT CAAGGAATTA CAGATTCCTT
1081 GATACTAACA CAGGTAAATC CCACACGTGT TTTGAGACTA CATTTGCTGG GATTTTATTG
1141 ATGTAATAGG TCACATGTTT TTCGGGCCAA TGTTGCTGTT ATTCGGTTAC TTCAAGAGAA
1201 TAGTGGCAAC TGATGCTATG TATTCTAGGG GTTTGAAGTG ATGTTTCATG ATTGAAATTT
1261 GTAAAAGAAT AACATCATCA TTCTTAACAA TAGAACATAT AAAGTCACAC AGAAGTGACA
1321 GTGTTTAAGC TGTACTATTG ATCAAAGAAA TTTATTACCT TCAGTTTCAA TGGAAATAAT
1381 TACTGATAAT ACAAACATGT GTGAACACAC ACTAATCCTA TCCAAATGCA CAGTGATACA
1441 CAGAAAATAT TAGCAAGTAG AATGCAATAT TTATATAACG ATTGTATTTA TCAATCAATT
1501 GTATGTATCA ATATATGGGC TATTTTCTTA CACATGATTT TATTCAAATT TACTCTAATC
1561 ATTGTTGAAC CATTTAGAAA AGGCATACTG GCAACTTTTC CTTACCTCAT CCAGCTGGGC
1621 AAAAGTCCCA GTGTGGAGTA AAGGATGCAA GATTTCCTGC TCTGTTAAGT ATAAAATAAT
1681 AGTATGAATT CAAAGGTGCC ATTCTTCTGC TTCTAGTTAT AAAGGCAGTG CTTGCTTCTT
1741 CCAGCACAGA TCTGGATCTC GAGGAGCTTG GCGAGATTTT CAGGAGCTAA GGAAGCTAAA
1801 AGCCGCCACC ATGAAAGCCA TCTTAATCCC ATTTTTATCT CTTCTGATTC CGTTAACCCC
1861 GCAATCTGCA TTCGCTCAGA GTGAGCCGGA GCTGAAGCTG GAAAGTGTGG TGATTGTCAG
1921 TCGTCATGGT GTGCGTGCTC CAACCAAGGC CACGCAACTG ATGCAGGATG TCACCCCAGA
1981 CGCATGGCCA ACCTGGCCGG TAAAACTGGG TTGGCTGACA CCGCGCGGTG GTGAGCTAAT
2041 CGCCTATCTC GGACATTACC AACGCCAGCG TCTGGTAGCC GACGGATTGC TGGCGAAAAA
2101 GGGCTGCCCG CAGTCTGGTC AGGTCGCGAT TATTGCTGAT GTCGACGAGC GTACCCGTAA
2161 AACAGGCGAA GCCTTCGCCG CCGGGCTGGC ACCTGACTGT GCAATAACCG TACATACCCA
2221 GGCAGATACG TCCAGTCCCG ATCCGTTATT TAATCCTCTA AAAACTGGCG TTTGCCAACT
2281 GGATAACGCG AACGTGACTG ACGCGATCCT CAGCAGGGCA GGAGGGTCAA TTGCTGACTT
2341 TACCGGGCAT CGGCAAACGG CGTTTCGCGA ACTGGAACGG GTGCTTAATT TTCCGCAATC
2401 AAACTTGTGC CTTAAACGTG AGAAACAGGA CGAAAGCTGT TCATTAACGC AGGCATTACC
2461 ATCGGAACTC AAGGTGAGCG CCGACAATGT CTCATTAACC GGTGCGGTAA GCCTCGCATC
2521 AATGCTGACG GAGATATTTC TCCTGCAACA AGCACAGGGA ATGCCGGAGC CGGGGTGGGG
2581 AAGGATCACC GATTCACACC AGTGGAACAC CTTGCTAAGT TTGCATAACG CGCAATTTTA
2641 TTTGCTACAA CGCACGCCAG AGGTTGCCCG CAGCCGCGCC ACCCCGTTAT TAGATTTGAT
2701 CAAGACAGCG TTGACGCCCC ATCCACCGCA AAAACAGGCG TATGGTGTGA CATTACCCAC
2761 TTCAGTGCTG TTTATCGCCG GACACGATAC TAATCTGGCA AATCTCGGCG GCGCACTGGA
2821 GCTCAACTGG ACGCTTCCCG GTCAGCCGGA TAACACGCCG CCAGGTGGTG AACTGGTGTT
2881 TGAACGCTGG CGTCGGCTAA GCGATAACAG CCAGTGGATT CAGGTTTCGC TGGTCTTCCA
2941 GACTTTACAG CAGATGCGTG ATAAAACGCC GCTGTCATTA AATACGCCGC CCGGAGAGGT
3001 GAAACTGACC CTGGCAGGAT GTGAAGAGCG AAATGCGCAG GGCATGTGTT CGTTGGCAGG
3061 TTTTACGCAA ATCGTGAATG AAGCACGCAT ACCCGCTTGC AGTTTGTAAG GTATAAGGCA
3121 GTTATTGGTG CCCTTAAACG CCTGGTGCTA CGCCTGAATA AGTGATAATA AGCGGATGAA
3181 TGGCAGAAAT TCGCCGGATC TTTGTGAAGG AACCTTACTT CTGTGGTGTG ACATAATTGG
3241 ACAAACTACC TACAGAGATT TAAAAAACCT CCCACACCTC CCCCTGAACC TGAAACATAA
3301 AATGAATGCA ATTGTTGTTG TTAACTTGTT TATTGCAGCT TATAATGGTT ACAAATAAAG
3361 CAATAGCATC ACAAATTTCA CAAATAAAGC ATTTTTTTCA CTGCATTCTA GTTGTGGTTT
3421 GTCCAAACTC ATCAATGTAT CTTATCATGT CTGGATCGAT CCCCGGGTAC
```

//

Figure 22: Nucleic acid sequence of the SV40/APPA+intron plasmid (SEQ ID NO:6).

```
LOCUS       SV40/APPA    5421 bp    DNA   CIRCULAR SYN       14-APR-2000
DEFINITION  Ligation of SV40 promoter/enhancer into CAT/APPA+intron
ACCESSION   SV40/APPA
REFERENCE   1  (bases 1 to 5421)
SOURCE      synthetic construct.
      ORGANISM  synthetic construct
                artificial sequence.
KEYWORDS    SV40 promoter/enhancer, acid glucose-1-phosphatase; appA gene;
            periplasmic phosphoanhydride phosphohydrolase; artificial
            sequence;
AUTHORS     Golovan, S., Forsberg, C.W., Phillips, J.
 JOURNAL  Unpublished.

DEFINITION  E. coli periplasmic phosphoanhydride phosphohydrolase (appA)
gene,

      ACCESSION    M58708 L03370 L03371 L03372 L03373 L03374 L03375
      VERSION      M58708.1  GI:145283
      SOURCE       Escherichia coli DNA.
      ORGANISM     Escherichia coli
            Bacteria; Proteobacteria; gamma subdivision; Enterobacteriaceae;
            Escherichia.

REFERENCE   1    (bases 40 1337)
      AUTHORS   Dassa,J., Marck,C. and Boquet,P.L.
      TITLE     The complete nucleotide sequence of the Escherichia coli gene appA
                   reveals significant homology between pH 2.5 acid phosphatase
                   and glucose-1-phosphatase
      JOURNAL   J. Bacteriol. 172 (9), 5497-5500 (1990)
      MEDLINE   90368616

FEATURES                Location/Qualifiers
      Source            40  1337
                        /organism="Escherichia coli"
                        /db_xref="taxon:562"
      sig_peptide       40.. 105
                        /gene="appA"
      CDS                40  1337
                              /gene="appA"
      /standard_name="acid phosphatase/phytase"
                        /transl_table=11
                        /product="periplasmic phosphoanhydride phosphohydrolase"
                        /protein_id="AAA72086.1"
                        /db_xref="GI:145285"

      mat_peptide       106   1334
                        /gene="appA"
```

Figure 22A:

```
                     /product="periplasmic phosphoanhydride phosphohydrolase"

     mutation      replace(46.. 48,"gcg changed to gcc")
                   /gene="appA"
                   /standard_name="A3 mutant"
                   /note="created by site directed mutagenesis"
                   /phenotype="silent mutation"
     mutation      replace(1320..1322," ccg changed to ccc")
                   /gene="appA"
                   /standard_name=" P428 mutant"
                   /note="created by site directed mutagenesis"
                   /phenotype=" silent mutation "
     mutation      replace(1323..1325," gcg changed to gct")
                   /gene="appA"
                   /standard_name=" A429 mutant"
                   /note="created by site directed mutagenesis"
                   /phenotype=" silent mutation "


DEFINITION  Plasmid pBLCAT3  (bases 2200 to 4924)
     ACCESSION   X64409
     VERSION     X64409.1  GI:58163
     SOURCE      synthetic construct.
       ORGANISM  synthetic construct
                 artificial sequence.
     REFERENCE   1  (bases 2200 to 4924)
       AUTHORS   Luckow,B.H.R.
       TITLE     Direct Submission
       JOURNAL   Submitted (06-FEB-1992) B.H.R. Luckow, German Cancer Res
                 Center, Im Neuenheimer Feld 280, W-6900 Heidelberg, FRG
     REFERENCE   2  (bases 2200 to 4924)
       AUTHORS   Luckow,B. and Schutz,G.
       TITLE     CAT constructions with multiple unique restriction sites
for
                 the functional analysis of eukaryotic promoters and
regulatory
                 elements
       JOURNAL   Nucleic Acids Res. 15 (13), 5490 (1987)
       MEDLINE   87260024
     COMMENT     Promoterless CAT vector for transient transfection
experiments
                  with eukaryotic cells. Allows the analysis of foreign
                  promoters and  enhancers.
     FEATURES             Location/Qualifiers
          source          2200 to 4924
                          /organism="synthetic construct"
                          /db_xref="taxon:32630"

          SV40 t intron   1380..1993
                          /note="SV40 signals"
          polyA_signal    1990..2230
                          /note="SV40 signals"
          CDS             complement(3471..4317)
                          /codon_start=1
                          /transl_table=11
                          /gene="Amp"
                          /product="beta-lactamase"
                          /protein_id="CAA45753.1"
                          /db_xref="GI:58165"
```

Figure 22B:

```
        SV40 promoter/enhancer   5023..5402
                         /note="SV40 signals"

BASE COUNT     1413 a   1321 c   1331 g   1355 t
ORIGIN
        1 CGAGATTTTC AGGAGCTAAG GAAGCTAAAA GCCGCCACCA TGAAAGCCAT CTTAATCCCA
       61 TTTTTATCTC TTCTGATTCC GTTAACCCCG CAATCTGCAT TCGCTCAGAG TGAGCCGGAG
      121 CTGAAGCTGG AAAGTGTGGT GATTGTCAGT CGTCATGGTG TGCGTGCTCC AACCAAGGCC
      181 ACGCAACTGA TGCAGGATGT CACCCCAGAC GCATGGCCAA CCTGGCCGGT AAAACTGGGT
      241 TGGCTGACAC CGCGNGGTGG TGAGCTAATC GCCTATCTCG GACATTACCA ACGCCAGCGT
      301 CTGGTAGCCG ACGGATTGCT GGCGAAAAAG GGCTGCCCGC AGTCTGGTCA GGTCGCGATT
      361 ATTGCTGATG TCGACGAGCG TACCCGTAAA ACAGGCGAAG CCTTCGCCGC CGGGCTGGCA
      421 CCTGACTGTG CAATAACCGT ACATACCCAG GCAGATACGT CCAGTCCCGA TCCGTTATTT
      481 AATCCTCTAA AAACTGGCGT TTGCCAACTG GATAACGCGA ACGTGACTGA CGCGATCCTC
      541 AGCAGGGCAG GAGGGTCAAT TGCTGACTTT ACCGGGCATC GGCAAACGGC GTTTCGCGAA
      601 CTGGAACGGG TGCTTAATTT TCCGCAATCA AACTTGTGCC TTAAACGTGA GAAACAGGAC
      661 GAAAGCTGTT CATTAACGCA GGCATTACCA TCGGAACTCA AGGTGAGCGC CGACAATGTC
      721 TCATTAACCG GTGCGGTAAG CCTCGCATCA ATGCTGACGG AGATATTTCT CCTGCAACAA
      781 GCACAGGGAA TGCCGGAGCC GGGGTGGGGA AGGATCACCG ATTCACACCA GTGGAACACC
      841 TTGCTAAGTT TGCATAACGC GCAATTTTAT TTGCTACAAC GCACGCCAGA GGTTGCCCGC
      901 AGCCGCGCCA CCCCGTTATT AGATTTGATC AAGACAGCGT TGACGCCCCA CCACCGCAAA
      961 AACAGGCGTA TGGTGTGACA TTACCCACTT CAGTGCTGTT TATCGCCGGA CACGATACTA
     1021 ATCTGGCAAA TCTCGGCGGC GCACTGGAGC TCAACTGGAC GCTTCCCGGT CAGCCGGATA
     1081 ACACGCCGCC AGGTGGTGAA CTGGTGTTTG AACGCTGGCG TCGGCTAAGC GATAACAGCC
     1141 AGTGGATTCA GGTTTCGCTG GTCTTCCAGA CTTTACAGCA GATGCGTGAT AAAACGCCGC
     1201 TGTCATTAAA TACGCCGCCC GGAGAGGTGA AACTGACCCT GGCAGGATGT GAAGAGCGAA
     1261 ATGCGCAGGG CATGTGTTCG TTGGCAGGTT TTACGCAAAT CGTGAATGAA GCACGCATAC
     1321 CCGCTTGCAG TTTGTAAGGC AGTTATTGGT GCCCTTAAAC GCCTGGTGCT ACGCCTGAAT
     1381 AAGTGATAAT AAGCGGATGA ATGGCAGAAA TTCGCCGGAT CTTTGTGAAG GAACCTTACT
     1441 TCTGTGGTGT GACATAATTG GACAAACTAC CTACAGAGAT TTAAAGCTCT AAGGTAAATA
     1501 TAAAATTTTT AAGTGTATAA TGTGTTAAAC TACTGATTCT AATTGTTTGT GTATTTTAGA
     1561 TTCCAACCTA TGGAACTGAT GAATGGGAGC AGTGGTGGAA TGCCTTTAAT GAGGAAAACC
     1621 TGTTTTGCTC AGAAGAAATG CCATCTAGTG ATGATGAGGC TACTGCTGAC TCTCAACATT
     1681 CTACTCCTCC AAAAAAGAAG AGAAAGGTAG AAGACCCCAA GGACTTTCCT TCAGAATTGC
     1741 TAAGTTTTTT GAGTCATGCT GTGTTTAGTA ATAGAACTCT TGCTTGCTTT GCTATTTACA
     1801 CCACAAAGGA AAAAGCTGCA CTGCTATACA AGAAAATTAT GGAAAAATAT TCTGTAACCT
     1861 TTATAAGTAG GCATAACAGT TATAATCATA ACATACTGTT TTTTCTTACT CCACACAGGC
     1921 ATAGAGTGTC TGCTATTAAT AACTATGCTC AAAAATTGTG TACCTTTAGC TTTTTAATTT
     1981 GTAAAGGGGT TAATAAGGAA TATTTGATGT ATAGTGCCTT GACTAGAGAT CATAATCAGC
     2041 CATACCACAT TTGTAGAGGT TTTACTTGCT TTAAAAAACC TCCCACACCT CCCCCTGAAC
     2101 CTGAAACATA AAATGAATGC AATTGTTGTT GTTAACTTGT TTATTGCAGC TTATAATGGT
     2161 TACAAATAAA GCAATAGCAT CACAAATTTC ACAAATAAAG CATTTTTTTC ACTGCATTCT
     2221 AGTTGTGGTT TGTCCAAACT CATCAATGTA TCTTATCATG TCTGGATCGA TCCCCGGGTA
     2281 CCGAGCTCGA ATTCGTAATC ATGGTCATAG CTGTTTCCTG TGTGAAATTG TTATCCGCTC
     2341 ACAATTCCAC ACAACATACG AGCCGGAAGC ATAAAGTGTA AAGCCTGGGG TGCCTAATGA
     2401 GTGAGCTAAC TCACATTAAT TGCGTTGCGC TCACTGCCCG CTTTCCAGTC GGGAAACCTG
     2461 TCGTGCCAGC TGCATTAATG AATCGGCCAA CGCGCGGGGA GAGGCGGTTT GCGTATTGGG
     2521 CGCTCTTCCG CTTCCTCGCT CACTGACTCG CTGCGCTCGG TCGTTCGGCT GCGGCGAGCG
     2581 GTATCAGCTC ACTCAAAGGC GGTAATACGG TTATCCACAG AATCAGGGGA TAACGCAGGA
     2641 AAGAACATGT GAGCAAAAGG CCAGCAAAAG GCCAGGAACC GTAAAAAGGC CGCGTTGCTG
     2701 GCGTTTTTCC ATAGGCTCCG CCCCCCTGAC GAGCATCACA AAAATCGACG CTCAAGTCAG
     2761 AGGTGGCGAA ACCCGACAGG ACTATAAAGA TACCAGGCGT TTCCCCCTGG AAGCTCCCTC
     2821 GTGCGCTCTC CTGTTCCGAC CCTGCCGCTT ACCGGATACC TGTCCGCCTT TCTCCCTTCG
     2881 GGAAGCGTGG CGCTTTCTCA ATGCTCACGC TGTAGGTATC TCAGTTCGGT GTAGGTCGTT
     2941 CGCTCCAAGC TGGGCTGTGT GCACGAACCC CCCGTTCAGC CCGACCGCTG CGCCTTATCC
     3001 GGTAACTATC GTCTTGAGTC CAACCCGGTA AGACACGACT TATCGCCACT GGCAGCAGCC
     3061 ACTGGTAACA GGATTAGCAG AGCGAGGTAT GTAGGCGGTG CTACAGAGTT CTTGAAGTGG
```

Figure 22C:

```
3121 TGGCCTAACT ACGGCTACAC TAGAAGGACA GTATTTGGTA TCTGCGCTCT GCTGAAGCCA
3181 GTTACCTTCG GAAAAAGAGT TGGTAGCTCT TGATCCGGCA AACAAACCAC CGCTGGTAGC
3241 GGTGGTTTTT TTGTTTGCAA GCAGCAGATT ACGCGCAGAA AAAAAGGATC TCAAGAAGAT
3301 CCTTTGATCT TTTCTACGGG GTCTGACGCT CAGTGGAACG AAAACTCACG TTAAGGGATT
3361 TTGGTCATGA GATTATCAAA AAGGATCTTC ACCTAGATCC TTTTAAATTA AAAATGAAGT
3421 TTTAAATCAA TCTAAAGTAT ATATGAGTAA ACTTGGTCTG ACAGTTACCA ATGCTTAATC
3481 AGTGAGGCAC CTATCTCAGC GATCTGTCTA TTTCGTTCAT CCATAGTTGC CTGACTCCCC
3541 GTCGTGTAGA TAACTACGAT ACGGGAGGGC TTACCATCTG GCCCCAGTGC TGCAATGATA
3601 CCGCGAGACC CACGCTCACC GGCTCCAGAT TTATCAGCAA TAAACCAGCC AGCCGGAAGG
3661 GCCGAGCGCA GAAGTGGTCC TGCAACTTTA TCCGCCTCCA TCCAGTCTAT TAATTGTTGC
3721 CGGGAAGCTA GAGTAAGTAG TTCGCCAGTT AATAGTTTGC GCAACGTTGT TGCCATTGCT
3781 ACAGGCATCG TGGTGTCACG CTCGTCGTTT GGTATGGCTT CATTCAGCTC CGGTTCCCAA
3841 CGATCAAGGC GAGTTACATG ATCCCCCATG TTGTGCAAAA AAGCGGTTAG CTCCTTCGGT
3901 CCTCCGATCG TTGTCAGAAG TAAGTTGGCC GCAGTGTTAT CACTCATGGT TATGGCAGCA
3961 CTGCATAATT CTCTTACTGT CATGCCATCC GTAAGATGCT TTTCTGTGAC TGGTGAGTAC
4021 TCAACCAAGT CATTCTGAGA ATAGTGTATG CGGCGACCGA GTTGCTCTTG CCCGGCGTCA
4081 ATACGGGATA ATACCGCGCC ACATAGCAGA ACTTTAAAAG TGCTCATCAT TGGAAAACGT
4141 TCTTCGGGGC GAAAACTCTC AAGGATCTTA CCGCTGTTGA GATCCAGTTC GATGTAACCC
4201 ACTCGTGCAC CCAACTGATC TTCAGCATCT TTTACTTTCA CCAGCGTTTC TGGGTGAGCA
4261 AAAACAGGAA GGCAAAATGC CGCAAAAAAG GGAATAAGGG CGACACGGAA ATGTTGAATA
4321 CTCATACTCT TCCTTTTTCA ATATTATTGA AGCATTTATC AGGGTTATTG TCTCATGAGC
4381 GGATACATAT TTGAATGTAT TTAGAAAAAT AAACAAATAG GGGTTCCGCG CACATTTCCC
4441 CGAAAAGTGC CACCTGACGT CTAAGAAACC ATTATTATCA TGACATTAAC CTATAAAAAT
4501 AGGCGTATCA CGAGGCCCTT TCGTCTCGCG CGTTTCGGTG ATGACGGTGA AAACCTCTGA
4561 CACATGCAGC TCCCGGAGAC GGTCACAGCT TGTCTGTAAG CGGATGCCGG GAGCAGACAA
4621 GCCCGTCAGG GCGCGTCAGC GGGTGTTGGC GGGTGTCGGG GCTGGCTTAA CTATGCGGCA
4681 TCAGAGCAGA TTGTACTGAG AGTGCACCAT ATGCGGTGTG AAATACCGCA CAGATGCGTA
4741 AGGAGAAAAT ACCGCATCAG GCGCCATTCG CCATTCAGGC TGCGCAACTG TTGGGAAGGG
4801 CGATCGGTGC GGGCCTCTTC GCTATTACGC CAGCTGGCGA AGGGGGGATG TGCTGCAAGG
4861 CGATTAAGTT GGGTAACGCC AGGGTTTTCC CAGTCACGAC GTTGTAAAAC GACGGCCAGT
4921 GCCAAGCTTT ACACTTTATG CTTCCGGCTC GTATGTTGTG TGGAATTGTG AGCGGATAAC
4981 AATTTCACAC AGGAAACAGC TATGACCATG ATTACGAATT CGGCGCAGCA CCATGGCCTG
5041 AAATAACCTC TGAAAGAGGA ACTTGGTTAG GTACCTTCTG AGGCGGAAAG AACCAGCTGT
5101 GGAATGTGTG TCAGTTAGGG TGTGGAAAGT CCCCAGGCTC CCCAGCAGGC AGAAGTATGC
5161 AAAGCATGCA TCTCAATTAG TCAGCAACCA GGTGTGGAAA GTCCCCAGGC TCCCCAGCAG
5221 GCAGAAGTAT GCAAAGCATG CATCTCAATT AGTCAGCAAC CATAGTCCCG CCCCTAACTC
5281 CGCCCATCCC GCCCCTAACT CCGCCCAGTT CCGCCCATTC TCCGCCCCAT GGCTGACTAA
5341 TTTTTTTTAT TTATGCAGAG GCCGAGGCCG CCTCGGCCTC TGAGCTATTC CAGAAGTAGT
5401 GAGGAGGCTC GAGGAGCTTG G
//
```

Figure 23. The nucleic acid sequence of the Lama2/APPA transgene used for the generation of transgenic mice and transgenic pigs (SEQ ID NO: 7)

```
LOCUS       transgene    17732 bp    DNA            SYN        14-APR-2000
DEFINITION  Lama-appA cut XhoI..20623 to NotI..17732
ACCESSION   transgene
KEYWORDS    parotid secretory protein; acid glucose-1-phosphatase; appA
            gene;
            periplasmic phosphoanhydride phosphohydrolase; artificial
            sequence;
            cloning vector
REFERENCE   1  (bases 1 to 17732)
AUTHORS     Golovan, S., Forsberg, C.W., Phillips, J.
JOURNAL     Unpublished.

FEATURES
DEFINITION  M. musculus Psp gene for parotid secretory protein.
   ACCESSION  X68699
   VERSION   X68699.1 GI:53809
   SOURCE      house mouse.
   ORGANISM  Mus musculus
      Eukaryota; Metazoa; Chordata; Craniata; Vertebrata; Mammalia;
      Eutheria; Rodentia; Sciurognathi; Muridae; Murinae; Mus.
      REFERENCE   1  (bases 3777 to 5332;)
      AUTHORS   Svendsen,P., Laursen,J., Krogh-Pedersen,H. and Hjorth,J.P.
      TITLE     Novel salivary gland specific binding elements located in
            the PSP proximal enhancer core
      JOURNAL   Nucleic Acids Res. 26 (11), 2761-2770 (1998)
      MEDLINE   98256451
      REFERENCE   2  (bases 7147 to 12653; 13952 to 17731)
      AUTHORS   Mikkelsen,T.R.
      TITLE     Direct Submission
      JOURNAL   Submitted (07-OCT-1992) T.R. Mikkelsen, Department of
                Molecular Biology, University of Aarhus, CF Mollers Alle
                130, 8000 Aarhus, DENMARK
      REFERENCE  3  (bases 7147 to 12653; 13952 to 17731)
      AUTHORS   Laursen J, Hjorth JP
      TITLE A cassette for high-level expression in the mouse salivary
 glands.
      JOURNAL   Gene 1997 Oct 1;198(1-2):367-72
      MEDLINE   9370303

 FEATURES              Location/Qualifiers
                    source         1.to 12653; 13952 to 17731
                   /organism="Mus musculus"
                   /strain="C3H/As"
                   /db_xref="taxon:10090"
                   /chromosome="2"
                   /map="Estimate: 69 cM from centromere"
                   /clone="Lambda YP1, Lambda YP3, Lambda YP7"
                   /clone_lib="Lambda-PHAGE (Lambda L47.1)"
                   /germline
                   /note="Allele: b"

      misc_feature    3777-5332
                   /gene="PSP"
                   /function="salivary gland specific positive acting
                   regulatory region"
      enhancer     7147..8724
```

Figure 23A:

```
                /evidence=experimental
     exon       11778..11824
                /gene="Psp"
                /note="exon a"
                /number=1
                /evidence=experimental
     exon       12626.. 14190
                /gene="Psp"
                /note="exon b fused with exons h and i"
     misc_feature      12644-12652
                /function=" consensus sequence for initiation in higher
                eukaryotes "
     misc_feature      13952-13965
                /function=" M13mp18 polylinker"


DEFINITION  E. coli periplasmic phosphoanhydride phosphohydrolase (appA)
gene,

     ACCESSION   M58708 L03370 L03371 L03372 L03373 L03374 L03375
     VERSION     M58708.1  GI:145283
     SOURCE            Escherichia coli DNA.
     ORGANISM    Escherichia coli
           Bacteria; Proteobacteria; gamma subdivision;
     Enterobacteriaceae;
           Escherichia.

REFERENCE   1  (bases 12653..13951)
     AUTHORS   Dassa,J., Marck,C. and Boquet,P.L.
     TITLE     The complete nucleotide sequence of the Escherichia coli
                 gene appA reveals significant homology between pH 2.5
                 acid phosphatase and glucose-1-phosphatase
     JOURNAL   J. Bacteriol. 172 (9), 5497-5500 (1990)
     MEDLINE   90368616

FEATURES              Location/Qualifiers
     Source                 12653..13951
                      /organism="Escherichia coli"
                      /db_xref="taxon:562"
     sig_peptide      12653..12718
     /gene="appA"
     CDS              12653       13951
                      /gene="appA"
                      /standard_name="acid phosphatase/phytase"
                      /transl_table=11
                      /product="periplasmic phosphoanhydride
                      phosphohydrolase"
                      /protein_id="AAA72086.1"
                      /db_xref="GI:145285"
```

Figure 23B:

```
mat_peptide         12719 13948
                    /gene="appA"
                    /product="periplasmic phosphoanhydride
                         phosphohydrolase"

mutation       replace(12659.. 12661,"gcg changed to gcc")
               /gene="appA"
               /standard_name="A3 mutant"
               /note="created by site directed mutagenesis"
               /citation=[3]
               /phenotype="silent mutation"
mutation       replace(13934..13936," ccg changed to ccc")
               /gene="appA"
               /standard_name=" P428 mutant"
               /note="created by site directed mutagenesis"
               /citation=[3]
               /phenotype=" silent mutation "
mutation       replace(13937..13939," gcg changed to gct")
               /gene="appA"
               /standard_name=" A429 mutant"
               /note="created by site directed mutagenesis"
               /citation=[3]
               /phenotype=" silent mutation "


BASE COUNT     4719 a   4125 c   4168 g   4719 t
ORIGIN
        1 TCGAGAGTAT CTTTGTCAGC TGTGCCTCCA ACAAAGGGGT ACTGTTGCCC ACATAGAAAG
       61 ATCTAAACTA ATTAATTAAT CCCTCACCCG CAAATCTTTC AGTCACTAAG TTAGCACGAT
      121 TGTTGAACAA GTTCTCCAAA GGAGAGATAC AGATGAGTGC GTATAGGGTG GACCTGGCTG
      181 CTGAGGAGAC ACCTGCATCT GACTAAGAAG AGCCACGGTG TTAGTTGAAT GGTGTGGAGT
      241 AGGGTGGTTC TGTGGGACAG TAGAAAATCG AGAGGCATGT GCCGTTTAGT GAACTGATGG
      301 AAGCTACCCC AAACGACAGA GATTGTCAGT CAGGCCAATC CGTTTCGAGT TTGATGGGCA
      361 GCCGGACAGT GAGACAGACA CACCTACTCA GTTGGAGGAA GGATGAGAAC AATGGCCAGC
      421 AGGGATTGAG AGACCCTGAC AGGCGCAAGG CCCTAACACA CACACCTACC ACCTCACTTG
      481 ACAAAGCTGC CAAAGACCAA AGACTTGTTC TCCATTAGAA ATGACAGCTG GCTTGACCCG
      541 ACAGCATAAT AAGCAGAGTG TACTCTGATT GGAGAACTTT AATGTGTTTC ATTCAGTATT
      601 ATAAAAGGAC AGTATTACAG ATTTTGTTGT ACACTGCTGT TACATGTGGG GCAGTGTGTC
      661 TTTAAGTAGG GTAAAGTACT CTTTAAAAAT GGGTCCTAGA TATTTTTTCC TTTAACTCAA
      721 GTCTCTTACT GTTTAAATGA TTTTTATTTT GTTTAATATG GAGGAAAAAG AAGCGTAAAT
      781 GGACAATATA TATTTAGAGA AAGATGGTTA GCTGTCAGAA AAATATGCAA ATCAAAATCA
      841 CACCAAGACT GCAGCACACC CCTGTCAGAT GGCTGTGATC AAGAAAATAA ATGACAATGA
      901 GTGGTGGTGA AGATGTACTA AAGGGAAACA CACACACACA CACACACACA CACACACACA
      961 CACACTGGAG CAACCACTGT GGAAATCAGT ATGAATGGTC CTCAAAAACC TGAAGATAGA
     1021 GCGGGGCGTG GTGGCATACA CTTTTATTCC CAGCACTGGG GAGGCAGAGG CAGGTGGATC
     1081 TCTGAGTTCC AGGCCAGCCT GGTCTATAGC ACAGGTTCTA GGACAGCCAG GGCTACACAG
     1141 AAAAACCCTG CCTTGATTAA ACCAAACCAA ACCAAACCAA ACCAAACCAA ACCAAACCAA
     1201 ACCAAACCAA ACCAAACCAG ACCAAACCAA AACACTGAAG ATAGAACTTC AGTATTCCAT
     1261 TCCTAGATAT ATACCCAATG GAGACTAAGT CAGCAAGACA CCTGCACAGC CATGTTCACT
     1321 ACTACACTGT TCACCACAGC CAGGCTGTGG AACCAGCCTG AGTGTCCATG ATAAATGAAT
```

Figure 23C:

```
1381 GGATAGGTAA CTTTCAAGGT AAATGGACTC TGCTGTGTAC ATGCCTCACA TTCTGTTTAT
1441 TCATTTTTCT TTATGAGGTG TCCATTCAGG AGTCACATGG TAGTTCTATT TTCAGTCTTC
1501 TGAAGATACT ACACTGGTCC CCACAGTTTA CACTTTTATC AGCAGTGAAT AAGGGTTCCT
1561 CTATCCTTAC CATCATTTGT TGTAATTTTT CTTGATGACC CTCTTTCTGA CAGGGATAGG
1621 ATGTAATATC AGTGTGAGGA AGTACAACTT GTTTTCTAAG TATTTATTGG CCCCTTGCAT
1681 TTCTTCTTTT GAAAACTGTC GGTTCCTGAC ATCTGCTCAG GTATTCATTG GATGTTGTTT
1741 CTTTGGTGTT TGAGTTCTTA TGAATTCTAG ATGTTAAATC CCTGCCTGTG GTTCTCTCCC
1801 ATTCTGTAGG CTGCCTCCTC ACCCTGGCAA TTGTTGTCCT TGTTTTGCAG AAACTTTTGA
1861 CTTCATGGAA TCTCATTTGT CAGTTTTCCC TCCTCTGCTA TAGCCTGAGC TAATGCACTG
1921 GTTTTTACAG AGCCCTGGTC TATGCCTTTA TCCTCCTCTG GCAGCTTCGG AGTTTCATTT
1981 CTTACATTTA GATCTTTGAT CCACTTTGAA CAAGTTTTGG AGCAGGGTGA GAGATACGAA
2041 TCTAGTTCCA TTCTTCCATA TGTGATCCTA GTTTACATAG CATCGTTGGT TGAAGAGGTT
2101 TTATTTTATT TTTAAATAAT GTGTCATAAA AAACGAGGTG GTTGTAGCAG TGTGGATTTG
2161 TTTCTTTGTC CTTTGATCTA CAGGTCTTGT TTTGTGTCAG TCTCATGATG TTTTATTGCT
2221 ATGGCTCTGT CATACAGTCT GAGGTCAGGT ATTGTGATAT ACCTTCAGTA TTGCTCCCTC
2281 AGACTCAGGT TTGCTTTGGC CAGGAGTCAT CTTACTCAGT GCTCTTAGAG CTCCCCCAGC
2341 ATGTAGCTGC TACTATTCTT AGTTGATAAA TCAGGAAACT GGGGCTCAGA GAGATTAACT
2401 GTCTTGAACT ACTTCTGGGG AGGTGAAACG TGGAGACACT AAACTGTGTT TACCCTGTAC
2461 TGCTCCAGTA GCTGTCGGGT GCTGGGCTAC AGCAAAGCAC CTATACTATA TATTACTCAG
2521 GAGGTGGAAA AACTCAGCCT CCCTTGGGGT TCCCAAGCTC CCAGGTGTCC AGTCACTGCT
2581 GGAAACCTCA TGGAGTCTGA AAGGAAGGGT TGAGGGTACA TGGGGCAGCG ATGAGGAGCC
2641 TGGGGCTGGG ATCTCCCAAA CACCTGGATA TCCAGATGCC ACTGGGTCAG GGGGAGTTGG
2701 GAACAGAGTT GGGATGTCCA TGGACCTGTG ACAAGGCCAG GGCCAGGGGG AGGATAACTC
2761 TGGCTTTACT AATTTGCGAA AGTCCTTAGC TTAGCAGCAG TTGTCTGGGA GCACAGAGGG
2821 GCCTTCTGTA AGAGGCTCAG GCAGTGCCGC TCTGTAGGCG AAGGTCTTCT CCATGTTCCC
2881 CATGGTGGTT CTTGATGAAA GAGACAGTCC TTGGCTCCAA ACTGGTTTAT TGATTGTTCA
2941 TTGTGGAAAA TGGGTGCACA CCACCTTCTC AGGGTGGACC AGAGATCAAA TACCTTTTGC
3001 AGGGAGGAAT ATCTGGGAAG GGACGCTTAC TGGCTAAACC CTCAGGGCCT CTAGATACAT
3061 CATTAGCATG GAGAACTCTG TTCTGGGCTA CATGACCACA GGCCACATTT CCACAAGCCA
3121 CATGTGGGAA GTGTGGCACA TGTTCTAGGC CAGGAATCTG GTAGGGAGCG TGGAGCCACC
3181 TACCATCCCA GGTGGGTGCC TGGGTGCCAG GGACCCTGAA CCCGCTCAAC CTTACCAAGT
3241 TTCCTGGCAG GGTCCACTGT CCTACACAGA AGCTGGAGGA GGTGTGAGGG TTGTGTCTTT
3301 GTGGAATGTC CCATGCTGCT TGGGGCTCAG TTTCTCCACC TGTACCTCAT TGGTTTGGGT
3361 ATAAAAAGTG GGGATACTTT ATTATTCTCT GACTCGGTCC TGAGGAAAAA GCATCGTGGC
3421 AGTCCAGGAA CCACACCCTG AGGTTCCTGC ACTGAAGGGA CTCCCTAAGT CTCTGGAGTC
3481 TCTCCCCTTC ACAGAGCTGC CAAAGTCTAG GTTCTTTTGA GGATAACAGA GCCATGCTTG
3541 GTAAGCAGAC AACAGCATTT GTTTACTCAA CCTTCTTTTG TCAGCTCCCT CTTCATAAAC
3601 AAGTTGAGAC ACCATGCTGG CTTGAGGAAG ACTTCTAAAG CCAGACAACT GTGCAAGGAA
3661 GAAGAAGAAG GGGCAAGTGG AGTTAGCCTG GATGTAGCCC TCAAAGTCTC CAGAGACCAG
3721 CCATGAAGGC TCAAGTGGAG GGCAAGACCT GCAGCAGCCA AGCATCTGGC AGGAGAGGAT
3781 CCTGGGAACC CCTCTACCAT GACACACATT CTTCCTGCAG GTCACACTTA ATAGGCCATT
3841 TCTTATTTGG ATCTATCATG GTGTTCTGTG CGAGATTAAT GAGGTGTTAT GCTGCGAACA
3901 GAAAGTTATA TAAAAACAAG TCCCCCCCCC TTGTCACTGC TGCTAAGAAT GTAGCAGAAA
3961 TTGTCTCAAG TGTCTCTCTA ATCAGAAACA ATAAAGGTCT CCTTGGATTC AAGCCCTCCA
4021 GTTTCCTCCT TCCTTGCTGA GCCTTGGACA CCCATACAAA CCTCCTGGAT GCTACAGCTC
4081 TGGGCAGAGA CTCCAAGGTG GGGAGAGACT GATGGTACAA AAGCAAAATA CTTGTTTGGG
4141 GGTACACCCA CTCCTCTGCC TGTGTGGTTC CTGCAGTCAG TCCTGCAGAC AGGCCCTCAG
4201 TGGGTCTTCC ATGGGCAACA CGCAGAGGGA GGCAATGGAT GGGAATACCC ACACCCTGGT
4261 TAGTTTACCC CGGCCATGCT CTCTGCTCTT CATCCCTCCT CTGCCCTCTG CCACGGCTTT
4321 CTCTGCAGGA ATCATATCTT CATATTGGCC CACAGGTGTT CTCCTCACCC TAGCTATGAT
4381 GTTTACTTTA GAGTGACCTT AGCAGGGCTG GTGGGAATGA GTTCTAGAAG GCTCACGGAG
4441 ATGCTAGGGA AGAAACGTCT TCTAACTACT GAGGTTACTA AGTTCCTGGT GGTTGTCTCT
4501 GCCTTTCCCT TGTTAAAGTC ACCTTGAAGT TAGTGCAGAA GAAATCAGAG CCCAGTCACA
4561 GAGTAAATAT GGTCCTGAAG ATTTCCTTTG AGTGCCCAGA ATCCATGACA TTTCAAGAGC
4621 CCTCTTTGTA CCTTAAGTCA TTTGGGGTTG TATCTTCTGC TTGATGTATG TGTGTGTGTT
4681 TATCAAAGAG TGAGATGGTT ACATAAGAGG TGCTCTAAAG GACAGAGAGG ATTTGCAATT
4741 GTGGCATGTG ACATCCTCAG GCCTTGCTCT GGTGCCAGGA GGAACTGATG CAGAAAAGAG
4801 TAAGAGGTCA TTTCCTGGAG GCTGTCACTA TAGAGGAGAT CTTAGAGTGC ATTCCCTCCT
```

Figure 23D:

```
4861 CCAGGCCCTG CCTGAGGATA GACATGTGCT GACTGCAACT GAAACAGAGG CTTGGGATGG
4921 AGAGTTAGGT TCACAGAAGG GAGGGTGGGA GATGGATGCT TGCTGGGTTC TGGGTCTCAT
4981 CACCAGCTCC TGACCACCCG GTCAGCCCAT GTGCTTATTC CATAGCTTTC TTTTGCTATG
5041 TTTACTCAGT GTGGTGTTTG TTGGGACCCA GCAGAAGCCA GTCCCAGGCT GACAGCTGTG
5101 GATACACAGG GCAGCATGAG GGTCCTCAGC CTGAAGCAGT CAGGCTGGCA GAAGAGAAAG
5161 ACCAGCACAC ATTCCTTCAA CCAACTATGT CTTGAAAAAC AAACATATTA TATCACATAT
5221 ATTGCATTTA TGAGACAGCT AAAATGTACT CGGGTAGCAT GACTCCAGGT GGGGATATCT
5281 GCAAGTGCCA TGAGTGGCAG AGGGACAGCC AATGTGAGGC AAGAAGGAAT TCTGGCTCAA
5341 CACAGCTTAG CTCCCTGGTG TTGGTTCAAA CTTTGAGAGT TTGACCACAA GCACTTTATT
5401 TTTGACATAT TTAAACAGAG CACAACTTTG GGAAAAAGTT TTCTTATGAA AATTATCACA
5461 ATAAAGCTTA AGGCATGACT ACATTAAAAT GCCTTTGCAA AGTATATGTG CCCTCTTCCA
5521 CAAGAATGGT TCTATTGACT GAGAAATAAT GTTCAGGATA AAGATCCAGG AAGAAAAGAT
5581 CAGGGATAAG TAAAATACTA AACTCTTTTG CAAAGTACAT AGACCCTCTT TCATAACAAT
5641 GGGTTCTATT GACTGACAAG CACTGCTCAG GAGTTGGGAA AGAGTCTAGC ATAAGCACGA
5701 TAGCCTGGAG ACTCTAGTGA GGTCTAGTCT TACAGACAGC AAAAATCACC AGGTTACAAA
5761 CTACATTCAT TTCCAGTTTT CTGATCAGGC ACAGGTATGA ATCCCTTCTG TTGAAGAGAA
5821 AAGTCCATGT GTTTAAAATA TCTGGTTTCT CCAGTGCTAT TAGCGAGAAG ACTTGAGCCC
5881 TATACAACTC CCACCTGGAG TGACATCCTG TCTTCATGGT ATATTACATA CCTAGACACG
5941 CTCATCTCAC AGACTTAGGA CTTTGTCTTC TGATCTCCAT TTCTGATCCC ACTTCCACCT
6001 TTGCCTTGAT AGTGTCATTT TCTTCACTGC CTTGGTGACA ACCATGTTAT CCTCTGTGTA
6061 TTTGAGTGTT ACCATTTTCA GATTTTACCT GTATGCAAGA TCACACAGTC TTTGTCTTTC
6121 TGTCTGGATG CATGCTAATC TCTACACAAC AACCCTTCCC CGTCACTCAG ATCTTCCTCC
6181 ATTAACACAT ACATGGTGCT GAAGAGGCTA GGGAGCTTCC CTTCAGTGGG GAGCTAGCTG
6241 GCTATTGGGC CTTTTTGACT GTCCAGGAAG GCCCCCAATT GCTGAGACAA GAACTTAGAT
6301 TCTTCATTAT TGACTCTAAC TCATGTATCA AGCAGAAGCT AATGAATAGT TATCAACAGG
6361 ATCAGAGGTT CCAGTGTAAG ACACTTTGAC ATGAAAGAAC GGAGGAAGGA CAGATGGATG
6421 CATAAAAGCA GGACCACTGC CCCAGGAAGG TCCTGGAAAC TGATGCAGGG CAAAGGACAG
6481 GTTATAAACC AAATCTTAGG GAGTCAGGAA GAGCACAGAG GAGCTCAACC AACTGACCAC
6541 TGCTTAGGGG CTACCAACCC AATCCTCCCT GTGGGAACAG CTAAGCTATC AGCCAAGGGT
6601 AATAAACAGG CAGGACCTGT GGATGACATG GAGAGCATAG GGACCCTGGG TCCAGCCTTT
6661 AGCACCTGCA CTCTCAGGAT ACTCCACCAT TGTGTCTTAG AGAGCCTAGG GATACTGGGT
6721 CCAGCCTTTG GTACCTTCAC TCTCAGGGTA CCCCATCACT GTGTCTTGGA GAGCCTAGGC
6781 ACCCTGGGTC CAGCCTTCAG TACCTGCGCT CTCAGGACAC CCCACCATTG TCTCTTGCCC
6841 CGTCTCTTCT TCCTCTTCCT CCCTTTCATT GTCTCTTCTC TGTTTCTTTC TTGACTCTCC
6901 TTTCCCCTCA CACCCTCACT CTAGTTCTCC CCTTCCCTCT CTGCATCACC CTATTCTCTC
6961 TGTGGTCCCT CCACTTTCCT TTATCTCTCA TGCTTCTCTC CTCCCTCAAA TACTTGTCAC
7021 CCACTATACT TCAGGGGCCA GCTCTAGTGA CAAAGCTGTT AATAGCAAGA CTCTCAGATC
7081 TCCAACGGCT CAGAGGAGCC AGACCCACCA AGAACTCTCT CCAGGTCCAA TTTCAGGTTC
7141 CTTCGAAAGC TTTCAGCAAA TGCTCAGGGA ACATGCCACT AACAAGAAGA TGCAAATTCC
7201 AGTTGAGAGT GGGAAAGGCC CTTGCGTAGG TCCCATCTTC CAGGCCAAGG TCAGAGGGGC
7261 TCTGTGTAAT CCGGATTGAC AGGGCTCAGA ACAATGTTTT GTTTTTAAGG TTTATTTATT
7321 TTAGGTGTTA GTGTCTTTGC TTGCATGACC TTATGTGCAT CATGTGTGTG CAGGTTCCTG
7381 ATGACAGTAG AGGAGGGCTT TGAATCCCTG GGGATAGGAA GTTACAGGAA ATTATAAGCT
7441 GCTTTGTGGG TCTTCTAGCT TTCCCAACAG AAGTGAATGC TCTTCACCAC TGAGCCATCT
7501 CTCTAGGCCC AAGAGACATT GCTTTATGGA TATAATTGTG TGTGTGTGTC AACATTGAGG
7561 AAAGGGAAAT AAAAAAAAAA CTTCAGCCGC TAAGGTTGTA CAGTTTCACT AATTGCTACT
7621 TTTAGTTGTG ATAAAATGGC AGGTGCTTCA ACATTTATAT ATACAAAAAC TTCCCTGCTG
7681 GTGGTTCAAC TGTGAGAACT GGGGTAAGTG GGTGAGTTCT CTTTTTCTGT CTCTGTCTCT
7741 GTCTCTCTCC TTCCATTCTT TCTTAAAGGA AATAAACATT GCAGCTGGGT TATAGCTCAT
7801 CAATATGGAA GTTACAGAAG TGAAAAAAGG CATTGCCTTG GTGGGTGGTG TTACCAGCTG
7861 ATTTTTGGTT GTCCTGCAAG GAGGTCTGGG GACTGGCTGC TCTGTCTCTG TCTGTATGAG
7921 TGAGGGAAGT CTGGGGAGCA GATTCCCTAA CCTTCAGCCT GGCCTGGTTC CTGAGTGAAC
7981 CCAGCCTCTC TGGTCCTAGT AGCTTTTTCC AAACAGGAAT CTGAGTGGTG ACAGGGAACA
8041 AGTACCAGCC CATTGCTTAA GTGCCAGGGT TAGTGAGGGC AGGAAGCTGC CATAGCTGGG
8101 ATTAGTAGTT GTATTGGATG TAGGAAGTCC TATCCTGGGA CAGCTAATCC TTAATGCTTC
8161 ACTGGAGATT TTCAATGAGA AATTTATCCC ACGGCCCATA TGGCCCCATC CTTTTGTCTC
8221 CAACAGCCAA GTATTTTCCA TTAGAGGAGA CTTCCTGTAC ACTTGATGGA TGCTCATTCC
8281 AAGGTGACTT GGGGCAGTCA GTACAGACTT GGGATGACCT CTGACAGGCT AACCTCTCCC
```

Figure 23E:

```
8341 CAACAAGGGC CCTCTATGTT TGCTATGTAA TGTAATGTCA GACATTGTCA GGAGTGTCCG
8401 CAGCACAGCC TGCCCAGTGT GAGGGCTCTC ATAGGTTTCC CACTGTCTTA TCTACACAGG
8461 GATAACGAGG AGGTAAGCTG CAGTTCCCAG TCTCACTTCA CAGAGGAAGA GATAACCCCA
8521 TCCCAGGTCA TGTAGCCAGC AGTGGAAAGA ATGAGGATTT GAACTCAGGT CTTCCAAGTC
8581 CCATTGATAG CATCTCCTCA CAAGTCCCTT GCCACCCTCA CGATGCCTTA GACACTTGCC
8641 TGCCCTTTAT ACTAAGGAGA TGCAGGTACA AGGGGTTTAC CCATGTAGCA GCTGAGGCAG
8701 CTGGGGATAG ATACCAGCAG CAGGCCTGAT GTCACCACTC TAACTCCAGC ATCCCCAGTC
8761 TGTGTTCCTG GAGTGTGAAA ATCCCTACTT AACAAGATTG TGCAACAGTC CTTGGCTCTG
8821 TGACCCATAG CTGGAAACAG GATTCTCATT GATTTGTGGA ACATGGTGGC AGCCAGCCAA
8881 AAAGAGGGTC TGCATACAGA AGACACGTGT GGCAAGGCCA CAGCAGACTC TGACTACCTT
8941 AGCTTACAGA ATTACAAGGT CATAATGTCC TCTGCTTTGG TCACCTCATG TTAAGGACAG
9001 GCCCTAATGA AGATGGGGCA GAAGACTGAA GGAATGGCCA ACCAATAACT GGCCCAACTT
9061 GAGACCCATC CTACAGGCAA GCATCAATTC CTGACACTAC TAATGATACT CTGTTATGCT
9121 TGCAGACAGA AGCCTAGCAT AACTATCCTC CGAGAGGTCC ACCCAGCAAC TGACTGAAAC
9181 AGAAAAAGAT ATCCACAGGC AAACAGTGGA TGGAGGTCAG GGACTATTAT GGGAGAGCTG
9241 TGGGAAGGAT TAAAAACCCT GAAGGGGATA GGAACCCCAC AGGAAGACCA ACAGAGTCAA
9301 CTAAGAGACC TGTGGGAGCT CTCAGAGACT GAGCCACCAA CCAAAGAGCA TACACAGGCC
9361 GGTCCGAGGC ACCTGGCACG TGTGAAGCAG ACATGCAGCT CAGTCTCCAT GTAGGTCCTC
9421 CAATAAGCGG TAGCCTGACT GCAGTATCCA ATCCCCAACA GGGCTGCATA GTCTGGCCTC
9481 AGTGGGGGAG GATGCCCCTA ATCCTGCAGA GACTTGATGA GTGGAGAGCT ATCCAGGGGG
9541 AACCCACCCT CTCTGAGAAG GGAATGGGGA TGGGGGAGGG ACTCTGTGAA GAGGGGACAA
9601 GGACAAACAA GAACCTCAAA TAGGTCAGGC CCTAAAGGCT TGCTAAGTAG CAGTGGCCCA
9661 GCTCTGTCCT GTTCCTCAGC CCAAGGCTCA GCTCCCACCT GTTTCTGTGT TTTTCTGGCT
9721 TTTCATGGGC CTAGGACTTG GTGACCAGTT CAAACAATGG GGCCTGTGGA AGACACAATA
9781 TACAAGACTA GGGACATTCC TGTTCTGCTG ACTATCCATA GCCTGATGTA GGTGGAAGGA
9841 CCCAATCACT GGATTTCTAC CCTTGCACAA CCTTGACAGC TGAGGGCCTC TCAGAAACCT
9901 ATTTCTTCCA CTGAAAAATG AGACTCTCAA ATGAACGTCG TGACAATCAT CAGGCTTATT
9961 AAAGAGGTGT ATCTAACCTG AATGGCAAGC AGACAGCAGG CAAATGTCTG TATCAACCTC
10021 TAGGAAGGAC AAGAACTGCT CACTGCTGCC CCCCAGGAGG CCATTTGCTG AAACAGCTGC
10081 TCTCCTGCTG GTGCACAGGC CCTGCCTTCT CATTGCAGCC ACAGCCCCTT CCTGTCTGAA
10141 CCTCCTGTCA GGTCACTGGG AAACAGATCA AGATGGAACA GGACAGCTCC TGATGGTAAA
10201 TAAAAAACAG TGGTCATGGC TATTCATAGG GGTTTATGCT TCTTCAGTCC ACACTGTGAA
10261 GAGCTGTGGG CATGAACCAC AGTGTTCGAG GTAGAGTTGG GGTTCTGAAA TTCACAGTGG
10321 GGTGAGCTCA GTAAATGTGA GCTGGAGGTC ACTCGTGAGA CACACAGTCC TGCTGCTTCT
10381 GTTCCCAATA TCCTGAGGAG ACGACACATC TACTTTGTTC AGAGGCCACA GTCTAGTTGA
10441 CCTGAGAGTT ACCAGTTTCT TATTTGTGTG TGTGTGTGTG TGTGTGTGTG TGTGTGTGTG
10501 TGTTGTTCGT GTGTGAGTGC AGGTGCACAT ATGATAGCGT ACACGTTGAG GTCAGAGGAT
10561 AACTATCAGG CGTTGTCCCC TCCTACTTTT CCTCGGACTC TGGAGAACAA ACATGGGTCC
10621 TTATTCCAGG GGAGCAAGTC GCTGTTGGCT GACACATCTT GCTCACATAC ATTTTACCTA
10681 GACAATGGAG CCTCCATCAG AGTATTACTT TAGCTCCTCA CCGATGGCAA TGCACCACCT
10741 CTCTACCCAC ATAGGAGTTG GGTCTCCACA CACCCCCACA CCCCCTTCAC CAAAACGTTT
10801 TCAGTTACTT TATCTGGTAA AGTTCATCAG AGAATGAAGC CAGTATTAAG AACATGGAAT
10861 CATTTGGGAA CCTGGATCTA GCAATACCCC ACCCTAGATG GAGTTGCTGA GTTTTCACCT
10921 CAGATTATAA TTCCCCCCTA GCTTCTATGG TTTATTCTGA AACCAGGGGA ACTCGATTCC
10981 TCCCTTTGGA CCACAGACAT CCTGGCTTGT GAATTCACAT GTCATCTACT GCTAATCCAT
11041 TGGTAGTATG TGGCTCACAG AGACACACTA CAGTCATGGC CAATGTCAAG GTAGGACAGA
11101 TGTGAATCAT TCCCCCAGTC CTGCTGTTTT CATGACTAAC CCTCCTCAGC ACAGTGACCA
11161 TGAACCTACT TTTCCCCTCC TTTTATTTTT AGAATTGCTG GAATTTTCTA TTTTGAGAAA
11221 TAATAGCCTT GGGCAGCATT AAACAAAATC ATCTAGAAAG CTGGTTTAAA ATACAGATGG
11281 TTGAGTCAGT GAAAGAGTGA GGAATGTCAT TATTGGCCCC TCACAGAGGC TGGCTCACTC
11341 CAGCAGAGGT GGTTGAAGCT CTTGGACACG GGTCAGGTGC ATAGGAAAGG TNGTCTGGGA
11401 CACTGAGAAC CACAATTGAA CAAACAGAAC TGTTGGCTTT TTTTTTTTTA AATGAGTTCT
11461 CAAAAAATGA CTGGCTAGCT TAGGCAAATA CTTCGAGCCA ACCCAACAGA ACATTCTTCC
11521 ATTGATTCAT TCTGGATCTT CTTTCTAGAC AATACTGAAC TGACCCCTTG TTGGCAGTCT
11581 CAAGTTTGAC AACATAGGGC TTTGAACTTG GCACAAGGTC CATCACTGTC ACCCAAGCAT
11641 CCTGGGTGAC CTTTGGGTTG GAATATCTTG GCTAACCTTA GATATTTTCT TTGGAGTATC
11701 TTTAGAACAT CCAGGAAATA GGGCTTGATT CTCATCCTGG GACCACAATA TAAGTCACCC
11761 TAGAATCCCA GGAGATCGTG CAGAGAAACA AGGATCTCTC TCGTGTGCAT CCTTCTTCAA
```

Figure 23F:

```
11821 AGCAGTGAGT AGTGACTCCA CTAAACTGAG TTCCCATCTG AGAGTCCACA GGAGGCTTTG
11881 GGGCAAGAAG CAGAGGGAAG GCACTGTTTG TGTTGGTAAA GTTTTGACTC TAACAAATTT
11941 GAAGACATAG ATGACATTGT GTCAGACTAA CAACAACCTA GACTCATGTG GGTTCTGTTT
12001 AGGGATCAGA TTTTATTCAT CAATGACTTG TCTTAGTGTA TAGAGAAAGG CTTCCTACTG
12061 GAGTGTAGGC TCAATAATGA CAGAAGAGAT AGCTATTTCC CCTAGGGACT GTGCTGCTCC
12121 AAGTTTGGTG GAGAAAGGCA GTGGGGAACC TAGATGTGCT CTCTGGGGAG GGGGTCTGAA
12181 GCTGGCTTCA TAGAAGGTGT GAAGTTTTGC TGAAACATCT AAACAGAATT ATAGCTTAGG
12241 AAAGTGAGCA GGCAAGGCAG GGAATGTGTT GCATATGTAT ATGTACATGA ATATATTATG
12301 TTATAGATAC ACACACATTT GAACCTCATT TGCAGATGAC AGAAAATAGG TTATTTTGCC
12361 TCTCTTAACT GCTAAGCACA ATGACTTCCA GTTCCATCCA TTTCCTGAAA TGCCACAATT
12421 TCATTTTTCA TTGTGGCTGA ATAAAATTCC ATTGCAGACT GGGCCCTACT TCATCCACTC
12481 CTGAGGGCAG GCATATCCCC TGGCTCCATT TCTTACCTAT TGTGAAGAGA AGTGCAACTG
12541 TCTTGTTGAA AGGCAAGCGT GAGAGAGGCA GGCACTAATT GTGGGTTTTT GTTTCTTCTT
12601 CCTGCTATGA CTCTCCATTT GTCAGAACCA AAGATCGATA AAAGCCGCCA CCATGAAAGC
12661 CATCTTAATC CCATTTTTAT CTCTTCTGAT TCCGTTAACC CCGCAATCTG CATTCGCTCA
12721 GAGTGAGCCG GAGCTGAAGC TGGAAAGTGT GGTGATTGTC AGTCGTCATG GTGTGCGTGC
12781 TCCAACCAAG GCCACGCAAC TGATGCAGGA TGTCACCCCA GACGCATGGC CAACCTGGCC
12841 GGTAAAACTG GGTTGGCTGA CACCGCGCGG TGGTGAGCTA ATCGCCTATC TCGGACATTA
12901 CCAACGCCAG CGTCTGGTAG CCGACGGATT GCTGGCGAAA AAGGGCTGCC CGCAGTCTGG
12961 TCAGGTCGCG ATTATTGCTG ATGTCGACGA GCGTACCCGT AAAACAGGCG AAGCCTTCGC
13021 CGCCGGGCTG GCACCTGACT GTGCAATAAC CGTACATACC CAGGCAGATA CGTCCAGTCC
13081 CGATCCGTTA TTTAATCCTC TAAAAACTGG CGTTTGCCAA CTGGATAACG CGAACGTGAC
13141 TGACGCGATC CTCAGCAGGG CAGGAGGGTC AATTGCTGAC TTTACCGGGC ATCGGCAAAC
13201 GGCGTTTCGC GAACTGGAAC GGGTGCTTAA TTTTCCGCAA TCAAACTTGT GCCTTAAACG
13261 TGAGAAACAG GACGAAAGCT GTTCATTAAC GCAGGCATTA CCATCGGAAC TCAAGGTGAG
13321 CGCCGACAAT GTCTCATTAA CCGGTGCGGT AAGCCTCGCA TCAATGCTGA CGGAGATATT
13381 TCTCCTGCAA CAAGCACAGG GAATGCCGGA GCCGGGGTGG GGAAGGATCA CCGATTCACA
13441 CCAGTGGAAC ACCTTGCTAA GTTTGCATAA CGCGCAATTT TATTTGCTAC AACGCACGCC
13501 AGAGGTTGCC CGCAGCCGCG CCACCCCGTT ATTAGATTTG ATCAAGACAG CGTTGACGCC
13561 CCATCCACCG CAAAAACAGG CGTATGGTGT GACATTACCC ACTTCAGTGC TGTTTATCGC
13621 CGGACACGAT ACTAATCTGG CAAATCTCGG CGGCGCACTG GAGCTCAACT GGACGCTTCC
13681 CGGTCAGCCG GATAACACGC CGCCAGGTGG TGAACTGGTG TTTGAACGCT GGCGTCGGCT
13741 AAGCGATAAC AGCCAGTGGA TTCAGGTTTC GCTGGTCTTC CAGACTTTAC AGCAGATGCG
13801 TGATAAAACG CCGCTGTCAT TAAATACGCC GCCCGGAGAG GTGAAACTGA CCCTGGCAGG
13861 ATGTGAAGAG CGAAATGCGC AGGGCATGTG TTCGTTGGCA GGTTTTACGC AAATCGTGAA
13921 TGAAGCACGC ATACCCGCTT GCAGTTTGTA AGGTACCCGG GGATCACAAC TTGCCCTCTG
13981 AAGAGGAAGA ACAGAAGGAT GCCACAACTC TCCTGCTGGC TACTCTCCAG TGGTTTCATC
14041 TTACTTCTGA TGGCATTTCC CTCTAGAAAG TGCTACTATC ATCCACACAT TTCTACCTGA
14101 GACCACCCAA AGGACCCTCC CAAATTCTCT TCCTCTCTGA GTAGTCTCCA CACCTGTTAC
14161 CACCATCCCA GAATTAAAAT CCTAACTGCA CTCTGGCGTG TGACTTGCCT CAGTCCTTGC
14221 AATAAGAGTT GTTGGCAGTG CCAGGCGTGG TGGCGCACGC CTTTAATTCC AGCACTTGGG
14281 AGGCAGAGGC AGGCGGATTT CTGAGTTCGA GGCCAGCCTG GTCTACAGAG TGAGTTCCAG
14341 GACAGCCAGG GCTATACAGA GAAACCCTGT GTCGAAAAAC CAAAAAAAAA AAAAAAAGTT
14401 GTTGGCAGAG TGTGGGTTAT ATACCAGGTG GAGATTTCAA ATGAGTGGCT GAAGCTGTAG
14461 CCAGAAGGAA CTTAGAGGAT AGCTCATAAC TTAAAAAGAA ATGTAGAGAG TAGCAGAAAC
14521 ATTGAGAGAG TGGGCACACA GCCACTGTGT GAATGTGGCA GAACACAATC CAGCCAGCTA
14581 TACATGCATA AGTGTATATT GGCGCCATCC TGACTGATGA GACACAGGAA AACAGATAGA
14641 CGGGGTTAGG TGGCCATGGC CTTTCCTGCC TGCCTCTTCC TAAGGGTCAT CTCAAGACCT
14701 TATGCTCTCT TAACTCTTCC ATTGCTACTT AGCTTCTAGA TATCACCTCC AGATTAGTCT
14761 CCTTGGGTAC ATCAGTGATC CTGGTGATAT CCAGGGCTTC CTGATTCCAT CTTTGTCATA
14821 GAGGCTGCAA CTAAAGAGGT CTTCTTAATA CTTCACACCC TGATGCCAAA AGGAAGACAC
14881 AGAAGTTCAC AGAGGTGAAG TGATTCATGT AGGACATACA GTGAGCAAGC ATCAGGGTCC
14941 GGATTATCTG ACTCTACTCT AACTTTTATG TAAATGTGCT TTATGCCATT AACACTGTCA
15001 TTCCTGTGCT TCAGCTCTGG GAGACTCCCA AGCACTCTTA GGCACAAGCC ACAATTAAGG
15061 GACTCTGACA CTCTGCATTG ATTAATTAGC ATGGTGGTCT CTATGTTTCC AGATTCATGA
15121 TTGTTTCACT TTCCATATAG GCTATGAAGG GTGTGAGGAA ATTTTTTGGG GACAGAATTG
15181 GAGGCAATCC ACCTCTCTCA GGAAGCCTCT ATCTGGAAAA GCTTACAACT CAGGGACAGT
15241 AACTGTAGGC CCAGTCCTTG GTGTCCAAAA TGGGTTTTAT GGTTTGAATC TGCAAAGCCT
```

Figure 23G:

```
15301 TCCATGTGCT CAAAGGTTTG AACATGGAGC CTCCTCCTGG TAACACTGTA TTGGAGGCTT
15361 TTGAGACTGG ATGCTCTTTG GTCCCATGTT TTGCTACATC ATCTGTCAAG ATATGACCCA
15421 GGCATGCTAC CAGCTACCAC AGACTATGCC TCTCCAGCTT TCATGTTCTC CCCACCATGA
15481 TAGACTTGTA TCTCCTAAAA ATGGAATCAA AGCAAACTTT TCCTGCATTA AGTTTTTTTT
15541 TTTCTGTTAA GTGTTTGGTC ACAGGGACAA GAAAACACTC AATACAGATA ATTAGTACCA
15601 GAGTTGAGGT TCATTGCTCT AGCAAGTTGG ATCAAATTTT TAGGGCTTTG GAACTGATTT
15661 ATAAGAGACA TGTAGAAGAG TCTGAAGCTG TGGGCTACAG AAGTGTCACC AGTTTTTAAG
15721 AATAGTTTAA TACACCATGG GAATTGTGAA AATCAGAATG CTCACACAAA GGCAGACAGG
15781 AAAACGTGAG CATGTGGCGT GTGAGAGGGC ATAAGAAGGA ACCTAGGGGG AAATGAGCTA
15841 GAAGCCATTC GGCTACGTTA GGGAACGTGT GTGGCTGTGC TTGGCCCATG CCCTGGCAAT
15901 CTGAATGAGG CCAAATTTTA AAGGAGTGGA CTAACTCGAT TGTCAGAGAA AATATCAAGA
15961 CAGACCACCA CTCAGGCTAT GCCGTGTTTG TGACCGACCA GCTACTCTTA GCCAGCTCTA
16021 TTGTGAAATT CCAGAGCAAT TATCAGAGCA TGAAGATACA TACAGTTTAG TGAAGTAAGG
16081 GGTGTGGGTC CCTAAGTGGA TGGTGCATAA ATCTATGTAG GTGATGCCTA AGTGACACTT
16141 GATAATCCAA AATATCAGCA ATGTGGAATG TCTTCCAAGG AGACCTGTAG ACACACATTT
16201 TAGAACTTTG CTCATGGCTG TAATAAATAG CTAGCTAGAA ATCATTTCCT GAAGAGGTTA
16261 GTCTGAGTTA CGGTTCCAGG GCAAACATTC AGTGATGGCA AGGAAGGCAT TGCAGTCAGG
16321 AGCCAAAGGT CAGCTGGTCA CATTGCATCA AGAGTAGAGA GTCAGAGTGT GAGTAGAAAG
16381 AGGATACAGG TTATAAAACC TCACTGTCCA CTCTCAGCAA TCCATTTTCT CCTAAAAGGC
16441 TTTACCTTCT AAAGATTTTA GTCTTCAAAA CCAGTACCAG TAGCCTGGGA ACAAAAGTTG
16501 AAACAAATGA GCCTTTGTGG GGCATTTCAC ACTTAAAACA GGGCATCACC TAGGAGGAGC
16561 CCTGTGTGCA GTAGGAAGTG TGGCCTCTGT GTCAGGAATG CTCAGGCTAA TAAGGGGTCC
16621 TCTATCTGAG GGACCCTATG AAGATTCAAC AAGTAGTTGT GAGAATTCCC TGTAAATGGA
16681 TGCTACCAAT TTGACATTTG TAGACCTGCT ATTGTGTGCT TCTTTATTGG GCTCTCCCAT
16741 CTCCCAACTT TCCAACCCAT ATTCCACATT AATCCCTTCC ACCACCATGC AACACTAGGT
16801 AGGAGAGAAG GAAGGTTAGA AGAGAAAGTG GGTATAGATC TATTTAGACT ACTTCCTGCT
16861 GATTAGGGGC AAGTCCAATC GTCATTGTCA GGATACCTCC AACCAGCAAC CAGCAAACCA
16921 GCAAATCAGA AACAGCAAAA GCAGCCAACA AGGCAGCACT AACCAGCAGG ATTGGGGTCG
16981 GTAGCGTGGG AGCAGTCACT ACTGGTCTTC TCATGGCTTT GGCATTAATA CTCTCTCAAG
17041 AAATTCCGTA ATTTTTTCCC CACCACCTGA AATTCCGTAA TTTTAAATGC AAACTATCTA
17101 CAGCTGGCAA AAATCACATC TCTCCTAGAG CACAAGACAA ATCATAGTTA CTGGCTATTT
17161 GCAATCTGAA GCATCTCAAT ATCCCACACC TGGGATTAAA ACAAAAACAT ATTCACATCA
17221 CATAACTGTT TTTTTTTTCC AATTTTTTAT TAGGTATTTT CTTTATTTAC ATTTCAAATG
17281 CTATCCCGAA AGTCCCCTAT ACCCTCCCAC CTCCCTGCTC CCCTACACAC CCACTCCCAC
17341 TTTTTGACCC TGGAGTTCCC CGGTACTGGG GCATATAAAG TTTGCAAGAC CAAGGGGCCT
17401 CTCTTCCCAG TGATGGCCGA CTAAGCCATC TTCTGCTACA TATGCAGATA GAGACACGAG
17461 CTCTGGGGGT ACTAGTTAGT TCATATTGTT GTTCCACCTA TAGGGTCGCA GACCCCTTCA
17521 GCTCCTTGGG TACTTTGTCT AGCTCCTCCA CTGGGGGCTC TGTGTTTTAT CTAATAGATG
17581 ACTGTGAGCA TCCACTTCTG TATTTGACAG GCACTGGCCT AGCGTCACAT GAGCCAGCTA
17641 TATCAGGGTC CTTTCAGCAA AACCTTGCTG GCATGTGCAA TAGTGTCTGC GTTTGGTGGT
17701 TGATTATGGG ATGGATCCAC TAGTTCTAGA GC
//
```

TRANSGENIC ANIMALS EXPRESSING SALIVARY PROTEINS

FIELD OF THE INVENTION

The present invention relates to transgenic animals and, more specifically, to animals genetically modified to express a desired protein.

BACKGROUND OF THE INVENTION

Phosphorus is an essential element for the growth of all organisms. In livestock production, phosphorus deficiency has been described as the most prevalent mineral deficiency throughout the world and feed must often be supplemented with inorganic phosphorus in order to obtain desired growth performance of monogastric animals (e.g. pigs, poultry etc.).

Phytic acid, or phytate, (myo-inositol 1,2,3,4,5,6-hexakis dihydrogen phosphate) is a major storage form of phosphorus in cereals and legumes, representing 18% to 88% of the total phosphorus content (Reddy et al. 1982). The enzyme phytase (myo-inositol hexakisphosphate phosphohydrolase) belongs to the group of phosphoric monoester hydrolases: it catalyzes the hydrolysis of phytate (myo-inositol hexakis phosphate) to inorganic monophosphate and lower phosphoric esters of myo-inositol or, in some cases, free myo-inositol. Phytases are classified either as 3-phytases or 6-phytases based on the first phosphate group attacked by the enzyme. 3-phytase is typical for microorganisms and 6-phytase for plants (Cosgrove, 1980).

Phytase is either absent or present at a very low levels in monogastric animals (Bitar and Reinhold 1972; Iqbal et al. 1994). Consequently, dietary phytate is not digested or absorbed from the small intestine and instead is concentrated in fecal material, thereby contributing to phosphorus pollution in areas of intensive livestock production. Runoff from animal farms leads to contamination of rivers and streams. Such runoff has resulted in rapid drops in the oxygen concentration in rivers and streams due to excessive algal growth in water, which, in turn, has led to an increase in the mortality rate of fish and existing flora and fauna. This is becoming a global problem as pig and poultry production is increased (Miner 1999; Mallin 2000). Furthermore, phytic acid is viewed as an anti-nutritional factor because it interacts with essential dietary minerals and proteins limiting the nutritional values of cereals and legumes in man and animals (Harland and Morris 1995).

For the above reasons, various attempts have been made to enable animals to utilize available phytate in feed. Such attempts have included production of low phytate plants (Abelson 1999), addition of phytase to the animal feed (Simons et al. 1990) (Stahl et al. 1999) or transformation of the fodder plants to produce the required phytase (Pen et al. 1993, Verwoerd et al. 1995). A combination of these options, the feeding of phytase to poultry receiving low phytate corn has also been tested (Huff et al. 1998). However, these solutions increase the cost of animal production. Also because phytase is an enzyme, it is susceptible to inactivation by heat and moisture and is generally unstable at the high temperatures used for feed pelleting.

The primary phytase used for supplementing animal feeds is from *Asperigillus* sp.; however, phytases are produced by a large number of plants and microorganisms (Wodzinski and Ullah 1996) (Dvorakova 1998). A phytase produced by *Escherichia coli* has been reported to exhibit the highest activity of those reported (Wodzinski and Ullah 1996). This phytase from *E. coli* was initially cloned as an acid phosphatase gene that was designated APPA (Dassa et al. 1990). Greiner et al. (1991; 1993) purified phytase from *E. coli* and reported that some of the kinetic properties of the acid phosphatase activity of the native phytase of *E. coli* were similar to those of the APPA-encoded acid phosphatase. However, the authors did not clone the phytase gene to prove that it was identical to APPA gene. We have subsequently cloned, overexpressed and characterized APPA gene, and shown that the *E. coli* gene APPA codes for a bifunctional enzyme exhibiting both phytase and acid phosphatase activities (Golovan et al. 2000). Phytases exhibit phosphatase activity, however the relative activities differ widely among enzymes (Wodzinski and Ullah 1996).

Therefore, there is a need for an improved method of allowing access by animals to phytase so as to enable efficient phytate metabolism and, thereby reducing phosphate pollution.

In the field of protein production using recombinant methods, one of the associated problems relates to the lack of required glycosylation. Therefore, a method of producing such glycoproteins is also needed.

SUMMARY OF THE INVENTION

In one embodiment, the invention provides a transgenic non-human animal that carries in the genome of its somatic and/or germ cells a nucleic acid sequence including a heterologous transgene construct, the construct including a trangene encoding a protein, the transgene being operably linked to a first regulatory sequence for salivary gland specific expression of the protein.

In another embodiment, the invention provides a transgenic non-human animal that carries in the genome of its somatic and/or germ cells a nucleic acid sequence including a heterologous transgene construct, the construct including a trangene encoding phytase or a homologue thereof.

In yet another embodiment, the invention provides a method of expressing a protein, the method comprising the steps of:

a) introducing a transgene construct into a non-human animal embryo such that a non-human transgenic animal that develops from the embryo has a genome that comprises the transgene construct, wherein the transgene construct comprises:

i) a transgene encoding the protein, and ii) at least one regulatory sequence for gastrointestinal tract specific expression of the protein, b) transferring the embryo to a foster female; and, c) developing the embryo into the transgenic animal wherein the transgene is produced in the gastrointestinal tract of the animal.

In a further embodiment, the invention provides a transgenic animal adapted for expressing a protein according to the above method. The invention also provides for the progeny of such animal.

In another embodiment, the invention provides a process for producing a protein comprising the steps of:

a) obtaining saliva containing the protein from a non-human transgenic animal, the animal containing within its genome a transgene construct, wherein the transgene construct comprises:

i) a transgene encoding the protein, and ii) at least one regulatory sequence for salivary gland specific expression of the protein, and extracting the protein from the saliva.

In a further embodiment, the invention provides a method for expressing a phytase or a homologue thereof in a non-human animal, the method comprising:

a) constructing a nucleic acid sequence including a transgene construct comprising:

i) a transgene encoding the phytase or a homologue thereof, and ii) at least one regulatory sequence for gastrointestinal tract specific expression of the protein, and b) transfecting the animal with the nucleic acid sequence;

whereby the animal carries within the genome of its somatic and/or germ cells the transgene construct and wherein the animal expresses the phytase or a homologue thereof in its gastrointestinal tract.

In another embodiment the invention provides a nucleic acid molecule comprising a nucleic acid sequence including a gene encoding a protein, the gene being operably linked to at least one regulatory sequence for gastrointestinal tract specific expression of the protein.

In another embodiment the invention provides an antibody specific to the protein expressed by the above nucleic acid sequence and a test kit for immunologically detecting such protein. The invention also provides for hybridomas secreting such antibodies.

In another embodiment the invention provides cells that are transfected with the above nucleic acid sequence.

In another embodiment, the invention provides a method for producing a protein molecule comprising a glycosylated protein secreted in the saliva that exhibits a novel physiological activity. One example of such an activity is phytase.

BRIEF DESCRIPTION OF THE DRAWINGS

These and other features of the preferred embodiments of the invention will become more apparent in the following detailed description in which reference is made to the appended drawings wherein:

FIG. 1 is a schematic diagram illustrating the steps in the construction of the transgenes R15/APPA+intron and R15/APPA used for the generation of transgenic mice. (SEQ ID NO: 36)

FIG. 2 is a schematic diagram illustrating the steps in construction of the plasmid containing the transgene SV40/APPA+intron that was introduced by transfection into mammalian cell lines.

FIG. 3 is a schematic diagram illustrating the steps in construction of the transgenes Lama2/APPA that codes for the native AppA phytase and the Lama2/PSP/APPA that codes for the AppA phytase with the PSP signal peptide sequence. (SEQ ID NOS: 37 & 38)

FIG. 4 is a schematic diagram of the Lama2-APPA plasmid containing the APPA transgene.

FIG. 5 illustrates the nucleic acid sequence of the Lama2/APPA plasmid containing the *E. coli* APPA gene (SEQ ID NO: 1).

FIG. 6 is a picture of an agarose gel illustrating APPA PCR products from genomic tail DNA of third generation offspring from the transgenic female founder mouse 3-1 generated using the Xho1 and Not1 fragment of the Lama2/APPA construct. A second generation phytase gene positive male was crossed with each of two phytase positive transgenic females 9f and 11f (Table 3). From litter 118m×9f offspring 3, 4, 5 & 6 are PCR positive and from litter 18m×11f offspring 2 and 3 are PCR positive. Std is the oligonucleotide standard and the numbers on the left are the bp sizes of the standard. Lane C is a negative control reaction mixture that lacks a DNA template and appA is a positive control containing an amplified segment of the phytase gene. The primers used were APPA-UP2 and APPA-KPN.

FIG. 7 is a picture of an agarose gel illustrating phytase gene PCR products and β-globin PCR products from genomic tail DNA of five founder piglets from litter 167. Std is a 1 kb ladder. Lane 2 using the phytase primer set is positive for the phytase gene, and all of the samples were positive for the β-globin gene. Lane C is a negative control not containing template DNA. The phytase transgene primer set included APPA-UP2 and APPA-KPN gave an expected fragment size of 750 bp. The primer set for the β-globin gene included PIG-BGF and PIG-BRG gives an expected fragment size of 207 bp.

FIG. 8 is a picture of an agarose gel showing the PCR products of four separate primer sets used to amplify different segments of the transgene introduced into pig 167-02. The Std contained a kilobase DNA ladder. The primers used included lane 1, APPA-UP2 and APPA-KPN (750 bp); lane 2, APPA-MATURE and APPA-KPN (1235 bp); lane 3 APPA MATURE and APPA-DOWN2 (608 bp); lane 4, PIG-BGF and PIG-BGR (207 bp). lane 5, a negative control without DNA template added; lane 6, the appA gene & primers APPA-UP2 and APPA-KPN. The numbers on the left indicate the sizes of the bands in the standard. No PCR products were detected in the absence of either DNA template or primers.

FIG. 14 is a picture of an agarose gel showing the PCR analysis of eight liter 154 piglets. The phytase transgenic boar 167-02 was used to breed a non-transgenic female. Std, 100 bp ladder, numbers on left are the sizes of the fragments in each band in bp; lane 167-02, DNA from boar 167-02 1, DNA from 167-02; lane C, is a lane without added DNA; lanes 1–8, are amplified DNA inserts from each of the offspring piglets of the litter. Phytase primers were Lama-UP and APPA-DOWN4. β-globin primers were PIG-BGF and PIG-BGR.

FIG. 15 is a picture of a sodium dodecylsulfate polyacrylamide gel electrophoresis (SDS-PAGE) profile of the purified AppA phytase produced in *E. coli* and the purified pig salivary phytase stained directly with silver (A) and a transfer from a similar SDS-PAGE gel transferred to nitrocellulose and stained for glyoproteins (B). Creatinase is not glycosylated while transferring is glycosylated. The numbers on the left are the masses in of the molecular mass standards (Std) expressed in kDa.

FIG. 6 is a Western blot of the AppA phytase from pig saliva after various purification steps and of purified phytase produced in *E. coli*. A monoclonal antibody prepared against the *E. coli* phytase was used as the primary antibody for detection. Lane 1, saliva from non-transgenic pig 164-04; lane 2, saliva from transgenic pig 167-02; Lane 3, saliva fraction not bound to DEAE-Sepharose; lane 4, salivary phytase bound to DEAE-Sepharose and released with an NaCl gradient; lane 5, salivary phytase further purified by Chromatofocusing with a pH gradient of 4 to 7; lane 6, phytase purified from *E. coli*. The numbers on the left are the masses of molecular mass standards (not shown) expressed in kDa.

FIG. 6 is a SDS-PAGE profile of the purified *E. coli* produced AppA phytase and the AppA phytases produced by pigs and mice stained with silver (A) and a Western blot of an identical set of protein samples (B). A polyclonal antibody prepared against the *E. coli* phytase was used as the primary antibody for detection. Lane 1, Purified AppA phytase produced in *E. coli*; lane 2, Saliva from a non-transgenic pig 164-01; lane 3, Saliva from a AppA producing transgenic pig 167-02; lane 4, Purified phytase from pig 167-02; lane 5, Saliva from a non-transgenic mouse; lane 6, Saliva from a transgenic mouse containing R15/APPA transgene induced with isoproterenol; lane 7, Saliva from a transgenic mouse containing the Lama/APPA transgene; Std, Molecular mass markers. The numbers on the left are the masses of molecular mass standards (not shown) expressed in kDa.

FIG. 18 illustrates the nucleic acid sequence of the known segment of the R15/APPA+ intron plasmid including the vector sequences of pBLCAT3 (SEQ ID NO:2).

FIG. 19 illustrates the nucleic acid sequence of the known segment of the R15/APPA+ intron transgene construct used for the generation of transgenic mice (SEQ ID NO:3).

FIG. 20 illustrates the nucleic acid sequence of the known segment of the R15/APPA plasmid including the vector sequences of pBLCAT3 (SEQ ID NO:4).

FIG. 21 illustrates the nucleic acid sequence of the known segment of the R15/APPA transgene construct used for the generation of transgenic mice (SEQ ID NO:5).

FIG. 22 illustrates the nucleic acid sequence of the SV40/APPA+ intron plasmid (SEQ ID NO:6).

FIG. 23 illustrates the nucleic acid sequence of the Lama2/APPA transgene construct used for the generation of transgenic mice and transgenic pigs (SEQ ID NO: 7).

DESCRIPTION OF THE PREFERRED EMBODIMENTS

Figure 1:
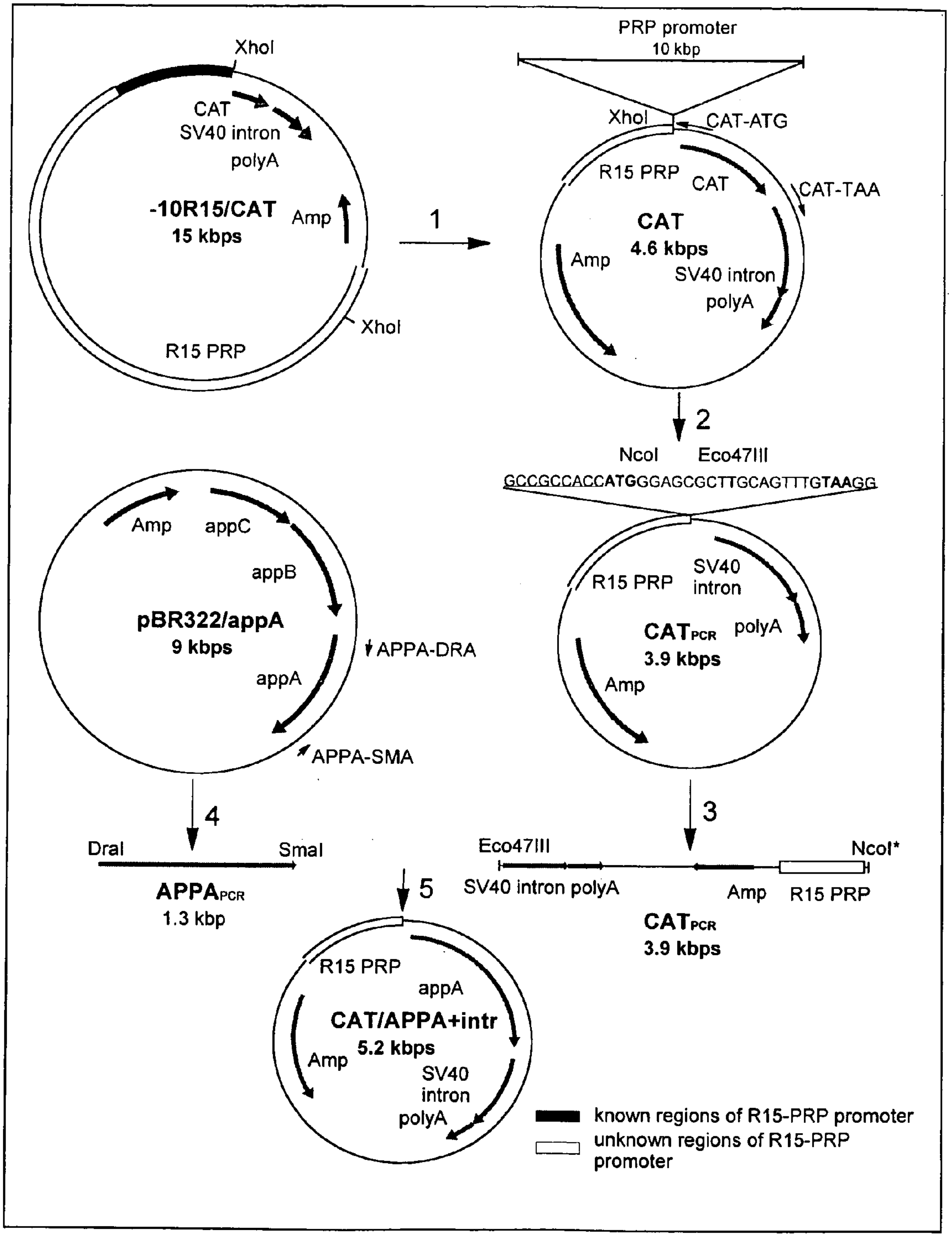
FIG. 1 is a schematic diagram representing a method for producing the gene construct of the present invention containing the inducible proline-rich protein (PRP) promoter/enhancer. More specifically.
Figure 1A:
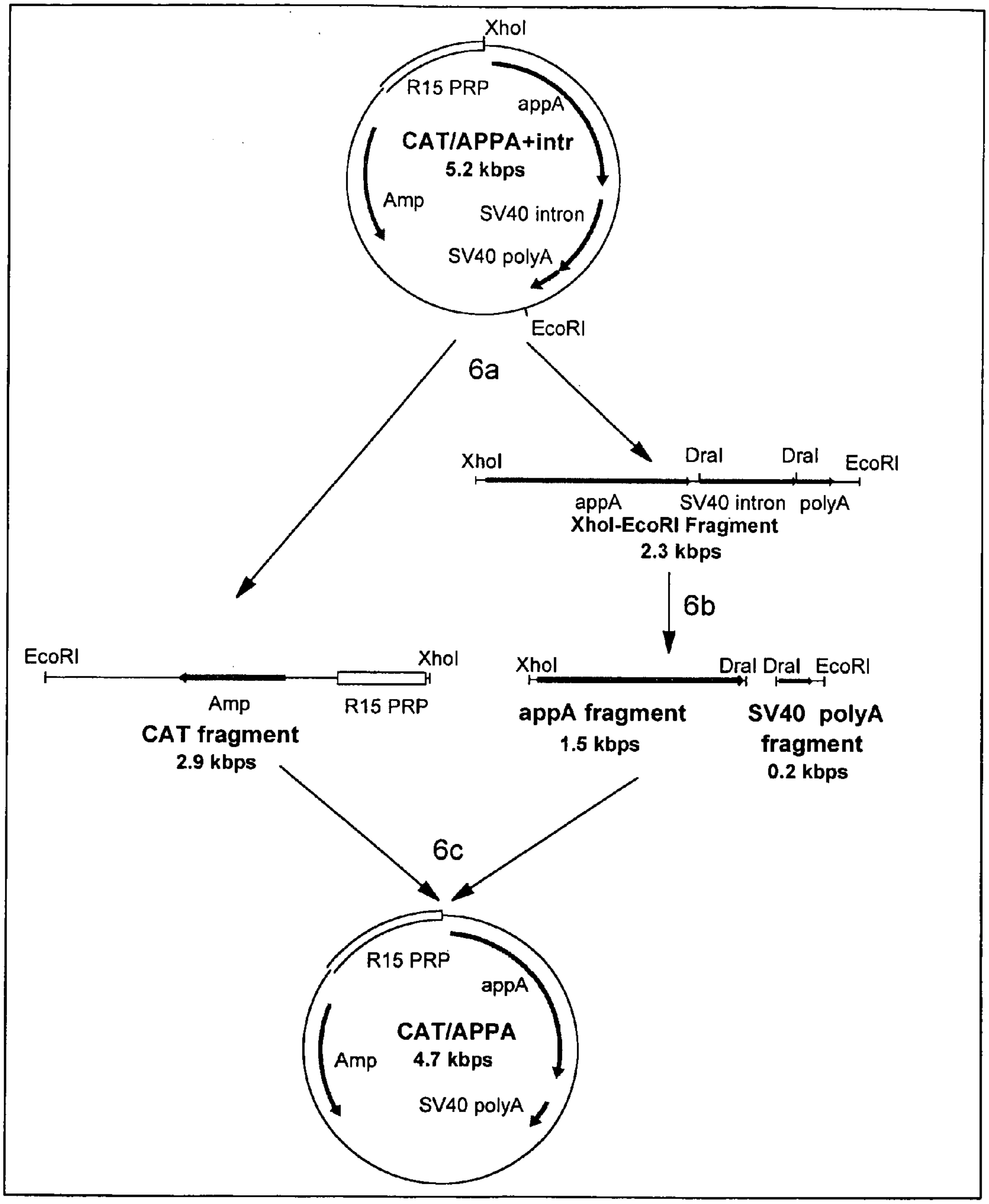
Figure 1B:
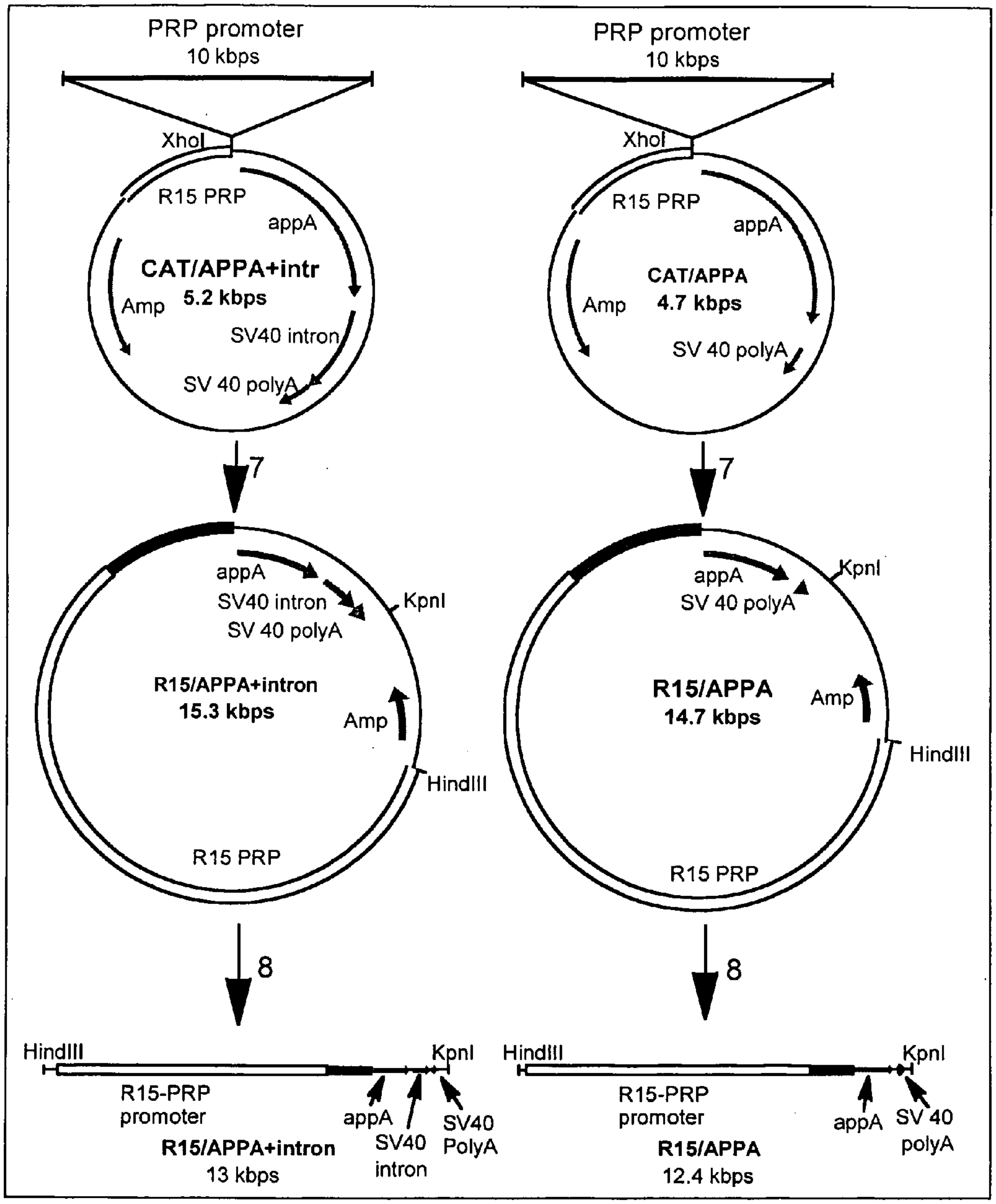

In the following description, a number of recombinant DNA technology terms are used. The following definitions have been provided in order to enable a clearer understanding of the specification and appended claims:

"Promoter"—a DNA sequence generally described as the 5' region of a gene and located proximal to the start codon. The transcription of an adjacent gene is initiated at the promoter region. If a promoter is an inducible promoter then the rate of transcription increases in response to an inducing agent. A constitutive promoter is one that initiates transcription of an adjacent gene without additional regulation.

"Operably Linked"—a nucleic acid sequence is "operably linked" when placed into a functional relationship with another nucleic acid sequence. For instance, a promoter or enhancer is "operably linked" to a coding sequence if the promoter causes the transcription of the sequence. Generally, operably linked means that the linked nucleic acid sequences are contiguous and, where it is necessary to join two protein coding regions, contiguous and in one reading frame.

"Phytase"—any protein that liberates phosphate from myo-inositolhexakis-phosphate or other inositol phosphates. Its catalytic capability may be limited to phytic acid or one of its salts, or it may show less specificity and hydrolyze a variety of phosphorylated compounds.

"Gene"—a DNA sequence that contains a template for an RNA polymerase and contains information needed for expressing a polypeptide or protein.

"Polynucleotide Molecule"—a polydeoxyribonucleic (DNA) acid molecule or a polyribonucleic acid (RNA) molecule.

"Expression"—the process by which a polypeptide is produced from a structural gene.

"Cloning vehicle"—is a plasmid or phage DNA or other DNA sequence which is capable of carrying genetic information into a host cell. A cloning vehicle is often characterized by one or more endonuclease recognition sites at which such DNA sequences may be cut in a determinable fashion without loss of an essential biological function of the vehicle. A cloning vehicle is a DNA sequence into which a desired DNA may be spliced in order to bring about its cloning into the host cell.

"Vector"—is a term also used to refer to a cloning vehicle.

"Plasmid"—is a cloning vehicle generally comprising a circular DNA molecule that is maintained and replicates autonomously in at least one host cell.

"Expression vehicle"—a vehicle or vector similar to a cloning vehicle but which supports expression of a gene that has been cloned into it, after transformation of a host. The cloned gene is usually placed under the control of (i.e. is operably linked to) certain control sequences such as promoter sequences.

"Host"—a cell that is utilized as the recipient and carrier of recombinant material.

"Homologous"—refers to a nucleic acid molecule that originates from the same genus or species as the host.

"Heterologous"—refers to a nucleic acid molecule that originates from a different genus or species than that of the host.

"Glycoprotein"—refers to a peptide molecule that has undergone glycosylation.

"Glycosylation"—refers to the addition of carbohydrate groups to a amino acid residues of a peptide molecule.

In recent years, transgenic animals have been developed for many purposes (Pinkert et al. 1990) (Wall et al. 1997). One premise, therefore, for the present invention is that by providing a transgenic animal capable of expressing phytase, the problems discussed above would be obviated. The options for heterologous phytase expression in animals include (i) salivary gland secretion of a phytase, (ii) pancreatic secretion of the enzyme into the small intestine along with the digestive enzymes, or (iii) secretion from the intestinal epithelial cells much like that of indigenous alkaline phosphatase and glycosidases (Low, 1989). The *E. coli* phytase would appear to be best suited for hydrolytic activity in the monogastric stomach because the enzyme has a pH optimum in the range of 2.5 to 4.5 and it is resistant to pepsin, the predominant protease active in the stomach. The phytase has a periplasmic location in *E. coli* and has an N-terminal signal peptide sequence (Golovan et al., 1999) that seemed optimally adapted for secretion from the parotid gland. Phytase could be expressed in either the pancreas for secretion into the small intestine or it could be expressed in the intestinal epithelial tissue and secreted into the intestinal milieu. However, if these choices of expression locations were chosen, it would be necessary to select an enzyme active at the more neutral pH of the small intestine and one which was more resistant to pancreatic enzymes including trypsin, chymotrypsin and elastase.

Factors of importance in terms of the expressed enzyme when selecting a phytase for expression in the gastrointestinal tract include a pH that is optimum for activity, high catalytic activity, broad substrate specificity, and protease resistance. If any of these properties, or indeed others, is not acceptable, there are now sophisticated molecular methods for modifying the properties of an enzyme. These include site directed mutagenesis, random mutagenesis and various modifications of DNA shuffling (Harayarna, 1998; Crameri et al., 1998).

Synthesis of phytase in the salivary gland and secretion in the saliva would, therefore, provide for early contact of the enzyme with phytic acid present in the feed and provide sufficient time for hydrolysis.

The salivary gland system of the pig consists of three pairs of glands, the parotid gland, which secretes through a duct on each cheek, and mandibular and submaxillary glands that have joint ducts that secrete beneath the front on the tongue. Saliva secreted in the pig via these ducts is discontinuous and is produced during consumption of solid foods, and can equal the weight of food consumed when water is limited during feed consumption (Corring, 1980; Arkhipovets, 1956). For example, the quantity of saliva produced by a 45 kg pig can vary from near zero when the pig receives a mainly liquid diet to 500 g when a dry diet is consumed without access to water. The salivary glands of the pig secrete amylase (Rozhkov and Galimov, 1990) and a variety of other salivary proteins and mucopolysaccharides.

To our knowledge no porcine genes coding for salivary proteins have been cloned. However, genes coding for major proteins secreted by the rat and mouse have been cloned and characterized. A multigene family encoding a group of unique proteins high in proline, the so-called proline-rich proteins (PRPs) are produced when either mice or rats consume tannins or are injected with isoproterenol.

It would be advantageous to develop an animal that is transformed to express phytase, preferably in the salivary gland. In such case, the phytate naturally occurring in the animal feed can be utilized by the animal without any additives being used. This will decrease the cost of animal production, and furthermore, will avoid polluting the environment with phosphorus. Therefore, the present invention aims to overcome the deficiencies of the prior art relating to increasing phytate utilization and, particularly, to provide transgenic animals which express phytase.

In the production of heterologous proteins by means of recombinant methods, several hurdles have been faced. One such hurdle that is often faced is the lack of required post-translational modification of the expressed protein thereby resulting in a protein that is structurally and/or functionally, different from the desired molecule. Glycosylation is one such post-translational modification that is desired. However, such modification is generally found to occur in more complex mammalian systems. Therefore in one embodiment of the present invention there is provided a method of producing recombinant glycoproteins.

In one embodiment, the present invention provides an animal capable of inducible or constitutive salivary expression of a heterologous protein. To illustrate this, the mouse was chosen as the animal model and the gene constructs used for transformation were created using the rat proline-rich protein (PRP) promoter/enhancer (inducible promoter) and the mouse parotid secretory protein (PSP) promoter/enhancer (constitutive promoter). In this illustration, phytase was used for expression in saliva.

After finding that an inducible phytase could be expressed in the parotid gland of mice the expression of the phytase transgene under the control of the constitutive PSP promoter was then tested. Two mice transgenic for the PSP construct were produced under contract at the University of Alabama.

Following the testing of the mice described above, transgenic pigs were developed by introduction into the genome a phytase transgene consisting of a constitutive promoter driving the synthesis of a highly active phytase. The pigs so generated were found to excrete less phosphorus in their feces than non-transgenic pigs.

Expression in the Salivary Glands

Saliva is a clear colorless fluid secreted by major salivary glands (parotid, submandibular, sublingual and minor salivary) that lubricates and cleans the oral structure, as well as initiates the process of digestion. The parotid glands are two of six major glands associated with the production of saliva. The parotid gland is composed mainly of two cell types: acinar and interglobular duct cells. The acinar cells, which represent 75 to 85% of the tissue, are the sites of secretory protein synthesis (Frandson and Spurgeon 1992). Two very abundant proteins are produced by these cells: α-amylase (AMY-1) (2% of polyA RNA) (Madsen and Hjorth 1985), and parotid secretory protein (PSP) (10% of polyA RNA) (Shaw and Schibler 1986). Several constructs are now available which allow tissue-specific expression of a transgene in the salivary glands of mice.

The salivary secretion in pigs has not received the attention given to that of mice and humans. It was suggested that salivary secretion is discontinuous (less secreted between periods of meal consumption). Up to 500 g of saliva may be secreted by a 45 kg pig upon consumption of 500 g of dry feed (Corring 1980). Wide variations were detected in both the flow rate and electrolytes in saliva between animals and even between samples taken from the same animal on separate days (Tryon and Bibby 1966). Very little is known about the composition of pig's saliva or salivary enzymes. Salivary amylase was detected, although the quantity was 250 000 times less than that of pancreatic amylase, and 100 times less than in human saliva (Low 1989). There are no constructs known which would allow salivary gland-specific expression of transgene in pigs.

I) APPA Gene Under Control of an Inducible Promoter

1) Construction of R15/APPA constructs (Inducible Promoter)

In this process, a plasmid is constructed by linking a promoter/enhancer for a saliva protein with the APPA gene, which codes for the bifunctional phytase, acid phosphatase. The APPA gene used in this construction was cloned from *E. coli* ATCC 33965 into pBR322. This is described above (Golovan et al., 2000).

Proteins, unusually high in proline, the so-called proline-rich proteins (PRPs), comprise about 70% of the total proteins in human saliva (Bennick 1982). Unlike the constitutive expression of the PRPs in humans, the salivary glands of mice, rats and hamster normally either do not express PRPs or express them in low levels. In the rat and mouse, PRP gene expression can be dramatically induced by diets high in tannins or by injection with the β-agonist isoproterenol (Carlson 1993). After 6 to 10 days of daily isoproterenol injection the PRPs comprised about 70% of the total soluble protein in parotid gland extracts. PRP cDNA and PRP genes have been cloned and characterized from rats (Clements et al. 1985), mice (Ann and Carlson 1985), hamsters (Mehansho et al. 1987), and humans (Kim and Maeda 1986).

Transgenic mice were used to locate the cis-acting DNA elements that are essential for salivary-specific and inducible expression of the rat proline-rich protein gene, R15. It was found that a parotid control region (−6 to −1.7 kb) upstream of the R15 promoter is capable of directing parotid-specific and isoproterenol-inducible expression of a heterologous promoter construct (Tu et al. 1993). The distal −10 to 6 kb region was shown to function as an enhancer, which can increase levels of expression more than 30-fold. The −6 to −1.7 kb region also seems to function as a locus control region (LCR), because it conferred copy number-dependent and chromosomal position-independent expression of a reporter gene in 15 out of 15 independent transgenic mice (Tu, Lazowski, Ehlenfeldt, Wu, Lin, Kousvelari, and Ann 1993).

We obtained the R15-PRP promoter from Dr. D. K. Ann as a plasmid −10R15/CAT, which placed the chloramphenicol acetyltransferase gene (CAT) under control of the inducible R15-PRP promoter. We decided to use the plasmid as a basis for transgene construction (FIG. 1). Due to the absence of complete sequence information about the R15-PRP promoter (only 2 kbp out of 10 kbp was sequenced) we removed the R15-PRP promoter by Xho I digestion (FIG. 1, step 1). Re-ligated plasmid was used as a template for PCR with CAT-ATG and CAT-TAA synthetic primers. The 4.3 kbp $CAT_{PCR}$ fragment had the initiation site of the CAT gene substituted with the optimal eukaryotic initiation sequence (Kozak 1987). The fragment was purified by agarose gel electrophoresis, re-ligated to itself and used to transform *E. coli* (FIG. 1, step 2). The $CAT_{PCR}$ plasmid was digested with Nco I and filled-in using T4 DNA polymerase to generate a blunt end. After that, the $CAT_{PCR}$ fragment was digested with Eco47III and purified by agarose gel electrophoresis (FIG. 1, step 3). Three rare codons in the APPA gene were modified during the sub-cloning steps leading to the construction of the transgene. Specifically, the $Ala_3$ coding sequence was changed from GCG to GCC, the $Pro_{428}$ sequence was changed from CCG to CCC, and the $Ala_{429}$ sequence was changed from GCG to GCT. This modification was made in order to increase the possibility of transcription of the gene in eukaryotic cells. The APPA gene was amplified by PCR using the previously cloned APPA gene from the pBR322/APPA plasmid with the synthetic primers APPA-DRA and APPA-SMA. The 1.3 kbp $APPA_{PCR}$ fragment generated by PCR was digested with Dra I and Sma I and gel-purified (FIG. 1, step 4). $APPA_{PCR}$ and $CAT_{PCR}$ fragments were blunt end ligated to produce CAT/APPA+intron vector (FIG. 1, step 5), which was introduced into a DH5α strain of *E. coli*. The insert orientation was checked by restriction digest with Sal I and EcoR I. The transgene in CAT/APPA+intron was checked by sequencing both strands. To remove the SV40 small t intron the 2.3 kbp APPA/intron/polyA fragment was excised from a plasmid by Xho I and EcoR I digestion (FIG. 1, step 6*a*), gel purified and digested by Dra I (FIG. 1, step 6*b*). The 1.5 kbp (APPA) and 0.2 kbp (polyA) fragments were gel-purified and linked together in three way ligation with $CAT_{PCR}$ digested with Xho I and EcoR I (FIG. 1, step 6*c*). The resulting plasmids CAT/APPA and CAT/APPA+intron were digested with Xho I, gel-purified and re-ligated with R15-PRP promoter digested with Xho I (FIG. 1, step 7). Because of the low efficiency of ligation the whole ligation mixture was used to transform *E. coli*, total plasmid DNA was prepared and run on the agarose gel. Plasmids which were larger than the original CAT/APPA (5.6 kbp) were eluted and re-transformed in *E. coli*. Plasmids with the R15-PRP insert (15 kbp) were identified by electrophoresing DNA from a single colony on an agarose gel. The correct orientation was identified by PCR with R15-UP1 and APPA-DOWN2 synthetic primers. The plasmids R15/APPA and R15/APPA+intron were both digested with Hind III and Kpn I; transgenes were gel-purified and further purified using a Qiagen column (FIG. 1, step 8).

FIG. 18 illustrates the nucleic acid sequence for the plasmid containing the known segment of the R15/APPA+ intron sequence including the vector sequences of pBLCAT3. The sequence of this plasmid is designated as SEQ ID NO:2.

FIG. 19 illustrates the nucleic acid sequence for the transgene construct containing the known segment of the R15/APPA+ intron sequence used for the generation of transgenic mice. The sequence of this transgene is designated as SEQ ID NO:3.

FIG. 20 illustrates the nucleic acid sequence for the plasmid containing the known segment of the R15/APPA sequence including the vector sequences of pBLCAT3. The sequence for this plasmid is designated as SEQ ID NO:4.

Figure 2:
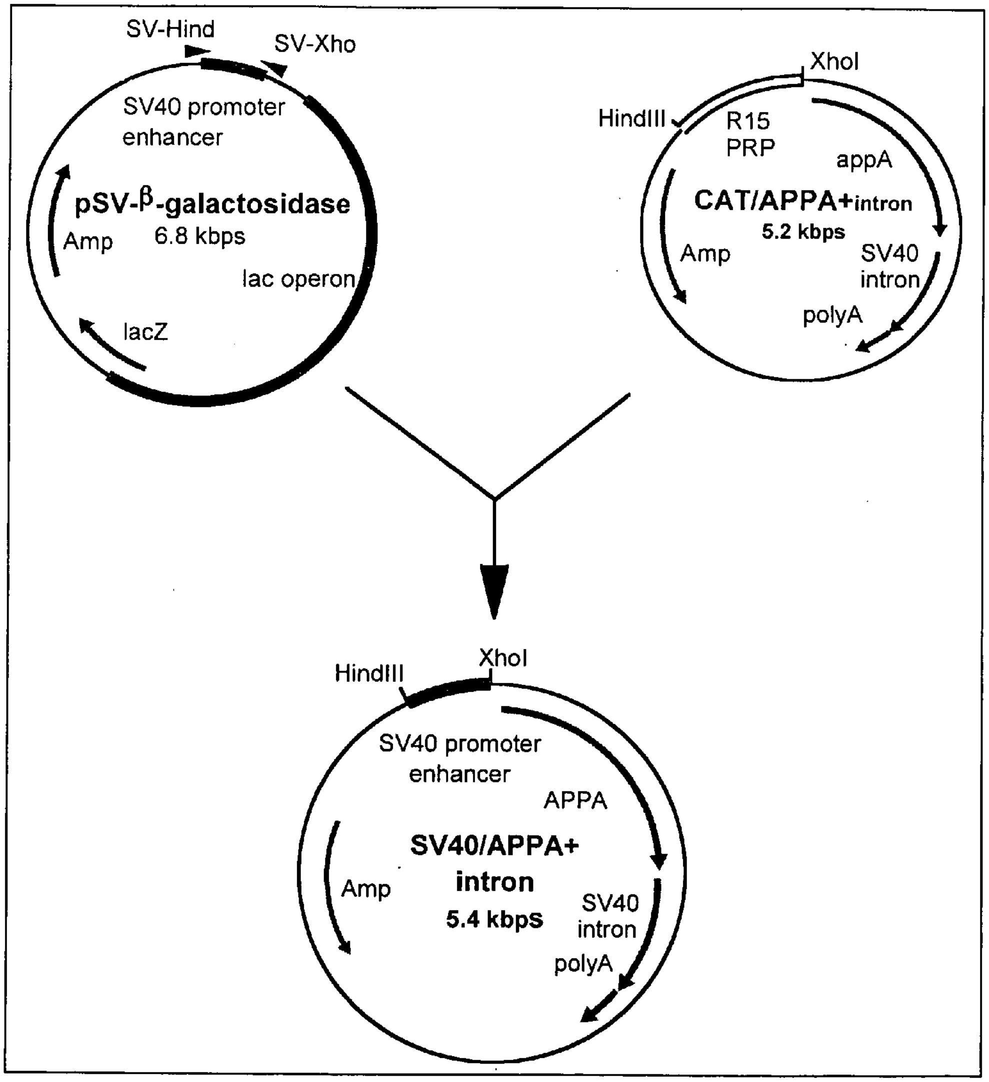
FIG. 2 is a schematic diagram representing a method for producing the gene construct of the present invention containing the SV40 promoter. More specifically.

The pBLCAT3 sequence indicated above is present in the CAT/APPA of FIG. 1 and in the CAT/APPA+intron of FIG. 2. This sequence was part of the original −10R15/CAT and a portion of it was carried through in the construction process.

FIG. 21 illustrates the nucleic acid sequence for the transgene construct containing the known segment of the R15/APPA sequence used for the generation of transgenic mice. The sequence of this transgene is designated as SEQ ID NO:5.

2) Expression of SV40/APPA+intron in Cell Culture

To produce an SV40/APPA plasmid for expression of APPA in cell culture, the SV40 promoter/enhancer was amplified by PCR from the pSV-β-galactosidase plasmid (Promega) using the synthetic primers SV-HIND and SV-XHO. The SV40 promoter/enhancer fragment was digested with Xho I and Hind III, gel purified, and ligated into CAT/APPA digested with Xho I and Hind III (FIG. 2).

FIG. 22 illustrates nucleic acid sequence for the SV40/APPA+intron. The sequence for this plasmid is designated as SEQ ID NO:6.

We obtained a rat parotid acinar cell line PARC 5.8 (Quissell et al. 1998) that we intended to use for transient expression of the phytase transgene. The purpose was to test the efficiency of different constructs for transgene expression and also to detect any deleterious effects of phytase expression before introduction into the animals. We tried transient expression of the APPA gene using R15/APPA and R15/APPA+ intron constructs but because of low transfection efficiency and/or low expression levels, we were unable to detect either phytase or β-galactosidase that we used as a control for transfection.

We exchanged the R15-PRP inducible promoter from the R15/APPA construct with the SV40 constitutive promoter-enhancer, which enables high level transient expression in different cell cultures. CHO, COS7 and HELAi cell lines were screened for transient expression of the APPA phytase using the SV40 promoter/enhancer. All cell lines were maintained on DMEM/F12 (Sigma) cell medium with 10% (wt/vol) heat-inactivated fetal bovine serum at 37° C. in 5% $CO_2$ and 95% air. Cells were grown to 70% confluence before transfection. Two hours before transfection the medium was exchanged with fresh medium. Cells were transformed with 5 μg of DNA per 60 mm culture plate (1:1 SV401APPA and SV40/β-galactosidase) using the DNA-Calcium-Phosphate method of transfection (Gorman et al. 1983). After 6 hours of incubation the medium was removed and cells were subjected to glycerol shock for 3 min (Ausbel et al. 1992). Cells were washed with phosphate-buffered saline (PBS) and incubated in fresh medium under standard growth conditions. After 48 hours of incubation cell-free culture fluid was collected, the cells washed two times with PBS and lysed with 1 ml of 1% (vol/vol) NP-40, 1 mM disodium EDTA in Hanks balanced salts (HBSS) for 1 hour at 4° C. The phytase assay was performed in a final volume of 100 μl of 0.1 M sodium acetate/acetic acid buffer (pH 4.5) using sodium phytate (4 mM) as a substrate at 37° C. After 6 hours of incubation the reaction was stopped with 67 μl ammonium molybdate/ammonium vanadate/nitric acid mixture and the concentration of liberated inorganic phosphate determined at 405 nm (Engelen et al. 1994). One unit (U) of enzyme activity was the amount of the enzyme releasing 1 μmol inorganic phosphate per minute. The assay was performed in triplicate. As a control for endogenous phytase activity, non-transfected cell lines were used.

We did not detect endogenous phytase activity in non-transfected cell lines. Phytase activity was detected in all transfected cell lines, with COS7 cells expressing a total of 0.35 U of phytase in cell-free culture fluid (4 ml) and 0.0034 U in the cell fraction (1.1 ml) obtained from the same plate. The phytase activity produced by COS7 cells was 7 times higher than that of CHO and 35 times more than the HELA cell line. More than 99% of activity was located in cell-free culture fluid, which suggests that the expressed enzyme was exported out of the cell using the bacterial signal sequence. We were unable to detect expression of cytoplasmic β-galactosidase, which we wanted to use as a control for transfection efficiency.

3) Expression of R15-PRP/APPA in Transgenic Mice

Transgenic mice were generated using the constructs R15/APPA and R15/APPA+ intron by Dr. C. A. Pinkert at the NICHD Transgenic Mouse Development Facility (NTMDF), University of Alabama at Birmingham, Ala. The procedures followed in generating the mice have been standardized by the NTMDF and further information concerning this can be obtained at: transgenics.bhs.uab.edu/page1.htm, the content of which is incorporated herein by reference. This procedure involved the microinjection technique for transfecting mice with the desired nucleic acid sequence. To summarize, the sequences are microinjected into mouse zygotes and the surviving eggs are implanted into pseudopregnant recipient mice. The recipient mice then give birth to the resulting founder transgenic mice. It will be appreciated that various other methods of generating transgenic mice may be used in the present invention.

The R15/APPA transgene in mice was detected by PCR using the primers CAT-UP1 and APPA-DOWN2 that gives rise to a 700 bp fragment using the standard PCR conditions, except that the hybridization step was set at 51° C. for 40 seconds and the polymerization step was at 72° C. for one minute.

For the R15/APPA construct 8 PCR positive founder mice were obtained of which 4 were males and 4 were females. Three of the founders did not pass the transgene to progeny and were probably mosaics. For R15/APPA+ intron 5 PCR positive founder mice were obtained, 3 were males and 2 were females, and one of them was found to be mosaic. At 10 to 12 weeks of age PRP production in the PCR positive progeny from different lines was induced for 10 days by daily intraperitoneal (ip) injection of 1 mg isoproterenol dissolved in 100 μl sterile saline. To serve as a control several PCR negative progeny were also induced. No significant differences in weight were noticed between PCR positive and PCR negative progeny at either the beginning or end of the induction period. Saliva was collected before induction and at the end of the 10 day induction period.

To collect saliva, mice were lightly anesthetized with a ketamine/xylazine mixture (ip injection of 50 mg ketamine and 5 mg xylazine per kg body weight diluted in water) and saliva flow was induced by injection with pilocarpine/ isoproterenol (ip injection of 0.5 mg pilocarpine and 2 mg isoproterenol per kg body weight dissolved in saline) (Hu et al. 1992). Between 100–250 μl of saliva was collected from each mouse over a 30 min period beginning 5 min after the pilocarpine/isoproterenol injection.

The saliva was collected from each mouse by holding it in one hand and withdrawing saliva from the corner of the mouth with a 20 μl pipetter. Collected saliva was transferred to a cold Eppendorf microcentrifuge tube containing 2 μl of 0.5 M EDTA (pH 8.0) and 4 μl of 10 mg/ml protease inhibitor Pefabloc (Boehringer Mannheim) dissolved in water. The tubes with saliva were kept on ice until assays were conducted. Phytase activity in the saliva was assayed as described for the SV40/APPA expressed in cell culture.

Phytase expression was not detected in either un-induced or in induced PCR negative mice. For PCR positive mice, phytase expression was not detected in those that were un-induced. However, phytase expression was observed for PCR positive mice that were induced. The results of this study are summarized in Table 1.

Even though it was possible to distinguish saliva from induced PCR positive from that of PCR negative mice in a phytase assay by a characteristic yellow color, saliva from some of the negative mice, when assayed, produced cloudiness that was impossible to remove by centrifugation and that affected spectrophotometer readings. We did not notice any gender differences in expression, both males and females were found to produce phytase in saliva. In three lines (all R15/APPA+intron) no phytase expression or very low level of expression (0.03–0.95 U/ml) was detected, in 4 lines the level of expression ranged from 7 to 87 U/ml, and two lines (both R15/APPA) produced very high levels of phytase in saliva, 252 and 547 U/ml.

These experiments demonstrated that phytase can be expressed at a very high level in the salivary glands of mice without detrimental effects on the animals. We also were able to produce progeny with an inducible salivary phytase from animals expressing the inducible phytase thereby documenting inheritance of the trait, and showing that the reproductive capability of animals was not affected. When the F2 generation of mice were tested for salivary phytase the level of phytase production was preserved.

Founders containing the transgene without the intron gave offspring that produced significantly higher levels of phytase. The SV40 intron in the R15/APPA+intron construct seems to cause a lower level of expression, and in three lines (A1f, A20f and B0m) the level of phytase was barely detectable. The level of phytase expression in A2m line (R15/APPA+intron) was 6.2 times lower than that of the BOm-intron line (R15/APPA).

Preliminary experiments showed that when the enzyme was analyzed by PAGE its size was increased from 42 kDa to 60 kDa. It is likely modified by glycosylation, but stable and active.

II) APPA Gene Under Control of a Constitutive Promoter

1) Construction of the Lama2/APPA Transgene (Constitutive Promoter)

The murine parotid secretory protein (PSP) is the most abundantly expressed protein in the parotid gland of mice (Madsen and Hjorth 1985). After an hour of pulse labeling, the mouse parotid gland incorporates 65 to 85% of $^{14}C$-leucine into this single protein (Owerbach and Hjorth 1980). It was estimated that PSP mRNA accumulates up to 50,000 molecules per cell and that from 3 to 5 molecules of PSP are produced for every molecule of amylase (Madsen and Hjorth 1985). Despite the predominance of the PSP in saliva its function is not well characterized.

The single-copy gene coding for PSP has been cloned and characterized. It has two alleles $PSP^a$ (Shaw and Schibler 1986) and $PSP^b$ (Owerbach and Hjorth 1980). The $PSP^b$ allele is also expressed in the sublingual gland, but at 1/10 of the level found in the parotid gland. It was shown that 4.6 kbp of 5' flanking sequence of $PSP^b$ is sufficient for salivary gland specific expression. The level of sublingual expression approached 100% of the PSP mRNA level, whereas the parotid expression did not exceed 1% (Mikkelsen et al. 1992), which demonstrates that regulatory sequences for sublingual and parotid expression are not identical. The level of expression was also dependent on the site of integration. The same construct was used for expression of the C-terminal chain of the human blood coagulation factor VIII, FVIII. A high level of FVIII mRNA was detected in the sublingual gland and a low level in the parotid gland. The transgenic lines also secreted the FVIII light chain into saliva at the level of about 10 units per salivation (about 0.05 ml of saliva) (Mikkelsen et al., 1992). Later the same group achieved a high level of parotid-specific expression that was similar or even exceeded that of the endogenous gene by using 11.4 kbp of 5' flanking sequences and 2.5 kbp of 3' flanking sequences (Larsen et al. 1994). The expression also seems to be position-independent and copy-number-dependent that could indicate the presence of a LCR in these sequences.

Lama 2 is a portion of the PSP gene and comprises an 18 kbp construct that is expressed in transgenic mice at up to 56% of the endogenous PSP gene.

Figure 3:
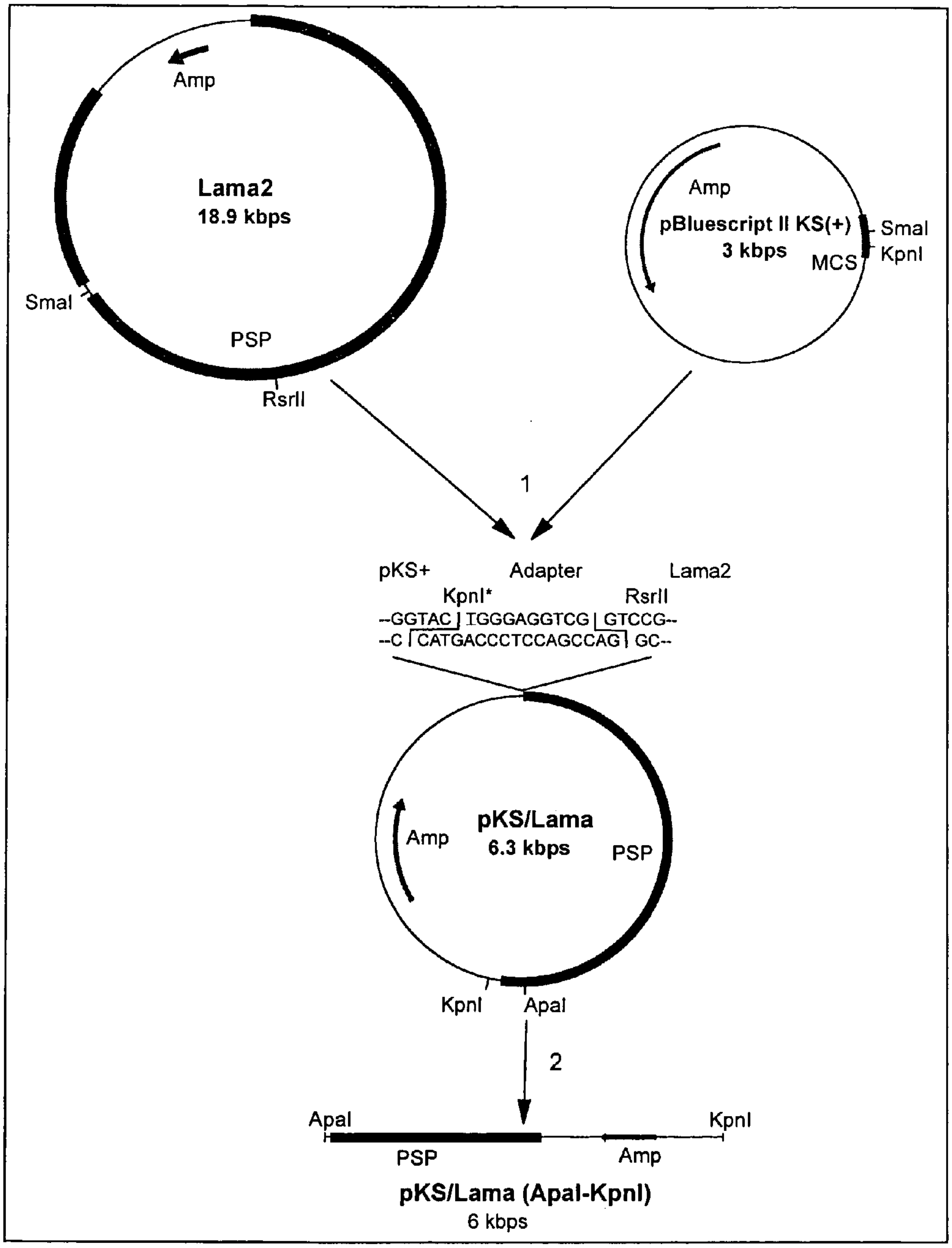
FIG. 3 is a schematic diagram representing a method for producing the gene construct of the present invention containing the constitutive parotid secretory protein (PSP) promoter/enhancer. More specifically.
Figure 3A:
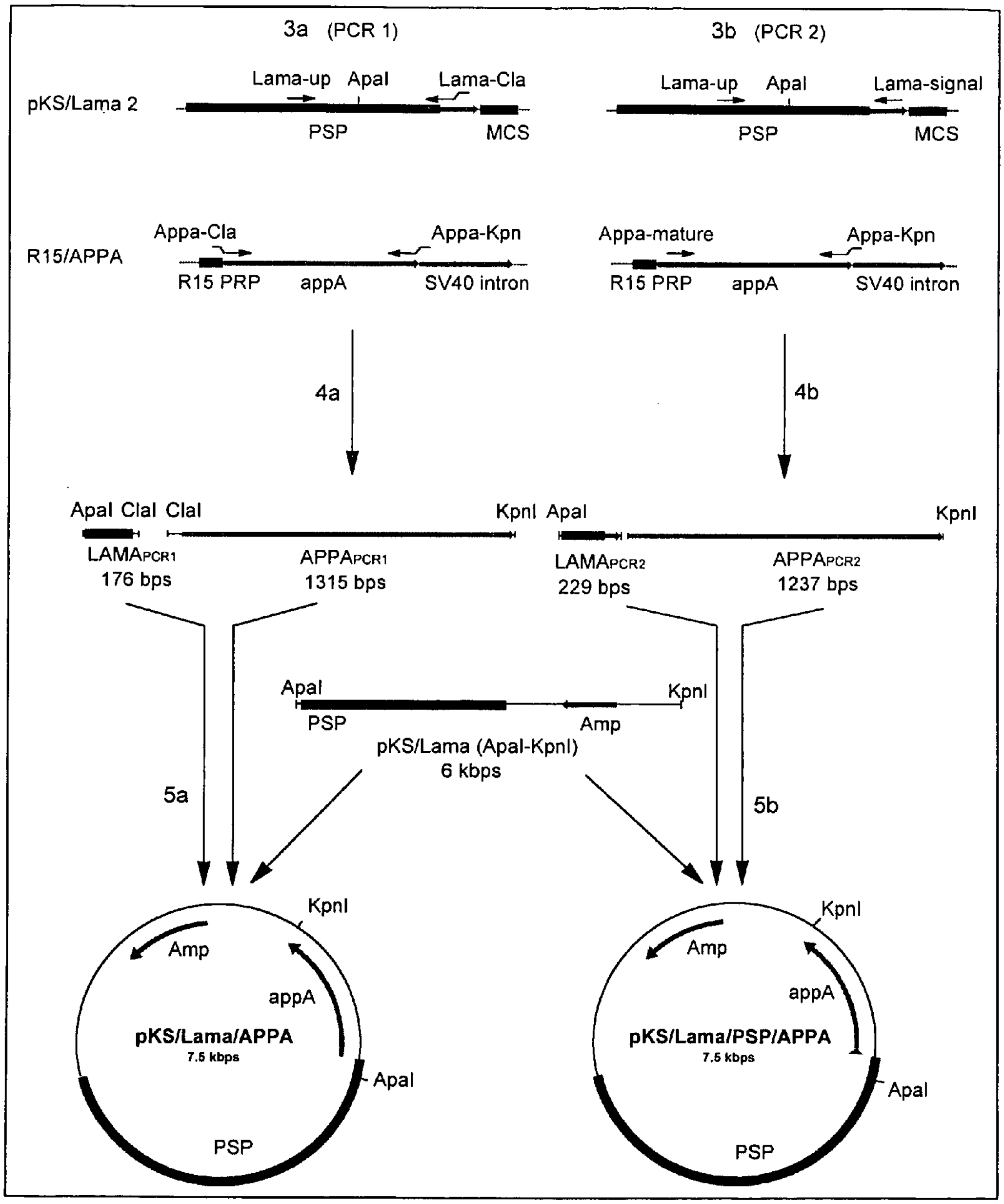
Figure 3B:
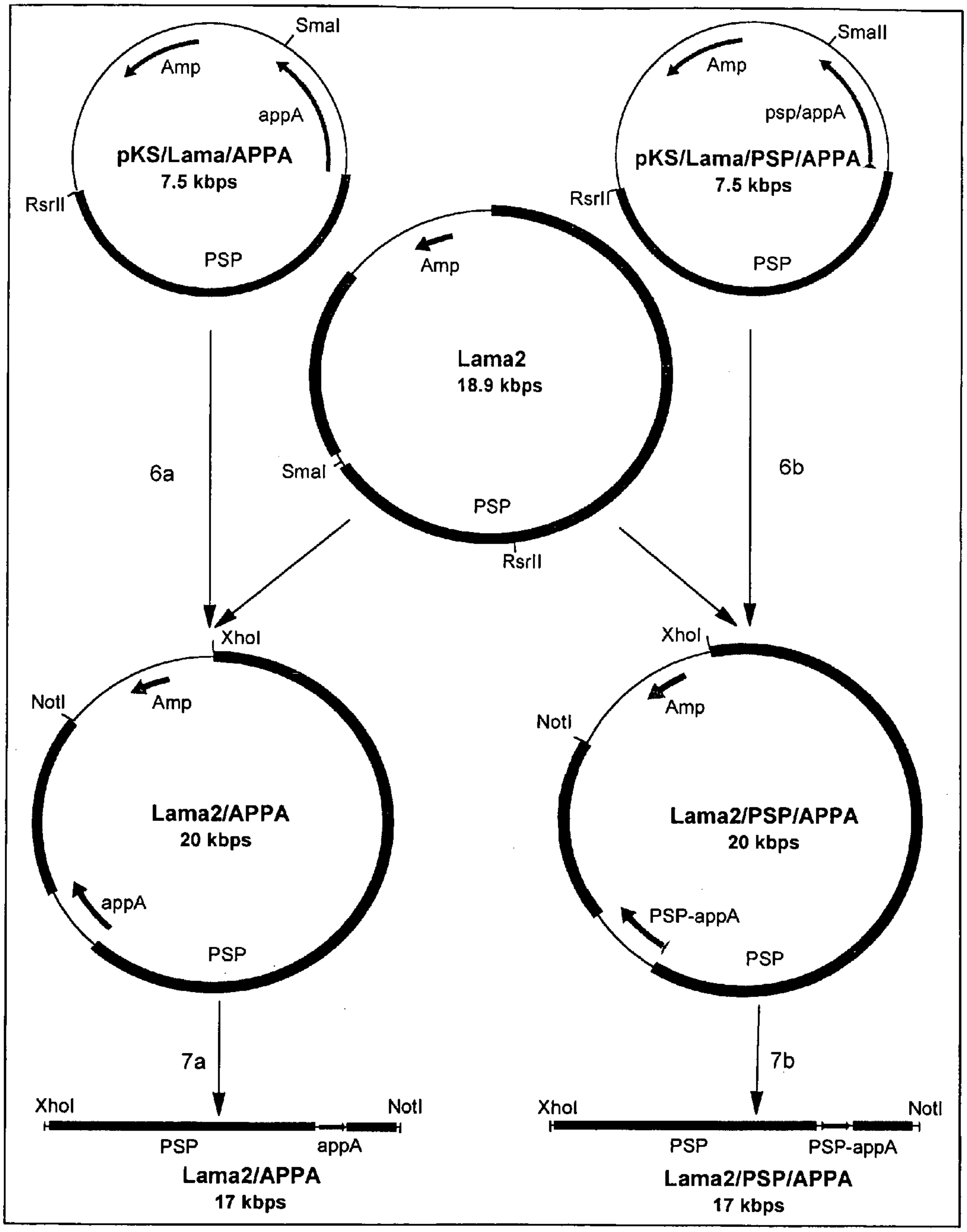

Because a large part of Lama 2 had not been sequenced, the construct was first disassembled and subcloned into pBluescript KS(+) and after incorporation of the APPA gene, the Lama 2 was reassembled back (FIG. 3). We used unique enzymes RsrII and Sma1 to remove a 3.4 kbp fragment from Lama2, which was subcloned into the multiple cloning site (MCS) of pBluescript II KS(+) that was previously digested with Kpn1 and Sma1, using a Kpn1-Rsril adapter (FIG. 3, step 1).

KpnI* RsrII
TGGGAGGTCG (SEQ ID NO: 8)
CATGACCCTCCAGCCAG (SEQ ID NO: 9)

That allowed us to preserve the RsrII (CG/GWCCG) (SEQ ID NO: 10) site and destroy the Kpn1 site (GGTAC/C (SEQ ID NO: 11)>GGTAC/T (SEQ ID NO: 12)), which would otherwise interfere with future cloning. The pKS/Lama construct was digested with Apa1 and Kpn1 and used in a three-way ligation with the modified APPA (FIG. 3, step 2). We designed two PSP/APPA constructs. One construct APPA-signal/APPA (FIG. 3, steps 3*a*–7*a*) had the original bacterial signal sequence from the APPA protein having the following amino acid sequence:

Met-Lys-Ala-Ile-Leu-Ile-Pro-Phe-Leu-Ser-Leu-Leu-Ile-Pro-Leu-Thr-Pro-Gln-Ser-Ala-Phe-Ala (SEQ ID NO: 13)

We also modified a sequence near the ATG codon to resemble the optimal mammalian Kozak sequence (GCC GCC A/GCC ATG G) (SEQ ID NO: 14) (Kozak 1987), but we did not mutagenize the +4 position because it would change Lys to Glu in the signal sequence with possible deleterious consequences for protein export. This optimized sequence was used in our previous construct R15/APPA and led to high levels of phytase production. We checked the APPA bacterial signal sequence using the PSORT computer neural network trained on eukaryotic signal sequences and further described at http://psort.nibb.ac.jp:8800/(Nakai and Kanehisa 1992). The APPA bacterial signal sequence was recognized as an efficient leader peptide and the cleavage site was correctly predicted. PSORT also predicted that there is a high probability that phytase would be exported correctly outside of the cell. There were also publications showing that some bacterial signal sequences might function efficiently in mammalian cells (Williamson et al. 1994) (Hall et al. 1990). Our experiments using cell culture demonstrated that the APPA signal was correctly processed with export of phytase outside of the cell.

Experiments using cell culture cannot predict the direction of export and if phytase were exported into blood vessels instead of salivary ducts that could lead to deleterious effects. That is why we also designed a second construct PSP-signal/APPA (FIG. 3, steps 3*b*–7*b*) that would preserve the original PSP signal amino acid sequence:

Met-Phe-Gln-Leu-Gly-Ser-Leu-Val-Val-Leu-Cys-Gly-Leu-Leu-Ile-Gly-Asn-Ser-Glu-Ser (SEQ ID NO: 15).

This leader peptide was also efficiently recognized by PSORT with the correct cleavage site (Nakai and Kanehisa 1992). In this construct we also preserved the original PSP sequences near the ATG start codons, which may not be optimal, but could be important in regulation of gene expression. The APPA gene for both constructs was amplified by PCR using as the template our previous transgenic construct R15/APPA that possessed the optimal Kozak sequence and the modified codons for residues Ala3, Pro428 and Ala429 as described earlier. For the APPA signal/APPA construct two synthetic primers were used which introduced a Cla1 site near the ATG codon (APPA-CLA) and a Kpn1 site near the TAA stop codon (APPA-KPN). The $APPA_{PCR}1$ product was digested with Cla1 and Kpn1. The Cla1 site was also introduced into Lama 2 using pKS/Lama 2 as template for PCR. LAMA-UP primer was located upstream of Apa1 site and the LAMA-CLA primer introduced the Cla1 site near ATG codon (FIG. 3, step 3*a*). $Lama_{PCR}1$ product was digested with Cla1 and Apa1 (FIG. 3, step 4*a*). pKS/Lama (Apa1-Kpn1), $Lama_{PCR}1$ (Apa1-Cla1) and $APPA_{PCR}1$ (Cla1-Kpn1) were combined together in a three-way ligation reaction (FIG. 3, step 5*a*). The recovered pKS/Lama/APPA plasmid was digested with RsrII, Sma1 and inserted back into Lama2 (FIG. 3, step 6*a*).

For the PSPsignal/APPA construct, the synthetic APPA-KPN primer was used with the synthetic APPA-MATURE primer, which produced phytase without a signal sequence. The $APPA_{PCR}2$ product was blunt-ended using T4 DNA polymerase and digested with Kpn1. The PSP signal sequence was produced using the LAMA-UP and LAMA-SIGNAL primer (FIG. 3, step 3*b*). The $Lama_{PCR}2$ was blunt-ended using T4 DNA polymerase and digested with Apa1 (FIG. 3, step 4*b*). pKS/Lama (Apa1-Kpn1), $Lama_{PCR}2$ (Apa1-blunt) and $APPA_{PCR}2$ (blunt-Kpn1) were combined together in a three-way ligation reaction (FIG. 3, step 5*b*). The recovered pKS/Lama/APPA plasmid was digested with RsrII, Sma1 and inserted back into Lama2 (FIG. 3, step 6*b*).

Even though both constructs were successfully produced we decided to use Lama2/APPAsignal/APPA for the generation of transgenic mice, because we have results from our previous transgenic constructs R15/APPA and R1S/APPA+ intron which demonstrated that phytase with optimized Kozak sequence and the APPA signal peptide was synthesized at a high level in salivary glands after induction and was efficiently exported into the salivary duct. The Lama2/APPA vector was digested with XhoI and NotI, and the transgene was gel-purified and further purified using a Qiagen column (FIG. 3, step 7*a*).

2) Sequence of the Lama2/APPA Construct

A large segment of the Lama2 construct (Laursen and Hjorth 1997) used for construction of the Lama2-APPA transgene had not been reported in GenBank prior to our research. To ensure that we could more clearly describe the transgene construct, and furthermore to avoid the introduction of deleterious DNA sequences from the mouse into the pig in the process of generating transgenic pigs, we sequenced the Lama2-APPA plasmid on both strands. FIG. 4 illustrates schematically the structure of the Lama2-APPA plasmid. FIG. 5 illustrates the nucleic acid sequence (SEQ ID NO:1) of such plasmid. The full transgene sequence was reconstructed from overlapping DNA sequences using the Contig Assembly Program (CAP) developed by Huang (1996; 1999) and then inspected manually for sequencing errors. The transgene sequence was checked for the presence of interspersed repetitive elements using the computer program RepeatMasker (Smith and Green, RepeatMasker). It was found that 26% of the transgene sequence was composed of repetitive elements (Table 2). However, such repetitive elements are widely present in all mammalian genomes. For example, up to 50% of the human genome is derived from repetitive elements (Smit 1996; Kazazian 1998).

FIG. 23 illustrates the nucleic acid sequence (SEQ ID NO:7) of the Lama2/APPA transgene construct.

The Lama2 high level expression cassette (Laursen and Hjorth 1997) contains the enhancer region and the promoter of the Psp gene in the parotid gland. High expression was shown to be dependent on regulatory elements between −11.5 kb and −6.5 kb and/or between +8.3 kb and +10.9 kb. Svendsen et al. (1998a) showed that a 1.5 kb sequence between −3.1 kb and −4.6 kb had properties of a parotid and sublingual specific enhancer and was designated as the PSP proximal enhancer. Furthermore, they showed that transgenes containing the PSP promoter and 5' flanking region located between −3.6 kb and −4.3 kb contained sequence information necessary to direct salivary gland specific expression.

Screening the transgene with RepeatMasker did not reveal the presence of any full-length active autonomous elements. The repeats present were extensively modified by insertions and deletions. The blastx program was also used to compare the transgene sequence translated in all reading frames against the National Center for Biotechnology Information (NCBI) protein sequence database (ncbi.nlm.nih.gov/BLAST/) (Altschul et al. 1990; Gish and States 1993; Terada and Nakanuma 1993). A region of DNA from 861 to 2180 was found that might code for parts of a protein with limited homology (38–58% identities) to the C-terminus of several human and mouse reverse transcriptases. However, the region was extensively modified by mutations with multiple frame shifts and inversions, and probably represented remnants left from the reverse transcriptase gene of a LINE element. It is unlikely that it would be active, due to extensive modifications in the amino acid sequence such that only 18% of the full reverse transcriptase sequence was present and the highly conserved amino acid motif (Y/FXDD) was absent from the sequence (Xiong and Eickbush 1990). The complete sequence was also scanned for the presence of open reading frames (ORFs) that code for proteins using the program GENSCAN (http://CCR-081.mit.edu/GENSCAN.html) (Burge and Karlin 1997). Only one gene was found and it corresponded to the APPA phytase gene. GENSCAN unexpectedly predicted a different N-terminus for the phytase than would have been expected from the sequence. However, that could have resulted from the lower accuracy of GENSCAN for detecting initiation sites (Burge and Karlin 1998).

3) Generation of Transgenic Mice Expressing a Constitutive Salivary Phytase In the following description, a pair of founder mice, incorporating the phytase gene and a constitutive promoter, were prepared under contract by the University of Alabama. As will be discussed, these founders were used to produce offspring, which were then analyzed for the presence of the phytase gene by PCR and animals containing the gene were then tested constitutive salivary phytase production.

Two transgenic founder mice (a black male and a white female, 3-1) containing the phytase transgene were received from the NICHD Transgenic Mouse Development Facility at the University of Alabama. The black male was negative for salivary phytase, but the female, 3-1, exhibited a salivary phytase activity of 30 U/ml. Progeny produced by crossing the black male with 4 CD-1 females produced 9 out of 25 females and 13 out of 26 males that were PCR positive. All progeny were negative for salivary phytase. The female founder, 3-1, was out-crossed with a CD-1 male to produce 3 litters for a total of 35 offspring. Of the progeny from these matings one phytase positive G1 male was obtained. When the G1 male was outcrossed with 6 CD-1 females, of the 6 litters 20/34 males were PCR positive and salivary phytase positive and 21/28 females were PCR positive and salivary phytase positive (Table 3) The salivary phytase activity of different offspring from the same first generation (G1) male ranged from 1.3 to 71.2 U/ml. There was no significant difference in the phytase activities between male or female mice.

Figure 6:
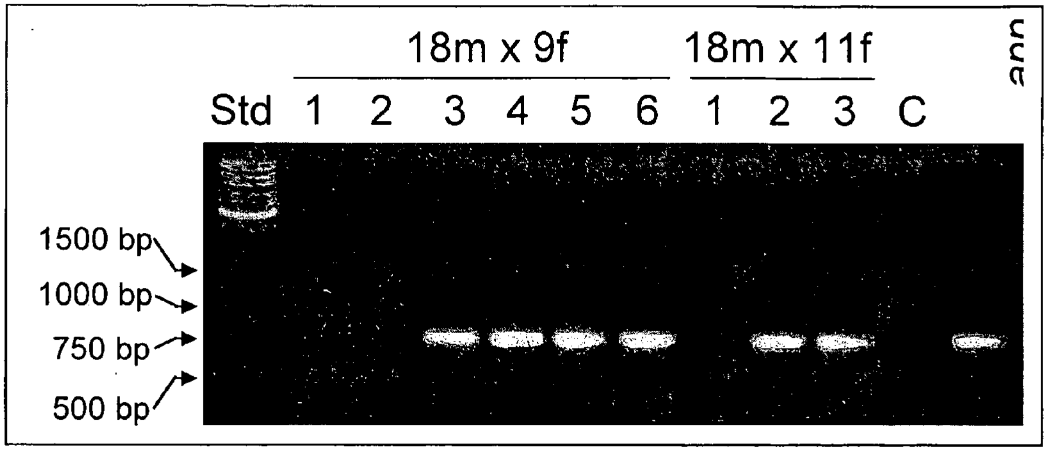
FIG. 6 illustrates the PCR results for transformed mice. More specifically.

PCR assays for identification of the transgenic mice were carried out with an initial heating step at 95° C. for 3 min, 40 cycles using 95° C. for 30 sec, 54° C. for 30 sec and 72° C. for 1 min) using the following primers: APPA-UP2 and APPA-KPN (FIG. 6).

The phytase assays were conducted as described above for the R15-PRP/APPA phytase expressed in cell culture.

4) Production of Transgenic Pigs Containing the Phytase Transgene Lama 2/APPA Transgenic pigs were produced using Yorkshire and Yorkshire/Landrace cross gilts as the embryo donors and Yorkshire sows as the recipients. The experimental procedure used was similar to that described by Wall et al. (1985). The detailed procedure is described below. The Lama2/APPA construct with the APPA signal peptide was used as the transgene for microinjection.

Methodology for the Generation of Transgenic Pigs

The following is a description of the preferred method of generating transgenic pigs according to the invention. However, it will be apparent to those skilled in the art that various other methods are also applicable.

a) Superovulation of prepuberal Gilts and Sows.

Selected Yorkshire or Yorkshire/Landrace cross gilts between 70 to 80 kg were superovulated by intramuscular injection of 2000 IU of pregnant mare's serum gonadotropin (PMSG, Ayerst Veterinary Laboratories), followed by 700 IU human chorionic gonadotropin (HCG, Ayerst Veterinary Laboratories) 60 to 72 hours later, administered in the same manner. The gilts were artificially inseminated three times with a 16 hour interval between inseminations using semen from a high breeding index Yorkshire boar. Twenty-four hours after the last insemination, the gilts were slaughtered and the reproductive tract recovered.

B) Synchronization of Estrus in Recipients

Estrus was synchronized in experienced recipient sows as described for donor sows. Since synchronization and not superovulation was the goal, hormone levels were reduced to 500 IU for PSMG and 500 IU for HCG. PMSG was given the day the sow's litter was weaned, followed in 72 hours by HCG and surgery for embryo transfer was performed 54 hours thereafter.

c) Embryo Collection

Reproductive tracts were collected at the abattoir, inserted into bags, sealed and the bags immersed in water at 39° C. for transport to the laboratory. Recovery of the embryos and microinjection with the transgene was conducted in a laboratory maintained at 32 to 33° C. The oviducts were dissected from the tracts and flushed, using a syringe and a feeding tube, with 15 ml of pre-warmed HBECM-3 medium (Dobrinsky et al. 1996). The media was collected in a 100 mm Petri dish and placed in an incubator at 38.5° C. with an atmosphere of 5% (vol/vol) of $CO_2$, 5% (vol/vol) $O_2$ and the balance $N_2$. After all tracts were flushed, embryos were individually collected from the flushed media using a polished transfer pipette. Embryos were rinsed twice in 3 ml volumes of pre-incubated BECM-3 and placed in 100 μl of pre-incubated BECM-3 under 3 ml of filter sterilized mineral oil until injected.

d) Pronuclear Injection

Embryos from one gilt were collected and placed in one ml of pre-warmed HBECM-3 in a 1.5 ml centrifuge tube and centrifuged for 6 min at 14,000×g (Wall et al. 1985). The embryos were then collected and placed in an injection dish with 40 μl of pre-warmed HBECM-3 covered with 2.5 ml of filter sterilized mineral oil. The pronucleus in each embryo was injected (Gordon et al. 1980) with three picolitres of Lama2/APPA DNA in solution at a concentration of 5 ng of DNA per μl in 10 mM Tris, pH 7.5, 0.1 mM EDTA. After injection, the embryos were placed in dishes containing 100 μl of pre-incubated BECM-3 under 3 ml of filter sterilized mineral oil. After all embryos were injected, which took no more than 4 hours since collection of reproductive tracts, the embryos were transferred to 1.8 ml cryotube (Nunc) containing 1 ml of pre-warmed HBECM-3 and transported in an incubator at 38.5° C. to the swine surgery.

e) Embryo Transfer

Recipient sows were anesthetized by intravenous injection of 500 mg Brietol and anesthesia maintained by inhalation of 3% halothane with 4 liters per min of nitrous oxide and 4 liters per min oxygen. The oviducts were exposed through a laparotomy, just off the dorsal midline, and a catheter, containing 20 to 35 injected embryos and 3 to 6 untreated embryos, was passed into the infindibulum and down the oviduct to the isthmus and emptied. The oviduct was returned to the abdominal cavity and the incision closed.

f) Growth of Pigs

New-born piglets were kept together until weaning. At that time males and females were separated and penned with non-transgenic same sex pigs of a similar age from other litters. The pigs are fed ad libitum starter rations until 25 kg wt, grower diet from 25 to 60 kg wt and finisher diet from 60 kg to market weight. Water is available ad libitum. Transgenic pigs 167-02, 282-02 and 282-04 were maintained on a low phytate ration until 85, 50, and 50 days of age, respectively, and then switched to the grower ration. All other transgenic pigs were given the standard high phosphorus diets.

The diets were provided as pelleted formulations during the weanling, grower and finishing phases are shown in Tables 4 and 5. The vitamin and mineral mixes included in the diets are shown in Tables 6 and 7.

PCR Analysis

Tail segments from newborn piglets were collected and slices of each placed in 600 µl of 50 mM NaOH and heating at for 95° C. for 15 minutes. The suspension was neutralized with 50 µl of 1 M Tris (pH 8.0) and insoluble materials removed by centrifugation for 5 min in a microcentrifuge. A 2 µl sample of each was used for PCR with primers APPA-UP2 and APPA-KPN.

The primers produce a 750 bp fragment if the transgene is present. As a positive control PIG-BGF and PIG-BGR primers were used to detect the porcine β-globin gene from the same DNA preparation (Heneine and Switzer 1996). The PCR reaction was performed using the same conditions as described for detection of the phytase transgene. As a negative control genomic DNA from a non-transgenic pig was used in the PCR reaction, for a positive control this DNA was spiked with a known amount of transgene (I gene copy/per genome).

When a positive signal was identified by PCR for pig 167-02 (FIG. 3) another DNA preparation was made and two more pairs of PCR primers were used to test for gene integrity (FIG. 4) APPA-MATURE with APPA-KPN, and APPA-MATURE with APPA-DOWN2

PCR conditions were similar to those described previously.

Extraction of DNA from Blood for PCR Analysis

The method for extraction of DNA from blood was based on a method described by Higuchi (1989) with some modifications. A 100 µl volume of whole blood was mixed with 200 µl of lysis buffer (10 mM Tris-HCl, 0.32 M sucrose, 5 mM $MgCl_2$, 1% (vol/vol) Triton X-100, pH 7.5.), mixed briefly and incubated on ice for 5 min. The sample was then centrifuged at 14,000×G for 3 min, and the supernate discarded. The sediment was suspended in lysis buffer, mixed, incubated and centrifuged. This procedure was repeated 2 more times, or until no hemoglobin remained. The sediment was dissociated in 100 µl of 50 mM NaOH, mixed and heated at 100° C. for 10 min. The contents were cooled, 10 µl of 1 M Tris-HCl (pH 8.5) added and mixed briefly. The sample was then centrifuged at 14,000×g for 2 min and 2 µl of the supernate used for analysis by PCR.

The PCR reaction mixture with a total volume of 40 µl consisted of; 23.8 µl of distilled water, 4 µl of 10× Gibco BRL PCR buffer, 1.2 µl of 50 mM $MgCl_2$, 0.8 µl of 10 mM dNTPs, 40 pmol of each of the forward and reverse primers in 8 µl, 2 µl of template DNA and 0.2 µl of Taq DNA polymerase (Gibco BRL, 5 U/µl). The amplification procedure was performed with an initial heating step at 95° C. for 3 min followed by 40 cycles of 95° C. for 30 sec, 54° C. for 30 sec and 72° C. for 60 sec.

The transgenic pigs were detected with primers for the APPA gene (APPA-KPN with APPA-UP2), and as a control PIG-BGF with PIG-BGR primers were used for detection of the porcine β-globin gene.

Saliva Collection from Pigs for Phytase Assays and Weighing of Pigs

Weanling pigs were sampled for salivary phytase by wiping under the tongue with a cotton tipped applicator, breaking the stick off and centrifuging the applicator tip in a 0.4 ml microcentrifuge tube, with a hole in the bottom, contained within a 1.5 ml microcentrifuge tube. Grower and finishing pigs were sampled using 1.5 inch long #2 dental cotton absorbent rolls (Ash Temple Sundries Ltd, Don Mills, ON) attached to dental floss. These were centrifuged in 1.5 ml microcentrifuge tubes with holes in the bottom while contained in larger tubes. The saliva was collected from the larger tube and stored at −20° C. until analyzed.

Saliva was collected and pigs were weighed at weekly intervals.

Analysis for Phytase Activity.

Saliva samples were either assayed directly or after dilution in 0.1 M acetate buffer pH 4.5. Phytase was assayed in 200 µl of 0.1 M sodium acetate buffer (pH 4.5) using sodium phytate (4 mM) as a substrate at 37° C. After 10 min of incubation the reaction was stopped by addition of 133 µl ammonium molybdate/ammonium vanadate/nitric acid mixture and the concentration of liberated inorganic phosphate determined at 405 n=(Engelen, van der Heeft, Randsdorp, and Smit 1994). This and all other assays were performed in triplicate. One unit (U) of enzyme activity was the amount of the enzyme releasing 1 µmol of inorganic phosphate per minute.

Assays for salivary phytase and for phytase in blood samples were conducted as previously described for saliva samples. A reagent blank with blood added at the same concentration as the samples assayed was subtracted from the sample readings.

Collection of Fecal Materials and Analysis for Total Phosphorus

Fresh feces were collected from each pig during the grower and finisher phases. Samples were placed in aluminum trays closed with a wax paper top and immediately frozen, and kept frozen until they were lyophilized for analysis. After lyophilization the samples were transferred to room conditions overnight to reach equilibrium in moisture content. The samples were separately ground with a mortar and pestle until homogenous and sealed in plastic containers until analyzed further. Dry matter content of samples was analyzed according to AOAC (Association of Official Analytical Chemists (AOAC) 1984) by heating 1 gram samples at 110° C. for 4 hours and cooling in a desiccator prior to weighing. To analyze total phosphorus content, samples were heated at 550° C. in a muffle furnace and 10 ml of 10 M HCl added and heated to boiling. The contents from each sample was quantitatively diluted to 250 ml with water and inorganic phosphorus content was measured by the method of Heinoen and Lahti (1981).

Purification of the *E. coli* Produced Phytase and Pig Salivary Phytase

The APPA phytase was over expressed in *E. coli* strain BL21(DE3) and the EDTA lysozyme extract fraction purified on DEAE-Sepharose and Sephadex-G75 as described by Jia et al. (1998). The pig phytase was purified by chromatography on DEAE-Sepharose and the band of enzyme eluted with a sodium chloride gradient was further purified by Chromatofocusing using a pH gradient from pH 4.0 to 7.0.

SDS-PAGE Analysis and Silver Staining

Sodium dodecylsulfate polyacrylamide gel electrophoresis was performed using a 10% gel as described by Laemmli (1970), except that protein in the sample buffer was heated at 70° C. for 10 minutes. Samples were stained with silver as described by Nesterenko et al. (1994).

Preparation of a Monoclonal Antibody Specific for the APPA Encoded *E. coli* Phytase Monoclonal antibodies specific to the *E. coli* APPA encoded phytase were prepared according to the procedures of Galfrè and Milstein (1981). Briefly, two female Balb/c mice were immunized 7 times over a period of 59 days with a purified APPA enzyme preparation. Mouse spleens were harvested, and the cells therein fused with an NS-1 myeloma cell line (Kohler and Milstein, 1976). Fused cells were selected for their ability to grow in media containing hypoxanthine, aminopterin, and thymidine (HAT). Western blotting and Enzyme-Linked Immunosorbent Assays (ELISA) were used identify those clones capable of secreting an antibody into the culture medium that recognized epitopes on both the *E. coli* and pig derived APPA enzyme. Clones secreting a desirable antibody were subcloned twice to ensure a pure culture of antibody secreting hybridomas.

Production of Polyclonal Antibodies Against the Purified *E. Coli* derived APPA Phytase Antibodies were prepared in two New Zealand White Rabbits by two intramuscular injections at different sites in the thigh of 50 μg of purified *Escherichia coli* derived APPA phytase in 0.5 ml of a 1:1 mixture of phosphate-buffered saline (PBS) and Freund's Complete Adjuvant. This was followed by repeat injections of 20 μg each of phytase in a 1:1 mixture of PBS and Freund's Incomplete Adjuvant on days 4, 19, 25, and 39. Blood was collected via heart puncture on day 42. The serum was separated from the cell fraction and used as the source of antibodies. The basic procedures for antibody production are described in Harlow and Lane (1988).

Western Blotting

Western blotting was performed as described by Towbin et al. (Towbin et al. 1979).

Deglycosylation of pig phytase was done according to protocols, Roche Molecular Biochemicals, with following modifications. Protein in 50 mM Tris (pH 8.0), 1 mM EDTA, 1% SDS, 1% 2-mercaptoethanol was denaturated by heating at 95° C. for 3 min. Than protein was precipitated with chloroform-methanol method (Wessel and Flugge 1984) and resuspended at 100 μg/mL in 20 mM Sodium Phosphate (pH 7.2) with 1% Triton X-100. Complete deglycosylation of 5 μg in 50 μL phytase was carried out overnight at 37° C. using 1 unit (U) N-glycosidase F, 1.2 mU O— glycosidase and 1 mU neuramimidase (Boehringer Mannheim GmbH). After incubation 0.5 μg of protein was run on the SDS gel.

Staining of Glycoproteins

This staining was done using DIG Glycan Detection Kit (Boehringer Mannheim) according to manufacture instructions (O'Shannessy et al. 1987).

Statistics on the Generation of Transgenic Pigs

The statistics on embryos recovered, microinjected and transferred into donor sows is shown in Table 8. A total of 4147 embryos injected with the transgene and 675 untreated embryos were introduced into 140 recipient sows with an average of 30 injected embryos and 5 uninjected embryos. All offspring were tested for the presence of the transgene in tissue biopsy, in blood by PCR analysis, and by an assay for phytase activity in the saliva.

Table 9 lists the transgenic pigs that were produced, their birth dates, sex and salivary phytase levels. There were 31 pigs transgenic for the phytase gene out of 203 live piglets born from embryos microinjected. These were detected by the presence of the gene in blood samples using the standard primer set, APPA-UP2 and APPA-KPN, but only 14 were detected by analysis of tail DNA preparations using the standard primer set. When the negative samples were reanalyzed using the primer set LAMA-UP1 and APPA-down4 (FIG. 8) a further 8 tail DNA samples were found to be positive. Purification of the tail biopsy DNA probably would have led to all being PCR positive for the phytase transgene.

Characteristics of the Phytase Transgene in Transgenic Pig 167-02

Figure 7:
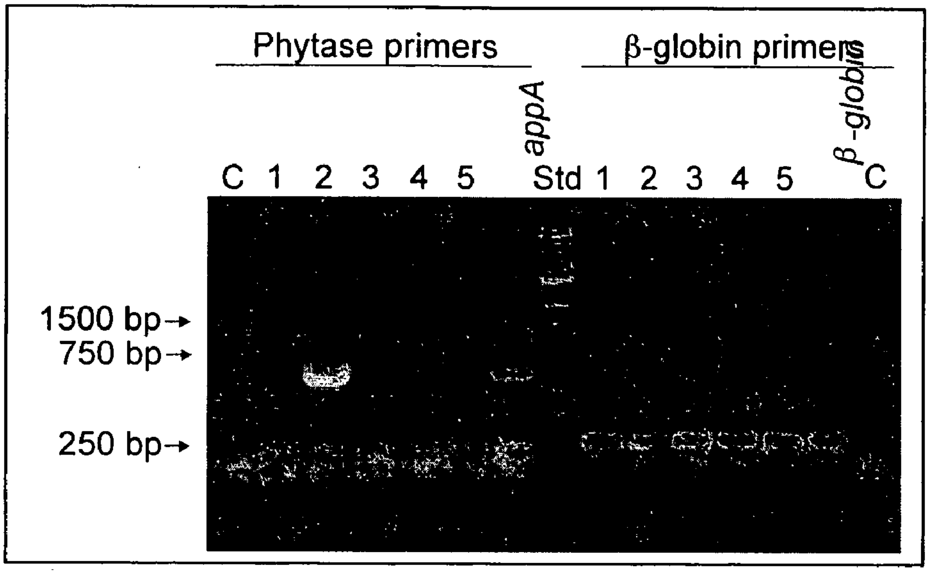
FIG. 7 illustrates the PCR results for transformed founder pigs. More specifically.
Figure 8:
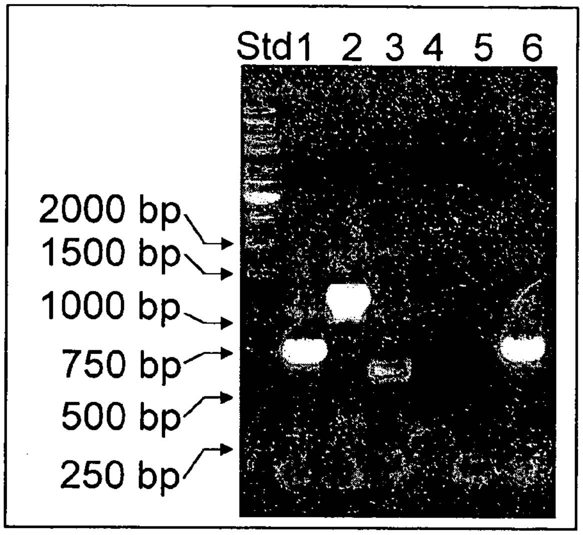
FIG. 8 illustrates the PCR results for transgene rearrangement tests. More specifically.
Figure 9:
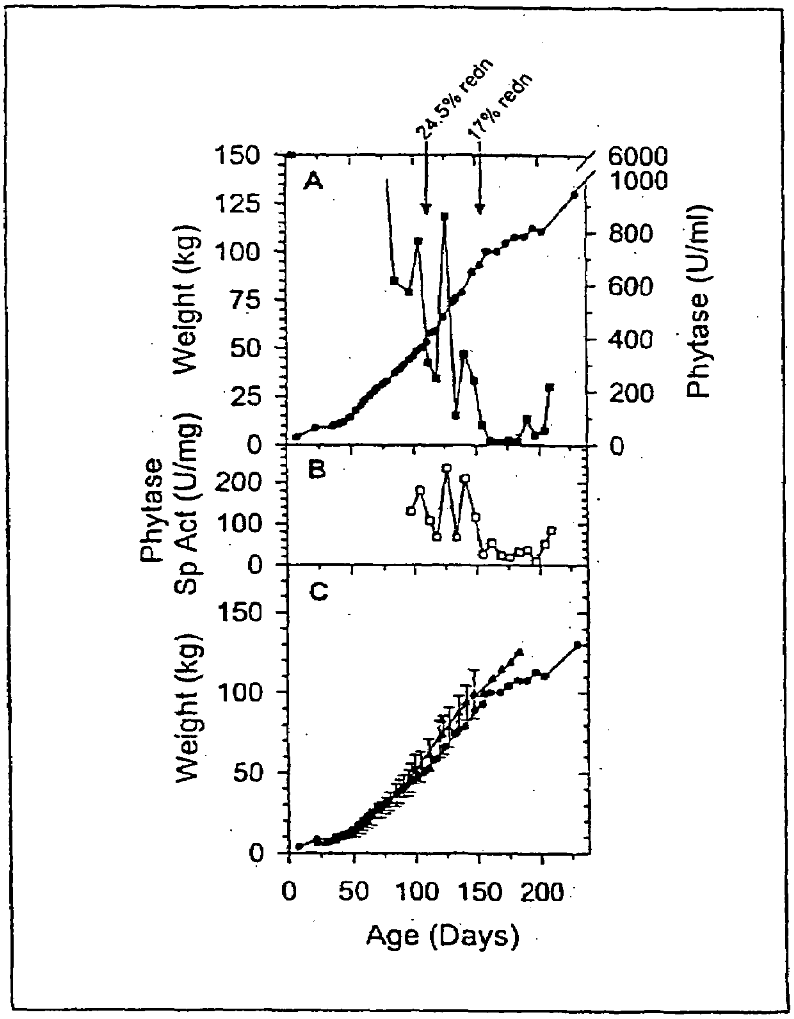
FIG. 9 illustrates weight and salivary phytase activity of the transgenic boar 167-02 and average weight of the pen-mates at intervals during growth. Symbols: Weight of 167-02, ;Average weight ±SD of four penmates, ▲; phytase activity of 167-02, ■; Phytase specific activity, □. Arrows indicate sampling for fecal phosphorus concentration.
Figure 10:
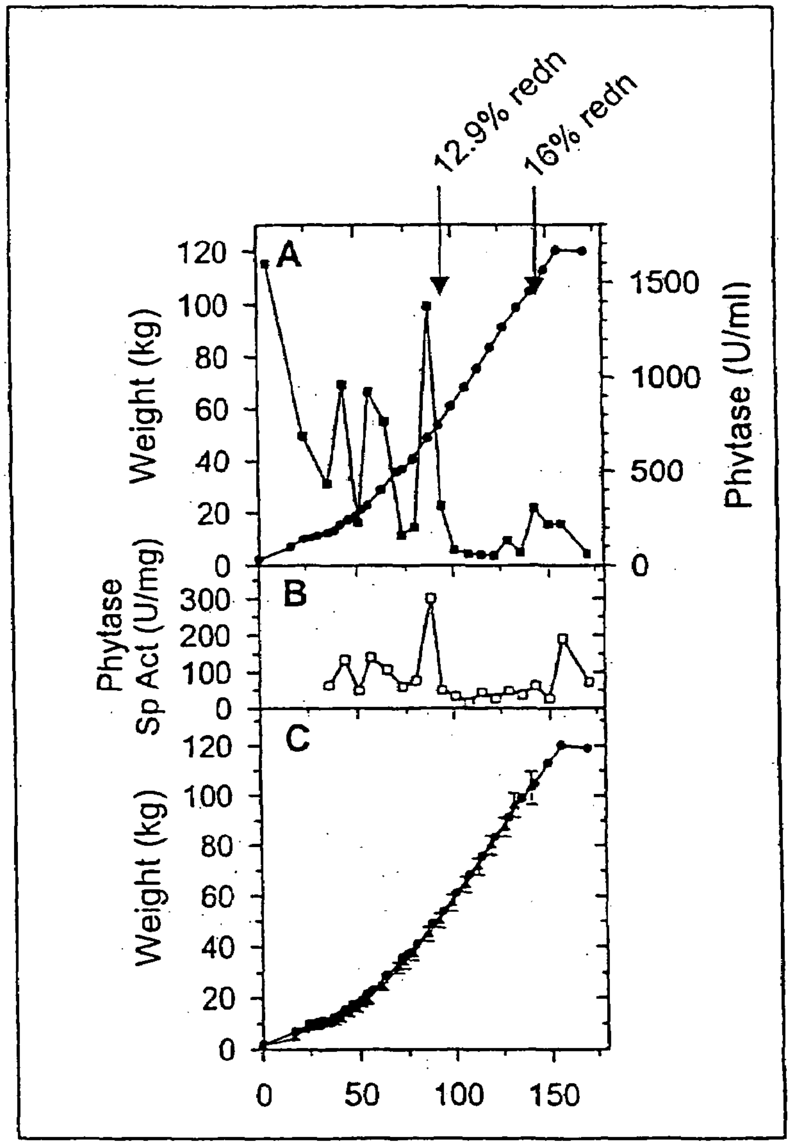
FIG. 10 illustrates weight and salivary phytase activity of the transgenic boar 282-02 and average weight of the pen-mates at intervals during growth. Symbols: Weight of 282-02, ◐; Average weight ±SD of five penmates, ▲; phytase activity of 282-02, ■; Phytase specific activity, □. Arrows indicate sampling for fecal phosphorus concentration.
Figure 11:
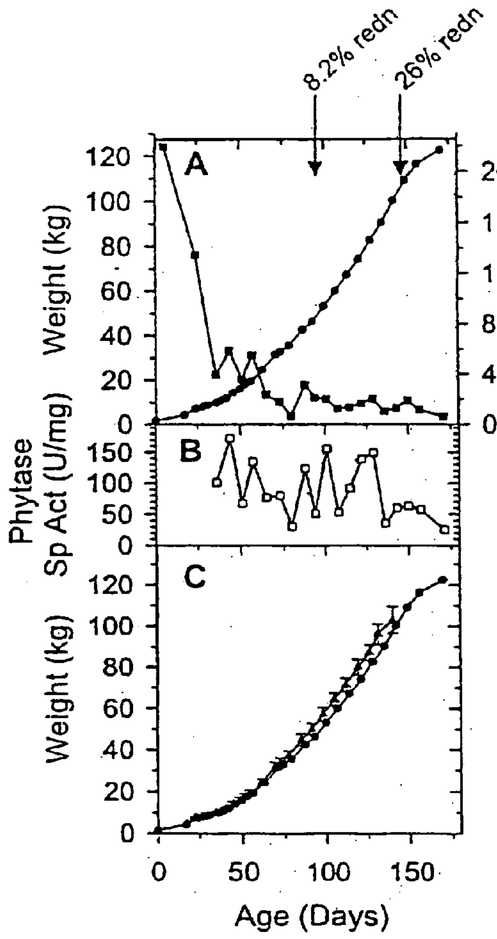
FIG. 11 illustrates weight and salivary phytase activity of the transgenic boar 282-04 and average weight of the pen-mates at intervals during growth. Symbols: Weight of 282-04, ◐; Average weight ±SD of five penmates, ▲; phytase activity of 282-04, ■; Phytase specific activity, □. Arrows indicate sampling for fecal phosphorus concentration.
Figure 12:
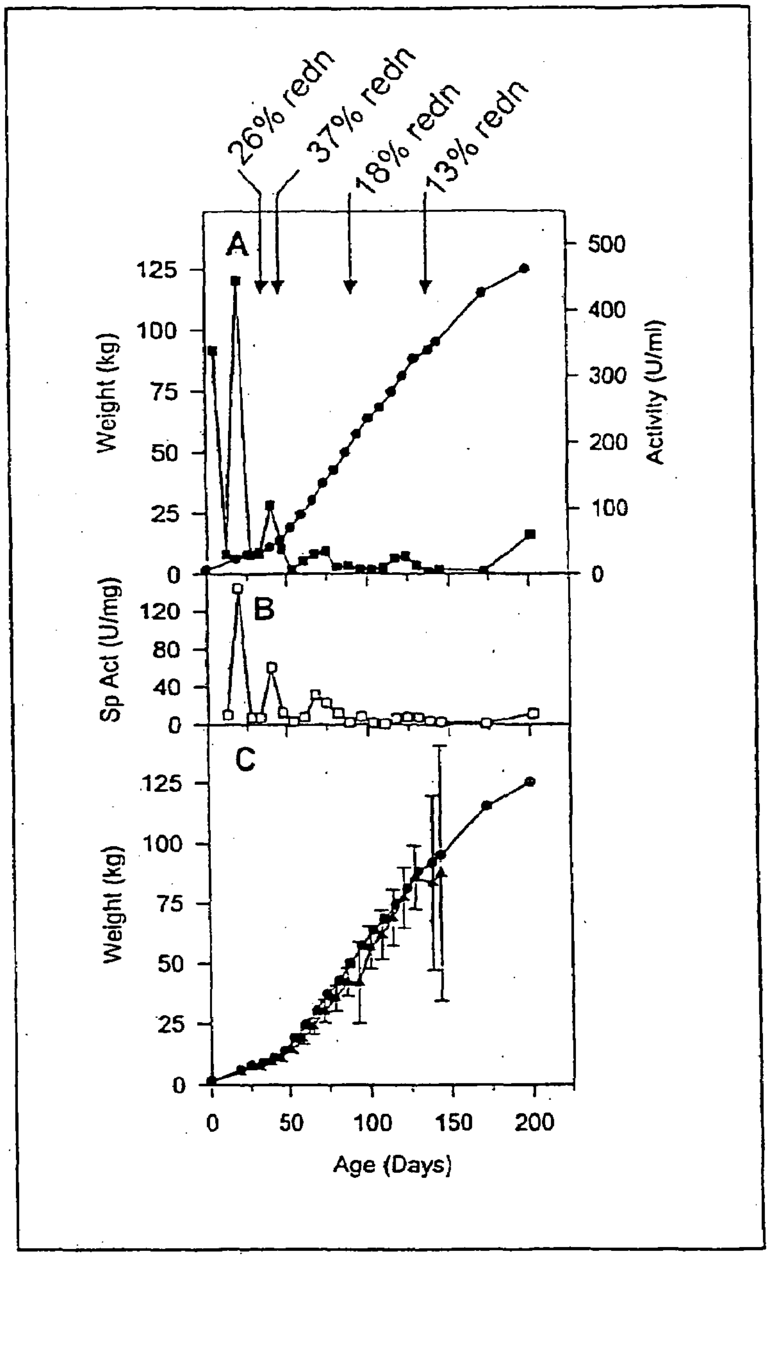
FIG. 12 illustrates weight and salivary phytase activity of the transgenic boar 405-02 and average weight of the pen-mates at intervals during growth. Symbols: Weight of 405-02, ●; Average weight ±SD of four penmates, ▲; phytase activity of 405-02, ■; Phytase specific activity, □. Arrows indicate sampling for fecal phosphorus concentration.
Figure 13:
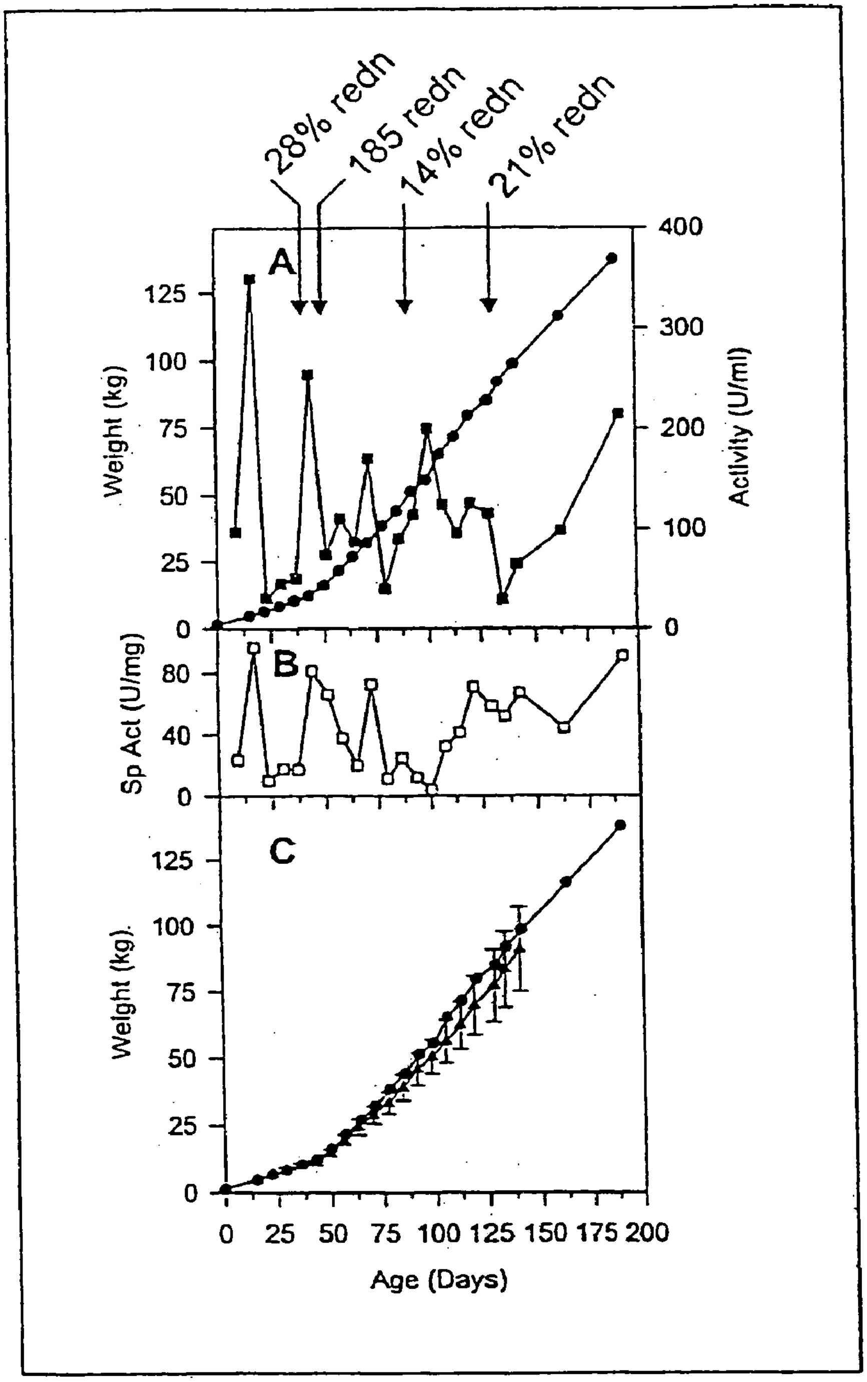
FIG. 13 illustrates weight and salivary phytase activity of the transgenic boar 421-06 and average weight of the pen-mates at intervals during growth. Symbols: Weight of 421-06, ●; Average weight ±SD of four penmates, ▲; phytase activity of 421-06, ■; Phytase specific activity, □. Arrows indicate sampling for fecal phosphorus concentration.

The application of PCR to detection of transgenic pigs is exemplified by analysis of litter 167 in which one of 7 piglets tested, including one that was stillborn and one that was crushed by the sow after birth, one live piglet designated 167-02 was identified as positive for the APPA gene by generation of a PCR product (Lane 2) of approximately 750 bps from the tail chromosomal DNA (FIG. 7). No rearrangements of the APPA gene were detected as documented by the positive PCR results using primers directed to the 3' region (lane 2) the whole gene (lane 3) and the 5' region (lane 4) of the APPA gene (FIG. 8).

Salivary Phytase and Weight Gain During Growth of Transgenic and Non-Transgenic Penmates.

Data on salivary phytase activity and weight gain are shown for five transgenic pigs and for weight gains of their non-transgenic penmates in FIGS. 9, 10, 11, 12 and 13. The phytase activity in the saliva varied substantially from one sampling time to the next. This variability was attributed to a combination of environmental factors including whether the animal had just consumed food or water, and regulation of parotid and saliva secretion in relation to food and water consumption. The weight gains during growth of the five transgenic pigs was within the range of the weight gains of the normal non-transgenic pigs.

With the exception of 167-02 the growth rate of the transgenic pigs was similar to that of the non-transgenic litter mates.

Phosphorus Content in the Fecal Materials from Transgenic and Non-Transgenic Pigs.

The phosphorus content of fresh fecal samples from three of the transgenic founder pigs, 167-02, 282-02, 282-04, 405-02 and 421-06 receiving weaning, grower or finisher ration is shown in Table 9. The phosphorus content of the feces of the transgenic pigs ranged from 1.59 to 2.26% while that of the non-transgenic penmates ranged from 1.61 to 2.76%. The reduction in fecal phosphorus ranged from a maximum of 26% to a minimum of 8%. In most cases the differences were at the 99% level of significance. The ages of the pigs at the time of fecal sampling and the corresponding phytase activities are shown in FIGS. 9, 10, 11, 12 & 13. The rations fed contained a supplement of readily available phosphorus suitable for maximizing growth of non-transgenic pigs. Since the reduction in fecal phosphorus is measured in transgenic pigs receiving a diet high in mineral phosphorus it is very likely that the fecal phosphorus would be substantially lower if the diet lacked mineral phosphorus. Under these conditions the phosphorus released from phytate would provide a substantial proportion of the dietary phosphorus and little would reach the large intestine and be excreted in the feces.

Transmission of the Phytase Transgene (to be Completed)

Figure 14:
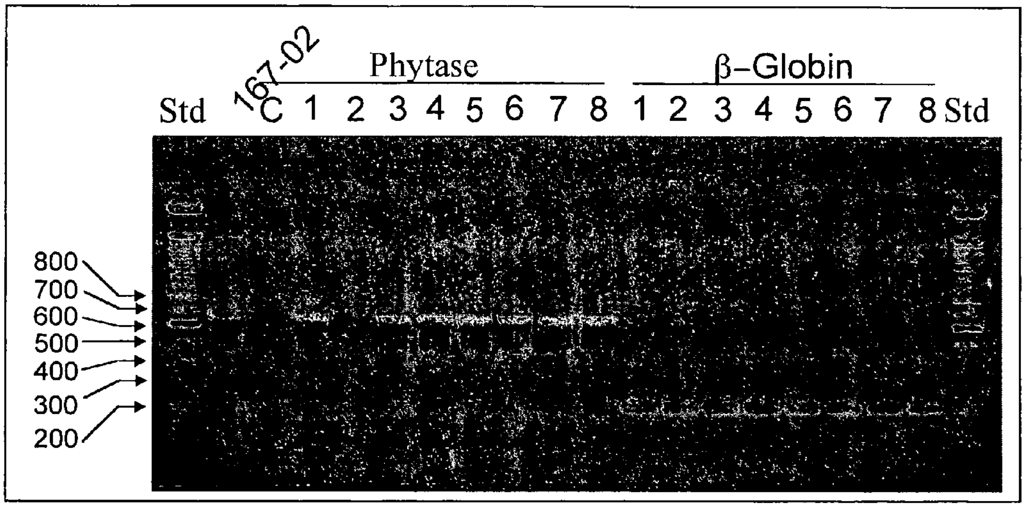
FIG. 14 illustrates the PCR results of first generation pigs. More specifically.

When semen from the transgenic boar 167-02 was used to inseminate four Yorkshire gilts all four sows had litters in which 4 out of 8, 2 out of 9, 7 out of 8 and 2 out of 5 of the piglets were transgenic for the phytase gene (Table 11). The PCR data for litter 154 that documents the presence of the transgene is shown in FIG. 14. All pigs containing the gene exhibited phytase activity in the saliva, and it ranged from 341 to 10,077 units per ml. Half of the transgenic piglets had salivary phytase activities of greater than 2000 units per ml. The specific activity of the phytase in the saliva ranged from 39 U/mg protein to a high of 706 units/mg protein.

This data documents that the gene was transferred and that the level of phytase expression observed in the founder was preserved in the first generation of pigs. Both male and female pigs at 11 days of age exhibited high phytase activity.

Figure 15:
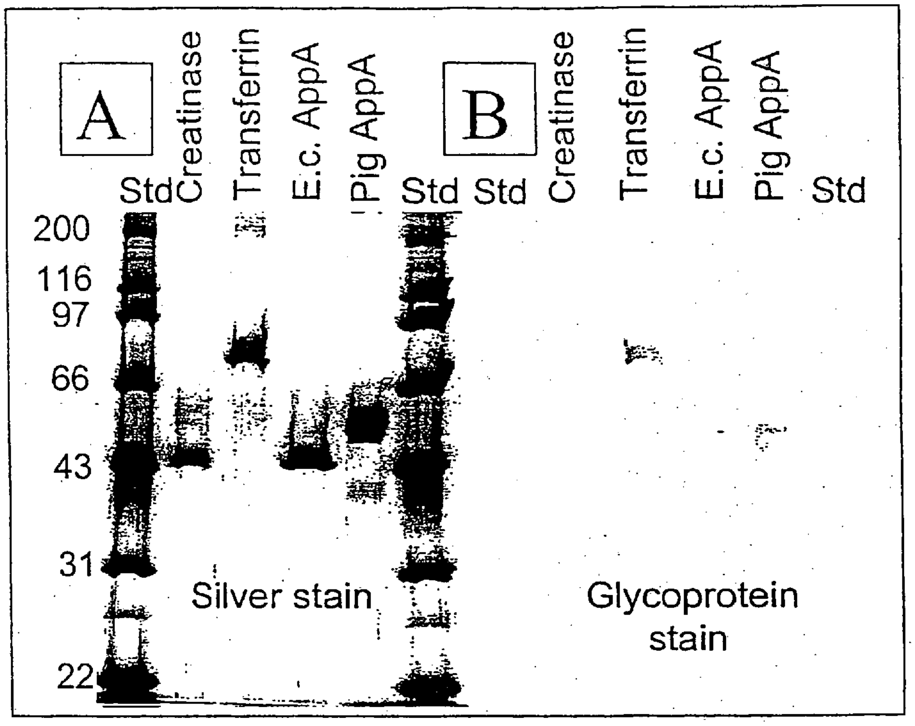
FIG. 15 illustrates a sodium dodecylsulfate gel stained with silver demonstrating the sizes of the *E. coli* produced APPA phytase and the APPA phytase produced by the pig and a demonstration that the pig phytase is glycosylated. More specifically.
Figure 15B:
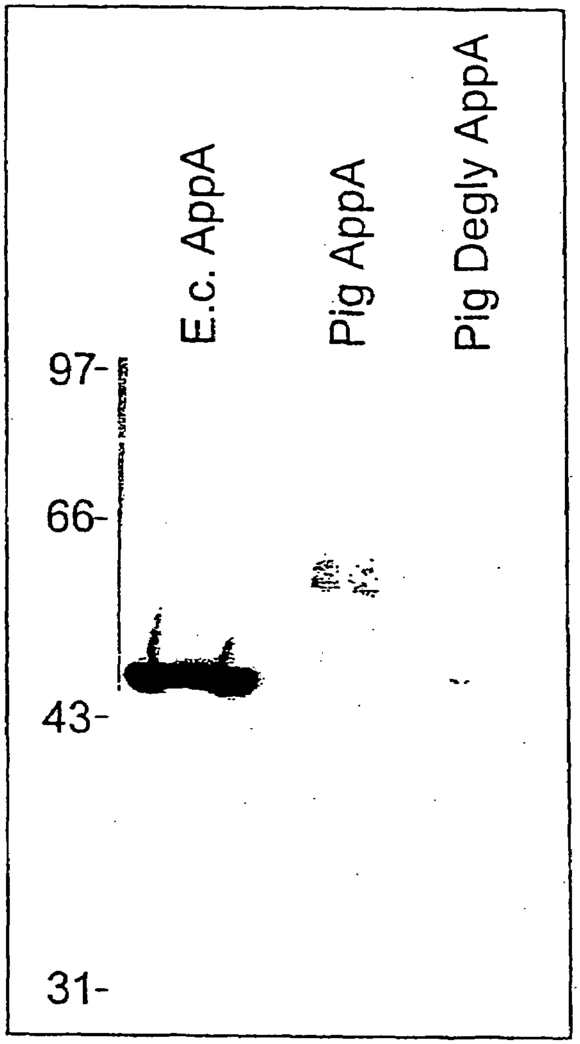
FIG. 15B is a picture of Western blot of the untreated pig AppA phytase and the same phytase after treatment with a combination of three deglycosylating enzymes. Lane 1, Purified AppA phytase produced in *E. coli* (untreated); lane 2, purified pig phytase (untreated); lane 3, purified pig phytase treated with the combination of deglycosylating enzymes including N-glycosidase F, O-glycosidase and neuraminidase.

Characteristics of the Phytase Enzyme Synthesized in the Salivary Glands of the Pig The phytase enzyme was purified to homogeneity from *E. coli* and from saliva collected from transgenic pig 167-02. Silver stains of the purified enzymes after SDS-PAGE are shown in FIG. 15. The *E. coli* derived enzyme has a molecular mass of approximately 45 kDa while that produced by the pig was about 55 kDa. The enzymes were also electrophoresed as before, transferred to nitrocellulose and stained for glycoproteins. The second part of FIG. 15 shows that the pig APPA protein is glycosylated. FIG. 15B shows that treatment of the pig phytase with deglycosylation enzymes changes the size of the phytase from 60 kDa to 45 kDa, an observation that confirms the glycosylated nature of the recombinant phytase produced in the saliva of the pig.

Figure 16:
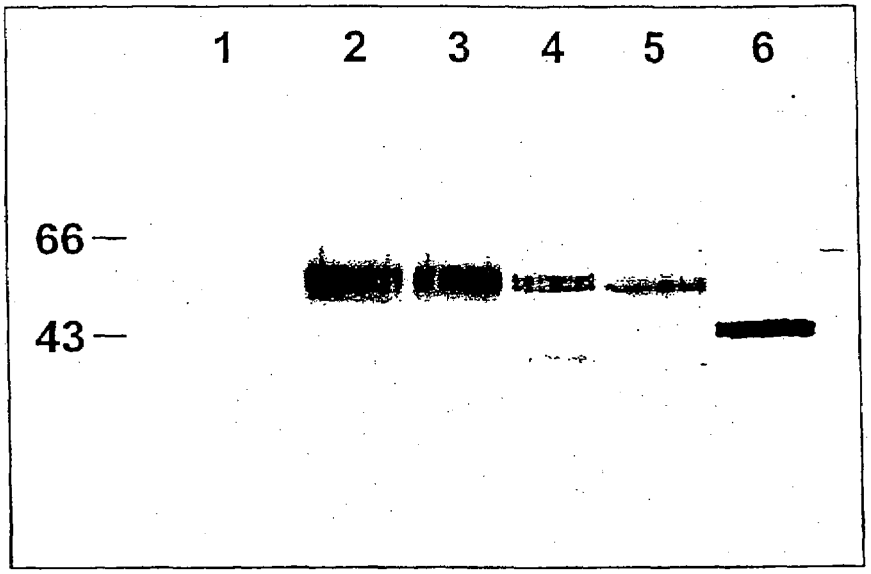
FIG. 16 illustrates a Western blot of the pig phytase and the *E. coli* produced APPA phytase using monoclonal antibodies directed to the APPA phytase documenting that they have homologous epitopes. More specifically.

The data in FIG. 16 shows that the pig phytase is homologous with the *E. Coli* enzyme despite their difference in size.

The purified pig phytase had $K_m$ and $V_{max}$ values of 0.33 mM and 624 units per mg of protein, respectively. Golovan et al. (2000) previously reported the $K_m$ and $V_{max}$ for the *E. coli* enzyme to be 0.63 mM and 2325 units per mg of protein. Thus the salivary phytase exhibits approximately 25% of the activity of the *E. coli* enzyme. This reduction in activity may be due to glycosylation that either modifies the catalytic site of the enzyme or otherwise leads to the formation of an enzyme with lower catalytic activity.

The latter finding of the production of a glycosylated protein suggests a method of producing such proteins using transgenic animals. Currently, although recombinant methods are available for producing proteins in host cells, it is often found that the mature peptide lacks the glycosylation normally associated with proteins produced by higher life forms. Insulin is an example of such protein. The findings of this study suggest that one means of producing the desired glycoproteins would be to generate transgenic animals such as the pig, that have been transformed, by known methods or the method described above, with a gene encoding the desired protein. When expressed by such animal, the subject protein would be produced and would undergo post-translational processing in the cell including the step of glycosylation. Thus, the invention contemplates a general method of producing such glycosylated proteins. Further, the invention contemplates a method of producing glycosylated proteins through the expression in and isolation from the saliva of an animal that has been transformed with a gene encoding such protein, and wherein such gene is operably linked to a saliva protein promoter or enhancer.

Various methods are known in the art for the collection of glycoproteins from the parotid gland of the pig for various applications. For example, surgical techniques have been published by Denny et al. (1972) for the collection of secretions from the parotid gland and submandibular salivary ducts.

Test Kit for Detection of the APPA Phytase Protein in Pigs

Figure 17:
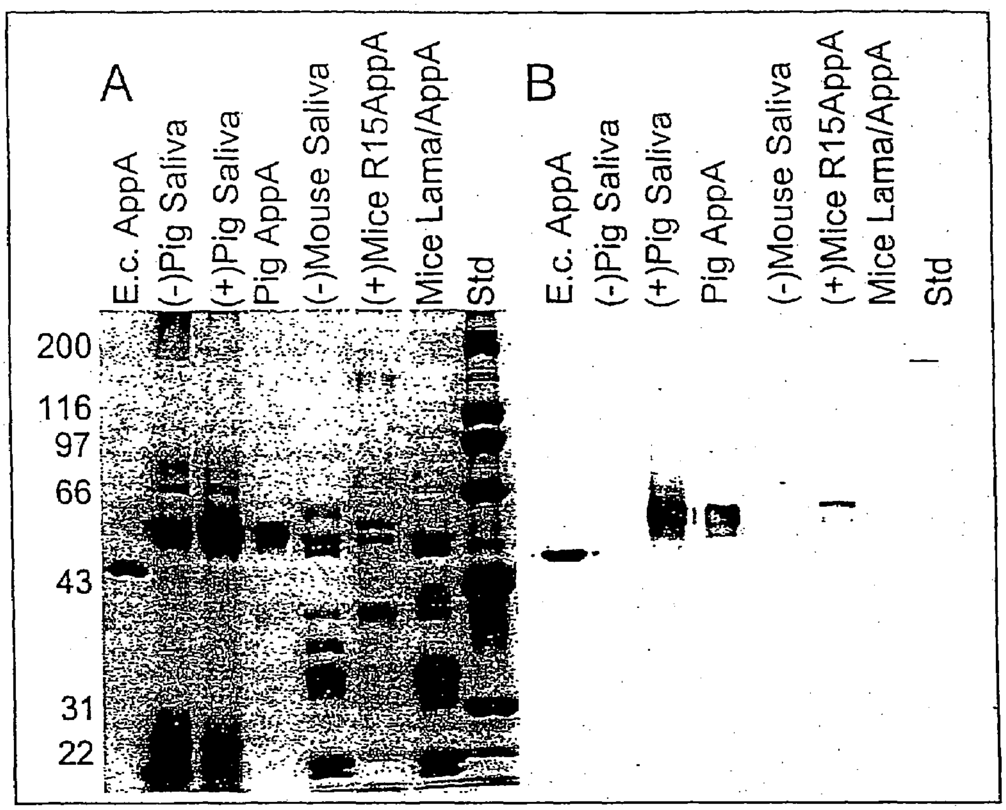
FIG. 17 illustrates an SDS-Page of the *E. coli* APPA phytase, saliva samples from phytase negative and positive pigs and mice and a corresponding Western blot documenting that phytases from all three sources have homologous antigenic epitopes, but the animal phytases are larger than that produced in *E. coli*. More specifically.

The monoclonal antibodies produced against the APPA phytase expressed in *E. coli* reacted with the APPA phytases produced in the saliva of transgenic mice and pigs (FIG. 17). Immunological detection of phytase in saliva provides definitive proof that the phytase secreted in transgenic pig saliva is a product of the APPA gene expressed in the pig salivary gland. This serves as a reliable method to document phytase production in transgenic pigs.

A further test would also be obtainable using the polyclonal antibodies discussed above.

The DNA sequence encoding phytase may be obtained from a variety of sources such as microbial, plant or animal sources. Preferably, the DNA sequence is obtained from a microbial source such as bacteria. Most preferred DNA sequences are obtained from *Escherichia coli.*

The cloning of a gene or a cDNA encoding a phytase protein may be achieved using various methods. One method is by purification of the phytase protein, subsequent determination of the N-terminal and several internal amino acid sequences and screening of a genomic or cDNA library of the organism producing the phytase using oligonucleotide probes based on the amino acid sequences. If at least a partial sequence of the gene is known, this information may be used to clone the corresponding cDNA using, for instance, the polymerase chain reaction (PCR) (PCR Technology: Principles and Applications for DNA Amplification, (1989) H. A. Ehrlich, ed., Stockton Press, New York; the contents of which are incorporated herein by reference). It will be evident to those skilled in the art that the cloned phytase gene described above may be used in heterologous hybridization experiments, directed to the isolation of phytase encoding genes from other microorganisms.

The DNAs encoding phytase or individual fragments or modified proteins thereof can be fused, in proper reading frame, with appropriate regulatory signals as described in detail below, to produce a genetic construct that is then amplified, for example, by preparation in a bacterial (e.g., *E. coli*) plasmid vector according to conventional methods. Such methods are described in, for example, Sambrook et al., Molecular Cloning: A Laboratory Manual (Cold Spring Harbor Press 1989), the contents of which are incorporated herein by reference. The amplified construct is thereafter excised from the vector and purified for use in producing transgenic animals.

The desired protein may also be produced as a fusion protein containing another protein. For example, the desired recombinant protein of this invention may be produced as part of a larger recombinant protein in order to stabilize the desired protein. Useful modifications within this context include, but are not limited to, those that alter post-translational modifications, size or active site, or that fuse the protein or portions thereof to another protein. Such modifications can be introduced into the protein by techniques well known in this art, such as by synthesizing modified genes by ligation of overlapping oligonucleotides or introducing mutations into the cloned genes by, for example, oligonucleotide-mediated mutagenesis.

The cloned phytase gene may be used as starting materials for the construction of improved phytases. Improved phytases are phytases, altered by mutagenesis techniques (e.g. site-directed mutagenesis, or directed evolution), which have properties that differ from those of wild-type phytases (Kuchner and Arnold 1997). For example, the temperature or pH optimum, specific activity, temperature or protease resistance may be altered so as to be better suited for a particular application.

A choice of expression in cellular compartments (such as cytosol, endoplasmic reticulum) or extracellular expression can be used in the present invention, depending on the iophysical and biochemical properties of the phytase. Such properties include, but are not limited to pH sensitivity, sensitivity to proteases, and sensitivity to the ionic strength of the preferred compartment. The DNA sequence encoding the enzyme of interest should be modified in such a way that the enzyme can exert its action at the desired location in the cell. To achieve extracellular expression of the phytase, the expression construct of the present invention utilizes a bacterial signal sequence. Although signal sequences that are homologous (native) to the animal host species are preferred, heterologous signal sequences, i.e. those originating from other animal species or of microbial origin, may be used as well. Such signal sequences are known to those skilled in the art.

All parts of the relevant DNA constructs (promoters, regulatory, secretory, stabilizing, targeting, or termination sequences) of the present invention may be modified, if desired, to affect their control characteristics using methods known to those skilled in the art. The cis-acting regulatory regions useful in the invention include the promoter that drives expression of the phytase gene. Highly preferred are promoters that are specifically active in salivary gland cells. Among such promoters, highly preferred are mouse parotid secretory protein (PSP) promoter, rat proline-rich protein (PRP) promoter, human salivary amylase promoter, mouse mammary tumor virus promoter (Samuelson 1996). Among the useful sequences that regulate transcription, in addition to the promoters discussed above, are enhancers, splice signals, transcription termination signals, and polyadenylation sites. Particularly useful in this regard are those that increase the efficiency of the transcription of the genes for phytase in the salivary gland or other cells of the transgenic animals listed above. Preferred are transcription regulatory sequences for proteins highly expressed in the salivary gland cells. Introns could be introduced to increase levels of expression. Such introns include the synthetic intron SIS, SV40 small t antigen intron and others (Whitelaw et al. 1991; Petitclerc et al. 1995).

Preferably, the expression system or construct of this invention also includes a 3' untranslated region downstream of the DNA sequence encoding the desired recombinant protein, or the salivary protein gene used for regulation. This region apparently stabilizes the RNA transcript of the expression system and thus increases the yield of the desired protein. Among the 3' untranslated regions useful in this regard are sequences that provide a polyA signal. Such sequences may be derived, e.g., from the SV 40 small t antigen late polyadenylation signal, synthetic polyadenylation signal or other 3' untranslated sequences well known in this art (Carswell and Alwine 1989; Levitt et al. 1989). Preferably, the 3' untranslated region is derived from a salivary-specific protein. The stabilizing effect of this region's polyA transcript is important in stabilizing the mRNA of the expression sequence. Further, the addition of locus control regions (LCRs), matrix attachment regions (MAR) and scaffold attachment regions (SARs) would allow position-independent, copy number dependent expression of the transgene with either homologous or heterologous promoters (Taboit-Dameron et al. 1999; Geyer 1997). Co-integration of an actively expressed gene with the transgene was also shown to increase expression levels of a poorly expressed transgene (Clark et al. 1993). Also important in increasing the efficiency of expression of phytase is a strong translation initiation site (Kozak 1987). Likewise, sequences that regulate the post-translational modification of phytase may be useful in the invention.

The term "animal" as used herein denotes all animals except humans. It also includes an individual animal in all stages of development, including embryonic and fetal stages.

A "transgenic" animal is any animal containing cells that bear genetic information received, directly or indirectly, by deliberate genetic manipulation at the subcellular level, such as by microinjection or infection with a recombinant virus. "Transgenic" in the present context does not encompass classical crossbreeding or in vitro fertilization, but rather denotes animals in which one or more cells receive a recombinant DNA molecule. Although it is highly preferred that this molecule be integrated within the animal's chromosomes, the invention also encompasses the use of extrachromosomally replicating DNA sequences, such as might be engineered into yeast artificial chromosomes. The information to be introduced into the animal may be foreign to the species of the animal to which the recipient belongs (i.e., "heterologous"), or the information may be foreign only to the particular individual recipient, or genetic information already possessed by the recipient. In the last case, the introduced gene may be expressed in a manner different than the native gene.

As indicated above, the transgenic animals of this invention are other than human. Farm animals (pigs, goats, sheep, cows, horses, rabbits and the like), rodents (such as mice and rats), domestic pets (eg. cats and dogs), fish and poultry (eg. chickens) are included in the scope of this invention. It is highly preferred that a transgenic animal of the present invention be produced by introducing into single cell embryos appropriate polynucleotides that encode phytase, or fragments or modified products thereof, in a manner such that these polynucleotides are stably integrated into the DNA of germ line cells of the mature animal, and are inherited in normal mendelian fashion. Advances in technologies for embryo micromanipulation now permit introduction of heterologous DNA into fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In one preferred method, developing embryos are infected with a retrovirus containing the desired DNA, and transgenic animals produced from the infected embryo. In a most preferred method, however, the appropriate DNAs are co-injected into the pronucleus or cytoplasm of embryos, preferably at the single cell stage, and the embryos allowed to develop into mature transgenic animals. Such techniques are well known (see reviews of standard laboratory procedures for microinjection of heterologous DNAs into mammalian fertilized ova, including Hogan et al., Manipulating The Mouse Embryo, (Cold Spring Harbor Press 1986); Krimpenfort et al., Bio/Technology 9:844 (1991); Palmiter et al., Cell, 41: 343 (1985); Kraemer et al., Genetic Manipulation Of The Early Mammalian Embryo, (Cold Spring Harbor Laboratory Press 1985); Hammer et al., Nature, 315: 680 (1985); Wagner et al., U.S. Pat. No. 5,175,385; Krimpenfort et al., U.S. Pat. No. 5,175,384, the respective contents of which are incorporated herein by reference).

For a person skilled in art, it will also be clear that the present invention provides for other proteins to be expressed in the salivary gland of the pig. Such proteins may be secreted into saliva to improve digestion and decrease pollution potential (for example, endoglucanases), or specifically targeted for secretion into blood and have effects on the growth and health of the animal (such as growth hormone).

Phytase activity may be measured via a number of assays, the choice of which is not critical to the present invention. For example, the phytase enzyme activity of the transgenic animal tissue may be tested with an ELISA-assay, Western blotting or direct enzyme assays using calorimetric techniques or gel assay system.

The examples included herein are provided so as to give those of ordinary skill in the art a complete disclosure and description of how to make and use the invention and are not intended to limit the scope of what the inventors regard as their invention. Efforts have been made to ensure accuracy with respect to numbers used (e.g., amounts, temperature, pH, etc.) but some experimental errors and deviation should be accounted for. Unless indicated otherwise, temperature is in degrees Centigrade and pressure is at or near atmospheric.

Although the invention has been described with reference to certain specific embodiments, various modifications thereof will be apparent to those skilled in the art without departing from the spirit and scope of the invention as outlined in the claims appended hereto.

TABLE 1

Secretion of phytase in the saliva of transgenic mice containing the R15-PRP/APPA transgene and non-transgenic mice induced with isoproterenol and pilocarpine.

| Founder | Mice | PCR | Gender | Generation | Transgene | Phytase activity micromoles/min/ml |
|---|---|---|---|---|---|---|
| A0m | 4bfr(+) | positive | F | 1 | APPA + intron | 39.73 |
| A0m | 2brm(+) | positive | M | 1 | APPA + intron | 24.29 |
| A0m | 2brm(+) | positive | M | 2 | APPA + intron | 14.42 |
| A0m | 5brf(+) | positive | F | 2 | APPA + intron | 7.36 |
| A0m | 1brm(−) | negative | M | 1 | APPA + intron | 0.00 |
| A1f | 9brf(+) | positive | F | 1 | APPA + intron | 0.08 |
| A1f | 11wf(+) | positive | F | 1 | APPA + intron | 0.07 |
| A1f | 5brm(+) | positive | M | 1 | APPA + intron | 0.03 |
| A1f | 10wf(−) | negative | F | 1 | APPA + intron | 0.02 |
| A20f | 1brm(+) | positive | M | 1 | APPA + intron | 0.53 |
| A20f | 5brf(+) | positive | F | 1 | APPA + intron | 0.12 |
| A20f | 4brf(−) | negative | F | 1 | APPA + intron | 0.03 |
| A2m | 13wf(+) | positive | F | 1 | APPA + intron | 87.70 |
| B0m | 5brf(+) | positive | F | 1 | APPA + intron | 0.95 |
| B0m | 3brm(+) | positive | M | 1 | APPA + intron | 0.73 |
| B0m | 6wf(−) | negative | F | 1 | APPA + intron | 0.00 |
| B0f | 3wf(+) | positive | F | 2 | APPA | 252.43 |
| B0m-intr | 9wf(+) | positive | F | 1 | APPA | 546.74 |
| W0m | 8wf(+) | positive | F | 1 | APPA | 60.42 |
| W30m | 1wm(+) | positive | M | 2 | APPA | 41.91 |
| W30m | 11wf(+) | positive | F | 1 | APPA | 43.44 |
| W30m | 4wm(−) | negative | M | 1 | APPA | 0.02 |
| W30m | 10wf(−) | negative | F | 1 | APPA | 0.02 |

TABLE 2

Repeat sequences found in the Lama2-APPA construct.

| Start | End | DNA strand | Repeat | Class/family | Substitutions % of consensus | Deletions % of consensus | Insertions % of consensus |
|---|---|---|---|---|---|---|---|
| 765 | 927 | + | L1M1 | LINE/L1 | 25 | 4.2 | 6.7 |
| 928 | 965 | + | (CA)n | Simple repeat | 0 | 0 | 0 |
| 966 | 1020 | + | L1M1 | LINE/L1 | 25 | 4.2 | 6.7 |
| 1021 | 1156 | + | B1_MM | SINE/Alu | 15.4 | 0 | 0 |
| 1159 | 1231 | + | CAAAC)n | Simple repeat | 1.4 | 0 | 0 |
| 1232 | 1385 | + | L1M1 | LINE/L1 | 25 | 4.2 | 6.7 |
| 1652 | 2308 | C | L1 | LINE/L1 | 28.5 | 11.9 | 1.7 |
| 2334 | 2406 | C | MIR | SINE/MIR | 27.4 | 4.1 | 0 |
| 2415 | 3266 | + | RMER13A | LTR | 17.7 | 4 | 6.1 |
| 6016 | 6127 | C | L1MA9 | LINE/L1 | 25.5 | 2 | 1 |
| 6831 | 7007 | + | CT-rich | Low complexity | 30.5 | 1.7 | 3.4 |
| 7299 | 7510 | C | B3 | SINE/B2 | 27.8 | 7.5 | 1.4 |
| 7718 | 7746 | + | (TCTCTG)n | Simple repeat | 6.9 | 0 | 0 |
| 8499 | 8581 | C | MIR | SINE/MIR | 24.1 | 12.1 | 3.6 |
| 9010 | 9603 | + | Lx4 | LINE/L1 | 21.7 | 6.4 | 0.2 |
| 10465 | 10519 | + | (TG)n | Simple repeat | 5.5 | 1.8 | 0 |
| 11235 | 11287 | C | MER5A | DNA/MER1 type | 28.3 | 0 | 1.9 |
| 12372 | 12537 | C | L1MA4A | LINE/L1 | 28.3 | 5.4 | 0 |
| 14240 | 14388 | + | B1_MM | SINE/Alu | 4 | 0 | 1.3 |
| 14869 | 14945 | C | MIR | SINE/MIR | 36.4 | 1.3 | 0 |
| 16391 | 16540 | C | ORR1D | LTR/MaLR | 29.3 | 0 | 6 |

TABLE 2-continued

Repeat sequences found in the Lama2-APPA construct.

| Start | End | DNA strand | Repeat | Class/family | Substitutions % of consensus | Deletions % of consensus | Insertions % of consensus |
|---|---|---|---|---|---|---|---|
| 16774 | 17214 | + | RMER4 | LTR | 21.3 | 10 | 11.8 |
| 17229 | 17718 | C | L1_MM | LINE/L1 | 15.3 | 0 | 0.8 |

TABLE 3

Salivary phytase activities of G2 mice from the founder female 3-1 generated using the construct Lama2-APPA. The mice were between 21 and 30 days of ace.

| male mouse # | Phytase (U/ml) | female mouse # | Phytase (U/ml) |
|---|---|---|---|
| 5 | 28.3 | 1 | 9.0 |
| 6 | 2.5 | 2 | 29.9 |
| 8 | 6.6 | 4 | 8.0 |
| 9 | 44.7 | 5 | 43.0 |
| 10 | 12.7 | 6 | 26.9 |
| 12 | 28.3 | 8 | 1.9 |
| 15 | 28.1 | 9 | 66.3 |
| 18 | 71.2 | 10 | 19.9 |
| 19 | 19.5 | 11 | 61.3 |
| 20 | 15.7 | 12 | 36.4 |
| 21 | 20.9 | 13 | 18.0 |
| 22 | 4.1 | 17 | 38.9 |
| 24 | 13.0 | 18 | 18.5 |
| 26 | 53.4 | 19 | 27.0 |
| 28 | 20.4 | 23 | 6.5 |
| 29 | 34.1 | 24 | 16.1 |
| 30 | 11.1 | 25 | 9.4 |
| 32 | 3.1 | 26 | 14.8 |
| 33 | 51.7 | 27 | 1.3 |
| 34 | 19.0 | 28 | 8.2 |

TABLE 4

Composition and nutrient levels of Phase II starter diet and low phytate starter diets fed to weanling pigs between 5–10 kg.

| Ingredients | Diet/Nutrient Levels[1] Phase II Starter Diet | Low Phytate Starter Diet |
|---|---|---|
| Corn | 33.15 | 25.44 |
| Barley | 8.00 | 8.00 |
| Wheat | 20.00 | 40.00 |
| Soybean meal | 21.00 | 8.00 |
| Fish meal | 5.00 | 5.00 |
| Meat and bone meal | — | 1.00 |
| Whey | 8.00 | 8.00 |
| Fat | 2.00 | 2.00 |
| Lysine-HCl | 0.10 | 0.28 |
| Dicalcium phosphate | 1.10 | — |
| $CaCO_3$ | 0.90 | 1.10 |
| Iodized salt | 0.30 | 0.30 |
| Vitamin premix[1] | 0.250 | 0.55 |
| Mineral premix[1] | 0.10 | 0.10 |
| Lincommix 44 | 0.10 | 0.10 |
| Total (kg) | 100.00 | 100.00 |
| Calculated nutritive values | | |
| DE (kcal/g) | 3.44 | 3.36 |
| CP (%) | 19.46 | 18.62 |
| CA (%) | 1.00 | 0.94 |
| Total P (%) | 0.74 | 0.66 |
| Ca/P | 1.35:1 | 1.42:1 |

TABLE 4-continued

Composition and nutrient levels of Phase II starter diet and low phytate starter diets fed to weanling pigs between 5–10 kg.

| Ingredients | Diet/Nutrient Levels[1] Phase II Starter Diet | Low Phytate Starter Diet |
|---|---|---|
| Total AA contents (%) | | |
| Arginine | 1.16 | 1.17 |
| Histidine | 0.50 | 0.48 |
| Isoleucine | 0.81 | 0.77 |
| Leucine | 1.58 | 1.54 |
| Lysine | 1.17 | 1.06 |
| Methionine | 0.34 | 0.29 |
| Cysteine | 0.34 | 0.34 |
| Methionine + Cysteine | 0.68 | 0.63 |
| Phenylalanine | 0.90 | 0.90 |
| Tyrosine | 0.65 | 0.65 |
| Threonine | 0.75 | 0.68 |
| Tryptophan | 0.23 | 0.23 |
| Valine | 0.91 | 0.86 |

[1]Minerals and vitamins meet or exceed levels recommended by NRC (1998).

TABLE 5

Composition and nutrient levels of grower and finisher diets.

| Ingredients | Diet/Nutrient Levels Grower Diet For pigs 20 to 50 kg | Finishing Diet For pigs 50 to 120 kg |
|---|---|---|
| Corn | 51.78 | 40.00 |
| Barley | 8.10 | 23.03 |
| Wheat | 20.00 | 23.00 |
| Soybean meal | 16.00 | 13.00 |
| Fat | 1.00 | 1.00 |
| Lysine-HCl | 0.12 | 0.12 |
| Dicalcium phosphate | 1.20 | 1.00 |
| $CaCO_3$ | 1.15 | 1.15 |
| Iodized salt | 0.50 | 0.50 |
| Vitamin premix[1] | 0.15 | 0.15 |
| Mineral premix[1] | 0.10 | 0.10 |
| Total (kg) | 100.00 | 100.05 |
| Calculated nutritive values | | |
| DE (kcal/g) | 3.39 | 3.33 |
| CP (%) | 14.76 | 14.17 |
| Ca (%) | 0.79 | 0.74 |
| Total P (%) | 0.57 | 0.53 |
| Ca/P | 1.39:1 | 1.39:1 |
| Total AA contents (%) | | |
| Arginine | 0.86 | 0.80 |
| Histidine | 0.38 | 0.36 |
| Isoleucine | 0.58 | 0.55 |
| Leucine | 1.28 | 1.18 |
| Lysine | 0.78 | 0.73 |
| Methionine | 0.24 | 0.23 |

TABLE 5-continued

Composition and nutrient levels of grower and finisher diets.

| Ingredients | Diet/Nutrient Levels<br>Grower Diet For pigs 20 to 50 kg | Finishing Diet For pigs 50 to 120 kg |
|---|---|---|
| Cysteine | 0.29 | 0.29 |
| Methionine + Cysteine | 0.53 | 0.52 |
| Phenylalanine | 0.70 | 0.68 |
| Tyrosine | 0.50 | 0.46 |
| Threonine | 0.52 | 0.49 |
| Tryptophan | 0.17 | 0.16 |
| Valine | 0.68 | 0.65 |

[1]Minerals and vitamins meet or exceed levels recommended by NRC (1998).

TABLE 6

Vitamin premix composition[1]

| Nutrient | Amount per 5 kg of premix |
|---|---|
| Wheat midds | 3.867 kg |
| Vitamin A | 10 million IU |
| Vitamin D | 1 million IU |
| Vitamin E | 40 thousand IU |
| Menadione | 2.5 g |
| Pantothenic acid | 15 g |
| Riboflavin | 5 g |
| Folic acid | 2 g |
| Niacin | 25 g |
| Thiamin | 1.5 g |
| Pyridoxine | 1.5 g |
| Vitamin $B_{12}$ | 25 mg |
| Biotin | 200 mg |
| Choline | 500 g |

[1]From Hoffman-LaRoche Limited, P.O. Box 877, Cambridge, ON. N1R5X9

TABLE 7

Composition of the mineral premix[1,2]

| Mineral component | Amount (%) |
|---|---|
| Limestone | 43.3 |
| Copper sulfate (25%) | 6.0 |

TABLE 7-continued

Composition of the mineral premix[1,2]

| Mineral component | Amount (%) |
|---|---|
| Ferrous sulfate (30%) | 33.4 |
| Zinc oxide (72%) | 13.9 |
| Manganous oxide (56%) | 3.4 |

[1]Mineral premix prepared at Arkell

[2]Dicalcium phosphate contained 18.5% calcium and 20.5% of phosphate and normally is added at a level of 1.2% to the pig grower diet, 1.0% to the finisher diet and 1.5% to the nursing sow diet.

TABLE 8

Statistics on embryo recovery and the introduction of embryos containing the transgene into recipient sows.

| Treatment | Number |
|---|---|
| Gilts used for embryo recovery: | |
| Yorkshire | 279 |
| Yorkshire x Landrace cross | 168 |
| Duroc | 12 |
| Total | 459 |
| Recipient sows[1] | 74 |
| Embryos transferred to recipients: | |
| Embryos microinjected with the transgene | 4147 |
| Uninjected carrier embryos | 675 |
| Total | 4543 |
| Total number of embryo transfers | 140 |

[1]Sows were used for up to three farrowings of potentially transgenic pigs. Sows were inseminated with Yorkshire semen from a high breeding value boars.

TABLE 9

Transgenic pigs containing a salivary phytase gene generated by microinjections of single cell zygotes using the Lama2-APPA transgene

| ID # of pig[1] | Birth Date | Presence of Transgene[2]Tail/Blood | Sex | Salivary phytase (U/ml)[3] | Zygote source[4] |
|---|---|---|---|---|---|
| 167-02 | Apr. 14, 1999 | +/+ | Boar | 6,000 | Yorkshire |
| 282-02 | Jun. 14, 1999 | +/+ | Boar | 618 | Yorkshire |
| 282-04 | Jun. 14, 1999 | +/+ | Boar | 1,349 | Yorkshire |
| 405-02 | Aug. 14, 1999 | +/+ | Gilt | 339 | York/Landrace |
| 421-02 | Aug. 24, 1999 | −/+ | Gilt | 0.8 | York/Landrace |
| 421-04 | Aug. 24, 1999 | −/+ | Gilt | 2.2 | York/Landrace |
| 421-06 | Aug. 24, 1999 | +/+ | Boar | 97 | York/Landrace |
| 448-01 | Sep. 03, 1999 | +/+ | Gilt | 0 | York/Landrace |
| 491-01 | Sep. 25, 1999 | +/+ | Gilt | 2.3 | York/Landrace |
| 491-02 | Sep. 25, 1999 | +/+ | Gilt | 0 | York/Landrace |
| 491-03 | Sep. 25, 1999 | +/+ | Gilt | 0.3 | York/Landrace |
| 491-05 | Sep. 25, 1999 | +/+ | Boar | 0 | York/Landrace |
| 496-05 | Sep. 26, 1999 | +/+ | Boar | 0 | York/Landrace |
| 500-03 | Sep. 28, 1999 | +/+ | Boar | 136 | York/Landrace |

TABLE 9-continued

Transgenic pigs containing a salivary phytase gene generated by microinjections of single cell zygotes using the Lama2-APPA transgene

| ID # of pig[1] | Birth Date | Presence of Transgene[2]Tail/Blood | Sex | Salivary phytase (U/ml)[3] | Zygote source[4] |
|---|---|---|---|---|---|
| 510-01 | Sep. 28, 1999 | +/+ | Boar | 0.2 | York/ |
| 559-05 | Nov. 01, 1999 | +*/+ | Boar | >418 | York/Landrace |
| 560-04 | Nov. 02, 1999 | +*/+ | Boar | 5 | Yorkshire |
| 594-03 | Nov. 18, 1999 | +/+ | Gilt | 2.3 | Yorkshire |
| 613-02 | Nov. 27, 1999 | −/+ | Gilt | 0.5 | York/Landrace |
| 613-03 | Nov. 27, 1999 | −/+ | Gilt | 0.3 | York/Landrace |
| 647-01 | Dec. 13, 1999 | −/+ | Gilt | 0.5 | York/Landrace |
| 647-03 | Dec. 13, 1999 | +*/+ | Gilt | 16.3 | York/Landrace |
| 647-04 | Dec. 13, 1999 | −*/+ | Gilt | 0.5 | York/Landrace |
| 647-08 | Dec. 13, 1999 | −*/+ | Boar | 0.4 | York/Landrace |
| 647-09 | Dec. 13, 1999 | +*/+ | Boar | 1.92 | York/Landrace |
| 668-01 | Dec. 17, 1999 | +*/+ | Gilt | 489 | Yorkshire |
| 671-02 | Dec. 19, 1999 | +*/+ | Boar | 6.9 | York/Landrace |
| 671-04 | Dec. 19, 1999 | +*/+ | Boar | 325 | York/Landrace |
| 675-03 | Dec. 21, 1999 | −*/+ | Gilt | 2.1 | York/Landrace |
| 675-04 | Dec. 21, 1999 | +*/+ | Boar | 42.6 | York/Landrace |
| 675-06 | Dec. 21, 1999 | −*/− | Boar | 5.0 | York/Landrace |

[1]The number preceeding the dash represents the litter number and the number following the dash is the pig number within the litter.
[2]All PCR assays were conducted with the primer APPA-up2-APPA-Kpn. Assays indicated with a star gave a negative result with the primer pair. However these samples gave a positive result for the primer set APPA-d4-Lama-up1. Samples 613-02 and 613-03 were negative with the latter primer set.
[3]Saliva was sampled and assayed for phytase 2 to 4 days after birth of the piglets.
[4]Zygotes used for microinjection were collected from superovulated Yorkshire or Yorkshire-Landrace cross gilts.

TABLE 10

Phosphorus content of feces collected from pigs producing a salivary phytase and non-transgenic pen-mates[1]. The data was subjected to a T-test analysis and the data recorded below.

| | Mean Fecal Phosphorus (%) | SE | Relative reduction in fecal phosphorus (%) | t | t (1%) |
|---|---|---|---|---|---|
| 1. 167-02 Grower Diet (122 days): | 1.59 | | 24.47 | | |
| Non-transgenic (n = 4) | 2.11 | 0.0604669 | | 8.517 | 4.6 |
| 2. 167-02 Finisher Diet (154 days): | 1.97 | | 16.97 | | |
| Non-transgenic (n = 4) | 2.37 | 0.0240767 | | 16.717 | 4.6 |
| 3. 282-02 Grower Diet (93 days): | 1.85 | | 12.90 | | |
| Non-transgenic (n = 5) | 2.124 | 0.022231964 | | 12.324 | 4.03 |
| 4. 282-02 Finisher Diet (145 days): | 1.76 | | 16.03 | | |
| Non-transgenic (n = 5) | 2.096 | 0.099153384 | | 3.389 | 4.03[2] |
| 5. 282-04 Grower Diet (93 days): | 1.95 | | 8.19 | | |
| Non-transgenic (n = 5) | 2.124 | 0.022231964 | | 7.827 | 4.03 |
| 6. 282-04 Finisher Diet (145 days): | 1.56 | | 25.57 | | |
| Non-transgenic (n = 5) | 2.096 | 0.099153384 | | 5.406 | 4.03 |
| 7. 421-06 Starter II Diet (40 days): | 1.17 | | 27.47 | | |
| Non-transgenic (n = 5) | 1.612 | 0.086155741 | | 5.140 | 4.03 |
| 8. 421-06 Start III Diet (48 days): | 1.57 | | 18.01 | | |
| Non-transgenic (n = 5) | 1.915 | 0.102884789 | | 3.351 | 4.03 |
| 9. 421-06 Grower Diet (81 days): | 2.00 | | 13.28 | | |
| Non-transgenic (n = 5) | 2.310 | 0.151658823 | | 2.022 | 4.03 |
| 10. 421-06 Finisher Diet (136 days): | 1.71 | | 21.20 | | |
| Non-transgenic (n = 5) | 2.173 | 0.053023237 | | 8.687 | 4.03 |
| 11. 405-02 Starter II Diet (40 days): | 1.81 | | 26.97 | | |
| Non-transgenic (n = 5) | 2.482 | 0.173625623 | | 3.856 | 4.03 |
| 12. 405-02 Starter III Diet (48 days): | 1.54 | | 36.58 | | |
| Non transgenic (n = 4) | 2.430 | 0.104642248 | | 8.496 | 4.6 |
| 13. 405-02 Grower Diet (80 days): | 2.26 | | 18.19 | | |
| Non-transgenic (n = 4) | 2.763 | 0.124724697 | | 4.209 | 4.6 |
| 14. 405-02 Finisher Diet (136 days): | 2.26 | | 13.24 | | |
| Non-transgenic (n = 4) | 2.605 | 0.217198066 | | 1.588 | 4.6 |

[1]Fresh fecal samples were collected on 3 different days was freeze-dried and then dried to constant weight at 110° C. for 24 h, and analyzed for total phosphorus.
[2]At the 5% level of confidence t = 2.57.

TABLE 11

Phytase activities of the first generation (G1) transgenic offspring obtained by the crossing the phytase positive boar 167-02 with non-transgenic Yorkshire gilts[1]

| ID # of pig | Birth Date | Sex | Salivary phytase (U/ml) | Specific Activity U/mg protein |
|---|---|---|---|---|
| 151-01 | Mar. 16, 2000 | F | 1193 | 126 |
| 151-02 | " | F | 736 | 63.3 |
| 151-05 | " | M | 710 | 109 |
| 151-07 | " | M | 8019 | 315 |
| 152-04 | " | M | 10077 | 364 |
| 152-09 | " | M | 3054 | 200 |
| 154-01 | Mar. 19, 2000 | F | 2472 | 256 |
| 154-03 | " | F | 6425 | 706 |
| 154-04 | " | F | n.d. | n.d. |
| 154-05 | " | M | 2767 | 213 |
| 154-06 | " | M | 341 | 39 |
| 154-07 | " | M | 4029 | 142 |
| 154-08 | " | M | 1184 | 47.4 |
| 159-03 | Mar. 20, 2000 | F | 1563 | 116 |
| 159-04 | " | M | 2285 | 201 |

[1]The number of males and females (M/F) in each litter were 5/3, 7/2, 5/4, and 2/3 for litter numbers 151, 152, 154 and 159, respectively. Saliva was collected from the piglets on day 11.

TABLE 12

Primers used for construction and detection of transpenic constructs.

| Name | Start-End[1] | Forward/ Reverse | |
|---|---|---|---|
| **Primers used in R15/APPA+intron and R15/APPA construction** | | | |
| APPA-DOWN2 | | R | TCGGCGCTCACCTTGAGTTC (SEQ ID NO: 16) |
| APPA-DRA | | F | CCGTTTAAAGCCATCTTAATCCCAT (SEQ ID NO: 17) |
| APPA-SMA | | R | GTCCCGGGTATGCGTGCTTCATTC (SEQ ID NO: 18) |
| CAT-ATG | | R | CCATGGTGGCGGCTTTTAGCTTCCTTAGCTCCTGA (SEQ ID NO: 19) |
| CAT-TAA | | F | AGCGCTTGCAGTTTGTAAGGCAGTTATTGGTGCCC (SEQ ID NO: 20) |
| CAT-UP1 | | F | TCG AGG AGC TTG GCG AGA TT (SEQ ID NO: 21) |
| R15-UP1 | | F | TTTCGGGCCAATGTTGCTGT (SEQ ID NO: 22) |
| **Primers used in SV40/APPA+intron construction** | | | |
| SV-HIND | | F | CCCAAGCTTTACACTTTATGC (SEQ ID NO: 23) |
| SV-XHO | | R | GCCCTCGAGCCTCCTCACTACTTCT (SEQ ID NO: 24) |
| **Primers used in Lama2/APPA and Lama2/PSP/APPA construction** | | | |
| APPA-CLA | 12635–12657 | F | GGATCGATAAAAGCCGCCACCATGAA (SEQ ID NO: 25) |
| APPA-DOWN2 | 13307–13326 | R | TCGGCGCTCACCTTGAGTTC (SEQ ID NO: 26) |
| APPA-DOWN4 | 12751–12780 | R | GCACGCACACCATGACGACTGACAATCACC (SEQ ID NO: 27) |
| APPA-KPN | 13935–13959 | R | CGGGTACCTTACAAACTGCAAGCGG (SEQ ID NO: 28) |
| APPA-MATURE | 12719–12738 | F | CAGAGTGAGCCGGAGCTGAA (SEQ ID NO: 29) |
| APPA-UP2 | 13210–13229 | F | CGAACTGGAACGGGTGCTTA (SEQ ID NO: 30) |
| LAMA-CLA | 12615–12639 | R | GCATCGATCTTTGGTTCTGACAAATGG (SEQ ID NO: 31) |
| LAMA-SIGNAL | | R | TGACTCTGAGTTCCCAATGA (SEQ ID NO: 32) |
| LAMA-UP | 12111–12130 | F | GTGCTGCTCCAAGTTTGGTG (SEQ ID NO: 33) |
| **Primers for detection of the porcine β-globin gene** | | | |
| PIG-BGF | | F | GCAGATTCCCAAACCTTCGCAGAG (SEQ ID NO: 34) |
| PIG-BGR | | R | TCTGCCCAAGTCCTAAATGTGCGT (SEQ ID NO: 35) |

[1]The location of the primers shown for Lama2/APPA sequence.

The start and stop codons of APPA are indicated in bold letters, the optimal initiation sequence for translation is italicized, and the restriction sites for restriction enzymes are underlined.

REFERENCE LIST

The following references have been referred to in the present application. The content of these references are incorporated herein by reference.

1. Abelson, P. H. 1999. A potential phosphate crisis [editorial]. Science 283: 2015.

2. Altschul, S. F., Gish, W., Miller, W., Myers, E. W., and Lipman, D. J. 1990. Basic local alignment search tool. J. Mol. Biol. 215: 403–410.

3. Ann, D. K. and Carlson, D. M. 1985. The structure and organization of a proline-rich protein gene of a mouse multigene family. J. Biol. Chem. 260: 15863–15872.

4. Arkhipovets, A. I. 1956. Age characteristics of salivary secretion in young pigs. Journal of Physiology of USSR 42: 882–886.

5. Association of Official Analytical Chemists (AOAC) 1984. Official methods of analysis of the Association of Official Analytical Chemists. Association of Official Analytical Chemists, Washington.

6. Ausbel, F. M., Brent, R., Kingston, R. E., Moore, D. D., Seidman, J. G., Smith, J. A., and Struhl, K. 1992. Short protocols in molecular biology. John Wiley & Sons, New York.

7. Barsh, G. S. and Epstein, C. J. 1989. Physical and genetic characterization of a 75-kilobase deletion associated with al, a recessive lethal allele at the mouse agouti locus. Genetics 121: 811–818.

8. Bennick, A. 1982. Salivary proline-rich proteins. Mol. Cell Biochem. 45: 83–99.

9. Bitar, K. and Reinhold, J. G. 1972. Phytase and alkaline phosphatase activities in intestinal mucosae of rat, chicken, calf, and man. Biochim. Biophys. Acta 268: 442–452.

10. Burge, C. and Karlin, S. 1997. Prediction of complete gene structures in human genomic DNA. J. Mol. Biol. 268: 78–94.

11. Burge, C. B. and Karlin, S. 1998. Finding the genes in genomic DNA. Curr. Opin. Struct. Biol. 8: 346–354.

12. Carlson, D. M. 1993. Salivary proline-rich proteins: biochemistry, molecular biology, and regulation of expression. Crit Rev. Oral Biol. Med. 4: 495–502.

13. Carswell, S. and Alwine, J. C. 1989. Efficiency of utilization of the simian virus 40 late polyadenylation site: effects of upstream sequences. Mol. Cell Biol. 9: 4248–4258.

14. Chi, T. H. and Crabtree, G. R. 2000. Perspectives: signal transduction. Inositol phosphates in the nucleus [comment]. Science 287: 1937–1939.

15. Clark, A. J., Archibald, A. L., McClenaghan, M., Simons, J. P., Wallace, R., and Whitelaw, C. B. 1993. Enhancing the efficiency of transgene expression. Philos. Trans. R. Soc. Lond B Biol. Sci. 339: 225–232.

16. Clements, S., Mehansho, H., and Carlson, D. M. 1985. Novel multigene families encoding highly repetitive peptide sequences. Sequence analyses of rat and mouse proline-rich protein cDNAs. J. Biol. Chem. 260: 13471–13477.

17. Corring, T. 1980. Endogenous secretions in the pig. In Current concepts of digestion and absorption in pigs. Edited by A. G. Low and I. G. Partridge. National Institute for Research in Dairying, Reading pp. 136–150.

18. Cosgrove, D. J. 1980. Inositol phosphates. Their chemistry, biochemistry and physiology. Elsevier, Amsterdam.

19. Crameri, A., Dawes, G., Rodriguez, E. Jr., Silver, S. and Stemmer, W. P. C. 1997. Molecular evolution of an arsenate detoxification pathway by DNA shuffling. Nature Biotechnol. 15: 436–438.

20. Dassa, J., Marck, C., and Boquet, P. L. 1990. The complete nucleotide sequence of the *Escherichia coli* gene APPA reveals significant homology between pH 2.5 acid phosphatase and glucose-1-phosphatase. J. Bacteriol. 172: 5497–5500.

21. Denny, H. R. and Messervy, A. 1972. Surgical techniques for the extirpation of the submandibular salivary glands and the collection of salivary secretions in the pig. Vet. Rec. 90: 650–654.

22. Dobrinsky, J. R., Johnson, L. A., and Rath, D. 1996. Development of a culture medium (BECM-3) for porcine embryos: Effect of bovine serum albumin and fetal bovine serum on embryo development. Biol. Reprod. 55: 1069–1074.

23. Dvorakova, J. 1998. Phytase: sources, preparation and exploitation. Folia Microbiol. (Praha) 43: 323–338.

24. Engelen, A. J., van der Heeft, F. C., Randsdorp, P. H., and Smit, E. L. 1994. Simple and rapid determination of phytase activity. J AOAC Int. 77: 760–764.

25. Frandson, R. D. and Spurgeon, T. L. 1992. Anatomy and physiology of farm animals. Lea & Febiger, Philadelphia.

26. Galfre, G. and Milstein, C. 1981. Preparation of monoclonal antibodies: strategies and procedures. Methods Enzymol. 73: 3–46.

27. Geyer, P. K. 1997. The role of insulator elements in defining domains of gene expression. Curr. Opin. Genet. Dev. 7: 242–248.

28. Gish, W. and States, D. J. 1993. Identification of protein coding regions by database similarity search. Nature Genetics 3: 266–272.

29. Golovan, S., Wang, G., Zhang, J., and Forsberg, C. W. 2000. Characterization and overproduction of the *Escherichia coli* APPA encoded bifunctional enzyme that exhibits both phytase and acid phosphatase activities [In Process Citation]. Can. J. Microbiol. 46: 59–71.

30. Gordon, J. W., Scangos, G. A., Plotkin, D. J., Barbosa, J. A., and Ruddle, F. H. 1980. Genetic transformation of mouse embryos by microinjection of purified DNA. Proc. Natl. Acad. Sci. USA 77: 7380–7384.

31. Gorman, C., Padmanabhan, R., and Howard, B. H. 1983. High efficiency DNA-mediated transformation of primate cells. Science 221: 551–553.

32. Greiner, R. and Jany, K.-D. Characterization of a phytase from *Escherichia coli*. Herbsttagung der Gesellschaft fur Biologische Chemie 372. 1991. Ref Type: Abstract 33. Greiner, R., Konietzny, U., and Jany, K. D. 1993. Purification and characterization of two phytases from *Escherichia coli*. Arch Biochem. Biophys. 303: 107–113.

34. Hall, J., Hazlewood, G. P., Surani, M. A., Hirst, B. H., and Gilbert, H. J. 1990. Eukaryotic and prokaryotic signal peptides direct secretion of a bacterial endoglucanase by mamalian cells. J. Biol. Chem. 275: 19996–19999.

35. Harland, B. F. and Morris, E. R. 1995. Phytate: A good or a bad food component? Nutr. Res. 15: 733–754.

36. Harlow, E., and Lane, D. 1988. Antibodies: a laboratory manual. Cold Spring Harbor Laboratory, New York.

37. Harayama, S. 1998. Artificial evolution by DNA shuffling. Trends Biotechnol. 16: 76–81.

38. Heinoen, J. K. and Lahti, R. J. 1981. A new and convenient colorimetric determination of inorganic orthophosphate and its application to the assay of inorganic pyrophosphate. Anal. Biochem. 133: 313–317.

39. Heneine, W. and Switzer, W. M. 1996. Highly sensitive and specific polymerase chain reaction assays for detection of baboon and pig cells following xenotransplantation in humans. Transplantation 62: 1360–1362.

40. Higuchi, R. 1989. Simple and rapid preparation of samples for PCR. In PCR technology: principles and applications for DNA amplification. Edited by H. A. Erlich. Macmillan Publishers; Stockton Press, New York, N.Y. pp. 31–38.

41. Hu, Y., Nakagawa, Y., Purushotham, K. R., and Humphreys-Beher, M. G. 1992. Functional changes in salivary glands of autoimmune disease-prone NOD mice. Am. J. Physiol. 263: E607–E614.

42. Huang, X. 1996. An improved sequence assembly program. Genomics 33: 21–31.

43. Huang, X. 1999. A contig assembly program based on sensitive detection of fragment overlaps. Genomics 14: 18–25.

44. Huff, W. E., Moore, P. A., Jr., Waldroup, P. W., Waldroup, A. L., Balog, J. M., Huff, G. R., Rath, N. C., Daniel, T. C., and Raboy, V. 1998. Effect of dietary phytase and high available phosphorus corn on broiler chicken performance. Poult Sci 77: 1899–1904.

45. Iqbal, T. H., Lewis, K. O., and Cooper, B. T. 1994. Phytase activity in the human and rat small intestine. Gut 35: 1233–1236.

46. Jia, Z., Golovan, S., Ye, Q., and Forsberg, C. W. 1998. Purification, crystallization and preliminary X-ray analysis of the *Escherichia coli* phytase. Acta Crystallogr. D. Biol. Crystallogr. 54 (Pt 4): 647–649.

47. Kazazian, H. H. J. 1998. Mobile elemants and disease. Curr. Opin. Genet. Dev. 8: 343–350.

48. Kim, H. S. and Maeda, N. 1986. Structures of two HaeIII-type genes in the human salivary proline-rich protein multigene family. J. Biol. Chem. 261: 6712–6718.

49. Kohler, G. and Milstein, C. 1976. Derivation of specific antibody-producing tissue culture and tumor lines by cell fusion. Eur. J. Immunol. 7: 511–519.

50. Kozak, M. 1987. At least six nucleotides preceding the AUG initiator codon enhance traslation in mammalian cells. Proc. Natl. Acad. Sci. USA 196: 947–950.

51. Kuchner, O. and Arnold, F. H. 1997. Directed evolution of enzyme catalysts. Trends Biotechnol. 15: 523–530.

52. Laemmli, U. K. 1970. Cleavage of structural proteins during the assembly of the head of bacteriophage T4. Nature 227: 680–785.

53. Larsen, H. J., Brodersen, C. H., and Hjorth, J. P. 1994. High-level salivary gland expression in transgenic mice. Transgenic Res. 3: 311–316.

54. Laursen, J. and Hjorth, J. P. 1997. A cassette for high-level expression in the mouse salivary glands. Gene 198: 367–372.

55. Levitt, N., Briggs, D., Gil, A., and Proudfoot, N. J. 1989. Definition of an efficient synthetic poly(A) site. Genes Dev. 3: 1019–1025.

56. Low, A. G. 1989. Research into the digestive physiology of pigs. In Nutrition and digestive physiology in monogastric farm animals. Edited by E. J. van Weerden and J. Huisman. Pudoc, Wageningen pp. 1–15.

57. Madsen, H. O. and Hjorth, J. P. 1985. Molecular cloning of mouse PSP mRNA. Nucleic Acids Res. 13: 1–13.

58. Mallin, M. A. 2000. Impacts of industrial animal production on rivers and estuaries. American Scientist 88: 26–37.

59. Mehansho, H., Ann, D. K., Butler, L. G., Rogler, J., and Carlson, D. M. 1987. Induction of proline-rich proteins in hamster salivary glands by isoproterenol treatment and an unusual growth inhibition by tannins. J. Biol. Chem. 262: 12344–12350.

60. Menniti, F. S., Oliver, K. G., Putney, J. W., Jr., and Shears, S. B. 1993. Inositol phosphates and cell signaling: new views of InsP5 and InsP6. Trends Biochem. Sci 18: 53–56.

61. Mikkelsen, T. R., Brandt, J., Larsen, H. J., Larsen, B. B., Poulsen, K., Ingerslev, J., Din, N., and Hjorth, J. P. 1992. Tissue-specific expression in the salivary glands of transgenic mice. Nucleic Acids Res. 20: 2249–2255.

62. Miner, J. R. 1999. Alternatives to minimize the environmental impact of large swine production units. J. Anim Sci. 77: 440–444.

63. Nakai, K. and Kanehisa, M. 1992. A knowledge base for predicting protein localization sites in eukaryotic cells. Genomics 14: 897–911.

64. Nesterenko, M. V., Tilley, M., and Upton, S. J. 1994. A simple modification of Blum's silver stain method allows for 30 minute detection of proteins in polyacrylamide gels. J. Biochem. Biophys. Methods 28: 239–242.

65. O'Shannessy, D. J., Voorstad, P. J., and Quarles, R. H. 1987. Quantitation of glycoproteins on electroblots using the biotin-streptavidin complex. Anal. Biochem. 163: 204–209.

66. Owerbach, D. and Hjorth, J. P. 1980. Inheritance of a parotid secretory protein in mice and its use in determining salivary amylase quantitative variants. Genetics 95: 129–141.

67. Pen, J., Verwoerd, T. C., Vanparidon, P. A., Beudeker, R. F., Vandenelzen, P. J. M., Geerse, K., Vanderklis, J. D., Versteegh, H. A. J., Vanooyen, A. J. J., and Hoekema, A. 1993. Phytase-containing transgenic seeds as a novel feed additive for improved phosphorus utilization. Biotechnology 11: 811–814.

68. Petitclerc, D., Attal, J., Theron, M. C., Bearzotti, M., Bolifraud, P., Kann, G., Stinnakre, M. G., Pointu, H., Puissant, C., and Houdebine, L. M. 1995. The effect of various introns and transcription terminators on the efficiency of expression vectors in various cultured cell lines and in the mammary gland of transgenic mice. J Biotechnol. 40: 169–178.

69. Pinkert, C. A., Dyer, T. J., Kooyman, D. L., and Kiehm, D. J. 1990. Characterization of transgenic livestock production. Domest. Anim Endocrinol. 7: 1–18.

70. Quissell, D. O., Barzen, K. A., Redman, R. S., Camden, J. M., and Turner, J. T. 1998. Development and characterization of SV40 immortalized rat parotid acinar cell lines. In Vitro Cell Dev. Biol.-Animal. 34: 58–67.

71. Reddy, N. R., Sathe, S. K., and Salunkhe, D. K. 1982. Phytates in legumes and cereals. Adv. Food Res. 28: 1–92.

72. Rozhkov, Y. I. and Galimov, I. R. 1990. Salivary gland polymorphism in pigs and cattle detected by affinity electrophoresis. Anim. Genet 21: 277–283.

73. Samuelson, L. C. 1996. Transgenic approaches to salivary gland research. Annu. Rev. Physiol. 58: 209–229.

74. Shaw, P. and Schibler, U. 1986. Structure and expression of the parotid secretory protein gene of mouse. J. Mol. Biol. 192: 567–576.

75. Simons, P. C., Versteegh, H. A., Jongbloed, A. W., Kemme, P. A., Slump, P., Bos, K. D., Wolters, M. G., Beudeker, R. F., and Verschoor, G. J. 1990. Improvement of phosphorus availability by microbial phytase in broilers and pigs. Br J Nutr. 64: 525–540.

76. Smit, A. F. A. 1996. The origin of interspersed repeats in the human genome. Curr. Opin. Genet. Dev. 6: 743–748.

77. Stahl, C. H., Han, Y. M., Roneker, K. R., House, W. A., and Lei, X. G. 1999. Phytase improves iron bioavailability for hemoglobin synthesis in young pigs. J Anim Sci 77: 2135–2142.

78. Svendsen, P., Laursen, J., Krogh-Pedersen, H., and Hjorth, J. P. 1998a. Novel salivary gland specific binding elements located in the PSP proximal enhancer core. Nucleic Acids Res. 26: 2761–2770.

79. Taboit-Dameron, F., Malassagne, B., Viglietta, C., Puissant, C., Leroux-Coyau, M., Chereau, C., Attal, J., Weill, B., and Houdebine, L. M. 1999. Association of the 5'HS4 sequence of the chicken beta-globin locus control region with human EF1 alpha gene promoter induces ubiquitous and high expression of human CD55 and CD59 cDNAs in transgenic rabbits. Transgenic Res. 8: 223–235.

80. Terada, T. and Nakanuma, Y. 1993. An immunohistochemical survey of amylase isoenzymes in cholangiocarcinoma and hepatocellular carcinoma. Arch Pathol. Lab Med. 117: 160–162.

81. Towbin, H., Staehelin, T., and Gordon, J. Electrophoretic transfer of proteins from polyacrylamide gels to nitrocellulose sheets: procedure and some applications. Proc. Natl. Acad. Sci. USA 76(9), 4350–4354. 1979.
Ref Type: Generic 82. Tryon, A. F. and Bibby, B. G. 1966. Preliminary studies on pig saliva. Arch. Oral Biol. 11: 527–531.

83. Tu, Z. J., Lazowski, K. W., Ehlenfeldt, R. G., Wu, G., Lin, H. H., Kousvelari, E., and Amm, D. K. 1993. Isoproterenol/tannin-dependent R15 expression in transgenic mice is mediated by an upstream parotid control region. Gene Expr. 3: 289–305.

84. Verwoerd, T. C., van Paridon, P. A., van Ooyen, A. J., van Lent, J. W., Hoekema, A., and Pen, J. 1995. Stable accumulation of *Aspergillus niger* phytase in transgenic tobacco leaves. Plant Physiol 109: 1199–1205.

85. Wall, R. J., Hyman, P., Kerr, D., Pintado, B., and Wells, K. 1997. Transgenic animal technology. J. Androl 18: 236–239.

86. Wall, R. J., Pursel, V. G., Hammer, R. E., and Prinster, R. L. (Editors). 1985. Development of porcine ova that were centrifuged to permit visualization of pronuclei and nuclei. Biol. Reprod. 32.

87. Wessel, D. and Flugge, U. I. 1984. A method for the quantitative recovery of protein in dilute solution in the presence of detergents and lipids. Anal. Biochem. 138: 141–143.

88. Whitelaw, C. B., Archibald, A. L., Harris, S., McClenaghan, M., Simons, J. P., and Clark, A. J. 1991. Targeting expression to the mammary gland: intronic sequences can enhance the efficiency of gene expression in transgenic mice. Transgenic Res. 1: 3–13.

89. Williamson, C. M., A. J. Bramley, and A. J. Lax 1994. Expression of the lysostaphin gene of *Staphylococcus simulans* in a eukaryotic system. Appl. Environ. Microbiol. 60: 771–776.

90. Wodzinski, R. J. and Ullah, A. H. 1996. Phytase. Adv. Appl. Microbiol. 42: 263–302.

91. Xiong, Y. and Eickbush, T. H. 1990. Origin and evolution of retroelements based upon their reverse transcriptase sequences. EMBO J. 9: 3353–3362.

The invention claimed is:

1. A transgenic non-human mammal that carries in the genome of its somatic and germ cells a transgene construct comprising (a) a transgene encoding a phytase protein operably linked to (b) a first mammalian regulatory sequence for salivary gland expression of said protein and (c) a signal sequence for secretion of said protein wherein said mammal is selected from the group consisting of pigs, goats, sheep, cows and horses and the mammal expresses and secretes the protein in its salivary glands.

2. The mammal of claim 1 wherein said first regulatory sequence comprises a salivary protein promoter/enhancer sequence.

3. The mammal of claim 2 wherein said salivary protein promoter/enhancer sequence comprises a parotid secretory protein (PSP) promoter/enhancer, a proline-rich protein (PRP) promoter/enhancer or a salivary amylase promoter/enhancer.

4. The mammal of claim 3 wherein said promoter/enhancer is a parotid secretory protein (PSP) promoter/enhancer.

5. The mammal of claim 4 wherein said parotid secretory protein (PSP) promoter/enhancer is from a mouse.

6. The mammal of claim 3 wherein said promoter/enhancer is a proline-rich protein (PRP) promoter/enhancer.

7. The mammal of claim 6 wherein said proline-rich protein (PRP) promoter/enhancer is from a rat.

8. The mammal of claim 1 wherein said transgene is further operably linked to (d) one or more second regulatory sequences including enhancers, transcription regulatory sequences, termination sequences, and polyadenylation sites.

9. The mammal of claim 1 wherein said mammal is a pig.

10. The mammal of claim 1 wherein said phytase is *Escherichia coli AppA phytase*.

11. The mammal of claim 1 wherein said mammal is a pig and said first regulatory sequence comprises a parotid secretory protein (PSP) promoter/enhancer or a proline-rich protein (PRP) promoter/enhancer.

12. The mammal of claim 1 wherein said transgene construct comprises a nucleic acid sequence according to SEQ ID NO:3, SEQ ID NO:5; or SEQ ID NO:7.

13. A method of expressing and secreting a phytase protein in the salivary gland of a non-human mammal, the method comprising the steps of:

a) introducing a transgene construct into a non-human mammalian embryo such that a non-human transgenic mammal that develops from said embryo has a genome that comprises said transgene construct wherein said transgene construct comprises:

i) a transgene encoding said phytase protein, ii) at least one mammalian regulatory sequence for salivary gland expression of said phytase protein, and (iii) a signal sequence for secretion of said phytase protein b) transferring said embryo to a foster female; and, c) developing said embryo into said transgenic mammal wherein said phytase is expressed and secreted in the salivary gland of said mammal, wherein said mammal is selected from the group consisting of pigs, goats, sheep, cows and horses.

14. The method of claim 13 wherein said salivary gland is a parotid gland, submaxillary gland, or a submandibular gland.

15. The method of claim 13 wherein said at least one regulatory sequence comprises a salivary protein promoter/enhancer sequence.

16. The method of claim 13 wherein said phytase is *Escherichia coli* AppA phytase.

17. The method of claim 13 wherein said transgene construct comprises a nucleic acid sequence according to SEQ ID NO:3, SEQ ID NO:5, or SEQ ID NO:7.

18. A transgenic mammal prepared according to the method of claim 13, or a progeny thereof.

19. A process for producing a phytase protein comprising the steps of:

a) obtaining salivary gland secretion containing said phytase protein from a non-human transgenic mammal selected from the group consisting of pigs, goats sheep, cows and horses, said mammal containing within its genome a transgene construct, wherein said transgene construct comprises:

i) a transgene encoding said phytase protein, ii) at least one mammalian regulatory sequence for salivary gland specific expression of said protein, and (iii) a signal sequence for secretion of said phytase protein; and extracting said protein from said saliva.

20. The process of claim 19 wherein said at least one regulatory sequence comprises a salivary protein promoter/enhancer sequence.

21. The process of claim 19 wherein said transgene construct comprises a nucleic acid sequence according to SEQ ID NO:3, SEQ ID NO:5; or SEQ ID NO:7.

22. The process of claim 19 wherein said phytase is *Escherichia coli* AppA phytase.

23. The process of claim 19 wherein said salivary gland secretion is from a parotid gland, submaxillary, or a submandibular gland.

* * * * *

SEQUENCE LISTING

```
<160> NUMBER OF SEQ ID NOS: 38

<210> SEQ ID NO 1
<211> LENGTH: 20623
<212> TYPE: DNA
<213> ORGANISM: Artificial Sequence
<220> FEATURE:
<223> OTHER INFORMATION: Lama2/APPA plasmid
<220> FEATURE:
<221> NAME/KEY: misc_feature
<222> LOCATION: (11392)..(11392)
<223> OTHER INFORMATION: n=any nucleic acid

<400> SEQUENCE: 1

tcgagagtat ctttgtcagc tgtgcctcca acaaaggggt actgttgccc acatagaaag      60

atctaaacta attaattaat ccctcacccg caaatctttc agtcactaag ttagcacgat     120

tgttgaacaa gttctccaaa ggagagatac agatgagtgc gtatagggtg gacctggctg     180

ctgaggagac acctgcatct gactaagaag agccacggtg ttagttgaat ggtgtggagt     240

agggtggttc tgtgggacag tagaaaatcg agaggcatgt gccgtttagt gaactgatgg     300

aagctacccc aaacgacaga gattgtcagt caggccaatc cgtttcgagt ttgatgggca     360

gccggacagt gagacagaca cacctactca gttggaggaa ggatgagaac aatggccagc     420

agggattgag agaccctgac aggcgcaagg ccctaacaca cacacctacc acctcacttg     480

acaaagctgc caaagaccaa agacttgttc tccattagaa atgacagctg gcttgacccg     540

acagcataat aagcagagtg tactctgatt ggagaacttt aatgtgtttc attcagtatt     600

ataaaaggac agtattacag attttgttgt acactgctgt tacatgtggg gcagtgtgtc     660
```

-continued

```
tttaagtagg gtaaagtact ctttaaaaat gggtcctaga tattttttcc tttaactcaa    720
gtctcttact gtttaaatga tttttatttt gtttaatatg gaggaaaaag aagcgtaaat    780
ggacaatata tatttagaga aagatggtta gctgtcagaa aaatatgcaa atcaaaatca    840
caccaagact gcagcacacc cctgtcagat ggctgtgatc aagaaaataa atgacaatga    900
gtggtggtga agatgtacta aagggaaaca cacacacaca cacacacaca cacacacaca    960
cacactggag caaccactgt ggaaatcagt atgaatggtc ctcaaaaacc tgaagataga   1020
gcggggcgtg gtggcataca cttttattcc cagcactggg gaggcagagg caggtggatc   1080
tctgagttcc aggccagcct ggtctatagc acaggttcta ggacagccag ggctacacag   1140
aaaaaccctg ccttgattaa accaaaccaa accaaaccaa accaaaccaa accaaaccaa   1200
accaaaccaa accaaaccag accaaaccaa aacactgaag atagaacttc agtattccat   1260
tcctagatat atacccaatg gagactaagt cagcaagaca cctgcacagc catgttcact   1320
actacactgt tcaccacagc caggctgtgg aaccagcctg agtgtccatg ataaatgaat   1380
ggataggtaa ctttcaaggt aaatggactc tgctgtgtac atgcctcaca ttctgtttat   1440
tcatttttct ttatgaggtg tccattcagg agtcacatgg tagttctatt ttcagtcttc   1500
tgaagatact acactggtcc ccacagttta cacttttatc agcagtgaat aagggttcct   1560
ctatccttac catcatttgt tgtaattttt cttgatgacc ctctttctga cagggatagg   1620
atgtaatatc agtgtgagga agtacaactt gttttctaag tatttattgg ccccttgcat   1680
ttcttctttt gaaaactgtc ggttcctgac atctgctcag gtattcattg gatgttgttt   1740
ctttggtgtt tgagttctta tgaattctag atgttaaatc cctgcctgtg gttctctccc   1800
attctgtagg ctgcctcctc accctggcaa ttgttgtcct tgttttgcag aaacttttga   1860
cttcatggaa tctcatttgt cagttttccc tcctctgcta tagcctgagc taatgcactg   1920
gtttttacag agccctggtc tatgccttta tcctcctctg gcagcttcgg agtttcattt   1980
cttacattta gatctttgat ccactttgaa caagttttgg agcagggtga gagatacgaa   2040
tctagttcca ttcttccata tgtgatccta gtttacatag catcgttggt tgaagaggtt   2100
ttattttatt tttaaataat gtgtcataaa aaacgaggtg gttgtagcag tgtggatttg   2160
tttctttgtc ctttgatcta caggtcttgt tttgtgtcag tctcatgatg ttttattgct   2220
atggctctgt catacagtct gaggtcaggt attgtgatat accttcagta ttgctccctc   2280
agactcaggt ttgctttggc caggagtcat cttactcagt gctcttagag ctcccccagc   2340
atgtagctgc tactattctt agttgataaa tcaggaaact ggggctcaga gagattaact   2400
gtcttgaact acttctgggg aggtgaaacg tggagacact aaactgtgtt taccctgtac   2460
tgctccagta gctgtcgggt gctgggctac agcaaagcac ctatactata tattactcag   2520
gaggtggaaa aactcagcct cccttggggt tcccaagctc ccaggtgtcc agtcactgct   2580
ggaaacctca tggagtctga aaggaagggt tgagggtaca tggggcagcg atgaggagcc   2640
tggggctggg atctcccaaa cacctggata tccagatgcc actgggtcag ggggagttgg   2700
gaacagagtt gggatgtcca tggacctgtg acaaggccag ggccaggggg aggataactc   2760
tggctttact aatttgcgaa agtccttagc ttagcagcag ttgtctggga gcacagaggg   2820
gccttctgta agaggctcag gcagtgccgc tctgtaggcg aaggtcttct ccatgttccc   2880
catggtggtt cttgatgaaa gagacagtcc ttggctccaa actggtttat tgattgttca   2940
ttgtggaaaa tgggtgcaca ccaccttctc agggtggacc agagatcaaa taccttttgc   3000
```

-continued

```
agggaggaat atctgggaag ggacgcttac tggctaaacc ctcagggcct ctagatacat   3060
cattagcatg gagaactctg ttctgggcta catgaccaca ggccacattt ccacaagcca   3120
catgtgggaa gtgtggcaca tgttctaggc caggaatctg gtagggagcg tggagccacc   3180
taccatccca ggtgggtgcc tgggtgccag ggaccctgaa cccgctcaac cttaccaagt   3240
ttcctggcag ggtccactgt cctacacaga agctggagga ggtgtgaggg ttgtgtcttt   3300
gtggaatgtc ccatgctgct tggggctcag tttctccacc tgtacctcat tggtttgggt   3360
ataaaaagtg gggatacttt attattctct gactcggtcc tgaggaaaaa gcatcgtggc   3420
agtccaggaa ccacaccctg aggttcctgc actgaaggga ctccctaagt ctctggagtc   3480
tctccccttc acagagctgc caaagtctag gttcttttga ggataacaga gccatgcttg   3540
gtaagcagac aacagcattt gtttactcaa ccttcttttg tcagctccct cttcataaac   3600
aagttgagac accatgctgg cttgaggaag acttctaaag ccagacaact gtgcaaggaa   3660
gaagaagaag gggcaagtgg agttagcctg gatgtagccc tcaaagtctc cagagaccag   3720
ccatgaaggc tcaagtggag ggcaagacct gcagcagcca agcatctggc aggagaggat   3780
cctgggaacc cctctaccat gacacacatt cttcctgcag gtcacactta ataggccatt   3840
tcttatttgg atctatcatg gtgttctgtg cgagattaat gaggtgttat gctgcgaaca   3900
gaaagttata taaaaacaag tccccccccc ttgtcactgc tgctaagaat gtagcagaaa   3960
ttgtctcaag tgtctctcta atcagaaaca ataaaggtct ccttggattc aagccctcca   4020
gtttcctcct tccttgctga gccttggaca cccatacaaa cctcctggat gctacagctc   4080
tgggcagaga ctccaaggtg gggagagact gatggtacaa aagcaaaata cttgtttggg   4140
ggtacaccca ctcctctgcc tgtgtggttc ctgcagtcag tcctgcagac aggccctcag   4200
tgggtcttcc atgggcaaca cgcagaggga ggcaatggat gggaataccc acaccctggt   4260
tagtttaccc cggccatgct ctctgctctt catccctcct ctgccctctg ccacggcttt   4320
ctctgcagga atcatatctt catattggcc cacaggtgtt ctcctcaccc tagctatgat   4380
gtttacttta gagtgacctt agcagggctg gtgggaatga gttctagaag gctcacggag   4440
atgctaggga agaaacgtct tctaactact gaggttacta agttcctggt ggttgtctct   4500
gcctttccct tgttaaagtc accttgaagt tagtgcagaa gaaatcagag cccagtcaca   4560
gagtaaatat ggtcctgaag atttcctttg agtgcccaga atccatgaca tttcaagagc   4620
cctctttgta ccttaagtca tttggggttg tatcttctgc ttgatgtatg tgtgtgtgtt   4680
tatcaaagag tgagatggtt acataagagg tgctctaaag gacagagagg atttgcaatt   4740
gtggcatgtg acatcctcag gccttgctct ggtgccagga ggaactgatg cagaaaagag   4800
taagaggtca tttcctggag gctgtcacta tagaggagat cttacagtgc attccctcct   4860
ccaggccctg cctgaggata gacatgtgct gactgcaact gaaacagagg cttgggatgg   4920
agagttaggt tcacagaagg gagggtggga gatggatgct tgctgggttc tgggtctcat   4980
caccagctcc tgaccacccg gtcagcccat gtgcttattc catagctttc ttttgctatg   5040
tttactcagt gtggtgtttg ttgggaccca gcagaagcca gtcccaggct gacagctgtg   5100
gatacacagg gcagcatgag ggtcctcagc ctgaagcagt caggctggca gaagagaaag   5160
accagcacac attccttcaa ccaactatgt cttgaaaaac aaacatatta tatcacatat   5220
attgcattta tgagacagct aaaatgtact cgggtagcat gactccaggt ggggatatct   5280
gcaagtgcca tgagtggcag agggacagcc aatgtgaggc aagaaggaat tctggctcaa   5340
cacagcttag ctccctggtg ttggttcaaa ctttgagagt ttgaccacaa gcactttatt   5400
```

-continued

```
tttgacatat ttaaacagag cacaactttg ggaaaaagtt ttcttatgaa aattatcaca   5460
ataaagctta aggcatgact acattaaaat gcctttgcaa agtatatgtg ccctcttcca   5520
caagaatggt tctattgact gagaaataat gttcaggata aagatccagg aagaaaagat   5580
cagggataag taaaatacta aactcttttg caaagtacat agaccctctt tcataacaat   5640
gggttctatt gactgacaag cactgctcag gagttgggaa agagtctagc ataagcacga   5700
tagcctggag actctagtga ggtctagtct tacagacagc aaaaatcacc aggttacaaa   5760
ctacattcat ttccagtttt ctgatcaggc acaggtatga atcccttctg ttgaagagaa   5820
aagtccatgt gtttaaaata tctggtttct ccagtgctat tagcgagaag acttgagccc   5880
tatacaactc ccacctggag tgacatcctg tcttcatggt atattacata cctagacacg   5940
ctcatctcac agacttagga ctttgtcttc tgatctccat ttctgatccc acttccacct   6000
ttgccttgat agtgtcattt tcttcactgc cttggtgaca accatgttat cctctgtgta   6060
tttgagtgtt accattttca gattttacct gtatgcaaga tcacacagtc tttgtctttc   6120
tgtctggatg catgctaatc tctacacaac aacccttccc cgtcactcag atcttcctcc   6180
attaacacat acatggtgct gaagaggcta gggagcttcc cttcagtggg gagctagctg   6240
gctattgggc ctttttgact gtccaggaag gcccccaatt gctgagacaa gaacttagat   6300
tcttcattat tgactctaac tcatgtatca agcagaagct aatgaatagt tatcaacagg   6360
atcagaggtt ccagtgtaag acactttgac atgaaagaac ggaggaagga cagatggatg   6420
cataaaagca ggaccactgc cccaggaagg tcctggaaac tgatgcaggg caaaggacag   6480
gttataaacc aaatcttagg gagtcaggaa gagcacagag gagctcaacc aactgaccac   6540
tgcttagggg ctaccaaccc aatcctccct gtgggaacag ctaagctatc agccaagggt   6600
aataaacagg caggacctgt ggatgacatg gagagcatag ggaccctggg tccagccttt   6660
agcacctgca ctctcaggat actccaccat tgtgtcttag agagcctagg gatactgggt   6720
ccagcctttg gtaccttcac tctcagggta ccccatcact gtgtcttgga gagcctaggc   6780
accctgggtc cagccttcag tacctgcgct ctcaggacac cccaccattg tctcttgccc   6840
cgtctcttct tcctcttcct ccctttcatt gtctcttctc tgtttctttc ttgactctcc   6900
tttcccctca caccctcact ctagttctcc ccttccctct ctgcatcacc ctattctctc   6960
tgtggtccct ccactttcct ttatctctca tgcttctctc ctccctcaaa tacttgtcac   7020
ccactatact tcaggggcca gctctagtga caaagctgtt aatagcaaga ctctcagatc   7080
tccaacggct cagaggagcc agacccacca agaactctct ccaggtccaa tttcaggttc   7140
cttcgaaagc tttcagcaaa tgctcaggga acatgccact aacaagaaga tgcaaattcc   7200
agttgagagt gggaaaggcc cttgcgtagg tcccatcttc caggccaagg tcagaggggc   7260
tctgtgtaat ccggattgac agggctcaga acaatgtttt gtttttaagg tttatttatt   7320
ttaggtgtta gtgtctttgc ttgcatgacc ttatgtgcat catgtgtgtg caggttcctg   7380
atgacagtag aggagggctt tgaatccctg gggataggaa gttacaggaa attataagct   7440
gctttgtggg tcttctagct ttcccaacag aagtgaatgc tcttcaccac tgagccatct   7500
ctctaggccc aagagacatt gctttatgga tataattgtg tgtgtgtgtc aacattgagg   7560
aaagggaaat aaaaaaaaaa cttcagccgc taaggttgta cagtttcact aattgctact   7620
tttagttgtg ataaaatggc aggtgcttca acatttatat atacaaaaac ttccctgctg   7680
gtggttcaac tgtgagaact ggggtaagtg ggtgagttct ctttttctgt ctctgtctct   7740
```

-continued

```
gtctctctcc ttccattctt tcttaaagga aataaacatt gcagctgggt tatagctcat   7800
caatatggaa gttacagaag tgaaaaaagg cattgccttg gtgggtggtg ttaccagctg   7860
atttttggtt gtcctgcaag gaggtctggg gactggctgc tctgtctctg tctgtatgag   7920
tgagggaagt ctggggagca gattccctaa ccttcagcct ggcctggttc ctgagtgaac   7980
ccagcctctc tggtcctagt agctttttcc aaacaggaat ctgagtggtg acagggaaca   8040
agtaccagcc cattgcttaa gtgccagggt tagtgagggc aggaagctgc catagctggg   8100
attagtagtt gtattggatg taggaagtcc tatcctggga cagctaatcc ttaatgcttc   8160
actggagatt ttcaatgaga aatttatccc acggcccata tggccccatc cttttgtctc   8220
caacagccaa gtattttcca ttagaggaga cttcctgtac acttgatgga tgctcattcc   8280
aaggtgactt ggggcagtca gtacagactt gggatgacct ctgacagcct aacctctccc   8340
caacaagggc cctctatgtt tgctatgtaa tgtaatgtca gacattgtca ggagtgtccg   8400
cagcacagcc tgcccagtgt gagggctctc ataggtttcc cactgtctta tctacacagg   8460
gataacgagg aggtaagctg cagttcccag tctcacttca cagaggaaga gataacccca   8520
tcccaggtca tgtagccagc agtggaaaga atgaggattt gaactcaggt cttccaagtc   8580
ccattgatag catctcctca caagtccctt gccaccctca cgatgcctta gacacttgcc   8640
tgccctttat actaaggaga tgcaggtaca aggggtttac ccatgtagca gctgaggcag   8700
ctggggatag ataccagcag caggcctgat gtcaccactc taactccagc atccccagtc   8760
tgtgttcctg gagtgtgaaa atccctactt aacaagattg tgcaacagtc cttggctctg   8820
tgacccatag ctggaaacag gattctcatt gatttgtgga acatggtggc agccagccaa   8880
aaagagggtc tgcatacaga agacacgtgt ggcaaggcca cagcagactc tgactacctt   8940
agcttacaga attacaaggt cataatgtcc tctgctttgg tcacctcatg ttaaggacag   9000
gccctaatga agatggggca gaagactgaa ggaatggcca accaataact ggcccaactt   9060
gagacccatc ctacaggcaa gcatcaattc ctgacactac taatgatact ctgttatgct   9120
tgcagacaga agcctagcat aactatcctc cgagaggtcc acccagcaac tgactgaaac   9180
agaaaaagat atccacaggc aaacagtgga tggaggtcag ggactattat gggagagctg   9240
tgggaaggat taaaaaccct gaaggggata ggaaccccac aggaagacca acagagtcaa   9300
ctaagagacc tgtgggagct ctcagagact gagccaccaa ccaaagagca tacacaggcc   9360
ggtccgaggc acctggcacg tgtgaagcag acatgcagct cagtctccat gtaggtcctc   9420
caataagcgg tagcctgact gcagtatcca atccccaaca gggctgcata gtctggcctc   9480
agtgggggag gatgccccta atcctgcaga gacttgatga gtggagagct atccaggggg   9540
aacccaccct ctctgagaag ggaatgggga tgggggaggg actctgtgaa gaggggacaa   9600
ggacaaacaa gaacctcaaa taggtcaggc cctaaaggct tgctaagtag cagtggccca   9660
gctctgtcct gttcctcagc ccaaggctca gctcccacct gtttctgtgt ttttctggct   9720
tttcatgggc ctaggacttg gtgaccagtt caaacaatgg ggcctgtgga agacacaata   9780
tacaagacta gggacattcc tgttctgctg actatccata gcctgatgta ggtggaagga   9840
cccaatcact ggatttctac ccttgcacaa ccttgacagc tgagggcctc tcagaaacct   9900
atttcttcca ctgaaaaatg agactctcaa atgaacgtcg tgacaatcat caggcttatt   9960
aaagaggtgt atctaacctg aatggcaagc agacagcagg caaatgtctg tatcaacctc  10020
taggaaggac aagaactgct cactgctgcc ccccaggagg ccatttgctg aaacagctgc  10080
tctcctgctg gtgcacaggc cctgccttct cattgcagcc acagcccctt cctgtctgaa  10140
```

-continued

```
cctcctgtca ggtcactggg aaacagatca agatggaaca ggacagctcc tgatggtaaa  10200
taaaaaacag tggtcatggc tattcatagg ggtttatgct tcttcagtcc acactgtgaa  10260
gagctgtggg catgaaccac agtgttcgag gtagagttgg ggttctgaaa ttcacagtgg  10320
ggtgagctca gtaaatgtga gctggaggtc actcgtgaga cacacagtcc tgctgcttct  10380
gttcccaata tcctgaggag acgacacatc tactttgttc agaggccaca gtctagttga  10440
cctgagagtt accagtttct tatttgtgtg tgtgtgtgtg tgtgtgtgtg tgtgtgtgtg  10500
tgttgttcgt gtgtgagtgc aggtgcacat atgatagcgt acacgttgag gtcagaggat  10560
aactatcagg cgttgtcccc tcctactttt cctcggactc tggagaacaa acatgggtcc  10620
ttattccagg ggagcaagtc gctgttggct gacacatctt gctcacatac attttaccta  10680
gacaatggag cctccatcag agtattactt tagctcctca ccgatggcaa tgcaccacct  10740
ctctacccac ataggagttg ggtctccaca cacccccaca ccccccttcac caaaacgttt  10800
tcagttactt tatctggtaa agttcatcag agaatgaagc cagtattaag aacatggaat  10860
catttgggaa cctggatcta gcaatacccc accctagatg gagttgctga gttttcacct  10920
cagattataa ttccccccta gcttctatgg tttattctga aaccagggga actcgattcc  10980
tccctttgga ccacagacat cctggcttgt gaattcacat gtcatctact gctaatccat  11040
tggtagtatg tggctcacag agacacacta cagtcatggc caatgtcaag gtaggacaga  11100
tgtgaatcat tcccccagtc ctgctgtttt catgactaac cctcctcagc acagtgacca  11160
tgaacctact tttcccctcc ttttattttt agaattgctg gaattttcta ttttgagaaa  11220
taatagcctt gggcagcatt aaacaaaatc atctagaaag ctggtttaaa atacagatgg  11280
ttgagtcagt gaaagagtga ggaatgtcat tattggcccc tcacagaggc tggctcactc  11340
cagcagaggt ggttgaagct cttggacacg ggtcaggtgc ataggaaagg tngtctggga  11400
cactgagaac cacaattgaa caaacagaac tgttggcttt tttttttttta aatgagttct  11460
caaaaaatga ctggctagct taggcaaata cttcgagcca acccaacaga acattcttcc  11520
attgattcat tctggatctt ctttctagac aatactgaac tgaccccttg ttggcagtct  11580
caagtttgac aacatagggc tttgaacttg gcacaaggtc catcactgtc acccaagcat  11640
cctgggtgac ctttgggttg gaatatcttg gctaacctta gatattttct ttggagtatc  11700
tttagaacat ccaggaaata gggcttgatt ctcatcctgg gaccacaata taagtcaccc  11760
tagaatccca ggagatcgtg cagagaaaca aggatctctc tcgtgtgcat ccttcttcaa  11820
agcagtgagt agtgactcca ctaaactgag ttcccatctg agagtccaca ggaggctttg  11880
gggcaagaag cagagggaag gcactgtttg tgttggtaaa gttttgactc taacaaattt  11940
gaagacatag atgacattgt gtcagactaa caacaaccta gactcatgtg ggttctgttt  12000
agggatcaga ttttattcat caatgacttg tcttagtgta tagagaaagg cttcctactg  12060
gagtgtaggc tcaataatga cagaagagat agctatttcc cctagggact gtgctgctcc  12120
aagtttggtg gagaaaggca gtggggaacc tagatgtgct ctctggggag ggggtctgaa  12180
gctggcttca tagaaggtgt gaagttttgc tgaaacatct aaacagaatt atagcttagg  12240
aaagtgagca ggcaaggcag ggaatgtgtt gcatatgtat atgtacatga atatattatg  12300
ttatagatac acacacattt gaacctcatt tgcagatgac agaaaatagg ttattttgcc  12360
tctcttaact gctaagcaca atgacttcca gttccatcca tttcctgaaa tgccacaatt  12420
tcatttttca ttgtggctga ataaaattcc attgcagact gggccctact tcatccactc  12480
```

-continued

```
ctgagggcag gcatatcccc tggctccatt tcttacctat tgtgaagaga agtgcaactg  12540
tcttgttgaa aggcaagcgt gagagaggca ggcactaatt gtgggttttt gtttcttctt  12600
cctgctatga ctctccattt gtcagaacca aagatcgata aaagccgcca ccatgaaagc  12660
catcttaatc ccatttttat ctcttctgat tccgttaacc ccgcaatctg cattcgctca  12720
gagtgagccg gagctgaagc tggaaagtgt ggtgattgtc agtcgtcatg gtgtgcgtgc  12780
tccaaccaag gccacgcaac tgatgcagga tgtcacccca gacgcatggc caacctggcc  12840
ggtaaaactg ggttggctga caccgcgcgg tggtgagcta atcgcctatc tcggacatta  12900
ccaacgccag cgtctggtag ccgacggatt gctggcgaaa aagggctgcc cgcagtctgg  12960
tcaggtcgcg attattgctg atgtcgacga gcgtacccgt aaaacaggcg aagccttcgc  13020
cgccgggctg gcacctgact gtgcaataac cgtacatacc caggcagata cgtccagtcc  13080
cgatccgtta tttaatcctc taaaaactgg cgtttgccaa ctggataacg cgaacgtgac  13140
tgacgcgatc ctcagcaggg caggagggtc aattgctgac tttaccgggc atcggcaaac  13200
ggcgtttcgc gaactggaac gggtgcttaa ttttccgcaa tcaaacttgt gccttaaacg  13260
tgagaaacag gacgaaagct gttcattaac gcaggcatta ccatcggaac tcaaggtgag  13320
cgccgacaat gtctcattaa ccggtgcggt aagcctcgca tcaatgctga cggagatatt  13380
tctcctgcaa caagcacagg gaatgccgga gccggggtgg ggaaggatca ccgattcaca  13440
ccagtggaac accttgctaa gtttgcataa cgcgcaattt tatttgctac aacgcacgcc  13500
agaggttgcc cgcagccgcg ccaccccgtt attagatttg atcaagacag cgttgacgcc  13560
ccatccaccg caaaaacagg cgtatggtgt gacattaccc acttcagtgc tgtttatcgc  13620
cggacacgat actaatctgg caaatctcgg cggcgcactg gagctcaact ggacgcttcc  13680
cggtcagccg gataacacgc cgccaggtgg tgaactggtg tttgaacgct ggcgtcggct  13740
aagcgataac agccagtgga ttcaggtttc gctggtcttc cagactttac agcagatgcg  13800
tgataaaacg ccgctgtcat taaatacgcc gcccggagag gtgaaactga ccctggcagg  13860
atgtgaagag cgaaatgcgc agggcatgtg ttcgttggca ggttttacgc aaatcgtgaa  13920
tgaagcacgc atacccgctt gcagtttgta aggtacccgg ggatcacaac ttgccctctg  13980
aagaggaaga acagaaggat gccacaactc tcctgctggc tactctccag tggtttcatc  14040
ttacttctga tggcatttcc ctctagaaag tgctactatc atccacacat ttctacctga  14100
gaccacccaa aggaccctcc caaattctct tcctctctga gtagtctcca cacctgttac  14160
caccatccca gaattaaaat cctaactgca ctctggcgtg tgacttgcct cagtccttgc  14220
aataagagtt gttggcagtg ccaggcgtgg tggcgcacgc ctttaattcc agcacttggg  14280
aggcagaggc aggcggattt ctgagttcga ggccagcctg gtctacagag tgagttccag  14340
gacagccagg gctatacaga gaaaccctgt gtcgaaaaac caaaaaaaaa aaaaaaagtt  14400
gttggcagag tgtgggttat ataccaggtg gagatttcaa atgagtggct gaagctgtag  14460
ccagaaggaa cttagaggat agctcataac ttaaaaagaa atgtagagag tagcagaaac  14520
attgagagag tgggcacaca gccactgtgt gaatgtggca gaacacaatc cagccagcta  14580
tacatgcata agtgtatatt ggcgccatcc tgactgatga gacacaggaa aacagataga  14640
cggggttagg tggccatggc ctttcctgcc tgcctcttcc taagggtcat ctcaagacct  14700
tatgctctct taactcttcc attgctactt agcttctaga tatcacctcc agattagtct  14760
ccttgggtac atcagtgatc ctggtgatat ccagggcttc ctgattccat ctttgtcata  14820
gaggctgcaa ctaaagaggt cttcttaata cttcacaccc tgatgccaaa aggaagacac  14880
```

-continued

```
agaagttcac agaggtgaag tgattcatgt aggacataca gtgagcaagc atcagggtcc  14940
ggattatctg actctactct aacttttatg taaatgtgct ttatgccatt aacactgtca  15000
ttcctgtgct tcagctctgg gagactccca agcactctta ggcacaagcc acaattaagg  15060
gactctgaca ctctgcattg attaattagc atggtggtct ctatgtttcc agattcatga  15120
ttgtttcact ttccatatag gctatgaagg gtgtgaggaa attttttggg gacagaattg  15180
gaggcaatcc acctctctca ggaagcctct atctggaaaa gcttacaact cagggacagt  15240
aactgtaggc ccagtccttg gtgtccaaaa tgggttttat ggtttgaatc tgcaaagcct  15300
tccatgtgct caaaggtttg aacatggagc ctcctcctgg taacactgta ttggaggctt  15360
ttgagactgg atgctctttg gtcccatgtt ttgctacatc atctgtcaag atatgaccca  15420
ggcatgctac cagctaccac agactatgcc tctccagctt tcatgttctc cccaccatga  15480
tagacttgta tctcctaaaa atggaatcaa agcaaacttt tcctgcatta agtttttttt  15540
tttctgttaa gtgtttggtc acagggacaa gaaaacactc aatacagata attagtacca  15600
gagttgaggt tcattgctct agcaagttgg atcaaatttt tagggctttg gaactgattt  15660
ataagagaca tgtagaagag tctgaagctg tgggctacag aagtgtcacc agtttttaag  15720
aatagtttaa tacaccatgg gaattgtgaa aatcagaatg ctcacacaaa ggcagacagg  15780
aaaacgtgag catgtggcgt gtgagagggc ataagaagga acctaggggg aaatgagcta  15840
gaagccattc ggctacgtta gggaacgtgt gtggctgtgc ttggcccatg ccctggcaat  15900
ctgaatgagg ccaaatttta aaggagtgga ctaactcgat tgtcagagaa aatatcaaga  15960
cagaccacca ctcaggctat gccgtgtttg tgaccgacca gctactctta gccagctcta  16020
ttgtgaaatt ccagagcaat tatcagagca tgaagataca tacagtttag tgaagtaagg  16080
ggtgtgggtc cctaagtgga tggtgcataa atctatgtag gtgatgccta agtgacactt  16140
gataatccaa aatatcagca atgtggaatg tcttccaagg agacctgtag acacacattt  16200
tagaactttg ctcatggctg taataaatag ctagctagaa atcatttcct gaagaggtta  16260
gtctgagtta cggttccagg gcaaacattc agtgatggca aggaaggcat tgcagtcagg  16320
agccaaaggt cagctggtca cattgcatca agagtagaga gtcagagtgt gagtagaaag  16380
aggatacagg ttataaaacc tcactgtcca ctctcagcaa tccattttct cctaaaaggc  16440
tttaccttct aaagatttta gtcttcaaaa ccagtaccag tagcctggga acaaaagttg  16500
aaacaaatga gcctttgtgg ggcatttcac acttaaaaca gggcatcacc taggaggagc  16560
cctgtgtgca gtaggaagtg tggcctctgt gtcaggaatg ctcaggctaa taaggggtcc  16620
tctatctgag ggaccctatg aagattcaac aagtagttgt gagaattccc tgtaaatgga  16680
tgctaccaat ttgacatttg tagacctgct attgtgtgct tctttattgg gctctcccat  16740
ctcccaactt tccaacccat attccacatt aatcccttcc accaccatgc aacactaggt  16800
aggagagaag gaaggttaga agagaaagtg ggtatagatc tatttagact acttcctgct  16860
gattaggggc aagtccaatc gtcattgtca ggatacctcc aaccagcaac cagcaaacca  16920
gcaaatcaga aacagcaaaa gcagccaaca aggcagcact aaccagcagg attggggtcg  16980
gtagcgtggg agcagtcact actggtcttc tcatggcttt ggcattaata ctctctcaag  17040
aaattccgta attttttccc caccacctga aattccgtaa ttttaaatgc aaactatcta  17100
cagctggcaa aaatcacatc tctcctagag cacaagacaa atcatagtta ctggctattt  17160
gcaatctgaa gcatctcaat atcccacacc tgggattaaa acaaaaacat attcacatca  17220
```

-continued

```
cataactgtt ttttttttcc aattttttat taggtatttt ctttatttac atttcaaatg  17280
ctatcccgaa agtcccctat accctcccac ctccctgctc ccctacacac ccactcccac  17340
tttttgaccc tggagttccc cggtactggg gcatataaag tttgcaagac caaggggcct  17400
ctcttcccag tgatggccga ctaagccatc ttctgctaca tatgcagata gagacacgag  17460
ctctggggt actagttagt tcatattgtt gttccaccta tagggtcgca gaccccttca  17520
gctccttggg tactttgtct agctcctcca ctgggggctc tgtgttttat ctaatagatg  17580
actgtgagca tccacttctg tatttgacag gcactggcct agcgtcacat gagccagcta  17640
tatcagggtc ctttcagcaa aaccttgctg gcatgtgcaa tagtgtctgc gtttggtggt  17700
tgattatggg atggatccac tagttctaga gcggccgcca ccgcggtgga gctccagctt  17760
ttgttccctt tagtgagggt taattgcgcg cttggcgtaa tcatggtcat agctgtttcc  17820
tgtgtgaaat tgttatccgc tcacaattcc acacaacata cgagccggaa gcataaagtg  17880
taaagcctgg ggtgcctaat gagtgagcta actcacatta attgcgttgc gctcactgcc  17940
cgctttccag tcgggaaacc tgtcgtgcca gctgcattaa tgaatcggcc aacgcgcggg  18000
gagaggcggt ttgcgtattg ggcgctcttc cgcttcctcg ctcactgact cgctgcgctc  18060
ggtcgttcgg ctgcggcgag cggtatcagc tcactcaaag gcggtaatac ggttatccac  18120
agaatcaggg gataacgcag gaaagaacat gtgagcaaaa ggccagcaaa aggccaggaa  18180
ccgtaaaaag gccgcgttgc tggcgttttt ccataggctc cgcccccctg acgagcatca  18240
caaaaatcga cgctcaagtc agaggtggcg aaacccgaca ggactataaa gataccaggc  18300
gtttccccct ggaagctccc tcgtgcgctc tcctgttccg accctgccgc ttaccggata  18360
cctgtccgcc tttctccctt cgggaagcgt ggcgctttct catagctcac gctgtaggta  18420
tctcagttcg gtgtaggtcg ttcgctccaa gctgggctgt gtgcacgaac cccccgttca  18480
gcccgaccgc tgcgccttat ccggtaacta tcgtcttgag tccaacccgg taagacacga  18540
cttatcgcca ctggcagcag ccactggtaa caggattagc agagcgaggt atgtaggcgg  18600
tgctacagag ttcttgaagt ggtggcctaa ctacggctac actagaagga cagtatttgg  18660
tatctgcgct ctgctgaagc cagttacctt cggaaaaaga gttggtagct cttgatccgg  18720
caaacaaacc accgctggta gcggtggttt ttttgtttgc aagcagcaga ttacgcgcag  18780
aaaaaaagga tctcaagaag atcctttgat cttttctacg gggtctgacg ctcagtggaa  18840
cgaaaactca cgttaaggga ttttggtcat gagattatca aaaaggatct tcacctagat  18900
ccttttaaat taaaaatgaa gttttaaatc aatctaaagt atatatgagt aaacttggtc  18960
tgacagttac caatgcttaa tcagtgaggc acctatctca gcgatctgtc tatttcgttc  19020
atccatagtt gcctgactcc ccgtcgtgta gataactacg atacgggagg gcttaccatc  19080
tggccccagt gctgcaatga taccgcgaga cccacgctca ccggctccag atttatcagc  19140
aataaaccag ccagccggaa gggccgagcg cagaagtggt cctgcaactt tatccgcctc  19200
catccagtct attaattgtt gccgggaagc tagagtaagt agttcgccag ttaatagttt  19260
gcgcaacgtt gttgccattg ctacaggcat cgtggtgtca cgctcgtcgt ttggtatggc  19320
ttcattcagc tccggttccc aacgatcaag gcgagttaca tgatccccca tgttgtgcaa  19380
aaaagcggtt agctccttcg gtcctccgat cgttgtcaga agtaagttgg ccgcagtgtt  19440
atcactcatg gttatggcag cactgcataa ttctcttact gtcatgccat ccgtaagatg  19500
cttttctgtg actggtgagt actcaaccaa gtcattctga gaatagtgta tgcggcgacc  19560
gagttgctct tgcccggcgt caatacggga taataccgcg ccacatagca gaactttaaa  19620
```

-continued

```
agtgctcatc attggaaaac gttcttcggg gcgaaaactc tcaaggatct taccgctgtt  19680
gagatccagt tcgatgtaac ccactcgtgc acccaactga tcttcagcat cttttacttt  19740
caccagcgtt tctgggtgag caaaaacagg aaggcaaaat gccgcaaaaa agggaataag  19800
ggcgacacgg aaatgttgaa tactcatact cttccttttt caatattatt gaagcattta  19860
tcagggttat tgtctcatga gcggatacat atttgaatgt atttagaaaa ataaacaaat  19920
aggggttccg cgcacatttc cccgaaaagt gccacctaaa ttgtaagcgt taatattttg  19980
ttaaaattcg cgttaaattt ttgttaaatc agctcatttt ttaaccaata ggccgaaatc  20040
ggcaaaatcc cttataaatc aaaagaatag accgagatag ggttgagtgt tgttccagtt  20100
tggaacaaga gtccactatt aaagaacgtg gactccaacg tcaaagggcg aaaaaccgtc  20160
tatcagggcg atggcccact acgtgaacca tcaccctaat caagtttttt ggggtcgagg  20220
tgccgtaaag cactaaatcg gaaccctaaa gggagccccc gatttagagc ttgacgggga  20280
aagccggcga acgtggcgag aaaggaaggg aagaaagcga aaggagcggg cgctagggcg  20340
ctggcaagtg tagcggtcac gctgcgcgta accaccacac ccgccgcgct taatgcgccg  20400
ctacagggcg cgtcccattc gccattcagg ctgcgcaact gttgggaagg gcgatcggtg  20460
cgggcctctt cgctattacg ccagctggcg aaagggggat gtgctgcaag gcgattaagt  20520
tgggtaacgc cagggttttc ccagtcacga cgttgtaaaa cgacggccag tgagcgcgcg  20580
taatacgact cactataggg cgaattgggt accgggcccc ccc                    20623

<210> SEQ ID NO 2
<211> LENGTH: 6708
<212> TYPE: DNA
<213> ORGANISM: Artificial Sequence
<220> FEATURE:
<223> OTHER INFORMATION: R15/APPA + intron plasmid with pBLCAT3 vector

<400> SEQUENCE: 2

ggatcccctt tgctatgtag tttttaatgg aaattacaac ccatagtgtg ttgataaata     60
gagagtcctg tttggtttaa gcaacctctg tttctcataa actccataaa aacaggaata    120
ctctttgttt ctagcataac caaaagattt agtgaattga aacaatgttt cccttagagt    180
ataggtctaa taaccccgaa aatattacca tgatactgag catttgtaag tatctcatag    240
catgtagtat ccatagtcca tcaatgagag agacatttaa catgattttc attaatcagg    300
tggaaaagac atgacaacat tcacaggcac tgcacagaac atagtggtcc accttgcaca    360
tatttcacta aactaggttt atctattttg ttgctttctc taacatctct gcaatgaagc    420
aggtcaacag tgccacatat cctttactta acctaaggaa cacaaaaaat tttctacata    480
tatcctggtt agagagtgct taaaataagt tttccaagaa tggaaaagaa atgttctgac    540
ttaacaatta agacagtatt tatttaaagc aagaaatatg aggcacacaa gaaaatattt    600
tgggaagaaa ccatttggtg aacaatattt caaataaaaa tagacaaaca tagttaattg    660
taaaacatat gtttgaccag cccttctttt caataggctt aatgtgaata aaatgttaaa    720
gattctcttt gggtggctgc aaattgtcca cgaataagac aaaatataaa aataaggact    780
gagtctcaca aaatgaaaag gaaatatatt cagaaagaga atcttgagag aatgtgttgt    840
cacaaattaa agaaaacctg tggtgaatga catcctgagg cctgagctat tactgacatt    900
taagataaag gtaactgtat acatttgtcc cattgagggg acaagaaagc tgctctcatg    960
ttcagctcta taattcttgc cttaaacaac ttaaatagaa tgatttaaaa tatggagctg   1020
```

-continued

```
tccatggacc tttgaaatat aaaatagtca agcaacttat caaggaatta cagattcctt   1080
gatactaaca caggtaaatc ccacacgtgt tttgagacta catttgctgg gattttattg   1140
atgtaatagg tcacatgttt ttcgggccaa tgttgctgtt attcggttac ttcaagagaa   1200
tagtggcaac tgatgctatg tattctaggg gtttgaagtg atgtttcatg attgaaattt   1260
gtaaaagaat aacatcatca ttcttaacaa tagaacatat aaagtcacac agaagtgaca   1320
gtgtttaagc tgtactattg atcaaagaaa tttattacct tcagtttcaa tggaaataat   1380
tactgataat acaaacatgt gtgaacacac actaatccta tccaaatgca cagtgataca   1440
cagaaaatat tagcaagtag aatgcaatat ttatataacg attgtattta tcaatcaatt   1500
gtatgtatca atatatgggc tattttctta cacatgattt tattcaaatt tactctaatc   1560
attgttgaac catttagaaa aggcatactg gcaacttttc cttacctcat ccagctgggc   1620
aaaagtccca gtgtggagta aaggatgcaa gatttcctgc tctgttaagt ataaaataat   1680
agtatgaatt caaaggtgcc attcttctgc ttctagttat aaaggcagtg cttgcttctt   1740
ccagcacaga tctggatctc gaggagcttg gcgagatttt caggagctaa ggaagctaaa   1800
agccgccacc atgaaagcca tcttaatccc atttttatct cttctgattc cgttaacccc   1860
gcaatctgca ttcgctcaga gtgagccgga gctgaagctg gaaagtgtgg tgattgtcag   1920
tcgtcatggt gtgcgtgctc caaccaaggc cacgcaactg atgcaggatg tcaccccaga   1980
cgcatggcca acctggccgg taaaactggg ttggctgaca ccgcgcggtg gtgagctaat   2040
cgcctatctc ggacattacc aacgccagcg tctggtagcc gacggattgc tggcgaaaaa   2100
gggctgcccg cagtctggtc aggtcgcgat tattgctgat gtcgacgagc gtacccgtaa   2160
aacaggcgaa gccttcgccg ccgggctggc acctgactgt gcaataaccg tacataccca   2220
ggcagatacg tccagtcccg atccgttatt taatcctcta aaaactggcg tttgccaact   2280
ggataacgcg aacgtgactg acgcgatcct cagcagggca ggagggtcaa ttgctgactt   2340
taccgggcat cggcaaacgg cgtttcgcga actggaacgg gtgcttaatt ttccgcaatc   2400
aaacttgtgc cttaaacgtg agaaacagga cgaaagctgt tcattaacgc aggcattacc   2460
atcggaactc aaggtgagcg ccgacaatgt ctcattaacc ggtgcggtaa gcctcgcatc   2520
aatgctgacg gagatatttc tcctgcaaca agcacaggga atgccggagc cggggtgggg   2580
aaggatcacc gattcacacc agtggaacac cttgctaagt ttgcataacg cgcaatttta   2640
tttgctacaa cgcacgccag aggttgcccg cagccgcgcc accccgttat tagatttgat   2700
caagacagcg ttgacgcccc atccaccgca aaaacaggcg tatggtgtga cattacccac   2760
ttcagtgctg tttatcgccg gacacgatac taatctggca aatctcggcg gcgcactgga   2820
gctcaactgg acgcttcccg gtcagccgga taacacgccg ccaggtggtg aactggtgtt   2880
tgaacgctgg cgtcggctaa gcgataacag ccagtggatt caggtttcgc tggtcttcca   2940
gactttacag cagatgcgtg ataaaacgcc gctgtcatta aatacgccgc ccggagaggt   3000
gaaactgacc ctggcaggat gtgaagagcg aaatgcgcag ggcatgtgtt cgttggcagg   3060
ttttacgcaa atcgtgaatg aagcacgcat acccgcttgc agtttgtaag gtataaggca   3120
gttattggtg cccttaaacg cctggtgcta cgcctgaata agtgataata agcggatgaa   3180
tggcagaaat tcgccggatc tttgtgaagg aaccttactt ctgtggtgtg acataattgg   3240
acaaactacc tacagagatt taaagctcta aggtaaatat aaaatttttta agtgtataat   3300
gtgttaaact actgattcta attgtttgtg tattttagat tccaacctat ggaactgatg   3360
aatgggagca gtggtggaat gcctttaatg aggaaaacct gttttgctca gaagaaatgc   3420
```

-continued

```
catctagtga tgatgaggct actgctgact ctcaacattc tactcctcca aaaaagaaga   3480
gaaaggtaga agaccccaag gactttcctt cagaattgct aagttttttg agtcatgctg   3540
tgtttagtaa tagaactctt gcttgctttg ctatttacac cacaaaggaa aaagctgcac   3600
tgctatacaa gaaaattatg gaaaaatatt ctgtaacctt tataagtagg cataacagtt   3660
ataatcataa catactgttt tttcttactc cacacaggca tagagtgtct gctattaata   3720
actatgctca aaaattgtgt acctttagct ttttaatttg taaaggggtt aataaggaat   3780
atttgatgta tagtgccttg actagagatc ataatcagcc ataccacatt tgtagaggtt   3840
ttacttgctt taaaaaacct cccacacctc cccctgaacc tgaaacataa aatgaatgca   3900
attgttgttg ttaacttgtt tattgcagct tataatggtt acaaataaag caatagcatc   3960
acaaatttca caaataaagc atttttttca ctgcattcta gttgtggttt gtccaaactc   4020
atcaatgtat cttatcatgt ctggatcgat ccccgggtac cgagctcgaa ttcgtaatca   4080
tggtcatagc tgtttcctgt gtgaaattgt tatccgctca caattccaca caacatacga   4140
gccggaagca taaagtgtaa agcctggggt gcctaatgag tgagctaact cacattaatt   4200
gcgttgcgct cactgcccgc tttccagtcg ggaaacctgt cgtgccagct gcattaatga   4260
atcggccaac gcgcggggag aggcggtttg cgtattgggc gctcttccgc ttcctcgctc   4320
actgactcgc tgcgctcggt cgttcggctg cggcgagcgg tatcagctca ctcaaaggcg   4380
gtaatacggt tatccacaga atcaggggat aacgcaggaa agaacatgtg agcaaaaggc   4440
cagcaaaagg ccaggaaccg taaaaaggcc gcgttgctgg cgtttttcca taggctccgc   4500
ccccctgacg agcatcacaa aaatcgacgc tcaagtcaga ggtggcgaaa cccgacagga   4560
ctataaagat accaggcgtt tccccctgga agctccctcg tgcgctctcc tgttccgacc   4620
ctgccgctta ccggatacct gtccgccttt ctcccttcgg gaagcgtggc gctttctcaa   4680
tgctcacgct gtaggtatct cagttcggtg taggtcgttc gctccaagct gggctgtgtg   4740
cacgaacccc ccgttcagcc cgaccgctgc gccttatccg gtaactatcg tcttgagtcc   4800
aacccggtaa gacacgactt atcgccactg gcagcagcca ctggtaacag gattagcaga   4860
gcgaggtatg taggcggtgc tacagagttc ttgaagtggt ggcctaacta cggctacact   4920
agaaggacag tatttggtat ctgcgctctg ctgaagccag ttaccttcgg aaaaagagtt   4980
ggtagctctt gatccggcaa acaaaccacc gctggtagcg gtggtttttt tgtttgcaag   5040
cagcagatta cgcgcagaaa aaaaggatct caagaagatc ctttgatctt ttctacgggg   5100
tctgacgctc agtggaacga aaactcacgt taagggattt tggtcatgag attatcaaaa   5160
aggatcttca cctagatcct tttaaattaa aaatgaagtt ttaaatcaat ctaaagtata   5220
tatgagtaaa cttggtctga cagttaccaa tgcttaatca gtgaggcacc tatctcagcg   5280
atctgtctat ttcgttcatc catagttgcc tgactccccg tcgtgtagat aactacgata   5340
cgggagggct taccatctgg ccccagtgct gcaatgatac cgcgagaccc acgctcaccg   5400
gctccagatt tatcagcaat aaaccagcca gccggaaggg ccgagcgcag aagtggtcct   5460
gcaactttat ccgcctccat ccagtctatt aattgttgcc gggaagctag agtaagtagt   5520
tcgccagtta atagtttgcg caacgttgtt gccattgcta caggcatcgt ggtgtcacgc   5580
tcgtcgtttg gtatggcttc attcagctcc ggttcccaac gatcaaggcg agttacatga   5640
tcccccatgt tgtgcaaaaa agcggttagc tccttcggtc ctccgatcgt tgtcagaagt   5700
aagttggccg cagtgttatc actcatggtt atggcagcac tgcataattc tcttactgtc   5760
```

-continued

```
atgccatccg taagatgctt ttctgtgact ggtgagtact caaccaagtc attctgagaa   5820

tagtgtatgc ggcgaccgag ttgctcttgc ccggcgtcaa tacgggataa taccgcgcca   5880

catagcagaa ctttaaaagt gctcatcatt ggaaaacgtt cttcggggcg aaaactctca   5940

aggatcttac cgctgttgag atccagttcg atgtaaccca ctcgtgcacc caactgatct   6000

tcagcatctt ttactttcac cagcgtttct gggtgagcaa aaacaggaag gcaaaatgcc   6060

gcaaaaaagg gaataagggc gacacggaaa tgttgaatac tcatactctt cctttttcaa   6120

tattattgaa gcatttatca gggttattgt ctcatgagcg gatacatatt tgaatgtatt   6180

tagaaaaata aacaaatagg ggttccgcgc acatttcccc gaaaagtgcc acctgacgtc   6240

taagaaacca ttattatcat gacattaacc tataaaaata ggcgtatcac gaggcccttt   6300

cgtctcgcgc gtttcggtga tgacggtgaa aacctctgac acatgcagct cccggagacg   6360

gtcacagctt gtctgtaagc ggatgccggg agcagacaag cccgtcaggg cgcgtcagcg   6420

ggtgttggcg ggtgtcgggg ctggcttaac tatgcggcat cagagcagat tgtactgaga   6480

gtgcaccata tgcggtgtga aataccgcac agatgcgtaa ggagaaaata ccgcatcagg   6540

cgccattcgc cattcaggct gcgcaactgt tgggaagggc gatcggtgcg ggcctcttcg   6600

ctattacgcc agctggcgaa agggggatgt gctgcaaggc gattaagttg ggtaacgcca   6660

gggttttccc agtcacgacg ttgtaaaacg acggccagtg ccaagctt                6708
```

<210> SEQ ID NO 3
<211> LENGTH: 4060
<212> TYPE: DNA
<213> ORGANISM: Artificial Sequence
<220> FEATURE:
<223> OTHER INFORMATION: R15/APPA + intron transgene

<400> SEQUENCE: 3

```
ggatcccctt tgctatgtag tttttaatgg aaattacaac ccatagtgtg ttgataaata     60

gagagtcctg tttggtttaa gcaacctctg tttctcataa actccataaa aacaggaata    120

ctctttgttt ctagcataac caaaagattt agtgaattga aaacaatgtt cccttagagt    180

ataggtctaa taaccccgaa aatattacca tgatactgag catttgtaag tatctcatag    240

catgtagtat ccatagtcca tcaatgagag agacatttaa catgattttc attaatcagg    300

tggaaaagac atgacaacat tcacaggcac tgcacagaac atagtggtcc accttgcaca    360

tatttcacta aactaggttt atctattttg ttgctttctc taacatctct gcaatgaagc    420

aggtcaacag tgccacatat cctttactta acctaaggaa cacaaaaaat tttctacata    480

tatcctggtt agagagtgct taaaataagt tttccaagaa tggaaaagaa atgttctgac    540

ttaacaatta agacagtatt tatttaaagc aagaaatatg aggcacacaa gaaaatattt    600

tgggaagaaa ccatttggtg aacaatattt caaataaaaa tagacaaaca tagttaattg    660

taaaacatat gtttgaccag cccttctttt caataggctt aatgtgaata aaatgttaaa    720

gattctcttt gggtggctgc aaattgtcca cgaataagac aaaatataaa aataaggact    780

gagtctcaca aaatgaaaag gaaatatatt cagaaagaga atcttgagag aatgtgttgt    840

cacaaattaa agaaaacctg tggtgaatga catcctgagg cctgagctat tactgacatt    900

taagataaag gtaactgtat acatttgtcc cattgagggg acaagaaagc tgctctcatg    960

ttcagctcta taattcttgc cttaaacaac ttaaatagaa tgatttaaaa tatggagctg   1020

tccatggacc tttgaaatat aaaatagtca agcaacttat caaggaatta cagattcctt   1080

gatactaaca caggtaaatc ccacacgtgt tttgagacta catttgctgg gattttattg   1140
```

-continued atgtaatagg tcacatgttt ttcgggccaa tgttgctgtt attcggttac ttcaagagaa 1200
tagtggcaac tgatgctatg tattctaggg gtttgaagtg atgtttcatg attgaaattt 1260
gtaaaagaat aacatcatca ttcttaacaa tagaacatat aaagtcacac agaagtgaca 1320
gtgtttaagc tgtactattg atcaaagaaa tttattacct tcagtttcaa tggaaataat 1380
tactgataat acaaacatgt gtgaacacac actaatccta tccaaatgca cagtgataca 1440
cagaaaatat tagcaagtag aatgcaatat ttatataacg attgtattta tcaatcaatt 1500
gtatgtatca atatatgggc tattttctta cacatgattt tattcaaatt tactctaatc 1560
attgttgaac catttagaaa aggcatactg gcaacttttc cttacctcat ccagctgggc 1620
aaaagtccca gtgtggagta aaggatgcaa gatttcctgc tctgttaagt ataaaataat 1680
agtatgaatt caaaggtgcc attcttctgc ttctagttat aaaggcagtg cttgcttctt 1740
ccagcacaga tctggatctc gaggagcttg gcgagatttt caggagctaa ggaagctaaa 1800
agccgccacc atgaaagcca tcttaatccc atttttatct cttctgattc cgttaacccc 1860
gcaatctgca ttcgctcaga gtgagccgga gctgaagctg gaaagtgtgg tgattgtcag 1920
tcgtcatggt gtgcgtgctc caaccaaggc cacgcaactg atgcaggatg tcaccccaga 1980
cgcatggcca acctggccgg taaaactggg ttggctgaca ccgcgcggtg gtgagctaat 2040
cgcctatctc ggacattacc aacgccagcg tctggtagcc gacggattgc tggcgaaaaa 2100
gggctgcccg cagtctggtc aggtcgcgat tattgctgat gtcgacgagc gtacccgtaa 2160
aacaggcgaa gccttcgccg ccgggctggc acctgactgt gcaataaccg tacataccca 2220
ggcagatacg tccagtcccg atccgttatt taatcctcta aaaactggcg tttgccaact 2280
ggataacgcg aacgtgactg acgcgatcct cagcagggca ggagggtcaa ttgctgactt 2340
taccgggcat cggcaaacgg cgtttcgcga actggaacgg gtgcttaatt ttccgcaatc 2400
aaacttgtgc cttaaacgtg agaaacagga cgaaagctgt tcattaacgc aggcattacc 2460
atcggaactc aaggtgagcg ccgacaatgt ctcattaacc ggtgcggtaa gcctcgcatc 2520
aatgctgacg gagatatttc tcctgcaaca agcacaggga atgccggagc cggggtgggg 2580
aaggatcacc gattcacacc agtggaacac cttgctaagt ttgcataacg cgcaatttta 2640
tttgctacaa cgcacgccag aggttgcccg cagccgcgcc accccgttat tagatttgat 2700
caagacagcg ttgacgcccc atccaccgca aaaacaggcg tatggtgtga cattacccac 2760
ttcagtgctg tttatcgccg gacacgatac taatctggca aatctcggcg gcgcactgga 2820
gctcaactgg acgcttcccg gtcagccgga taacacgccg ccaggtggtg aactggtgtt 2880
tgaacgctgg cgtcggctaa gcgataacag ccagtggatt caggtttcgc tggtcttcca 2940
gactttacag cagatgcgtg ataaaacgcc gctgtcatta aatacgccgc ccggagaggt 3000
gaaactgacc ctggcaggat gtgaagagcg aaatgcgcag ggcatgtgtt cgttggcagg 3060
ttttacgcaa atcgtgaatg aagcacgcat acccgcttgc agtttgtaag gtataaggca 3120
gttattggtg cccttaaacg cctggtgcta cgcctgaata agtgataata agcggatgaa 3180
tggcagaaat tcgccggatc tttgtgaagg aaccttactt ctgtggtgtg acataattgg 3240
acaaactacc tacagagatt taaagctcta aggtaaatat aaaattttta agtgtataat 3300
gtgttaaact actgattcta attgtttgtg tattttagat tccaacctat ggaactgatg 3360
aatgggagca gtggtggaat gcctttaatg aggaaaacct gttttgctca gaagaaatgc 3420
catctagtga tgatgaggct actgctgact ctcaacattc tactcctcca aaaaagaaga 3480

-continued

```
gaaaggtaga agaccccaag gactttcctt cagaattgct aagttttttg agtcatgctg   3540
tgtttagtaa tagaactctt gcttgctttg ctatttacac cacaaaggaa aaagctgcac   3600
tgctatacaa gaaaattatg gaaaaatatt ctgtaacctt tataagtagg cataacagtt   3660
ataatcataa catactgttt tttcttactc cacacaggca tagagtgtct gctattaata   3720
actatgctca aaaattgtgt acctttagct ttttaatttg taaaggggtt aataaggaat   3780
atttgatgta tagtgccttg actagagatc ataatcagcc ataccacatt tgtagaggtt   3840
ttacttgctt taaaaaacct cccacacctc cccctgaacc tgaaacataa aatgaatgca   3900
attgttgttg ttaacttgtt tattgcagct tataatggtt acaaataaag caatagcatc   3960
acaaatttca caaataaagc atttttttca ctgcattcta gttgtggttt gtccaaactc   4020
atcaatgtat cttatcatgt ctggatcgat ccccgggtac                         4060
```

<210> SEQ ID NO 4
<211> LENGTH: 6116
<212> TYPE: DNA
<213> ORGANISM: Artificial Sequence
<220> FEATURE:
<223> OTHER INFORMATION: R15/APPA plasmid with pBLCAT3 vector

<400> SEQUENCE: 4

```
ggatcccctt tgctatgtag tttttaatgg aaattacaac ccatagtgtg ttgataaata     60
gagagtcctg tttggtttaa gcaacctctg tttctcataa actccataaa aacaggaata    120
ctctttgttt ctagcataac caaaagattt agtgaattga aaacaatgtt cccttagagt    180
ataggtctaa taaccccgaa aatattacca tgatactgag catttgtaag tatctcatag    240
catgtagtat ccatagtcca tcaatgagag agacatttaa catgattttc attaatcagg    300
tggaaaagac atgacaacat tcacaggcac tgcacagaac atagtggtcc accttgcaca    360
tatttcacta aactaggttt atctattttg ttgctttctc taacatctct gcaatgaagc    420
aggtcaacag tgccacatat cctttactta acctaaggaa cacaaaaaat tttctacata    480
tatcctggtt agagagtgct taaaataagt tttccaagaa tggaaaagaa atgttctgac    540
ttaacaatta agacagtatt tatttaaagc aagaaatatg aggcacacaa gaaaatattt    600
tgggaagaaa ccatttggtg aacaatattt caaataaaaa tagacaaaca tagttaattg    660
taaaacatat gtttgaccag cccttctttt caataggctt aatgtgaata aaatgttaaa    720
gattctcttt gggtggctgc aaattgtcca cgaataagac aaaatataaa aataaggact    780
gagtctcaca aaatgaaaag gaaatatatt cagaaagaga atcttgagag aatgtgttgt    840
cacaaattaa agaaaacctg tggtgaatga catcctgagg cctgagctat tactgacatt    900
taagataaag gtaactgtat acatttgtcc cattgagggg acaagaaagc tgctctcatg    960
ttcagctcta taattcttgc cttaaacaac ttaaatagaa tgatttaaaa tatggagctg   1020
tccatggacc tttgaaatat aaaatagtca agcaacttat caaggaatta cagattcctt   1080
gatactaaca caggtaaatc ccacacgtgt tttgagacta catttgctgg gattttattg   1140
atgtaatagg tcacatgttt ttcgggccaa tgttgctgtt attcggttac ttcaagagaa   1200
tagtggcaac tgatgctatg tattctaggg gtttgaagtg atgtttcatg attgaaattt   1260
gtaaaagaat aacatcatca ttcttaacaa tagaacatat aaagtcacac agaagtgaca   1320
gtgtttaagc tgtactattg atcaaagaaa tttattacct tcagtttcaa tggaaataat   1380
tactgataat acaaacatgt gtgaacacac actaatccta tccaaatgca cagtgataca   1440
cagaaaatat tagcaagtag aatgcaatat ttatataacg attgtattta tcaatcaatt   1500
```

-continued

```
gtatgtatca atatatgggc tattttctta cacatgattt tattcaaatt tactctaatc   1560
attgttgaac catttagaaa aggcatactg gcaacttttc cttacctcat ccagctgggc   1620
aaaagtccca gtgtggagta aaggatgcaa gatttcctgc tctgttaagt ataaaataat   1680
agtatgaatt caaaggtgcc attcttctgc ttctagttat aaaggcagtg cttgcttctt   1740
ccagcacaga tctggatctc gaggagcttg gcgagatttt caggagctaa ggaagctaaa   1800
agccgccacc atgaaagcca tcttaatccc atttttatct cttctgattc cgttaacccc   1860
gcaatctgca ttcgctcaga gtgagccgga gctgaagctg gaaagtgtgg tgattgtcag   1920
tcgtcatggt gtgcgtgctc caaccaaggc cacgcaactg atgcaggatg tcaccccaga   1980
cgcatggcca acctggccgg taaaactggg ttggctgaca ccgcgcggtg gtgagctaat   2040
cgcctatctc ggacattacc aacgccagcg tctggtagcc gacggattgc tggcgaaaaa   2100
gggctgcccg cagtctggtc aggtcgcgat tattgctgat gtcgacgagc gtacccgtaa   2160
aacaggcgaa gccttcgccg ccgggctggc acctgactgt gcaataaccg tacataccca   2220
ggcagatacg tccagtcccg atccgttatt taatcctcta aaaactggcg tttgccaact   2280
ggataacgcg aacgtgactg acgcgatcct cagcagggca ggagggtcaa ttgctgactt   2340
taccgggcat cggcaaacgg cgtttcgcga actggaacgg gtgcttaatt ttccgcaatc   2400
aaacttgtgc cttaaacgtg agaaacagga cgaaagctgt tcattaacgc aggcattacc   2460
atcggaactc aaggtgagcg ccgacaatgt ctcattaacc ggtgcggtaa gcctcgcatc   2520
aatgctgacg gagatatttc tcctgcaaca agcacaggga atgccggagc cggggtgggg   2580
aaggatcacc gattcacacc agtggaacac cttgctaagt ttgcataacg cgcaatttta   2640
tttgctacaa cgcacgccag aggttgcccg cagccgcgcc accccgttat tagatttgat   2700
caagacagcg ttgacgcccc atccaccgca aaaacaggcg tatggtgtga cattacccac   2760
ttcagtgctg tttatcgccg gacacgatac taatctggca aatctcggcg gcgcactgga   2820
gctcaactgg acgcttcccg gtcagccgga taacacgccg ccaggtggtg aactggtgtt   2880
tgaacgctgg cgtcggctaa gcgataacag ccagtggatt caggtttcgc tggtcttcca   2940
gactttacag cagatgcgtg ataaaacgcc gctgtcatta aatacgccgc ccggagaggt   3000
gaaactgacc ctggcaggat gtgaagagcg aaatgcgcag ggcatgtgtt cgttggcagg   3060
ttttacgcaa atcgtgaatg aagcacgcat acccgcttgc agtttgtaag gtataaggca   3120
gttattggtg cccttaaacg cctggtgcta cgcctgaata agtgataata agcggatgaa   3180
tggcagaaat tcgccggatc tttgtgaagg aaccttactt ctgtggtgtg acataattgg   3240
acaaactacc tacagagatt taaaaaacct cccacacctc cccctgaacc tgaaacataa   3300
aatgaatgca attgttgttg ttaacttgtt tattgcagct tataatggtt acaaataaag   3360
caatagcatc acaaatttca caaataaagc atttttttca ctgcattcta gttgtggttt   3420
gtccaaactc atcaatgtat cttatcatgt ctggatcgat ccccgggtac cgagctcgaa   3480
ttcgtaatca tggtcatagc tgtttcctgt gtgaaattgt tatccgctca caattccaca   3540
caacatacga gccggaagca taaagtgtaa agcctggggt gcctaatgag tgagctaact   3600
cacattaatt gcgttgcgct cactgcccgc tttccagtcg ggaaacctgt cgtgccagct   3660
gcattaatga atcggccaac gcgcggggag aggcggtttg cgtattgggc gctcttccgc   3720
ttcctcgctc actgactcgc tgcgctcggt cgttcggctg cggcgagcgg tatcagctca   3780
ctcaaaggcg gtaatacggt tatccacaga atcaggggat aacgcaggaa agaacatgtg   3840
```

-continued

```
agcaaaaggc cagcaaaagg ccaggaaccg taaaaaggcc gcgttgctgg cgtttttcca   3900

taggctccgc ccccctgacg agcatcacaa aaatcgacgc tcaagtcaga ggtggcgaaa   3960

cccgacagga ctataaagat accaggcgtt tccccctgga agctccctcg tgcgctctcc   4020

tgttccgacc ctgccgctta ccggatacct gtccgccttt ctcccttcgg gaagcgtggc   4080

gctttctcaa tgctcacgct gtaggtatct cagttcggtg taggtcgttc gctccaagct   4140

gggctgtgtg cacgaacccc ccgttcagcc cgaccgctgc gccttatccg gtaactatcg   4200

tcttgagtcc aacccggtaa gacacgactt atcgccactg gcagcagcca ctggtaacag   4260

gattagcaga gcgaggtatg taggcggtgc tacagagttc ttgaagtggt ggcctaacta   4320

cggctacact agaaggacag tatttggtat ctgcgctctg ctgaagccag ttaccttcgg   4380

aaaaagagtt ggtagctctt gatccggcaa acaaaccacc gctggtagcg gtggtttttt   4440

tgtttgcaag cagcagatta cgcgcagaaa aaaaggatct caagaagatc ctttgatctt   4500

ttctacgggg tctgacgctc agtggaacga aaactcacgt taagggattt tggtcatgag   4560

attatcaaaa aggatcttca cctagatcct tttaaattaa aaatgaagtt ttaaatcaat   4620

ctaaagtata tatgagtaaa cttggtctga cagttaccaa tgcttaatca gtgaggcacc   4680

tatctcagcg atctgtctat ttcgttcatc catagttgcc tgactccccg tcgtgtagat   4740

aactacgata cgggagggct taccatctgg ccccagtgct gcaatgatac cgcgagaccc   4800

acgctcaccg gctccagatt tatcagcaat aaaccagcca gccggaaggg ccgagcgcag   4860

aagtggtcct gcaactttat ccgcctccat ccagtctatt aattgttgcc gggaagctag   4920

agtaagtagt tcgccagtta atagtttgcg caacgttgtt gccattgcta caggcatcgt   4980

ggtgtcacgc tcgtcgtttg gtatggcttc attcagctcc ggttcccaac gatcaaggcg   5040

agttacatga tcccccatgt tgtgcaaaaa agcggttagc tccttcggtc ctccgatcgt   5100

tgtcagaagt aagttggccg cagtgttatc actcatggtt atggcagcac tgcataattc   5160

tcttactgtc atgccatccg taagatgctt ttctgtgact ggtgagtact caaccaagtc   5220

attctgagaa tagtgtatgc ggcgaccgag ttgctcttgc ccggcgtcaa tacgggataa   5280

taccgcgcca catagcagaa ctttaaaagt gctcatcatt ggaaaacgtt cttcggggcg   5340

aaaactctca aggatcttac cgctgttgag atccagttcg atgtaaccca ctcgtgcacc   5400

caactgatct tcagcatctt ttactttcac cagcgtttct gggtgagcaa aaacaggaag   5460

gcaaaatgcc gcaaaaaagg gaataagggc gacacggaaa tgttgaatac tcatactctt   5520

cctttttcaa tattattgaa gcatttatca gggttattgt ctcatgagcg gatacatatt   5580

tgaatgtatt tagaaaaata aacaaatagg ggttccgcgc acatttcccc gaaaagtgcc   5640

acctgacgtc taagaaacca ttattatcat gacattaacc tataaaaata ggcgtatcac   5700

gaggcccttt cgtctcgcgc gtttcggtga tgacggtgaa aacctctgac acatgcagct   5760

cccggagacg gtcacagctt gtctgtaagc ggatgccggg agcagacaag cccgtcaggg   5820

cgcgtcagcg ggtgttggcg ggtgtcgggg ctggcttaac tatgcggcat cagagcagat   5880

tgtactgaga gtgcaccata tgcggtgtga aataccgcac agatgcgtaa ggagaaaata   5940

ccgcatcagg cgccattcgc cattcaggct gcgcaactgt tgggaagggc gatcggtgcg   6000

ggcctcttcg ctattacgcc agctggcgaa agggggatgt gctgcaaggc gattaagttg   6060

ggtaacgcca gggttttccc agtcacgacg ttgtaaaacg acggccagtg ccaagc       6116
```

<210> SEQ ID NO 5
<211> LENGTH: 3470

-continued

```
<212> TYPE: DNA
<213> ORGANISM: Artificial Sequence
<220> FEATURE:
<223> OTHER INFORMATION: R15/APPA transgene

<400> SEQUENCE: 5

ggatcccctt tgctatgtag tttttaatgg aaattacaac ccatagtgtg ttgataaata     60

gagagtcctg tttggtttaa gcaacctctg tttctcataa actccataaa aacaggaata    120

ctctttgttt ctagcataac caaaagattt agtgaattga aaacaatgtt cccttagagt    180

ataggtctaa taaccccgaa aatattacca tgatactgag catttgtaag tatctcatag    240

catgtagtat ccatagtcca tcaatgagag agacatttaa catgattttc attaatcagg    300

tggaaaagac atgacaacat tcacaggcac tgcacagaac atagtggtcc accttgcaca    360

tatttcacta aactaggttt atctattttg ttgctttctc taacatctct gcaatgaagc    420

aggtcaacag tgccacatat cctttactta acctaaggaa cacaaaaaat tttctacata    480

tatcctggtt agagagtgct taaaataagt tttccaagaa tggaaaagaa atgttctgac    540

ttaacaatta agacagtatt tatttaaagc aagaaatatg aggcacacaa gaaaatattt    600

tgggaagaaa ccatttggtg aacaatattt caaataaaaa tagacaaaca tagttaattg    660

taaaacatat gtttgaccag cccttctttt caataggctt aatgtgaata aaatgttaaa    720

gattctcttt gggtggctgc aaattgtcca cgaataagac aaaatataaa aataaggact    780

gagtctcaca aaatgaaaag gaaatatatt cagaaagaga atcttgagag aatgtgttgt    840

cacaaattaa agaaaacctg tggtgaatga catcctgagg cctgagctat tactgacatt    900

taagataaag gtaactgtat acatttgtcc cattgagggg acaagaaagc tgctctcatg    960

ttcagctcta taattcttgc cttaaacaac ttaaatagaa tgatttaaaa tatggagctg   1020

tccatggacc tttgaaatat aaaatagtca agcaacttat caaggaatta cagattcctt   1080

gatactaaca caggtaaatc ccacacgtgt tttgagacta catttgctgg gattttattg   1140

atgtaatagg tcacatgttt ttcgggccaa tgttgctgtt attcggttac ttcaagagaa   1200

tagtggcaac tgatgctatg tattctaggg gtttgaagtg atgtttcatg attgaaattt   1260

gtaaaagaat aacatcatca ttcttaacaa tagaacatat aaagtcacac agaagtgaca   1320

gtgtttaagc tgtactattg atcaaagaaa tttattacct tcagtttcaa tggaaataat   1380

tactgataat acaaacatgt gtgaacacac actaatccta tccaaatgca cagtgataca   1440

cagaaaatat tagcaagtag aatgcaatat ttatataacg attgtattta tcaatcaatt   1500

gtatgtatca atatatgggc tattttctta cacatgattt tattcaaatt tactctaatc   1560

attgttgaac catttagaaa aggcatactg gcaacttttc cttacctcat ccagctgggc   1620

aaaagtccca gtgtggagta aaggatgcaa gatttcctgc tctgttaagt ataaaataat   1680

agtatgaatt caaaggtgcc attcttctgc ttctagttat aaaggcagtg cttgcttctt   1740

ccagcacaga tctggatctc gaggagcttg gcgagatttt caggagctaa ggaagctaaa   1800

agccgccacc atgaaagcca tcttaatccc atttttatct cttctgattc cgttaacccc   1860

gcaatctgca ttcgctcaga gtgagccgga gctgaagctg gaaagtgtgg tgattgtcag   1920

tcgtcatggt gtgcgtgctc caaccaaggc cacgcaactg atgcaggatg tcaccccaga   1980

cgcatggcca acctggccgg taaaactggg ttggctgaca ccgcgcggtg gtgagctaat   2040

cgcctatctc ggacattacc aacgccagcg tctggtagcc gacggattgc tggcgaaaaa   2100

gggctgcccg cagtctggtc aggtcgcgat tattgctgat gtcgacgagc gtacccgtaa   2160
```

-continued

```
aacaggcgaa gccttcgccg ccgggctggc acctgactgt gcaataaccg tacataccca   2220

ggcagatacg tccagtcccg atccgttatt taatcctcta aaaactggcg tttgccaact   2280

ggataacgcg aacgtgactg acgcgatcct cagcagggca ggagggtcaa ttgctgactt   2340

taccgggcat cggcaaacgg cgtttcgcga actggaacgg gtgcttaatt ttccgcaatc   2400

aaacttgtgc cttaaacgtg agaaacagga cgaaagctgt tcattaacgc aggcattacc   2460

atcggaactc aaggtgagcg ccgacaatgt ctcattaacc ggtgcggtaa gcctcgcatc   2520

aatgctgacg gagatatttc tcctgcaaca agcacaggga atgccggagc cggggtgggg   2580

aaggatcacc gattcacacc agtggaacac cttgctaagt ttgcataacg cgcaatttta   2640

tttgctacaa cgcacgccag aggttgcccg cagccgcgcc accccgttat tagatttgat   2700

caagacagcg ttgacgcccc atccaccgca aaaacaggcg tatggtgtga cattacccac   2760

ttcagtgctg tttatcgccg gacacgatac taatctggca aatctcggcg gcgcactgga   2820

gctcaactgg acgcttcccg gtcagccgga taacacgccg ccaggtggtg aactggtgtt   2880

tgaacgctgg cgtcggctaa gcgataacag ccagtggatt caggtttcgc tggtcttcca   2940

gactttacag cagatgcgtg ataaaacgcc gctgtcatta aatacgccgc ccggagaggt   3000

gaaactgacc ctggcaggat gtgaagagcg aaatgcgcag ggcatgtgtt cgttggcagg   3060

ttttacgcaa atcgtgaatg aagcacgcat acccgcttgc agtttgtaag gtataaggca   3120

gttattggtg cccttaaacg cctggtgcta cgcctgaata agtgataata agcggatgaa   3180

tggcagaaat tcgccggatc tttgtgaagg aaccttactt ctgtggtgtg acataattgg   3240

acaaactacc tacagagatt taaaaaacct cccacacctc cccctgaacc tgaaacataa   3300

aatgaatgca attgttgttg ttaacttgtt tattgcagct tataatggtt acaaataaag   3360

caatagcatc acaaatttca caaataaagc atttttttca ctgcattcta gttgtggttt   3420

gtccaaactc atcaatgtat cttatcatgt ctggatcgat ccccgggtac              3470
```

<210> SEQ ID NO 6
<211> LENGTH: 5421
<212> TYPE: DNA
<213> ORGANISM: Artificial Sequence
<220> FEATURE:
<223> OTHER INFORMATION: SV40/APPA + intron plasmid
<220> FEATURE:
<221> NAME/KEY: misc_feature
<222> LOCATION: (255)..(255)
<223> OTHER INFORMATION: n=any nucleic acid

<400> SEQUENCE: 6

```
cgagattttc aggagctaag gaagctaaaa gccgccacca tgaaagccat cttaatccca     60

tttttatctc ttctgattcc gttaaccccg caatctgcat tcgctcagag tgagccggag    120

ctgaagctgg aaagtgtggt gattgtcagt cgtcatggtg tgcgtgctcc aaccaaggcc    180

acgcaactga tgcaggatgt caccccagac gcatggccaa cctggccggt aaaactgggt    240

tggctgacac cgcgnggtgg tgagctaatc gcctatctcg gacattacca acgccagcgt    300

ctggtagccg acggattgct ggcgaaaaag ggctgcccgc agtctggtca ggtcgcgatt    360

attgctgatg tcgacgagcg tacccgtaaa acaggcgaag ccttcgccgc cgggctggca    420

cctgactgtg caataaccgt acatacccag gcagatacgt ccagtcccga tccgttattt    480

aatcctctaa aaactggcgt ttgccaactg gataacgcga acgtgactga cgcgatcctc    540

agcagggcag gagggtcaat tgctgacttt accgggcatc ggcaaacggc gtttcgcgaa    600

ctggaacggg tgcttaattt tccgcaatca aacttgtgcc ttaaacgtga gaaacaggac    660
```

-continued

```
gaaagctgtt cattaacgca ggcattacca tcggaactca aggtgagcgc cgacaatgtc    720
tcattaaccg gtgcggtaag cctcgcatca atgctgacgg agatatttct cctgcaacaa    780
gcacagggaa tgccggagcc ggggtgggga aggatcaccg attcacacca gtggaacacc    840
ttgctaagtt tgcataacgc gcaattttat ttgctacaac gcacgccaga ggttgcccgc    900
agccgcgcca ccccgttatt agatttgatc aagacagcgt tgacgcccca ccaccgcaaa    960
aacaggcgta tggtgtgaca ttacccactt cagtgctgtt tatcgccgga cacgatacta   1020
atctggcaaa tctcggcggc gcactggagc tcaactggac gcttcccggt cagccggata   1080
acacgccgcc aggtggtgaa ctggtgtttg aacgctggcg tcggctaagc gataacagcc   1140
agtggattca ggtttcgctg gtcttccaga ctttacagca gatgcgtgat aaaacgccgc   1200
tgtcattaaa tacgccgccc ggagaggtga aactgaccct ggcaggatgt gaagagcgaa   1260
atgcgcaggg catgtgttcg ttggcaggtt ttacgcaaat cgtgaatgaa gcacgcatac   1320
ccgcttgcag tttgtaaggc agttattggt gcccttaaac gcctggtgct acgcctgaat   1380
aagtgataat aagcggatga atggcagaaa ttcgccggat ctttgtgaag gaaccttact   1440
tctgtggtgt gacataattg gacaaactac ctacagagat ttaaagctct aaggtaaata   1500
taaaattttt aagtgtataa tgtgttaaac tactgattct aattgtttgt gtattttaga   1560
ttccaaccta tggaactgat gaatgggagc agtggtggaa tgcctttaat gaggaaaacc   1620
tgttttgctc agaagaaatg ccatctagtg atgatgaggc tactgctgac tctcaacatt   1680
ctactcctcc aaaaaagaag agaaaggtag aagaccccaa ggactttcct tcagaattgc   1740
taagtttttt gagtcatgct gtgtttagta atagaactct tgcttgcttt gctatttaca   1800
ccacaaagga aaaagctgca ctgctataca agaaaattat ggaaaaatat tctgtaacct   1860
ttataagtag gcataacagt tataatcata acatactgtt ttttcttact ccacacaggc   1920
atagagtgtc tgctattaat aactatgctc aaaaattgtg tacctttagc tttttaattt   1980
gtaaaggggt taataaggaa tatttgatgt atagtgcctt gactagagat cataatcagc   2040
cataccacat ttgtagaggt tttacttgct ttaaaaaacc tcccacacct cccccctgaac  2100
ctgaaacata aaatgaatgc aattgttgtt gttaacttgt ttattgcagc ttataatggt   2160
tacaaataaa gcaatagcat cacaaatttc acaaataaag catttttttc actgcattct   2220
agttgtggtt tgtccaaact catcaatgta tcttatcatg tctggatcga tccccgggta   2280
ccgagctcga attcgtaatc atggtcatag ctgtttcctg tgtgaaattg ttatccgctc   2340
acaattccac acaacatacg agccggaagc ataaagtgta aagcctgggg tgcctaatga   2400
gtgagctaac tcacattaat tgcgttgcgc tcactgcccg ctttccagtc gggaaacctg   2460
tcgtgccagc tgcattaatg aatcggccaa cgcgcgggga gaggcggttt gcgtattggg   2520
cgctcttccg cttcctcgct cactgactcg ctgcgctcgg tcgttcggct gcggcgagcg   2580
gtatcagctc actcaaaggc ggtaatacgg ttatccacag aatcagggga taacgcagga   2640
aagaacatgt gagcaaaagg ccagcaaaag gccaggaacc gtaaaaaggc cgcgttgctg   2700
gcgtttttcc ataggctccg cccccctgac gagcatcaca aaaatcgacg ctcaagtcag   2760
aggtggcgaa acccgacagg actataaaga taccaggcgt ttccccctgg aagctccctc   2820
gtgcgctctc ctgttccgac cctgccgctt accggatacc tgtccgcctt tctcccttcg   2880
ggaagcgtgg cgctttctca atgctcacgc tgtaggtatc tcagttcggt gtaggtcgtt   2940
cgctccaagc tgggctgtgt gcacgaaccc cccgttcagc ccgaccgctg cgccttatcc   3000
```

-continued

```
ggtaactatc gtcttgagtc caacccggta agacacgact tatcgccact ggcagcagcc   3060
actggtaaca ggattagcag agcgaggtat gtaggcggtg ctacagagtt cttgaagtgg   3120
tggcctaact acggctacac tagaaggaca gtatttggta tctgcgctct gctgaagcca   3180
gttaccttcg gaaaaagagt tggtagctct tgatccggca aacaaaccac cgctggtagc   3240
ggtggttttt ttgtttgcaa gcagcagatt acgcgcagaa aaaaaggatc tcaagaagat   3300
cctttgatct tttctacggg gtctgacgct cagtggaacg aaaactcacg ttaagggatt   3360
ttggtcatga gattatcaaa aaggatcttc acctagatcc ttttaaatta aaaatgaagt   3420
tttaaatcaa tctaaagtat atatgagtaa acttggtctg acagttacca atgcttaatc   3480
agtgaggcac ctatctcagc gatctgtcta tttcgttcat ccatagttgc ctgactcccc   3540
gtcgtgtaga taactacgat acgggagggc ttaccatctg gccccagtgc tgcaatgata   3600
ccgcgagacc cacgctcacc ggctccagat ttatcagcaa taaaccagcc agccggaagg   3660
gccgagcgca gaagtggtcc tgcaacttta tccgcctcca tccagtctat taattgttgc   3720
cgggaagcta gagtaagtag ttcgccagtt aatagtttgc gcaacgttgt tgccattgct   3780
acaggcatcg tggtgtcacg ctcgtcgttt ggtatggctt cattcagctc cggttcccaa   3840
cgatcaaggc gagttacatg atcccccatg ttgtgcaaaa aagcggttag ctccttcggt   3900
cctccgatcg ttgtcagaag taagttggcc gcagtgttat cactcatggt tatggcagca   3960
ctgcataatt ctcttactgt catgccatcc gtaagatgct tttctgtgac tggtgagtac   4020
tcaaccaagt cattctgaga atagtgtatg cggcgaccga gttgctcttg cccggcgtca   4080
atacgggata ataccgcgcc acatagcaga actttaaaag tgctcatcat tggaaaacgt   4140
tcttcggggc gaaaactctc aaggatctta ccgctgttga gatccagttc gatgtaaccc   4200
actcgtgcac ccaactgatc ttcagcatct tttactttca ccagcgtttc tgggtgagca   4260
aaaacaggaa ggcaaaatgc cgcaaaaaag ggaataaggg cgacacggaa atgttgaata   4320
ctcatactct tcctttttca atattattga agcatttatc agggttattg tctcatgagc   4380
ggatacatat ttgaatgtat ttagaaaaat aaacaaatag gggttccgcg cacatttccc   4440
cgaaaagtgc cacctgacgt ctaagaaacc attattatca tgacattaac ctataaaaat   4500
aggcgtatca cgaggccctt tcgtctcgcg cgtttcggtg atgacggtga aaacctctga   4560
cacatgcagc tcccggagac ggtcacagct tgtctgtaag cggatgccgg gagcagacaa   4620
gcccgtcagg gcgcgtcagc gggtgttggc gggtgtcggg gctggcttaa ctatgcggca   4680
tcagagcaga ttgtactgag agtgcaccat atgcggtgtg aaataccgca cagatgcgta   4740
aggagaaaat accgcatcag gcgccattcg ccattcaggc tgcgcaactg ttgggaaggg   4800
cgatcggtgc gggcctcttc gctattacgc cagctggcga aagggggatg tgctgcaagg   4860
cgattaagtt gggtaacgcc agggttttcc cagtcacgac gttgtaaaac gacggccagt   4920
gccaagcttt acactttatg cttccggctc gtatgttgtg tggaattgtg agcggataac   4980
aatttcacac aggaaacagc tatgaccatg attacgaatt cggcgcagca ccatggcctg   5040
aaataacctc tgaaagagga acttggttag gtaccttctg aggcggaaag aaccagctgt   5100
ggaatgtgtg tcagttaggg tgtggaaagt ccccaggctc cccagcaggc agaagtatgc   5160
aaagcatgca tctcaattag tcagcaacca ggtgtggaaa gtccccaggc tccccagcag   5220
gcagaagtat gcaaagcatg catctcaatt agtcagcaac catagtcccg cccctaactc   5280
cgcccatccc gcccctaact ccgcccagtt ccgcccattc tccgccccat ggctgactaa   5340
ttttttttat ttatgcagag gccgaggccg cctcggcctc tgagctattc cagaagtagt   5400
```

-continued gaggaggctc gaggagcttg g 5421

<210> SEQ ID NO 7
<211> LENGTH: 17732
<212> TYPE: DNA
<213> ORGANISM: Artificial Sequence
<220> FEATURE:
<223> OTHER INFORMATION: Lama2/APPA transgene
<220> FEATURE:
<221> NAME/KEY: misc_feature
<222> LOCATION: (11392)..(11392)
<223> OTHER INFORMATION: n=any nucleic acid

<400> SEQUENCE: 7
tcgagagtat ctttgtcagc tgtgcctcca acaaaggggt actgttgccc acatagaaag 60
atctaaacta attaattaat ccctcacccg caaatctttc agtcactaag ttagcacgat 120
tgttgaacaa gttctccaaa ggagagatac agatgagtgc gtatagggtg gacctggctg 180
ctgaggagac acctgcatct gactaagaag agccacggtg ttagttgaat ggtgtggagt 240
agggtggttc tgtgggacag tagaaaatcg agaggcatgt gccgtttagt gaactgatgg 300
aagctacccc aaacgacaga gattgtcagt caggccaatc cgtttcgagt ttgatgggca 360
gccggacagt gagacagaca cacctactca gttggaggaa ggatgagaac aatggccagc 420
agggattgag agaccctgac aggcgcaagg ccctaacaca cacacctacc acctcacttg 480
acaaagctgc caaagaccaa agacttgttc tccattagaa atgacagctg gcttgacccg 540
acagcataat aagcagagtg tactctgatt ggagaacttt aatgtgtttc attcagtatt 600
ataaaaggac agtattacag attttgttgt acactgctgt tacatgtggg gcagtgtgtc 660
tttaagtagg gtaaagtact ctttaaaaat gggtcctaga tattttttcc tttaactcaa 720
gtctcttact gtttaaatga tttttatttt gtttaatatg gaggaaaaag aagcgtaaat 780
ggacaatata tatttagaga aagatggtta gctgtcagaa aaatatgcaa atcaaaatca 840
caccaagact gcagcacacc cctgtcagat ggctgtgatc aagaaaataa atgacaatga 900
gtggtggtga agatgtacta aagggaaaca cacacacaca cacacacaca cacacacaca 960
cacactggag caaccactgt ggaaatcagt atgaatggtc ctcaaaaacc tgaagataga 1020
gcggggcgtg gtggcataca cttttattcc cagcactggg gaggcagagg caggtggatc 1080
tctgagttcc aggccagcct ggtctatagc acaggttcta ggacagccag ggctacacag 1140
aaaaaccctg ccttgattaa accaaaccaa accaaaccaa accaaaccaa accaaaccaa 1200
accaaaccaa accaaaccag accaaaccaa aacactgaag atagaacttc agtattccat 1260
tcctagatat atacccaatg gagactaagt cagcaagaca cctgcacagc catgttcact 1320
actacactgt tcaccacagc caggctgtgg aaccagcctg agtgtccatg ataaatgaat 1380
ggataggtaa ctttcaaggt aaatggactc tgctgtgtac atgcctcaca ttctgtttat 1440
tcatttttct ttatgaggtg tccattcagg agtcacatgg tagttctatt ttcagtcttc 1500
tgaagatact acactggtcc ccacagttta cacttttatc agcagtgaat aagggttcct 1560
ctatccttac catcatttgt tgtaattttt cttgatgacc ctctttctga cagggatagg 1620
atgtaatatc agtgtgagga agtacaactt gttttctaag tatttattgg ccccttgcat 1680
ttcttctttt gaaaactgtc ggttcctgac atctgctcag gtattcattg gatgttgttt 1740
ctttggtgtt tgagttctta tgaattctag atgttaaatc cctgcctgtg gttctctccc 1800
attctgtagg ctgcctcctc accctggcaa ttgttgtcct tgttttgcag aaacttttga 1860

-continued

```
cttcatggaa tctcatttgt cagttttccc tcctctgcta tagcctgagc taatgcactg   1920
gtttttacag agccctggtc tatgccttta tcctcctctg gcagcttcgg agtttcattt   1980
cttacattta gatctttgat ccactttgaa caagttttgg agcagggtga gagatacgaa   2040
tctagttcca ttcttccata tgtgatccta gtttacatag catcgttggt tgaagaggtt   2100
ttattttatt tttaaataat gtgtcataaa aaacgaggtg gttgtagcag tgtggatttg   2160
tttctttgtc ctttgatcta caggtcttgt tttgtgtcag tctcatgatg ttttattgct   2220
atggctctgt catacagtct gaggtcaggt attgtgatat accttcagta ttgctccctc   2280
agactcaggt ttgctttggc caggagtcat cttactcagt gctcttagag ctcccccagc   2340
atgtagctgc tactattctt agttgataaa tcaggaaact ggggctcaga gagattaact   2400
gtcttgaact acttctgggg aggtgaaacg tggagacact aaactgtgtt taccctgtac   2460
tgctccagta gctgtcgggt gctgggctac agcaaagcac ctatactata tattactcag   2520
gaggtggaaa aactcagcct cccttggggt tcccaagctc ccaggtgtcc agtcactgct   2580
ggaaacctca tggagtctga aaggaagggt tgagggtaca tggggcagcg atgaggagcc   2640
tggggctggg atctcccaaa cacctggata tccagatgcc actgggtcag gggagttggg   2700
gaacagagtt gggatgtcca tggacctgtg acaaggccag ggccaggggg aggataactc   2760
tggctttact aatttgcgaa agtccttagc ttagcagcag ttgtctggga gcacagaggg   2820
gccttctgta agaggctcag gcagtgccgc tctgtaggcg aaggtcttct ccatgttccc   2880
catggtggtt cttgatgaaa gagacagtcc ttggctccaa actggtttat tgattgttca   2940
ttgtggaaaa tgggtgcaca ccaccttctc agggtggacc agagatcaaa taccttttgc   3000
agggaggaat atctgggaag ggacgcttac tggctaaacc ctcagggcct ctagatacat   3060
cattagcatg gagaactctg ttctgggcta catgaccaca ggccacattt ccacaagcca   3120
catgtgggaa gtgtggcaca tgttctaggc caggaatctg gtagggagcg tggagccacc   3180
taccatccca ggtgggtgcc tgggtgccag ggaccctgaa cccgctcaac cttaccaagt   3240
ttcctggcag ggtccactgt cctacacaga agctggagga ggtgtgaggg ttgtgtcttt   3300
gtggaatgtc ccatgctgct tggggctcag tttctccacc tgtacctcat tggtttgggt   3360
ataaaaagtg gggatacttt attattctct gactcggtcc tgaggaaaaa gcatcgtggc   3420
agtccaggaa ccacaccctg aggttcctgc actgaaggga ctccctaagt ctctggagtc   3480
tctccccttc acagagctgc caaagtctag gttcttttga ggataacaga gccatgcttg   3540
gtaagcagac aacagcattt gtttactcaa ccttcttttg tcagctccct cttcataaac   3600
aagttgagac accatgctgg cttgaggaag acttctaaag ccagacaact gtgcaaggaa   3660
gaagaagaag gggcaagtgg agttagcctg gatgtagccc tcaaagtctc cagagaccag   3720
ccatgaaggc tcaagtggag ggcaagacct gcagcagcca agcatctggc aggagaggat   3780
cctgggaacc cctctaccat gacacacatt cttcctgcag gtcacactta ataggccatt   3840
tcttatttgg atctatcatg gtgttctgtg cgagattaat gaggtgttat gctgcgaaca   3900
gaaagttata taaaaacaag tccccccccc ttgtcactgc tgctaagaat gtagcagaaa   3960
ttgtctcaag tgtctctcta atcagaaaca ataaaggtct ccttggattc aagccctcca   4020
gtttcctcct tccttgctga gccttggaca cccatacaaa cctcctggat gctacagctc   4080
tgggcagaga ctccaaggtg gggagagact gatggtacaa aagcaaaata cttgtttggg   4140
ggtacaccca ctcctctgcc tgtgtggttc ctgcagtcag tcctgcagac aggccctcag   4200
tgggtcttcc atgggcaaca cgcagaggga ggcaatggat gggaataccc acaccctggt   4260
```

-continued

```
tagtttaccc cggccatgct ctctgctctt catccctcct ctgccctctg ccacggcttt   4320
ctctgcagga atcatatctt catattggcc cacaggtgtt ctcctcaccc tagctatgat   4380
gtttacttta gagtgacctt agcagggctg gtgggaatga gttctagaag gctcacggag   4440
atgctaggga agaaacgtct tctaactact gaggttacta agttcctggt ggttgtctct   4500
gcctttccct tgttaaagtc accttgaagt tagtgcagaa gaaatcagag cccagtcaca   4560
gagtaaatat ggtcctgaag atttcctttg agtgcccaga atccatgaca tttcaagagc   4620
cctctttgta ccttaagtca tttggggttg tatcttctgc ttgatgtatg tgtgtgtgtt   4680
tatcaaagag tgagatggtt acataagagg tgctctaaag gacagagagg atttgcaatt   4740
gtggcatgtg acatcctcag gccttgctct ggtgccagga ggaactgatg cagaaaagag   4800
taagaggtca tttcctggag gctgtcacta tagaggagat cttacagtgc attccctcct   4860
ccaggccctg cctgaggata gacatgtgct gactgcaact gaaacagagg cttgggatgg   4920
agagttaggt tcacagaagg gagggtggga gatggatgct tgctgggttc tgggtctcat   4980
caccagctcc tgaccacccg gtcagcccat gtgcttattc catagctttc ttttgctatg   5040
tttactcagt gtggtgtttg ttgggaccca gcagaagcca gtcccaggct gacagctgtg   5100
gatacacagg gcagcatgag ggtcctcagc ctgaagcagt caggctggca gaagagaaag   5160
accagcacac attccttcaa ccaactatgt cttgaaaaac aaacatatta tatcacatat   5220
attgcattta tgagacagct aaaatgtact cgggtagcat gactccaggt ggggatatct   5280
gcaagtgcca tgagtggcag agggacagcc aatgtgaggc aagaaggaat tctggctcaa   5340
cacagcttag ctccctggtg ttggttcaaa ctttgagagt ttgaccacaa gcactttatt   5400
tttgacatat ttaaacagag cacaactttg ggaaaaagtt ttcttatgaa aattatcaca   5460
ataaagctta aggcatgact acattaaaat gcctttgcaa agtatatgtg ccctcttcca   5520
caagaatggt tctattgact gagaaataat gttcaggata aagatccagg aagaaaagat   5580
cagggataag taaaatacta aactcttttg caaagtacat agaccctctt tcataacaat   5640
gggttctatt gactgacaag cactgctcag gagttgggaa agagtctagc ataagcacga   5700
tagcctggag actctagtga ggtctagtct tacagacagc aaaaatcacc aggttacaaa   5760
ctacattcat ttccagtttt ctgatcaggc acaggtatga atcccttctg ttgaagagaa   5820
aagtccatgt gtttaaaata tctggtttct ccagtgctat tagcgagaag acttgagccc   5880
tatacaactc ccacctggag tgacatcctg tcttcatggt atattacata cctagacacg   5940
ctcatctcac agacttagga ctttgtcttc tgatctccat ttctgatccc acttccacct   6000
ttgccttgat agtgtcattt tcttcactgc cttggtgaca accatgttat cctctgtgta   6060
tttgagtgtt accattttca gattttacct gtatgcaaga tcacacagtc tttgtctttc   6120
tgtctggatg catgctaatc tctacacaac aacccttccc cgtcactcag atcttcctcc   6180
attaacacat acatggtgct gaagaggcta gggagcttcc cttcagtggg gagctagctg   6240
gctattgggc ctttttgact gtccaggaag gcccccaatt gctgagacaa gaacttagat   6300
tcttcattat tgactctaac tcatgtatca agcagaagct aatgaatagt tatcaacagg   6360
atcagaggtt ccagtgtaag acactttgac atgaaagaac ggaggaagga cagatggatg   6420
cataaaagca ggaccactgc cccaggaagg tcctggaaac tgatgcaggg caaaggacag   6480
gttataaacc aaatcttagg gagtcaggaa gagcacagag gagctcaacc aactgaccac   6540
tgcttagggg ctaccaaccc aatcctccct gtgggaacag ctaagctatc agccaagggt   6600
```

-continued

```
aataaacagg caggacctgt ggatgacatg gagagcatag ggaccctggg tccagccttt   6660
agcacctgca ctctcaggat actccaccat tgtgtcttag agagcctagg gatactgggt   6720
ccagcctttg gtaccttcac tctcagggta ccccatcact gtgtcttgga gagcctaggc   6780
accctgggtc cagccttcag tacctgcgct ctcaggacac cccaccattg tctcttgccc   6840
cgtctcttct tcctcttcct ccctttcatt gtctcttctc tgtttctttc ttgactctcc   6900
tttcccctca caccctcact ctagttctcc ccttccctct ctgcatcacc ctattctctc   6960
tgtggtccct ccactttcct ttatctctca tgcttctctc ctccctcaaa tacttgtcac   7020
ccactatact tcaggggcca gctctagtga caaagctgtt aatagcaaga ctctcagatc   7080
tccaacggct cagaggagcc agacccacca agaactctct ccaggtccaa tttcaggttc   7140
cttcgaaagc tttcagcaaa tgctcaggga acatgccact aacaagaaga tgcaaattcc   7200
agttgagagt gggaaaggcc cttgcgtagg tcccatcttc caggccaagg tcagaggggc   7260
tctgtgtaat ccggattgac agggctcaga acaatgtttt gtttttaagg tttatttatt   7320
ttaggtgtta gtgtctttgc ttgcatgacc ttatgtgcat catgtgtgtg caggttcctg   7380
atgacagtag aggagggctt tgaatccctg gggataggaa gttacaggaa attataagct   7440
gctttgtggg tcttctagct ttcccaacag aagtgaatgc tcttcaccac tgagccatct   7500
ctctaggccc aagagacatt gctttatgga tataattgtg tgtgtgtgtc aacattgagg   7560
aaagggaaat aaaaaaaaaa cttcagccgc taaggttgta cagtttcact aattgctact   7620
tttagttgtg ataaaatggc aggtgcttca acatttatat atacaaaaac ttccctgctg   7680
gtggttcaac tgtgagaact ggggtaagtg ggtgagttct ctttttctgt ctctgtctct   7740
gtctctctcc ttccattctt tcttaaagga aataaacatt gcagctgggt tatagctcat   7800
caatatggaa gttacagaag tgaaaaaagg cattgccttg gtgggtggtg ttaccagctg   7860
atttttggtt gtcctgcaag gaggtctggg gactggctgc tctgtctctg tctgtatgag   7920
tgagggaagt ctggggagca gattccctaa ccttcagcct ggcctggttc ctgagtgaac   7980
ccagcctctc tggtcctagt agctttttcc aaacaggaat ctgagtggtg acagggaaca   8040
agtaccagcc cattgcttaa gtgccagggt tagtgagggc aggaagctgc catagctggg   8100
attagtagtt gtattggatg taggaagtcc tatcctggga cagctaatcc ttaatgcttc   8160
actggagatt ttcaatgaga aatttatccc acggcccata tggccccatc cttttgtctc   8220
caacagccaa gtattttcca ttagaggaga cttcctgtac acttgatgga tgctcattcc   8280
aaggtgactt ggggcagtca gtacagactt gggatgacct ctgacagcct aacctctccc   8340
caacaagggc cctctatgtt tgctatgtaa tgtaatgtca gacattgtca ggagtgtccg   8400
cagcacagcc tgcccagtgt gagggctctc ataggtttcc cactgtctta tctacacagg   8460
gataacgagg aggtaagctg cagttcccag tctcacttca cagaggaaga gataacccca   8520
tcccaggtca tgtagccagc agtggaaaga atgaggattt gaactcaggt cttccaagtc   8580
ccattgatag catctcctca caagtccctt gccaccctca cgatgcctta gacacttgcc   8640
tgccctttat actaaggaga tgcaggtaca aggggtttac ccatgtagca gctgaggcag   8700
ctggggatag ataccagcag caggcctgat gtcaccactc taactccagc atccccagtc   8760
tgtgttcctg gagtgtgaaa atccctactt aacaagattg tgcaacagtc cttggctctg   8820
tgacccatag ctggaaacag gattctcatt gatttgtgga acatggtggc agccagccaa   8880
aaagagggtc tgcatacaga agacacgtgt ggcaaggcca cagcagactc tgactacctt   8940
agcttacaga attacaaggt cataatgtcc tctgctttgg tcacctcatg ttaaggacag   9000
```

-continued

```
gccctaatga agatggggca gaagactgaa ggaatggcca accaataact ggcccaactt   9060
gagacccatc ctacaggcaa gcatcaattc ctgacactac taatgatact ctgttatgct   9120
tgcagacaga agcctagcat aactatcctc cgagaggtcc acccagcaac tgactgaaac   9180
agaaaaagat atccacaggc aaacagtgga tggaggtcag ggactattat gggagagctg   9240
tgggaaggat taaaaaccct gaaggggata ggaaccccac aggaagacca acagagtcaa   9300
ctaagagacc tgtgggagct ctcagagact gagccaccaa ccaaagagca tacacaggcc   9360
ggtccgaggc acctggcacg tgtgaagcag acatgcagct cagtctccat gtaggtcctc   9420
caataagcgg tagcctgact gcagtatcca atccccaaca gggctgcata gtctggcctc   9480
agtgggggag gatgccccta atcctgcaga gacttgatga gtggagagct atccaggggg   9540
aacccaccct ctctgagaag ggaatgggga tgggggaggg actctgtgaa gaggggacaa   9600
ggacaaacaa gaacctcaaa taggtcaggc cctaaaggct tgctaagtag cagtggccca   9660
gctctgtcct gttcctcagc ccaaggctca gctcccacct gtttctgtgt ttttctggct   9720
tttcatgggc ctaggacttg gtgaccagtt caaacaatgg ggcctgtgga agacacaata   9780
tacaagacta gggacattcc tgttctgctg actatccata gcctgatgta ggtggaagga   9840
cccaatcact ggatttctac ccttgcacaa ccttgacagc tgagggcctc tcagaaacct   9900
atttcttcca ctgaaaaatg agactctcaa atgaacgtcg tgacaatcat caggcttatt   9960
aaagaggtgt atctaacctg aatggcaagc agacagcagg caaatgtctg tatcaacctc  10020
taggaaggac aagaactgct cactgctgcc ccccaggagg ccatttgctg aaacagctgc  10080
tctcctgctg gtgcacaggc cctgccttct cattgcagcc acagcccctt cctgtctgaa  10140
cctcctgtca ggtcactggg aaacagatca agatggaaca ggacagctcc tgatggtaaa  10200
taaaaaacag tggtcatggc tattcatagg ggtttatgct tcttcagtcc acactgtgaa  10260
gagctgtggg catgaaccac agtgttcgag gtagagttgg ggttctgaaa ttcacagtgg  10320
ggtgagctca gtaaatgtga gctggaggtc actcgtgaga cacacagtcc tgctgcttct  10380
gttcccaata tcctgaggag acgacacatc tactttgttc agaggccaca gtctagttga  10440
cctgagagtt accagtttct tatttgtgtg tgtgtgtgtg tgtgtgtgtg tgtgtgtgtg  10500
tgttgttcgt gtgtgagtgc aggtgcacat atgatagcgt acacgttgag gtcagaggat  10560
aactatcagg cgttgtcccc tcctactttt cctcggactc tggagaacaa acatgggtcc  10620
ttattccagg ggagcaagtc gctgttggct gacacatctt gctcacatac attttaccta  10680
gacaatggag cctccatcag agtattactt tagctcctca ccgatggcaa tgcaccacct  10740
ctctacccac ataggagttg ggtctccaca cacccccaca ccccccttcac caaaacgttt  10800
tcagttactt tatctggtaa agttcatcag agaatgaagc cagtattaag aacatggaat  10860
catttgggaa cctggatcta gcaatacccc accctagatg gagttgctga gttttcacct  10920
cagattataa ttccccccta gcttctatgg tttattctga aaccagggga actcgattcc  10980
tcccttttgga ccacagacat cctggcttgt gaattcacat gtcatctact gctaatccat  11040
tggtagtatg tggctcacag agacacacta cagtcatggc caatgtcaag gtaggacaga  11100
tgtgaatcat tcccccagtc ctgctgtttt catgactaac cctcctcagc acagtgacca  11160
tgaacctact tttcccctcc ttttattttt agaattgctg gaattttcta ttttgagaaa  11220
taatagcctt gggcagcatt aaacaaaatc atctagaaag ctggtttaaa atacagatgg  11280
ttgagtcagt gaaagagtga ggaatgtcat tattggcccc tcacagaggc tggctcactc  11340
```

-continued cagcagaggt ggttgaagct cttggacacg ggtcaggtgc ataggaaagg tngtctggga 11400
cactgagaac cacaattgaa caaacagaac tgttggcttt ttttttttta aatgagttct 11460
caaaaaatga ctggctagct taggcaaata cttcgagcca acccaacaga acattcttcc 11520
attgattcat tctggatctt ctttctagac aatactgaac tgaccccttg ttggcagtct 11580
caagtttgac aacatagggc tttgaacttg gcacaaggtc catcactgtc acccaagcat 11640
cctgggtgac ctttgggttg gaatatcttg gctaacctta gatattttct ttggagtatc 11700
tttagaacat ccaggaaata gggcttgatt ctcatcctgg gaccacaata taagtcaccc 11760
tagaatccca ggagatcgtg cagagaaaca aggatctctc tcgtgtgcat ccttcttcaa 11820
agcagtgagt agtgactcca ctaaactgag ttcccatctg agagtccaca ggaggctttg 11880
gggcaagaag cagagggaag gcactgtttg tgttggtaaa gttttgactc taacaaattt 11940
gaagacatag atgacattgt gtcagactaa caacaaccta gactcatgtg ggttctgttt 12000
agggatcaga ttttattcat caatgacttg tcttagtgta tagagaaagg cttcctactg 12060
gagtgtaggc tcaataatga cagaagagat agctatttcc cctagggact gtgctgctcc 12120
aagtttggtg gagaaaggca gtggggaacc tagatgtgct ctctggggag ggggtctgaa 12180
gctggcttca tagaaggtgt gaagttttgc tgaaacatct aaacagaatt atagcttagg 12240
aaagtgagca ggcaaggcag ggaatgtgtt gcatatgtat atgtacatga atatattatg 12300
ttatagatac acacacattt gaacctcatt tgcagatgac agaaaatagg ttattttgcc 12360
tctcttaact gctaagcaca atgacttcca gttccatcca tttcctgaaa tgccacaatt 12420
tcatttttca ttgtggctga ataaaattcc attgcagact gggccctact tcatccactc 12480
ctgagggcag gcatatcccc tggctccatt tcttacctat tgtgaagaga agtgcaactg 12540
tcttgttgaa aggcaagcgt gagagaggca ggcactaatt gtgggttttt gtttcttctt 12600
cctgctatga ctctccattt gtcagaacca aagatcgata aaagccgcca ccatgaaagc 12660
catcttaatc ccatttttat ctcttctgat tccgttaacc ccgcaatctg cattcgctca 12720
gagtgagccg gagctgaagc tggaaagtgt ggtgattgtc agtcgtcatg gtgtgcgtgc 12780
tccaaccaag gccacgcaac tgatgcagga tgtcacccca gacgcatggc caacctggcc 12840
ggtaaaactg ggttggctga caccgcgcgg tggtgagcta atcgcctatc tcggacatta 12900
ccaacgccag cgtctggtag ccgacggatt gctggcgaaa aagggctgcc cgcagtctgg 12960
tcaggtcgcg attattgctg atgtcgacga gcgtacccgt aaaacaggcg aagccttcgc 13020
cgccgggctg gcacctgact gtgcaataac cgtacatacc caggcagata cgtccagtcc 13080
cgatccgtta tttaatcctc taaaaactgg cgtttgccaa ctggataacg cgaacgtgac 13140
tgacgcgatc ctcagcaggg caggagggtc aattgctgac tttaccgggc atcggcaaac 13200
ggcgtttcgc gaactggaac gggtgcttaa ttttccgcaa tcaaacttgt gccttaaacg 13260
tgagaaacag gacgaaagct gttcattaac gcaggcatta ccatcggaac tcaaggtgag 13320
cgccgacaat gtctcattaa ccggtgcggt aagcctcgca tcaatgctga cggagatatt 13380
tctcctgcaa caagcacagg gaatgccgga gccggggtgg ggaaggatca ccgattcaca 13440
ccagtggaac accttgctaa gtttgcataa cgcgcaattt tatttgctac aacgcacgcc 13500
agaggttgcc cgcagccgcg ccaccccgtt attagatttg atcaagacag cgttgacgcc 13560
ccatccaccg caaaaacagg cgtatggtgt gacattaccc acttcagtgc tgtttatcgc 13620
cggacacgat actaatctgg caaatctcgg cggcgcactg gagctcaact ggacgcttcc 13680
cggtcagccg gataacacgc cgccaggtgg tgaactggtg tttgaacgct ggcgtcggct 13740

-continued

```
aagcgataac agccagtgga ttcaggtttc gctggtcttc cagactttac agcagatgcg  13800
tgataaaacg ccgctgtcat taaatacgcc gcccggagag gtgaaactga ccctggcagg  13860
atgtgaagag cgaaatgcgc agggcatgtg ttcgttggca ggttttacgc aaatcgtgaa  13920
tgaagcacgc atacccgctt gcagtttgta aggtacccgg ggatcacaac ttgccctctg  13980
aagaggaaga acagaaggat gccacaactc tcctgctggc tactctccag tggtttcatc  14040
ttacttctga tggcatttcc ctctagaaag tgctactatc atccacacat ttctacctga  14100
gaccacccaa aggaccctcc caaattctct tcctctctga gtagtctcca cacctgttac  14160
caccatccca gaattaaaat cctaactgca ctctggcgtg tgacttgcct cagtccttgc  14220
aataagagtt gttggcagtg ccaggcgtgg tggcgcacgc ctttaattcc agcacttggg  14280
aggcagaggc aggcggattt ctgagttcga ggccagcctg gtctacagag tgagttccag  14340
gacagccagg gctatacaga gaaaccctgt gtcgaaaaac caaaaaaaaa aaaaaaagtt  14400
gttggcagag tgtgggttat ataccaggtg gagatttcaa atgagtggct gaagctgtag  14460
ccagaaggaa cttagaggat agctcataac ttaaaaagaa atgtagagag tagcagaaac  14520
attgagagag tgggcacaca gccactgtgt gaatgtggca gaacacaatc cagccagcta  14580
tacatgcata agtgtatatt ggcgccatcc tgactgatga gacacaggaa aacagataga  14640
cggggttagg tggccatggc ctttcctgcc tgcctcttcc taagggtcat ctcaagacct  14700
tatgctctct taactcttcc attgctactt agcttctaga tatcacctcc agattagtct  14760
ccttgggtac atcagtgatc ctggtgatat ccagggcttc ctgattccat ctttgtcata  14820
gaggctgcaa ctaaagaggt cttcttaata cttcacaccc tgatgccaaa aggaagacac  14880
agaagttcac agaggtgaag tgattcatgt aggacataca gtgagcaagc atcagggtcc  14940
ggattatctg actctactct aacttttatg taaatgtgct ttatgccatt aacactgtca  15000
ttcctgtgct tcagctctgg gagactccca agcactctta ggcacaagcc acaattaagg  15060
gactctgaca ctctgcattg attaattagc atggtggtct ctatgtttcc agattcatga  15120
ttgtttcact ttccatatag gctatgaagg gtgtgaggaa attttttggg gacagaattg  15180
gaggcaatcc acctctctca ggaagcctct atctggaaaa gcttacaact cagggacagt  15240
aactgtaggc ccagtccttg gtgtccaaaa tgggttttat ggtttgaatc tgcaaagcct  15300
tccatgtgct caaaggtttg aacatggagc ctcctcctgg taacactgta ttggaggctt  15360
ttgagactgg atgctctttg gtcccatgtt ttgctacatc atctgtcaag atatgaccca  15420
ggcatgctac cagctaccac agactatgcc tctccagctt tcatgttctc cccaccatga  15480
tagacttgta tctcctaaaa atggaatcaa agcaaacttt tcctgcatta agttttttttt  15540
tttctgttaa gtgtttggtc acagggacaa gaaaacactc aatacagata attagtacca  15600
gagttgaggt tcattgctct agcaagttgg atcaaatttt tagggctttg gaactgattt  15660
ataagagaca tgtagaagag tctgaagctg tgggctacag aagtgtcacc agtttttaag  15720
aatagtttaa tacaccatgg gaattgtgaa aatcagaatg ctcacacaaa ggcagacagg  15780
aaaacgtgag catgtggcgt gtgagagggc ataagaagga acctaggggg aaatgagcta  15840
gaagccattc ggctacgtta gggaacgtgt gtggctgtgc ttggcccatg ccctggcaat  15900
ctgaatgagg ccaaatttta aaggagtgga ctaactcgat tgtcagagaa aatatcaaga  15960
cagaccacca ctcaggctat gccgtgtttg tgaccgacca gctactctta gccagctcta  16020
ttgtgaaatt ccagagcaat tatcagagca tgaagataca tacagtttag tgaagtaagg  16080
```

-continued

```
ggtgtgggtc cctaagtgga tggtgcataa atctatgtag gtgatgccta agtgacactt  16140

gataatccaa aatatcagca atgtggaatg tcttccaagg agacctgtag acacacattt  16200

tagaactttg ctcatggctg taataaatag ctagctagaa atcatttcct gaagaggtta  16260

gtctgagtta cggttccagg gcaaacattc agtgatggca aggaaggcat tgcagtcagg  16320

agccaaaggt cagctggtca cattgcatca agagtagaga gtcagagtgt gagtagaaag  16380

aggatacagg ttataaaacc tcactgtcca ctctcagcaa tccattttct cctaaaaggc  16440

tttaccttct aaagatttta gtcttcaaaa ccagtaccag tagcctggga acaaaagttg  16500

aaacaaatga gcctttgtgg ggcatttcac acttaaaaca gggcatcacc taggaggagc  16560

cctgtgtgca gtaggaagtg tggcctctgt gtcaggaatg ctcaggctaa taaggggtcc  16620

tctatctgag ggaccctatg aagattcaac aagtagttgt gagaattccc tgtaaatgga  16680

tgctaccaat ttgacatttg tagacctgct attgtgtgct tctttattgg gctctcccat  16740

ctcccaactt tccaacccat attccacatt aatcccttcc accaccatgc aacactaggt  16800

aggagagaag gaaggttaga agagaaagtg ggtatagatc tatttagact acttcctgct  16860

gattaggggc aagtccaatc gtcattgtca ggatacctcc aaccagcaac cagcaaacca  16920

gcaaatcaga aacagcaaaa gcagccaaca aggcagcact aaccagcagg attggggtcg  16980

gtagcgtggg agcagtcact actggtcttc tcatggcttt ggcattaata ctctctcaag  17040

aaattccgta attttttccc caccacctga aattccgtaa ttttaaatgc aaactatcta  17100

cagctggcaa aaatcacatc tctcctagag cacaagacaa atcatagtta ctggctattt  17160

gcaatctgaa gcatctcaat atcccacacc tgggattaaa acaaaaacat attcacatca  17220

cataactgtt tttttttcc aattttttat taggtatttt ctttatttac atttcaaatg  17280

ctatcccgaa agtcccctat accctcccac ctccctgctc ccctacacac ccactcccac  17340

tttttgaccc tggagttccc cggtactggg gcatataaag tttgcaagac caaggggcct  17400

ctcttcccag tgatggccga ctaagccatc ttctgctaca tatgcagata gagacacgag  17460

ctctgggggt actagttagt tcatattgtt gttccaccta tagggtcgca gaccccttca  17520

gctccttggg tactttgtct agctcctcca ctgggggctc tgtgttttat ctaatagatg  17580

actgtgagca tccacttctg tatttgacag gcactggcct agcgtcacat gagccagcta  17640

tatcagggtc ctttcagcaa aaccttgctg gcatgtgcaa tagtgtctgc gtttggtggt  17700

tgattatggg atggatccac tagttctaga gc                                17732
```

<210> SEQ ID NO 8
<211> LENGTH: 10
<212> TYPE: DNA
<213> ORGANISM: Mus musculus

<400> SEQUENCE: 8

```
tgggaggtcg                                                            10
```

<210> SEQ ID NO 9
<211> LENGTH: 17
<212> TYPE: DNA
<213> ORGANISM: Mus musculus

<400> SEQUENCE: 9

```
catgaccctc cagccag                                                    17
```

<210> SEQ ID NO 10
<211> LENGTH: 7

-continued

<212> TYPE: DNA
<213> ORGANISM: Mus musculus

<400> SEQUENCE: 10 cggwccg 7

<210> SEQ ID NO 11
<211> LENGTH: 6
<212> TYPE: DNA
<213> ORGANISM: Mus musculus

<400> SEQUENCE: 11 ggtacc 6

<210> SEQ ID NO 12
<211> LENGTH: 6
<212> TYPE: DNA
<213> ORGANISM: Mus musculus

<400> SEQUENCE: 12 ggtact 6

<210> SEQ ID NO 13
<211> LENGTH: 22
<212> TYPE: PRT
<213> ORGANISM: E. coli

<400> SEQUENCE: 13

```
Met Lys Ala Ile Leu Ile Pro Phe Leu Ser Leu Leu Ile Pro Leu Thr
1               5                   10                  15

Pro Gln Ser Ala Phe Ala
            20
```

<210> SEQ ID NO 14
<211> LENGTH: 13
<212> TYPE: DNA
<213> ORGANISM: E. coli
<220> FEATURE:
<221> NAME/KEY: misc_feature
<222> LOCATION: (7)..(7)
<223> OTHER INFORMATION: n=a or g

<400> SEQUENCE: 14
gccgccncca tgg 13

<210> SEQ ID NO 15
<211> LENGTH: 20
<212> TYPE: PRT
<213> ORGANISM: Mus musculus

<400> SEQUENCE: 15

```
Met Phe Gln Leu Gly Ser Leu Val Val Leu Cys Gly Leu Leu Ile Gly
1               5                   10                  15

Asn Ser Glu Ser
            20
```

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16

-continued tcggcgctca ccttgagttc 20

<210> SEQ ID NO 17
<211> LENGTH: 25
<212> TYPE: DNA
<213> ORGANISM: Artificial Sequence
<220> FEATURE:
<223> OTHER INFORMATION: Synthetic primer

<400> SEQUENCE: 17
ccgtttaaag ccatcttaat cccat 25

<210> SEQ ID NO 18
<211> LENGTH: 24
<212> TYPE: DNA
<213> ORGANISM: Artificial Sequence
<220> FEATURE:
<223> OTHER INFORMATION: Synthetic primer

<400> SEQUENCE: 18
gtcccgggta tgcgtgcttc attc 24

<210> SEQ ID NO 19
<211> LENGTH: 35
<212> TYPE: DNA
<213> ORGANISM: Artificial Sequence
<220> FEATURE:
<223> OTHER INFORMATION: Synethtic primer

<400> SEQUENCE: 19
ccatggtggc ggcttttagc ttccttagct cctga 35

<210> SEQ ID NO 20
<211> LENGTH: 35
<212> TYPE: DNA
<213> ORGANISM: Artificial Sequence
<220> FEATURE:
<223> OTHER INFORMATION: Synthetic primer

<400> SEQUENCE: 20
agcgcttgca gtttgtaagg cagttattgg tgccc 35

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
tcgaggagct tggcgagatt 20

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
tttcgggcca atgttgctgt 20

<210> SEQ ID NO 23
<211> LENGTH: 21
<212> TYPE: DNA
<213> ORGANISM: Artificial Sequence -continued
<220> FEATURE:
<223> OTHER INFORMATION: Synthetic primer

<400> SEQUENCE: 23
cccaagcttt acactttatg c 21

<210> SEQ ID NO 24
<211> LENGTH: 25
<212> TYPE: DNA
<213> ORGANISM: Artificial Sequence
<220> FEATURE:
<223> OTHER INFORMATION: Synthetic primer

<400> SEQUENCE: 24
gccctcgagc ctcctcacta cttct 25

<210> SEQ ID NO 25
<211> LENGTH: 26
<212> TYPE: DNA
<213> ORGANISM: Artificial Sequence
<220> FEATURE:
<223> OTHER INFORMATION: Synthetic primer

<400> SEQUENCE: 25
ggatcgataa aagccgccac catgaa 26

<210> SEQ ID NO 26
<211> LENGTH: 20
<212> TYPE: DNA
<213> ORGANISM: Artificial Sequence
<220> FEATURE:
<223> OTHER INFORMATION: Synthetic primer

<400> SEQUENCE: 26
tcggcgctca ccttgagttc 20

<210> SEQ ID NO 27
<211> LENGTH: 30
<212> TYPE: DNA
<213> ORGANISM: Artificial Sequence
<220> FEATURE:
<223> OTHER INFORMATION: Synthetic primer

<400> SEQUENCE: 27
gcacgcacac catgacgact gacaatcacc 30

<210> SEQ ID NO 28
<211> LENGTH: 25
<212> TYPE: DNA
<213> ORGANISM: Artificial Sequence
<220> FEATURE:
<223> OTHER INFORMATION: Synthetic primer

<400> SEQUENCE: 28
cgggtacctt acaaactgca agcgg 25

<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29
cagagtgagc cggagctgaa 20

-continued

<210> SEQ ID NO 30
<211> LENGTH: 20
<212> TYPE: DNA
<213> ORGANISM: Artificial Sequence
<220> FEATURE:
<223> OTHER INFORMATION: Synthetic primer

<400> SEQUENCE: 30
cgaactggaa cgggtgctta 20

<210> SEQ ID NO 31
<211> LENGTH: 27
<212> TYPE: DNA
<213> ORGANISM: Artificial Sequence
<220> FEATURE:
<223> OTHER INFORMATION: Synthetic primer

<400> SEQUENCE: 31
gcatcgatct ttggttctga caaatgg 27

<210> SEQ ID NO 32
<211> LENGTH: 20
<212> TYPE: DNA
<213> ORGANISM: Artificial Sequence
<220> FEATURE:
<223> OTHER INFORMATION: Synthetic primer

<400> SEQUENCE: 32
tgactctgag ttcccaatga 20

<210> SEQ ID NO 33
<211> LENGTH: 20
<212> TYPE: DNA
<213> ORGANISM: Artificial Sequence
<220> FEATURE:
<223> OTHER INFORMATION: Synthetic primer

<400> SEQUENCE: 33
gtgctgctcc aagtttggtg 20

<210> SEQ ID NO 34
<211> LENGTH: 24
<212> TYPE: DNA
<213> ORGANISM: Artificial Sequence
<220> FEATURE:
<223> OTHER INFORMATION: Synthetic primer

<400> SEQUENCE: 34
gcagattccc aaaccttcgc agag 24

<210> SEQ ID NO 35
<211> LENGTH: 24
<212> TYPE: DNA
<213> ORGANISM: Artificial Sequence
<220> FEATURE:
<223> OTHER INFORMATION: Synthetic primer

<400> SEQUENCE: 35
tctgcccaag tcctaaatgt gcgt 24

<210> SEQ ID NO 36
<211> LENGTH: 34
<212> TYPE: DNA
<213> ORGANISM: Rattus norvegicus

<400> SEQUENCE: 36

-continued

```
gccgccacca tgggagcgct tgcagtttgt aagg                             34


<210> SEQ ID NO 37
<211> LENGTH: 20
<212> TYPE: DNA
<213> ORGANISM: Mus musculus

<400> SEQUENCE: 37

ggtactggga ggtcggtccg                                             20


<210> SEQ ID NO 38
<211> LENGTH: 20
<212> TYPE: DNA
<213> ORGANISM: Mus musculus

<400> SEQUENCE: 38

ccatgaccct ccagccaggc                                             20
```